US012290574B2

(12) United States Patent
Anguela et al.

(10) Patent No.: US 12,290,574 B2
(45) Date of Patent: May 6, 2025

(54) OPTIMIZED PROMOTER SEQUENCES, INTRON-FREE EXPRESSION CONSTRUCTS AND METHODS OF USE

(71) Applicant: SPARK THERAPEUTICS, INC., Philadelphia, PA (US)

(72) Inventors: Xavier Anguela, Barcelona (ES); Liron Elkouby, Modi'in-Maccabim-Reut (IL)

(73) Assignee: Spark Therapeutics, Inc., Philadelphia, PA (US)

( * ) Notice: Subject to any disclaimer, the term of this patent is extended or adjusted under 35 U.S.C. 154(b) by 985 days.

(21) Appl. No.: 17/250,712

(22) PCT Filed: Aug. 23, 2019

(86) PCT No.: PCT/US2019/048032

§ 371 (c)(1),
(2) Date: Feb. 23, 2021

(87) PCT Pub. No.: WO2020/041773

PCT Pub. Date: Feb. 27, 2020

(65) Prior Publication Data

US 2022/0362408 A1 Nov. 17, 2022

Related U.S. Application Data

(60) Provisional application No. 62/784,116, filed on Dec. 21, 2018, provisional application No. 62/725,096, filed on Aug. 30, 2018, provisional application No. 62/722,547, filed on Aug. 24, 2018.

(51) Int. Cl.

| | |
|---|---|
| ***A61K 48/00*** | (2006.01) |
| ***A61K 9/00*** | (2006.01) |
| ***A61P 7/04*** | (2006.01) |
| ***C07K 14/755*** | (2006.01) |
| ***C07K 14/775*** | (2006.01) |
| ***C07K 14/81*** | (2006.01) |
| ***C12N 7/00*** | (2006.01) |
| ***C12N 15/86*** | (2006.01) |
| *A61K 38/00* | (2006.01) |

(52) U.S. Cl.

CPC ........ *A61K 48/0066* (2013.01); *A61K 9/0019* (2013.01); *A61K 48/0058* (2013.01); *A61P 7/04* (2018.01); *C07K 14/755* (2013.01); *C07K 14/775* (2013.01); *C07K 14/8125* (2013.01); *C12N 7/00* (2013.01); *C12N 15/86* (2013.01); *A61K 38/00* (2013.01); *C07K 2319/00* (2013.01); *C12N 2750/14143* (2013.01); *C12N 2800/22* (2013.01)

(58) Field of Classification Search

CPC .............. A61K 48/0066; A61K 9/0019; A61K 48/0058; A61K 38/00; A61P 7/04; C07K 14/755; C07K 14/775; C07K 14/8125; C07K 2319/00; C12N 7/00; C12N 15/86; C12N 2750/14143; C12N 2800/22

See application file for complete search history.

(56) References Cited

U.S. PATENT DOCUMENTS

| | | | | |
|---|---|---|---|---|
| 8,008,468 | B2 | 8/2011 | Roelvink | |
| 11,110,153 | B2 | 9/2021 | High | |
| 11,814,642 | B2 | 11/2023 | Hebben | |
| 11,857,641 | B2 | 1/2024 | Ando | |
| 2006/0189561 | A1* | 8/2006 | Roelvink | C12N 15/1131 435/320.1 |
| 2008/0025952 | A1* | 1/2008 | Scheule | A61K 48/0075 514/44 R |
| 2014/0271550 | A1 | 9/2014 | Rabinowitz et al. | |
| 2016/0347822 | A1* | 12/2016 | Crystal | A01K 67/0275 |
| 2017/0043036 | A1* | 2/2017 | Hoffman | A61K 39/0008 |
| 2017/0216408 | A1* | 8/2017 | Anguela | A61K 38/37 |

FOREIGN PATENT DOCUMENTS

| | | | |
|---|---|---|---|
| EP | 2542247 | A1 | 1/2013 |
| EP | 3293203 | A1 | 3/2018 |
| EP | 3293259 | A1 | 3/2018 |
| EP | 3293260 | A1 | 3/2018 |
| EP | 3794043 | A1 | 3/2021 |
| JP | 2018522529 | A | 6/2018 |
| JP | 2021514201 | A | 6/2021 |
| JP | 2022544004 | A | 10/2022 |
| KR | 20190056388 | A | 5/2019 |
| KR | 20190057327 | A | 5/2019 |
| KR | 20200118468 | A | 10/2020 |
| KR | 20210040984 | A | 4/2021 |

(Continued)

OTHER PUBLICATIONS

Alzheimer's Disease 101: Symptoms, risk factors, treatments and prevention. Mount Sinai Medical Center (accessed at: https://www.msmc.com/alzheimers-disease-101-symptoms-risk-factors-treatments-and-prevention/#:~:text=While%20there%20are%20no%20surefire,of%20smoking%20and%20excess%20alcohol) (Year: 2016).*

(Continued)

*Primary Examiner* — Valarie E Bertoglio
*Assistant Examiner* — Briana N Ebbinghaus
(74) *Attorney, Agent, or Firm* — Ice Miller LLP

(57) ABSTRACT

The disclosure includes CpG reduced regulatory elements, polynucleotides comprising such CpG reduced regulatory elements, expression cassettes comprising such CpG reduced regulatory elements, and recombinant AAV vectors comprising such CpG reduced regulatory elements. The regulatory elements can be, for example, operably coupled to a transgene.

35 Claims, 12 Drawing Sheets

Specification includes a Sequence Listing.

(56) References Cited

FOREIGN PATENT DOCUMENTS

| | | | |
|---|---|---|---|
| KR | 20210153069 | A | 12/2021 |
| KR | 20230026504 | A | 2/2023 |
| KR | 20230029624 | A | 3/2023 |
| WO | 2001/75092 | A2 | 10/2001 |
| WO | 2011109380 | A1 | 9/2011 |
| WO | 2016/210170 | A9 | 12/2016 |
| WO | 2016210170 | A1 | 12/2016 |
| WO | 2017/053677 | A1 | 3/2017 |
| WO | 2017/074526 | A1 | 5/2017 |
| WO | 2017/075619 | A1 | 5/2017 |
| WO | 2018046772 | A1 | 3/2018 |
| WO | 2018046774 | A1 | 3/2018 |
| WO | 2018046775 | A1 | 3/2018 |
| WO | 2019154939 | A1 | 8/2019 |
| WO | 2019157324 | A1 | 8/2019 |
| WO | 2019222411 | A1 | 11/2019 |
| WO | 2020023857 | A1 | 1/2020 |
| WO | 2020161483 | A1 | 8/2020 |
| WO | 2020162978 | A1 | 8/2020 |
| WO | 2020212626 | A1 | 10/2020 |
| WO | 2020219868 | A1 | 10/2020 |
| WO | 2021021661 | A1 | 2/2021 |
| WO | 2021078833 | A1 | 4/2021 |
| WO | 2021078834 | A1 | 4/2021 |
| WO | 2021084277 | A2 | 5/2021 |
| WO | 2021087361 | A1 | 5/2021 |
| WO | 2021234176 | A1 | 11/2021 |
| WO | 2021260394 | A1 | 12/2021 |

OTHER PUBLICATIONS

Autoimmune disorders. Better Health Channel (accessed at: https://web.archive.org/web/20170715000127/https://www.betterhealth.vic.gov.au/health/conditionsandtreatments/autoimmune-disorders) (Year: 2017).*

Systemic lupus erythematosus. Mount Sinai (accessed at: https://web.archive.org/web/20180202165358/https://www.mountsinai.org/health-library/condition/systemic-lupus-erythematosus) (Year: 2018).*

Spring Allergies Nothing to Sneeze At. NMHealth (accessed at: https://www.nmhealth.org/news/healthy/2014/4/?view=59) (Year: 2014).*

Borish. Allergic rhinitis: Systemic inflammation and implications for management. J Allergy Clin Immunol. Dec. 2003; 112(6):1021-31. (Year: 2003).*

MacGinnitie. Pediatric hereditary angioedema. Pediatr Allergy Immunol. Aug. 2014;25(5):420-7. Epub Dec. 9, 2013. (Year: 2013).*

Fryxell et al. CpG Mutation Rates in the Human Genome Are Highly Dependent on Local GC Content. Mol Biol Evol. Mar. 2005;22(3 ):650-8. (Year: 2005).*

Wolf et al. Plasmid CpG Depletion Improves Degree and Duration of Tumor Gene Expression After Intravenous Administration of Polyplexes. Pharm Res. Jul. 2008;25(7):1654-62. (Year: 2008).*

Marsh et al. Distribution of an NMDA receptor:GFP fusion protein in sensory neurons is altered by a C-terminal construct. J Neurochem. Apr. 2001;77(1):23-33. (Year: 2001).*

NM_000295.4(SERPINA1):c.-208C>T And Alpha-1-antitrypsin deficiency. National Library of Medicine. (accessed at: https://www.ncbi.nlm.nih.gov/clinvar/RCV000301367.5/ (Year: 2018).*

Choi, Jun-Hyeok, et al., Optimization of AAV expression cassettes to improve packaging capacity and transgene expression in neurons, Molecular Brain, Mar. 11, 2014, p. 17; vol. 7., No. 1.

NCBI Blast:58, Aug. 16, 2024, retrieved from Internet "https://blast.ncbi.nlm.nih.gov/blast/Blast.cgi#", 20 pages.

* cited by examiner

OPTIMIZED PROMOTER SEQUENCES, INTRON-FREE EXPRESSION CONSTRUCTS AND METHODS OF USE

RELATED APPLICATIONS

This patent application is the National Phase of International Application No. PCT/US2019/048032, filed Aug. 23, 2019, which designated the U.S. and that International Application was published under PCT Article 21(2) in English, which claims the benefit of priority to U.S. Provisional Patent Application No. 62/722,547, filed Aug. 24, 2018, U.S. Provisional Patent Application No. 62/725,096, filed Aug. 30, 2018, and U.S. Provisional Patent Application No. 62/784,116, filed Dec. 21, 2018. The entire contents of the foregoing applications are incorporated herein by reference, including all text, tables, sequence listings and drawings.

INTRODUCTION

Gene therapy shows great promise in therapeutic applications involving loss of protein function or activity, for example, due to a genetic deficiency or defect, or the aberrant function or activity of a protein in which it is desired to suppress the expression of the aberrant protein. Improvements in transgene expression, enhancer and promoter function that drive transgene expression will enhance gene therapy therapeutic applications. The instant invention addresses, inter alia, this need.

SEQUENCE LISTING

The instant application contains a Sequence Listing which has been submitted electronically in ASCII format and is hereby incorporated by reference in its entirety. Said ASCII copy, created on Feb. 22, 2021, is named "023637-0559972_SL.txt" and is 201 KB in size.

SUMMARY

In accordance with the instant invention expression cassettes comprising a nucleic acid sequence encoding a Factor VIII protein having a B domain deletion (FVIII-BDD) are provided.

In certain embodiments, the expression cassette comprises a sequence at least 98% identical to the sequence of SEQ ID NO:1, is at least 99% identical to the sequence of SEQ ID NO:1, comprises the sequence of SEQ ID NO:1, or consists of the sequence of SEQ ID NO:1.

In certain embodiments, the expression cassette comprises a regulatory element operably linked to a nucleic acid sequence encoding a Factor VIII protein having a B domain deletion (FVIII-BDD), wherein no intron is present between the regulatory element and the nucleic acid sequence, and wherein the expression cassette comprises a sequence at least 91% identical to the sequence of SEQ ID NO:1.

In certain embodiments, the expression cassette comprises (a) a regulatory element at least 90% identical to the sequence of any of SEQ ID NOs:2-67, and (b) a nucleic acid sequence encoding a Factor VIII protein having a B domain deletion (FVIII-BDD), wherein the nucleic acid sequence of (a) is at least 90% identical to the sequence of SEQ ID NO:77, and wherein the regulatory element is operably linked to the nucleic acid sequence, and wherein no intron is present between the regulatory element and the nucleic acid sequence encoding FVIII-BDD.

In certain embodiments, the expression cassette comprises (a) a regulatory element at least 90% identical to the sequence of any of SEQ ID NOs:2-67, and (b) a nucleic acid sequence encoding a Factor VIII protein having a B domain deletion (FVIII-BDD), wherein the nucleic acid sequence is at least 90% identical to the sequence of SEQ ID NO:77, and wherein the regulatory element is operably linked to the nucleic acid sequence, and wherein no more than 0-5, 5-10, 10-15, 15-20, 20-25, 25-30, 30-35, 35-40, 40-45, 45-50, 50-55, 55-60, 60-65, 65-70, 70-75, 75-80, 80-85, 85-90, 90-95, 95-100, 100-105, 106 or 107 nucleotides of untranslated nucleic acid is between the regulatory element and the nucleic acid sequence that encodes FVIII-BDD.

In certain embodiments, the regulatory element in the expression cassette comprises a nucleotide sequence at least 95% identical to any of SEQ ID NOs:2-67.

In certain embodiments, the regulatory element in the expression cassette has the same total number of reduced CpGs as set forth in the sequence of any of SEQ ID NOs:4-21 or 24-67.

In certain embodiments, the regulatory element in the expression cassette comprises the sequence of any of SEQ ID NOs:2-21 or 24-67 having CpG(s) substituted to be CpT, CpA, TpG, or ApG at the same position(s) as set forth in the sequence of any of SEQ ID NOs:4-21 or 24-67.

In certain embodiments, the nucleic acid sequence in the expression cassette exhibits greater expression when compared to expression from an expression cassette having (a) an intron, or (b) 108 or more nucleotides of untranslated nucleic acid, between the regulatory element and the nucleic acid sequence.

In certain embodiments, the encoded FVIII-BDD in the expression cassette exhibits greater biological activity as compared to expression from an expression cassette having (a) an intron, or (b) 108 or more nucleotides of untranslated nucleic acid, between the regulatory element and the nucleic acid sequence.

In certain embodiments, biological activity is determined by a clotting assay or reduced bleeding in a FVIII assay or FVIII deficiency model.

In certain embodiments, the expression cassette is more efficiently packaged into an AAV vector when compared to packaging of an expression cassette having (a) an intron, or (b) 108 or more nucleotides of untranslated nucleic acid, between the regulatory element and the nucleic acid sequence.

In accordance with the instant invention, cytosine-guanine dinucleotide (CpG) reduced nucleic acid sequences of regulatory elements (promoters) are provided. Exemplary promoters include the TTR (transthyretin gene) promoter and ApoE/hAAT (human apolipoprotein E gene/human alpha-1 antitrypsin gene) promoter. Exemplary promoters also include the fibrinogen gamma chain gene (FGG) promoter, the albumin promoter, and the serum amyloid A1 gene (SAA1) promoter. Exemplary promoters further include the TTR promoter fused to one or more of a hAAT promoter, FGG promoter, albumin promoter, and/or SAA1 promoter that result in a hybrid promoter or a promoter chimera.

CpG reduced nucleic acid regulatory elements include variants that exhibit altered gene expression levels compared to non-CpG reduced regulatory elements when transferred into cells. In certain embodiments, CpG reduced regulatory elements can provide for increased expression of a transgene or heterologous nucleic acid, such as a transgene encoding a protein such as a blood clotting factor (e.g., FVIII), in a mammal, as well as provide increased efficacy in the context of gene transfer by increased circulating levels of the protein, such as a blood clotting factor, and achieving hemostasis for beneficial therapeutic outcomes.

In certain embodiments, a nucleic acid sequence has at least 1 fewer CpGs than a wild-type non-CpG reduced regulatory element (e.g., any of SEQ ID NOs:2, 3, 22 and 23).

In certain embodiments, a nucleic acid sequence has at least 2 fewer CpGs than a wild-type non-CpG reduced regulatory element (e.g., any of SEQ ID NOs:2, 3, 22 and 23).

In certain embodiments, a nucleic acid sequence has at least 3 fewer CpGs than a wild-type non-CpG reduced regulatory element (e.g., any of SEQ ID NOs:2, 3, 22 and 23).

In certain embodiments, a nucleic acid sequence has at least 4 fewer CpGs than a wild-type non-CpG reduced regulatory element (e.g., any of SEQ ID NOs:2, 3, 22 and 23).

In certain embodiments, a nucleic acid sequence has at least 5 fewer CpGs than a wild-type non-CpG reduced regulatory element (e.g., any of SEQ ID NOs:22 and 23).

In certain embodiments, a nucleic acid sequence has at least 6 fewer CpGs than a wild-type non-CpG reduced regulatory element (e.g., any of SEQ ID NOs:22 and 23).

In certain embodiments, a nucleic acid sequence has at least 7 fewer CpGs than a wild-type non-CpG reduced regulatory element (e.g., any of SEQ ID NOs:22 and 23).

In certain embodiments, a nucleic acid sequence has at least 8 fewer CpGs than a wild-type non-CpG reduced regulatory element (e.g., any of SEQ ID NOs:22 and 23).

In certain embodiments, a nucleic acid sequence has at least 9 fewer CpGs than a wild-type non-CpG reduced regulatory element (e.g., any of SEQ ID NOs:22 and 23).

In certain embodiments, a nucleic acid sequence has at least 10 fewer CpGs than a wild-type non-CpG reduced regulatory element (e.g., any of SEQ ID NOs:22 and 23).

In certain embodiments, a nucleic acid sequence has at least 11 fewer CpGs than a wild-type non-CpG reduced regulatory element (e.g., any of SEQ ID NOs:22 and 23).

In certain embodiments, a nucleic acid sequence has at least 12 fewer CpGs than a wild-type non-CpG reduced regulatory element (e.g., any of SEQ ID NOs:22 and 23).

In certain embodiments, a nucleic acid sequence has at least 13 fewer CpGs than a wild-type non-CpG reduced regulatory element (e.g., any of SEQ ID NOs:22 and 23).

In certain embodiments, a nucleic acid sequence has at least 14 fewer CpGs than a wild-type non-CpG reduced regulatory element (e.g., any of SEQ ID NOs:22 and 23).

In certain embodiments, a nucleic acid sequence has at least 15 fewer CpGs than a wild-type non-CpG reduced regulatory element (e.g., any of SEQ ID NOs:22 and 23).

In certain embodiments, a nucleic acid sequence has at least 16 fewer CpGs than a wild-type non-CpG reduced regulatory element (e.g., any of SEQ ID NOs:22 and 23).

In certain embodiments, a nucleic acid sequence has no more than 16 CpGs; has no more than 15 CpGs; has no more than 14 CpGs; has no more than 13 CpGs; has no more than 12 CpG; has no more than 11 CpGs; has no more than 10 CpGs; has no more than 9 CpGs; has no more than 8 CpGs; has no more than 7 CpGs; has no more than 6 CpGs; has no more than 5 CpGs; has no more than 4 CpGs; has no more than 3 CpGs; has no more than 2 CpGs; or has no more than 1 CpG.

In certain embodiments, a nucleic acid sequence has at most 15 CpGs; 14 CpGs; 13 CpGs; 12 CpGs; 11 CpG; 10 CpGs; 9 CpGs; 8 CpGs; 7 CpGs; 6 CpGs; 5 CpGs; 4 CpGs; 3 CpGs; 2 CpGs; or 1 CpG. In certain embodiments, a nucleic acid sequence has no CpGs.

In certain embodiments, a nucleic acid sequence comprising SEQ ID NO:22 or 23 is modified to have 15 or fewer cytosine-guanine dinucleotides (CpGs); 14 or fewer CpGs; 13 or fewer CpGs; 12 or fewer CpGs; 11 or fewer CpGs; 10 or fewer CpGs; 9 or fewer CpGs; 8 or fewer CpGs; 7 or fewer CpGs; 6 or fewer CpGs; 5 or fewer CpGs; 4 or fewer CpGs; 3 or fewer CpGs; 2 or fewer CpGs; or 1 or 0 CpGs. In certain embodiments, the nucleic acid sequence in any of SEQ ID NOs:2, 3, 22 and 23 is modified to have 0 CpG.

In certain embodiments, the nucleic acid sequence in any of SEQ ID NOs:2, 3, 22 and 23 is modified such that the C in every CpG site is modified to a T, optionally excluding the C in the C/EBP site.

In certain embodiments, the nucleic acid sequence in any of SEQ ID NOs:2, 3, 22 and 23 is modified such that the C in every CpG site is modified to a T, optionally excluding the C in the C/EBP site, except that the first CpG site is left unmodified.

In certain embodiments, the nucleic acid sequence in any of SEQ ID NOs:2, 3, 22 and 23 is modified such that the C in every CpG site is modified to a T, optionally excluding the C in the C/EBP site, except that the second CpG site is left unmodified.

In certain embodiments, the nucleic acid sequence in any of SEQ ID NOs:2, 3, 22 and 23 is modified such that the C in every CpG site is modified to a T, optionally excluding the C in the C/EBP site, except that the third CpG site is left unmodified.

In certain embodiments, the nucleic acid sequence in any of SEQ ID NOs:2, 3, 22 and 23 is modified such that the C in every CpG site is modified to a T, optionally excluding the C in the C/EBP site, except that the fourth CpG site is left unmodified.

In certain embodiments, the nucleic acid sequence in any of SEQ ID NOs:22 and 23 is modified such that the C in every CpG site is modified to a T, optionally excluding the C in the C/EBP site, except that the fifth CpG site is left unmodified.

In certain embodiments, the nucleic acid sequence in any of SEQ ID NOs:22 and 23 is modified such that the C in every CpG site is modified to a T, optionally excluding the C in the C/EBP site, except that the sixth CpG site is left unmodified.

In certain embodiments, the nucleic acid sequence in any of SEQ ID NOs:22 and 23 is modified such that the C in every CpG site is modified to a T, except that the seventh CpG site is left unmodified.

In certain embodiments, the nucleic acid sequence in any of SEQ ID NOs:22 and 23 is modified such that the C in every CpG site is modified to a T, optionally excluding the C in the C/EBP site, except that the eighth CpG site is left unmodified.

In certain embodiments, the nucleic acid sequence in any of SEQ ID NOs:22 and 23 is modified such that the C in every CpG site is modified to a T, optionally excluding the C in the C/EBP site, except that the ninth CpG site is left unmodified.

In certain embodiments, the nucleic acid sequence in any of SEQ ID NOs:22 and 23 is modified such that the C in every CpG site is modified to a T, optionally excluding the C in the C/EBP site, except that the tenth CpG site is left unmodified.

In certain embodiments, the nucleic acid sequence in any of SEQ ID NOs:22 and 23 is modified such that the C in every CpG site is modified to a T, optionally excluding the C in the C/EBP site, except that the eleventh CpG site is left unmodified.

In certain embodiments, the nucleic acid sequence in any of SEQ ID NOs:22 and 23 is modified such that the C in every CpG site is modified to a T, optionally excluding the C in the C/EBP site, except that the twelfth CpG site is left unmodified.

In certain embodiments, the nucleic acid sequence in any of SEQ ID NOs:22 and 23 is modified such that the C in every CpG site is modified to a T, optionally excluding the C in the C/EBP site, except that the thirteenth CpG site is left unmodified.

In certain embodiments, the nucleic acid sequence in any of SEQ ID NOs:22 and 23 is modified such that the C in every CpG site is modified to a T, optionally excluding the C in the C/EBP site, except that the fourteenth CpG site is left unmodified.

In certain embodiments, the nucleic acid sequence in any of SEQ ID NOs:22 and 23 is modified such that the C in every CpG site is modified to a T, optionally excluding the C in the C/EBP site, except that the fifteenth CpG site is left unmodified.

In certain embodiments, the nucleic acid sequence in any of SEQ ID NOs:22 and 23 is modified such that the C in every CpG site is modified to a T, optionally excluding the C in the C/EBP site, except that the sixteenth CpG site is left unmodified.

In certain embodiments, the nucleic acid sequence is modified such that at least the $1^{st}$ CpG from the 5' end in any of SEQ ID NOs:2, 3, 22 and 23 is modified to not be CpG.

In certain embodiments, the nucleic acid sequence is modified such that at least the $2^{nd}$ CpG from the 5' end in in any of SEQ ID NOs:2, 3, 22 and 23 is modified to not be CpG.

In certain embodiments, the nucleic acid sequence is modified such that at least the $3^{rd}$ CpG from the 5' end in in any of SEQ ID NOs:2, 3, 22 and 23 is modified to not be CpG.

In certain embodiments, the nucleic acid sequence is modified such that at least the $4^{th}$ CpG from the 5' end in in any of SEQ ID NOs:2, 3, 22 and 23 is modified to not be CpG.

In certain embodiments, the nucleic acid sequence is modified such that at least the $5^{th}$ CpG from the 5' end in in any of SEQ ID NOs:22 and 23 is modified to not be CpG.

In certain embodiments, the nucleic acid sequence is modified such that at least the $6^{th}$ CpG from the 5' end in in any of SEQ ID NOs:22 and 23 is modified to not be CpG.

In certain embodiments, the nucleic acid sequence is modified such that at least the $7^{th}$ CpG from the 5' end in in any of SEQ ID NOs:22 and 23 is modified to not be CpG.

In certain embodiments, the nucleic acid sequence is modified such that at least the $8^{th}$ CpG from the 5' end in in any of SEQ ID NOs:22 and 23 is modified to not be CpG.

In certain embodiments, the nucleic acid sequence is modified such that at least the $9^{th}$ CpG from the 5' end in in any of SEQ ID NOs:22 and 23 is modified to not be CpG.

In certain embodiments, the nucleic acid sequence is modified such that at least the $10^{th}$ CpG from the 5' end in in any of SEQ ID NOs:22 and 23 is modified to not be CpG.

In certain embodiments, the nucleic acid sequence is modified such that at least the $11^{th}$ CpG from the 5' end in in any of SEQ ID NOs:22 and 23 is modified to not be CpG.

In certain embodiments, the nucleic acid sequence is modified such that at least the $12^{th}$ CpG from the 5' end in in any of SEQ ID NOs:22 and 23 is modified to not be CpG.

In certain embodiments, the nucleic acid sequence is modified such that at least the $13^{th}$ CpG from the 5' end in in any of SEQ ID NOs:22 and 23 is modified to not be CpG.

In certain embodiments, the nucleic acid sequence is modified such that at least the $14^{th}$ CpG from the 5' end in in any of SEQ ID NOs:22 and 23 is modified to not be CpG.

In certain embodiments, the nucleic acid sequence is modified such that at least the $15^{th}$ CpG from the 5' end in in any of SEQ ID NOs:22 and 23 is modified to not be CpG.

In certain embodiments, the nucleic acid sequence is modified such that at least the $16^{th}$ CpG from the 5' end in in any of SEQ ID NOs:22 and 23 is modified to not be CpG.

In certain embodiments, the cytosine of one or more CpGs in any of SEQ ID NOs:2, 3, 22 and 23 is modified to a thymine. In certain embodiments, the cytosine of one or more CpGs in any of SEQ ID NOs:2, 3, 22 and 23 is modified to adenine.

In certain embodiments, the nucleic acid sequence in any of SEQ ID NOs:2, 3, 22 and 23 is modified such that the C in one or more CpGs is deleted.

In certain embodiments, the nucleic acid sequence in any of SEQ ID NOs:2, 3, 22 and 23 is modified such that the G in one or more CpGs is deleted.

In certain embodiments, the nucleic acid sequence in any of SEQ ID NOs:2, 3, 22 and 23 is modified such that the C and G in one or more CpGs are deleted.

Exemplary CpG reduced TTR promoters are set forth in SEQ ID NOs:4-13.

Exemplary CpG reduced hybrid promoters are set forth in SEQ ID NOs:14-21.

Exemplary CpG reduced ApoE/hAAT promoters are set forth in SEQ ID NOs:24-67.

In certain embodiments, the cytosine of one or more CpGs in a hybrid promoter, comprising all or a portion of the TTR promoter fused to all or a portion of at least one of the hAAT promoter, and/or the FGG promoter, and/or the albumin promoter, and/or the SAA1 promoter, is modified to a thymine (C→T) or an adenine (G→A). The TTR promoter can be fused to any one or a combination of the foregoing promoters in any 5'→3' orientation.

In certain embodiments, a hybrid promoter has a 5'→3' orientation, TTR/hAAT or hAAT/TTR. In certain embodiments, a hybrid promoter has a 5'→3' orientation, TTR/FGG or FGG/TTR. In certain embodiments, a hybrid promoter has a 5'→3' orientation, TTR/hAAT/albumin or hAAT/TTR/albumin or albumin/TTR/hAAT or TTR/albumin/hAAT, hAAT/albumin/TTR or albumin/hAAT/TTR, etc.

In certain embodiments, a hybrid promoter has a 5'→3' orientation, TTR/FGG/albumin or hAAT/TTR/FGG or FGG/TTR/hAAT or TTR/FGG/hAAT, etc.

In certain embodiments, a hybrid promoter has a TTR promoter fused to all or a portion of all 4 of the hAAT promoter, the FGG promoter, the albumin promoter, and the SAA1 promoter. The TTR promoter can be fused to all or a portion of the foregoing promoters in any 5'→3' orientation and in any promoter order.

In certain embodiments, a nucleic acid sequence or polynucleotide of the instant invention, such as a CPG reduced nucleic acid sequence, is operably linked to a transgene.

In certain embodiments, a nucleic acid sequence or polynucleotide of the instant invention, such as modified SEQ ID NO:2, 3, 22 or 23 as set forth herein, is operably linked to transgene.

In certain embodiments, a nucleic acid sequence or polynucleotide of the instant invention, such as modified SEQ ID NO:2, 3, 22 or 23 as set forth herein, confers transcription on an operably linked transgene that is within about 5-100% of the transcription conferred by unmodified SEQ ID NO:2, 3, 22 or 23, or that is within about 50% of the transcription conferred by unmodified SEQ ID NO:2, 3, 22 or 23, or that is within about 25-50% of the transcription conferred by unmodified SEQ ID NO:2, 3, 22 or 2.

In certain embodiments, a nucleic acid sequence or polynucleotide, such as modified SEQ ID NO:2, 3, 22 or 23 as set forth herein, is positioned 5' of a transgene.

In certain embodiments, a transgene encodes a blood coagulation or clotting protein.

In certain embodiments, a transgene encodes Factor IX (FIX), Factor VIII (FVIII), Factor VII (FVII) or Protein C.

In certain embodiments, a transgene encodes Factor VIII having a sequence at least 95% identical to the sequence of SEQ ID NO:68.

In certain embodiments, a transgene is transcribed into an inhibitory RNA. In certain embodiments, an inhibitory RNA comprises antisense RNA, a microRNA (miRNA), or a small interfering RNA (siRNA).

In certain embodiments, a transgene encodes a therapeutic protein that is expressed in liver cells and secreted into the systemic circulation.

In certain embodiments, the therapeutic protein treats or prevents a neurodegenerative or central nervous system (CNS) disease.

In certain embodiments, the therapeutic protein is a protective ApoE isoform.

In certain embodiments, the therapeutic protein is ApoE ε2 isoform.

In certain embodiments, the therapeutic protein treats or prevents an autoimmune disease or allergic disease.

In certain embodiments, the therapeutic protein is a fusion protein comprising an unwanted antigen and a leader sequence that drives secretion of said therapeutic protein from the cell.

In certain embodiments, the unwanted antigen is the extracellular domain of myelin oligodendrocyte glycoprotein (MOG) or a fragment thereof.

In certain embodiments, an expression cassette comprises a nucleic acid sequence or polynucleotide of the instant invention, such as a modified SEQ ID NO:2, 3, 22 or 23 as set forth herein, operably linked to a transgene, in which the nucleic acid sequence or polynucleotide is positioned upstream of the 5' end of the transgene and optionally wherein there are no more than 0-5, 5-10, 10-15, 15-20, 20-25, 25-30, 30-35, 35-40, 40-45, 45-50, 50-55, 55-60, 60-65, 65-70, 70-75, 75-80, 80-85, 85-90, 90-95, 95-100, 100-105, 106 or 107 nucleotides of untranslated nucleic acid sequence positioned between the nucleic acid sequence or polynucleotide and the 5' end of the transgene.

In certain embodiments, an expression cassette comprises a first nucleotide sequence having 95% or greater sequence identity to the sequence of any of SEQ ID NOs:4-21 or 24-67, in which the first nucleotide sequence positioned upstream of the 5' end of a second nucleotide sequence has 95% or greater sequence identity to the sequence of SEQ ID NO:77, and optionally wherein there are no more than 0-5, 5-10, 10-15, 15-20, 20-25, 25-30, 30-35, 35-40, 40-45, 45-50, 50-55, 55-60, 60-65, 65-70, 70-75, 75-80, 80-85, 85-90, 90-95, 95-100, 100-105, 106 or 107 nucleotides of untranslated nucleic acid sequence positioned between the first nucleotide sequence and the 5' end of the second nucleotide sequence.

In certain embodiments, the expression cassette comprises the sequence of SEQ ID NO:1 or a polynucleotide having at least 98% sequence identity to the sequence of SEQ ID NO:1.

In certain embodiments, the expression cassette comprises a polynucleotide having at least 99% sequence identity to the sequence of SEQ ID NO:1.

In certain embodiments, the expression cassette consists essentially of SEQ ID NO:1.

In certain embodiments, the transgene or second nucleotide sequence comprises a nucleic acid sequence encoding Factor VIII (FVIII) having a B-domain deletion (FVIII-BDD), and the nucleic acid sequence encodes a FVII-BDD protein with FVIII blood coagulation activity and having at least 90% sequence identity to the sequence of SEQ ID NO:68.

In certain embodiments, the transgene or second nucleotide sequence comprises a nucleic acid sequence encoding Factor VIII (FVIII) having a B-domain deletion (FVIII-BDD), and the nucleic acid sequence has 90% or greater sequence identity to the sequence of SEQ ID NO:77 and encodes a protein having FVIII blood coagulation activity.

In certain embodiments, the untranslated nucleic acid sequence is not an intron or is intron-free.

In certain embodiments, the first nucleotide sequence comprises a nucleic acid sequence at least 95% identical to any of SEQ ID NOs:4-21 or 24-67.

In certain embodiments, the first nucleotide sequence comprises a nucleic acid sequence at least 95% identical to the sequence of any of SEQ ID NOs:4-21 or 24-67, and has the same total number of reduced CpGs as set forth in the sequence of any of SEQ ID NOs:4-21 or 24-67.

In certain embodiments, the first nucleotide sequence comprises a nucleic acid sequence at least 95% identical to the sequence of any of SEQ ID NOs:4-21 or 24-67, and having CpG(s) substituted to be CpT, CpA, TpG, or ApG at the same position(s) as set forth in the sequence of any of SEQ ID NOs:4-21 or 24-67.

In certain embodiments, the second nucleotide sequence exhibits greater expression when compared to expression from a polynucleotide having 108 or more nucleotides between the first nucleotide sequence and the 5' end of the second nucleotide sequence.

In certain embodiments, the second nucleotide sequence exhibits greater biological activity when compared to expression from a polynucleotide having 108 or more nucleotides between the first nucleotide sequence and the 5' end of the second nucleotide sequence.

In certain embodiments, biological activity is determined by a clotting assay or reduced bleeding in a FVIII assay or FVIII deficiency model.

In certain embodiments, the second nucleotide sequence is more efficiently packaged into an AAV vector when compared to packaging of a polynucleotide having 108 or more nucleotides between the first nucleotide sequence and the 5' end of the second nucleotide sequence.

In certain embodiments, an adeno-associated virus (AAV) vector comprises the nucleic acid sequence, or polynucleotide or expression cassette as set forth herein.

In certain embodiments, the AAV vector comprises one or more of: a) an AAV capsid; and b) one or more AAV inverted terminal repeats (ITRs), wherein the AAV ITR(s) flanks the 5' or 3' terminus of the nucleic acid sequence, the polynucleotide, and/or the transgene.

In certain embodiments, the AAV vector further comprises an intron positioned within the flanking 5' or 3' ITR.

In certain embodiments, the intron or one or more ITRs is modified to have reduced CpGs.

In certain embodiments, the AAV capsid serotype comprises a modified or variant AAV VP1, VP2 and/or VP3 capsid having 90% or more sequence identity to AAV1, AAV2, AAV3, AAV3B, AAV4, AAV5, AAV6, AAV7, AAV8, AAV9, AAV10, AAV11, AAV12, Rh10, Rh74, AAV-2i8, SEQ ID NO:91 or SEQ ID NO:92 VP1, VP2 and/or VP3 sequences, or a capsid having 95% or more sequence identity to AAV1, AAV2, AAV3, AAV3B, AAV4, AAV5, AAV6, AAV7, AAV8, AAV9, AAV10, AAV11, AAV12, Rh10, Rh74, AAV-2i8, SEQ ID NO:91 or SEQ ID NO:92 VP1, VP2 and/or VP3 sequences, or a capsid having 100% sequence identity to AAV1, AAV2, AAV3, AAV3B, AAV4, AAV5, AAV6, AAV7, AAV8, AAV9, AAV10, AAV11, AAV12, Rh10, Rh74, AAV-2i8, SEQ ID NO:91 or SEQ ID NO:92 VP1, VP2 and/or VP3 sequences.

In certain embodiments, the ITRs comprise one or more ITRs of any of: AAV1, AAV2, AAV3, AAV3B, AAV4, AAV5, AAV6, AAV7, AAV8, AAV9, AAV10, AAV11, AAV12, Rh10, or Rh74 AAV serotypes, or a combination thereof.

In certain embodiments, the AAV vector further comprises an ITR, a polyA signal and/or intron sequence.

In certain embodiments, the AAV vectors as set forth herein are any pharmaceutical composition.

In certain embodiments, a pharmaceutical composition comprises a biologically compatible carrier or excipient.

In certain embodiments, a pharmaceutical composition further comprises empty AAV capsids.

In certain embodiments, a composition or a pharmaceutical composition comprises a ratio of empty AAV capsids to AAV vectors within or between about 100:1-50:1, from about 50:1-25:1, from about 25:1-10:1, from about 10:1-1:1, from about 1:1-1:10, from about 1:10-1:25, from about 1:25-1:50, or from about 1:50-1:100.

In certain embodiments, the ratio of the empty AAV capsids to the AAV vectors in a composition or pharmaceutical composition is about 2:1, 3:1, 4:1, 5:1, 6:1, 7:1, 8:1, 9:1, or 10:1

In certain embodiments, a composition or a pharmaceutical composition set forth herein further comprises a surfactant.

In certain embodiments, methods of treating a human in need of gene therapy are provided.

In certain embodiments, the human is in need of a blood coagulation or clotting factor.

In certain embodiments, a method of treating a human includes (a) providing an expression cassette as set forth herein, a polynucleotide as set forth herein, an AAV vector as set forth herein, or a pharmaceutical composition as set forth herein; and (b) administering an amount of the expression cassette, polynucleotide, AAV vector, or pharmaceutical composition to the human, wherein the blood coagulation or clotting factor is expressed in the human.

In certain embodiments, the human has hemophilia A or B.

In certain embodiments, the AAV vector is administered to the human intravenously, intraarterially, intra-cavity, intramucosally, or via catheter.

In certain embodiments, the blood coagulation or clotting factor is expressed at increased levels after administration.

In certain embodiments, the blood coagulation or clotting factor is expressed at greater than 1% of the levels of the blood coagulation or clotting factor found in a human not in need of blood coagulation or clotting factor.

In certain embodiments, the blood coagulation or clotting factor is expressed at about 1%-40% of the levels of the blood coagulation or clotting factor found in a human not in need of blood coagulation or clotting factor.

In certain embodiments, the blood coagulation or clotting factor is expressed at about 5%-30% of the levels of the blood coagulation or clotting factor found in a human not in need of blood coagulation or clotting factor.

In certain embodiments, the AAV vector is administered in a range from about $1\times10^{8}$ to about $1\times10^{14}$ vector genomes per kilogram (vg/kg) of the weight of the human.

DETAILED DESCRIPTION

Figure 1:
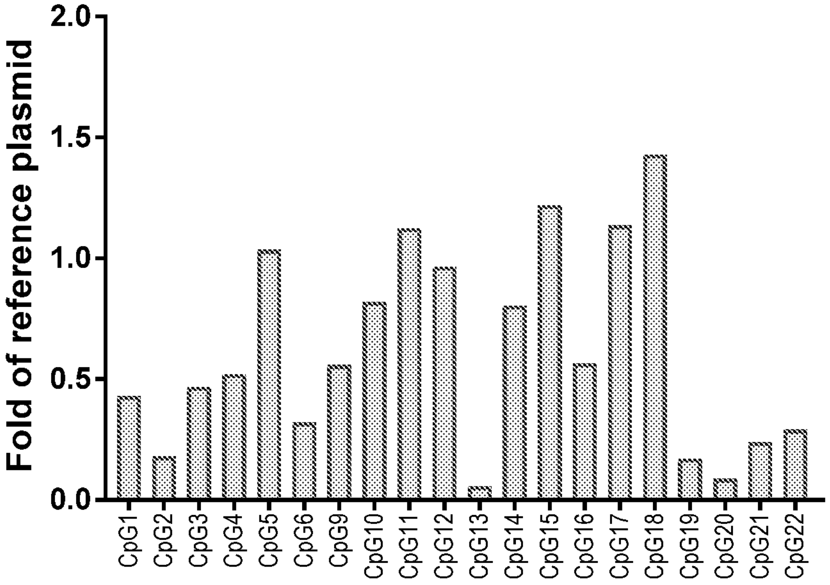
FIG. 1 shows human Factor IX (hFIX) levels, measured by an activity assay, in the plasma of mice 24 hours post hydrodynamic delivery of CpG reduced ApoE/hAAT regulatory element-hFIX encoding constructs, labeled "CpG1" through "CpG22". SEQ ID NOs:24-67 correspond to regulatory elements CpG1-ApoE/hAAT through CpG22-ApoE/hAAT, respectively, with and without restriction enzyme sites, and are further described in Example 13. Levels hFIX are presented as fold of a reference plasmid containing non-CpG reduced ApoE/hAAT (SEQ ID NO:23).
Figure 2:
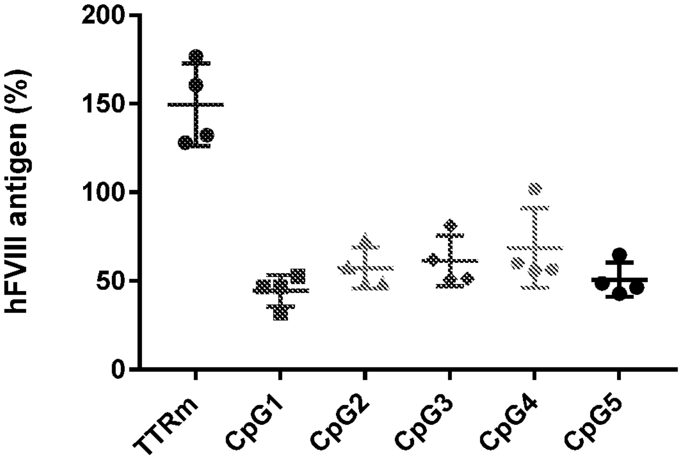
FIG. 2 shows human Factor VIII (hFVIII) antigen levels, measured by an ELISA assay, in the plasma of mice 24 hours post hydrodynamic delivery of CpG reduced TTRm promoter hFVIII-encoding constructs, labeled "CpG1" through "CpG5". SEQ ID NOs:4-21 correspond to the promoters CpG1-TTRm through CpG5-TTRm, respectively, with and without flanking restriction enzyme sites, and are further described in Example 13. Levels are presented as percentage of normal human plasma FVIII, where 100%=150 ng/mL. "TTRm" refers to a hFVIII-encoding construct containing a non-CpG reduced TTRm promoter (SEQ ID NO:3).
Figure 3:
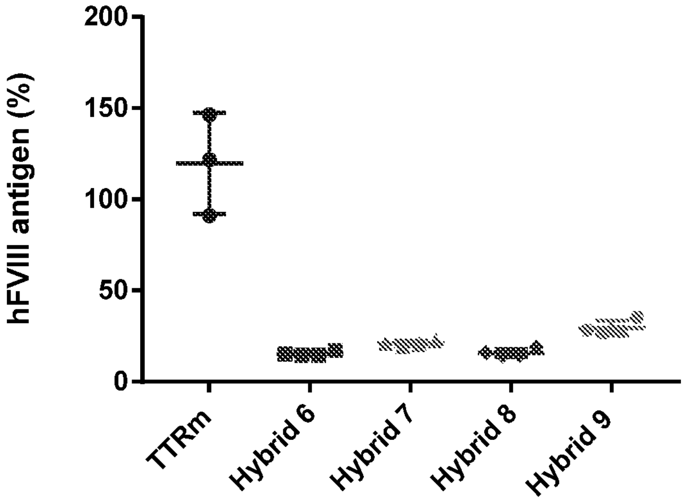
FIG. 3 shows hFVIII antigen levels, measured by an ELISA assay, in plasma of mice 24 hours post hydrodynamic delivery of CpG reduced hybrid promoter hFVIII-encoding constructs, labeled "Hybrid 6" through "Hybrid 9." SEQ ID NOs:14-21 correspond to CpG reduced promoters Hybrid6 through Hybrid9, respectively. Levels are presented as percentage of normal human plasma FVIII, where 100%=150 ng/mL. "TTRm" refers to hFVIII-encoding construct containing a non-CpG reduced TTRm promoter (SEQ ID NO:3).
Figure 4:
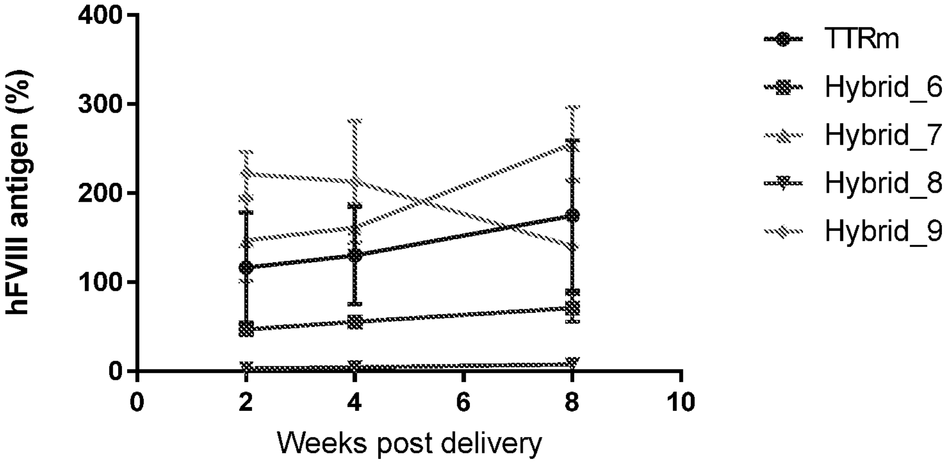
FIG. 4 shows hFVIII antigen levels, measured by an ELISA assay, in the plasma of mice 2, 4 and 8 weeks post-delivery of AAV encapsidated non-CpG reduced (TTRm) and CpG reduced Hybrid 6, 7, 8 and 9 promoter-hFVIII constructs, at a dose of 6.4e11 vector genomes (vg)/kg. Levels are presented as percentage of normal human plasma FVIII, where 100%=150 ng/mL.
Figure 5:
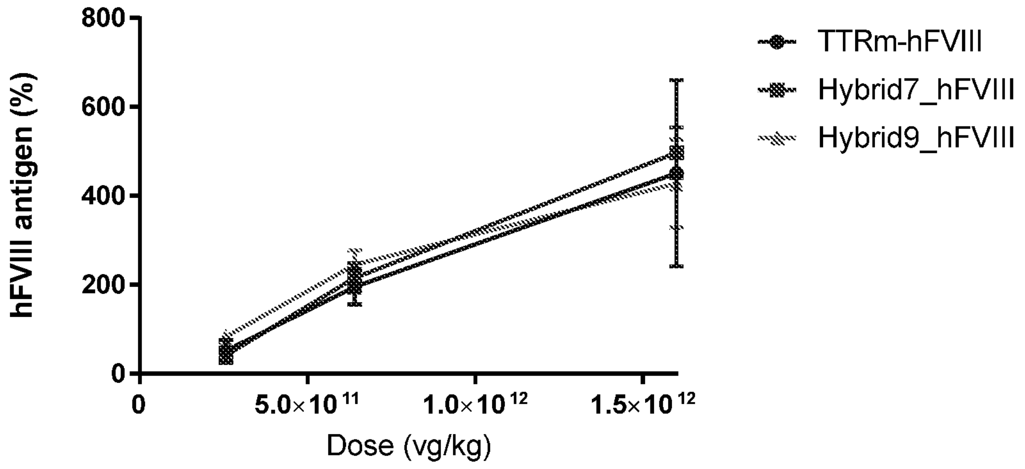
FIG. 5 shows hFVIII antigen levels measured by an ELISA assay, in the plasma of mice 8 weeks post-delivery of AAV encapsidated non-CpG reduced (TTRm-hFVIII), Hybrid 7 and Hybrid 9 promoter-hFVIII constructs, at a dose range of 2.56e11, 6.4e11 and 1.6e12 vg/kg. Levels are presented as percentage of normal human plasma FVIII, where 100%=150 ng/mL.

Disclosed herein are intron-free expression cassettes for the expression of Factor VIII (FVIII) and FVIII having a deleted B-domain (FVIII-BBD) (e.g., human FVIII (hFVIII) and human FVIII-BDD (hFVIII-BDD)). Investigators have reported that inclusion of an intron in an expression cassette, including in AAV delivery vectors, can contribute to increased transgene expression (Huang et al., 1990, Nucl. Acid Res., 18:937-947; Choi et al., 2014, Mol. Brain, 7:17; Powell et al., 2015, Discov. Med., 19:49-57; Lu et al., 2017, Hum. Gene Ther., 28:125-134). Surprisingly, as disclosed herein, partial or complete removal of an intron led to increased AAV vector potency and transgene (in this case Factor VIII) expression levels in cell culture, mice and non-human primates. The "intron-free" expression cassette design is an improvement in vectors for treatment of blood clotting disorders such as Hemophilia A, and may provide efficacy at lower vector doses, potentially offering benefits to patient safety and outcomes, in addition to decreasing barriers to manufacturing, such as costs and time.

Also disclosed herein are nucleic acid sequences having reduced CpGs compared with a reference wild-type mammalian (e.g., human) sequence and/or less than 100% sequence identity with a reference wild-type mammalian (e.g., human) sequence. Nucleic acid sequences having reduced CpGs include one or more the following promoters: TTR promoter, ApoE/hAAT promoter, FGG promoter, albumin promoter, and SAA1 promoter. Nucleic acid sequences having reduced CPGs include fusions or hybrids of TTR promoter and at least one or more the following promoters: ApoE/hAAT promoter, FGG promoter, albumin promoter, and SAA1 promoter.

The terms "polynucleotide" and "nucleic acid" are used interchangeably herein to refer to all forms of nucleic acid, oligonucleotides, including deoxyribonucleic acid (DNA) and ribonucleic acid (RNA). Polynucleotides include genomic DNA, cDNA and antisense DNA, and spliced or unspliced mRNA, rRNA tRNA and inhibitory DNA or RNA (RNAi, e.g., small or short hairpin (sh)RNA, microRNA (miRNA), small or short interfering (si)RNA, trans-splicing RNA, or antisense RNA). Polynucleotides include naturally occurring, synthetic, and intentionally modified or altered polynucleotides (e.g., variant nucleic acid). Polynucleotides can be single, double, or triplex, linear or circular, and can be of any length. In discussing polynucleotides, a sequence or structure of a particular polynucleotide may be described herein according to the convention of providing the sequence in the 5' to 3' direction.

As used herein, the terms "modify" or "variant" and grammatical variations thereof, mean that a nucleic acid, polypeptide or subsequence thereof deviates from a reference sequence. Modified and variant sequences may therefore have substantially the same, greater or less expression, activity or function than a reference sequence, but at least retain partial activity or function of the reference sequence. Particular examples of a modification or variant are a CpG reduced TTR promoter, ApoE/hAAT promoter, FGG promoter, albumin promoter and SAA1 promoter.

A "nucleic acid" or "polynucleotide" variant refers to a modified sequence which has been genetically altered compared to wild-type. A nucleic acid or polynucleotide variant can refer to a sequence which has been codon modified but still retains at least partial sequence identity to a reference sequence, such as wild-type sequence. A nucleic acid or polynucleotide that encodes a protein may be genetically modified without altering the encoded protein sequence. Alternatively, the sequence may be genetically modified to encode a variant protein. For example, some codons of such a nucleic acid variant will be changed (e.g. CpG reduced) without altering the amino acids of the protein encoded thereby.

Expression vectors with promoters having reduced CpG content can exhibit improvements compared to promoters in which CpG content has not been reduced. When comparing expression, a CpG reduced promoter is compared to a wild-type or non-CpG reduced promoter.

The term "variant" or "modified" need not appear in each instance of a reference made to CpG reduced nucleic acid sequence herein. Likewise, the term "CpG reduced nucleic acid" or the like may omit the term "variant" or "modified" but it is intended that reference to "CpG reduced nucleic acid" includes variants at the genetic level.

A particular example of a variant is a CpG reduced nucleic acid. CpG reduction can be achieved by changing the C or G nucleotide to a different nucleotide, such as changing a C to a T, or changing a G to an A. CpG reduction can also be achieved by deleting a C nucleotide, or deleting a G nucleotide, or deleting both C and G nucleotides.

A "variant or modified" FVIII refers to a FVIII or FVIII-BDD which has been genetically altered as compared to unmodified wild-type FVIII or FVIII-BDD (SEQ ID NO:68). Such a variant can be referred to as a "nucleic acid variant encoding Factor VIII (FVIII)."

A "variant Factor VIII (FVIII)" can also mean a modified FVIII protein such that the modified protein has an amino acid alteration compared to wild-type FVIII. When comparing activity and/or stability, if the encoded variant FVIII protein retains the B-domain, it is appropriate to compare it to wild-type FVIII; and if the encoded variant FVIII protein has a B-domain deletion, it is compared to wild-type FVIII that also has a B-domain deletion.

A variant FVIII can include a portion of the B-domain. Thus, FVIII-BDD includes a portion of the B-domain. Typically, in FVIII-BDD most of the B-domain is deleted.

A variant FVIII can include an "SQ" sequence set forth as SFSQNPPVLKRHQR (SEQ ID NO:69). Typically, such a variant FVIII with an SQ (FVIII/SQ) has a BDD, e.g., at least all or a part of BD is deleted. Variant FVIII, such as FVIII-BDD can have all or a part of the "SQ" sequence, i.e. all or a part of SEQ ID NO:69. Thus, for example, a variant FVIII-BDD with an SQ sequence (SFSQNPPVLKRHQR, SEQ ID NO: 69) can have all or just a portion of the amino acid sequence SFSQNPPVLKRHQR (SEQ ID NO:69). For example, FVIII-BDD can have 1, 2, 3, 4, 5, 6, 7, 8, 9, 10, 11, 12 or 13 amino acid residues of SFSQNPPVLKRHQR (SEQ ID NO:69) included. Thus, SFSQNPPVLKRHQR (SEQ ID NO:69) with 1, 2, 3, 4, 5, 6, 7, 8, 9, 10, 11, 12 or 13 internal deletions as well as 1, 2, 3, 4, 5, 6, 7, 8, 9, 10, 11, 12 or 13 amino- or carboxy terminal deletions are included in the variant FVIII proteins set forth herein.

The "polypeptides," "proteins" and "peptides" encoded by the "nucleic acid" or "polynucleotide" sequences," include full-length native sequences, as with naturally occurring wild-type proteins, as well as functional subsequences, modified forms or sequence variants so long as the subsequence, modified form or variant retain some degree of functionality of the native full-length protein. For example, a nucleic acid (e.g., CpG reduced nucleic acid) encoding FVIII protein can have a B-domain deletion as set forth herein and retain clotting function. In methods and uses of the instant invention, such polypeptides, proteins and peptides encoded by the nucleic acid sequences can be but are not required to be identical to the endogenous protein that is defective, or whose expression is insufficient, or deficient in the treated mammal.

For example, and without limitation, modifications include one or more nucleotide or amino acid substitutions (e.g., 1-3, 3-5, 5-10, 10-15, 15-20, 20-25, 25-30, 30-40, 40-50, 50-100, 100-150, 150-200, 200-250, 250-500, 500-750, 750-850 or more nucleotides or residues). As set forth herein, an example of a nucleic acid modification is CpG reduction.

An example of an amino acid modification is a conservative amino acid substitution or a deletion (e.g., subsequences or fragments) of a reference sequence, e.g. FVIII, such as FVIII with a B-domain deletion. In certain embodiments, a modified or variant sequence retains at least part of a function or activity of unmodified sequence.

All mammalian and non-mammalian forms of nucleic acids, including other mammalian forms of the CpG reduced promoters herein are expressly included, either known or unknown.

The term "vector" refers to small carrier nucleic acid molecule, a plasmid, virus (e.g., AAV), or other vehicle that can be manipulated by insertion or incorporation of a nucleic acid. Vectors can be used for genetic manipulation (i.e., "cloning vectors"), to introduce/transfer polynucleotides into cells and/or organs, and to transcribe or translate the inserted polynucleotide in cells. An "expression vector" is a vector that contains a gene or nucleic acid sequence with the necessary regulatory regions needed for expression in a host cell. A vector nucleic acid sequence generally contains at least an origin of replication for propagation in a cell and optionally additional elements, such as a heterologous nucleic acid sequence, expression control element (e.g., a promoter, enhancer), intron, inverted terminal repeat(s) (ITRs), optional selectable marker, polyadenylation signal.

As disclosed herein, a vector lacking an intron exhibited superior characteristics compared to the same vector with a synthetic intron. Accordingly, the instant invention provides expression cassettes comprising a transgene operably linked to a regulatory element, wherein the regulatory element (e.g., a CpG reduced promoter as set forth in herein) is positioned upstream of the 5' end of the transgene and in which there are no more than 0-5, 5-10, 10-15, 15-20, 20-25, 25-30, 30-35, 35-40, 40-45, 45-50, 50-55, 55-60, 60-65, 65-70, 70-75, 75-80, 80-85, 85-90, 90-95, 95-100, 100-105, 106 or 107 nucleotides of untranslated nucleic acid sequence between the regulatory element and the 5' end of the transgene.

The instant invention also provides expression cassettes comprising a first nucleotide sequence having 95% or greater sequence identity to the sequence of any of SEQ ID NOs:2-67, in which the first nucleotide sequence is positioned upstream of the 5' end of a second nucleotide sequence having 95% or greater sequence identity to the sequence of SEQ ID NO:77, and in which no more than 0-5, 5-10, 10-15, 15-20, 20-25, 25-30, 30-35, 35-40, 40-45, 45-50, 50-55, 55-60, 60-65, 65-70, 70-75, 75-80, 80-85, 85-90, 90-95, 95-100, 100-105, 106 or 107 nucleotides of untranslated nucleic acid sequence is between the first nucleotide sequence and the 5' end of the second nucleotide sequence.

The instant invention additionally provides expression cassettes comprising a first nucleotide sequence having 95% or greater sequence identity to the sequence of any of SEQ ID NOs:2-67, in which the first nucleotide sequence is positioned upstream of the 5' end of a second nucleotide sequence having 95% or greater sequence identity (e.g., 95%, 96%, 97%, 98%, 99% or greater sequence identity) to the sequence of any of SEQ ID NOs:71-88, and in which no more than 0-5, 5-10, 10-15, 15-20, 20-25, 25-30, 30-35, 35-40, 40-45, 45-50, 50-55, 55-60, 60-65, 65-70, 70-75, 75-80, 80-85, 85-90, 90-95, 95-100, 100-105, 106 or 107 nucleotides of untranslated nucleic acid sequence is between the first nucleotide sequence and the 5' end of the second nucleotide sequence.

The instant invention further provides expression cassettes with an untranslated (non-coding) nucleic acid positioned between a regulatory element and a transgene, wherein the untranslated nucleic acid is not an intron. Such an expression cassette can be referred to as an intron-free cassette.

An intron is a sequence with a donor site and splice acceptor site that allows cellular machinery to splice out untranslated nucleotide sequence during the process of RNA maturation to mRNA. As used herein, "intron-free" refers to an untranslated nucleic acid sequence that lacks donor and splice acceptor sites, but does not mean that the untranslated nucleic acid sequence is devoid of other sites such as restriction enzyme recognition/cleavage sites, Kozak sequences, transcription factor recognition/binding sites. In other words, intron-free does not mean that the nucleic acid sequence is completely devoid of any untranslated nucleic acid sequence(s).

An AAV vector is derived from adeno-associated virus. AAV vectors are useful as gene therapy vectors as they can penetrate cells and introduce nucleic acid/genetic material so that the nucleic acid/genetic material may be stably maintained in cells. Because AAV is not associated with pathogenic disease in humans, AAV vectors are able to deliver heterologous nucleic acid sequences (e.g., that encode therapeutic proteins and inhibitory RNA) to human patients without causing substantial AAV pathogenesis or disease.

The term "recombinant," as a modifier of a vector, such as a recombinant AAV (rAAV) vector, as well as a modifier of sequences such as recombinant polynucleotides and polypeptides, means that the compositions have been manipulated (i.e., engineered) in a fashion that generally does not occur in nature. A particular example of a recombinant AAV vector would be where a nucleic acid that is not normally present in the wild-type AAV genome (heterologous sequence) is inserted within the viral genome. An example of would be where a nucleic acid (e.g., gene) encoding a therapeutic protein or polynucleotide sequence is cloned into a vector, with or without 5', 3' and/or intron regions that the gene is normally associated within the AAV genome. Although the term "recombinant" is not always used herein in reference to an AAV vector, as well as sequences such as polynucleotides, recombinant forms including AAV vectors, polynucleotides, etc., are expressly included in spite of any such omission.

A "rAAV vector" is derived from the wild type genome of AAV by using molecular methods to remove all or a part of the wild type AAV genome, and replacing with a non-native (heterologous) nucleic acid, such as a nucleic acid encoding a therapeutic protein or polynucleotide sequence. Typically, for a rAAV vector one or both inverted terminal repeat (ITR) sequences of AAV genome are retained. A rAAV is distinguished from an AAV genome since all or a part of the AAV genome has been replaced with a non-native sequence with respect to the AAV genomic nucleic acid, such as with a heterologous nucleic acid encoding a therapeutic protein or polynucleotide sequence. Incorporation of a non-native (heterologous) sequence therefore defines the AAV as a "recombinant" AAV vector, which can be referred to as a "rAAV vector."

A recombinant AAV vector sequence can be packaged-referred to herein as a "particle" for subsequent infection (transduction) of a cell, ex vivo, in vitro or in vivo. Where a recombinant vector sequence is encapsidated or packaged into an AAV particle, the particle can also be referred to as a "rAAV" or "rAAV particle" or "rAAV virion." Such rAAV, rAAV particles and rAAV virions include proteins that encapsidate or package the vector genome. Particular examples include in the case of AAV, capsid proteins.

A "vector genome" or conveniently abbreviated as "vg" refers to the portion of the recombinant plasmid sequence that is ultimately packaged or encapsidated to form a rAAV particle. In cases where recombinant plasmids are used to construct or manufacture recombinant AAV vectors, the AAV vector genome does not include the portion of the "plasmid" that does not correspond to the vector genome sequence of the recombinant plasmid. This non vector genome portion of the recombinant plasmid is referred to as the "plasmid backbone," which is important for cloning and amplification of the plasmid, a process that is needed for propagation and recombinant AAV vector production, but is not itself packaged or encapsidated into rAAV particles. Thus, a "vector genome" refers to the nucleic acid that is packaged or encapsidated by rAAV.

"AAV helper functions" refer to AAV-derived coding sequences (proteins) which can be expressed to provide AAV gene products and AAV vectors that, in turn, function in trans for productive AAV replication and packaging. Thus, AAV helper functions include both of the major AAV open reading frames (ORFs), rep and cap. The Rep expression products have been shown to possess many functions, including, among others: recognition, binding and nicking of the AAV origin of DNA replication; DNA helicase activity; and modulation of transcription from AAV (or other heterologous) promoters. The Cap expression products (capsids) supply necessary packaging functions. AAV helper functions are used to complement AAV functions in trans that are missing from AAV vector genomes.

An "AAV helper construct" refers generally to a nucleic acid sequence that includes nucleotide sequences providing AAV functions deleted from an AAV vector which is to be used to produce a transducing AVV vector for delivery of a nucleic acid sequence of interest, by way of gene therapy to a subject, for example. AAV helper constructs are commonly used to provide transient expression of AAV rep and/or cap genes to complement missing AAV functions that are necessary for AAV vector replication and encapsidation. Helper constructs generally lack AAV ITRs and can neither replicate nor package themselves. AAV helper constructs can be in the form of a plasmid, phage, transposon, cosmid, virus, or virion. A number of AAV helper constructs have been described, such as plasmids pAAV/Ad and pIM29+45 which encode both Rep and Cap expression products (See, e.g., Samulski et al. (1989) J. Virol. 63:3822-3828; and McCarty et al. (1991) J. Virol. 65:2936-2945). A number of other vectors have been described which encode Rep and/or Cap expression products (See, e.g., U.S. Pat. Nos. 5,139,941 and 6,376,237).

The term "accessory functions" refers to non-AAV derived viral and/or cellular functions upon which AAV is dependent for replication. The term includes proteins and RNAs that are required in AAV replication, including moieties involved in activation of AAV gene transcription, stage specific AAV mRNA splicing, AAV DNA replication, synthesis of Cap expression products and AAV capsid packaging. Viral-based accessory functions can be derived from any of the known helper viruses such as adenovirus, herpesvirus (other than herpes simplex virus type-1) and vaccinia virus.

An "accessory function vector" refers generally to a nucleic acid molecule that includes polynucleotide sequences providing accessory functions. Such sequences can be on an accessory function vector, and transfected into a suitable host cell. The accessory function vector is capable of supporting rAAV virion production in the host cell. Accessory function vectors can be in the form of a plasmid, phage, transposon or cosmid. In addition, the full-complement of adenovirus genes are not required for accessory functions. For example, adenovirus mutants incapable of DNA replication and late gene synthesis have been reported to be permissive for AAV replication (Ito et al., (1970) J. Gen. Virol. 9:243; Ishibashi et al., (1971) Virology 45:317). Similarly, mutants within E2B and E3 regions have been shown to support AAV replication, indicating that the E2B and E3 regions are probably not involved in providing accessory functions (Carter et al., (1983) Virology 126:505). Adenoviruses defective in the E1 region, or having a deleted E4 region, are unable to support AAV replication. Thus, E1A and E4 regions appear necessary for AAV replication, either directly or indirectly (Laughlin et al., (1982) J. Virol. 41:868; Janik et al., (1981) Proc. Natl. Acad. Sci. USA 78:1925; Carter et al., (1983) Virology 126:505). Other characterized adenovirus mutants include: E1B (Laughlin et al. (1982), supra; Janik et al., (1981), supra; Ostrove et al., (1980) Virology 104:502); E2A (Handa et al., (1975) J. Gen. Virol. 29:239; Strauss et al., (1976) J. Virol. 17:140; Myers et al., (1980) J. Virol. 35:665; Jay et al., (1981) Proc. Natl. Acad. Sci. USA 78:2927; Myers et al., (1981) J. Biol. Chem. 256:567); E2B (Carter, Adeno-Associated Virus Helper Functions, in I CRC Handbook of Parvoviruses (P. Tijssen ed., 1990)); E3 (Carter et al., (1983), supra); and E4 (Carter et al., (1983), supra; Carter (1995)). Studies of the accessory functions provided by adenoviruses having mutations in the E1B coding region have produced conflicting results, but E1B55k may be required for AAV virion production, while E1B19k is not (Samulski et al., (1988) J. Virol. 62:206-210). In addition, International Publication WO 97/17458 and Matshushita et al., (1998) Gene Therapy 5:938-945, describe accessory function vectors encoding various adenovirus genes. Exemplary accessory function vectors comprise an adenovirus VA RNA coding region, an adenovirus E4 ORF6 coding region, an adenovirus E2A 72 kD coding region, an adenovirus E1A coding region, and an adenovirus E1B region lacking an intact E1B55k coding region. Such accessory function vectors are described, for example, in International Publication No. WO 01/83797.

As used herein, the term "serotype" is a distinction used to refer to an AAV having a capsid that is serologically distinct from other AAV serotypes. Serologic distinctiveness is determined on the basis of the lack of cross-reactivity between antibodies to one AAV as compared to another AAV. Cross-reactivity differences are usually due to differences in capsid protein sequences/antigenic determinants (e.g., due to VP1, VP2, and/or VP3 sequence differences of AAV serotypes).

Under the traditional definition, a serotype means that the virus of interest has been tested against serum specific for all existing and characterized serotypes for neutralizing activity and no antibodies have been found that neutralize the virus of interest. As more naturally occurring virus isolates of are discovered and/or capsid mutants generated, there may or may not be serological differences with any of the currently existing serotypes. Thus, in cases where the new virus (e.g., AAV) has no serological difference, this new virus (e.g., AAV) would be a subgroup or variant of the corresponding serotype. In many cases, serology testing for neutralizing activity has yet to be performed on mutant viruses with capsid sequence modifications to determine if they are of another serotype according to the traditional definition of serotype. Accordingly, for the sake of convenience and to avoid repetition, the term "serotype" broadly refers to both serologically distinct viruses (e.g., AAV) as well as viruses (e.g., AAV) that are not serologically distinct that may be within a subgroup or a variant of a given serotype.

rAAV vectors include any viral strain or serotype. For example, and without limitation, a rAAV vector genome or particle (capsid, such as VP1, VP2 and/or VP3) can be based upon any AAV serotype, such as AAV-1, -2, -3, -4, -5, -6, -7, -8, -9, -10, -11, -12, -rh74, -rh10 or AAV-2i8, for example. Such vectors can be based on the same of strain or serotype (or subgroup or variant), or be different from each other. For example, and without limitation, a rAAV plasmid or vector genome or particle (capsid) based upon one serotype genome can be identical to one or more of the capsid proteins that package the vector. In addition, a rAAV plasmid or vector genome can be based upon an AAV serotype genome distinct from one or more of the capsid proteins that package the vector genome, in which case at least one of the three capsid proteins could be a different AAV serotype, e.g., AAV1, AAV2, AAV3, AAV3B, AAV4, AAV5, AAV6, AAV7, AAV8, AAV9, AAV10, AAV11, AAV12, -rh74, -rh10, AAV-2i8, LK03 (SEQ ID NO:91), SPK (SEQ ID NO:92), or variant thereof, for example. More specifically, a rAAV2 vector genome can comprise AAV2 ITRs but capsids from a different serotype, such as AAV1, AAV3, AAV3B, AAV4, AAV5, AAV6, AAV7, AAV8, AAV9, AAV10, AAV11, AAV12, -rh74, -rh10, AAV-2i8, LK03 (SEQ ID NO:91), SPK (SEQ ID NO:92) or variant thereof, for example. Accordingly, rAAV vectors include gene/protein sequences identical to gene/protein sequences characteristic for a particular serotype, as well as mixed serotypes also referred to as pseudotypes.

In certain embodiments, a rAAV vector includes or consists of a capsid sequence at least 70% or more (e.g., 75%, 80%, 85%, 90%, 95%, 96%, 97%, 98%, 99%, 99.5%, etc.) identical to one or more AAV1, AAV2, AAV3, AAV3B, AAV4, AAV5, AAV6, AAV7, AAV8, AAV9, AAV10, AAV11, AAV12, -rh74, -rh10, AAV-2i8, LK03 (SEQ ID NO:91), SPK (SEQ ID NO:92) capsid proteins (VP1, VP2, and/or VP3 sequences). In certain embodiments, a rAAV vector includes or consists of a sequence at least 70% or more (e.g., 75%, 80%, 85%, 90%, 95%, 96%, 97%, 98%, 99%, 99.5%, etc.) identical to one or more AAV1, AAV2, AAV3, AAV3B, AAV4, AAV5, AAV6, AAV7, AAV8, AAV9, AAV10, AAV11, AAV12, -rh74, or -rh10 ITR(s).

In certain embodiments, rAAV vectors include AAV1, AAV2, AAV3, AAV3B, AAV4, AAV5, AAV6, AAV7, AAV8, AAV9, AAV10, AAV11, AAV12, Rh10, Rh74 and AAV-2i8 variants (e.g., ITR and capsid variants, such as amino acid insertions, additions, substitutions and deletions) thereof, for example, as set forth in WO 2013/158879 (International Application PCT/US2013/037170), WO 2015/013313 (International Application PCT/US2014/047670) and US 2013/0059732 (US application Ser. No. 13/594,773, discloses LK01, LK02, LK03 (SEQ ID NO:91), etc.).

rAAV, such as AAV1, AAV2, AAV3, AAV3B, AAV4, AAV5, AAV6, AAV7, AAV8, AAV9, AAV10, AAV11, AAV12, -rh74, -rh10, AAV-2i8, LK03 (SEQ ID NO:91), SPK (SEQ ID NO:92) and variants, hybrids and chimeric sequences, can be constructed using recombinant techniques that are known to the skilled artisan, to include one or more heterologous polynucleotide sequences (transgenes) flanked with one or more functional AAV ITR sequences. Such AAV vectors typically retain at least one functional flanking ITR sequence(s), as necessary for the rescue, replication, and packaging of the recombinant vector into a rAAV vector particle. A rAAV vector genome would therefore include sequences required in cis for replication and packaging (e.g., functional ITR sequences).

As used herein the phrase "bona fide AAV vector" or "bona fide rAAV vector" refers to AAV vectors comprising a heterologous nucleic acid which are capable of infecting target cells. The phrase excludes empty AAV vectors (no heterologous nucleic acid), and AAV vectors lacking full inserts (e.g., heterologous nucleic acid fragments) or those AAV vectors containing host cell nucleic acids.

The terms "nucleic acid" and "polynucleotide" are used interchangeably herein to refer to all forms of nucleic acid, oligonucleotides, including deoxyribonucleic acid (DNA) and ribonucleic acid (RNA).

Nucleic acids include genomic DNA, cDNA and antisense DNA, and spliced or unspliced mRNA, rRNA tRNA and inhibitory DNA or RNA (RNAi, e.g., small or short hairpin (sh)RNA, microRNA (miRNA), small or short interfering (si)RNA, trans-splicing RNA, or antisense RNA).

Nucleic acids include naturally occurring, synthetic, and intentionally modified or altered polynucleotides. Nucleic acids can be single, double, or triplex, linear or circular, and can be of any length. In discussing nucleic acids, a sequence or structure of a particular polynucleotide may be described herein according to the convention of providing the sequence in the 5' to 3' direction.

A "heterologous" nucleic acid sequence refers to a polynucleotide inserted into an AAV plasmid or vector for purposes of vector mediated transfer/delivery of the polynucleotide into a cell. Heterologous nucleic acid sequences are distinct from AAV nucleic acid, i.e., are non-native with respect to AAV nucleic acid. Once transferred/delivered into the cell, a heterologous nucleic acid sequence, contained within the vector, can be expressed (e.g., transcribed, and translated if appropriate). Alternatively, a transferred/delivered heterologous polynucleotide in a cell, contained within the vector, need not be expressed. Although the term "heterologous" is not always used herein in reference to nucleic acid sequences and polynucleotides, reference to a nucleic acid sequence or polynucleotide even in the absence of the modifier "heterologous" is intended to include heterologous nucleic acid sequences and polynucleotides in spite of the omission.

A "transgene" is used herein to conveniently refer to a nucleic acid that is intended or has been introduced into a cell or organism. Transgenes include any nucleic acid, such as a heterologous nucleic acid encoding a therapeutic protein or polynucleotide sequence. The term transgene and heterologous nucleic acid/polynucleotide sequences are used interchangeably herein.

In a cell having a transgene, the transgene has been introduced/transferred by way of a plasmid or a AAV vector, "transduction" or "transfection" of the cell. The terms "transduce" and "transfect" refer to introduction of a molecule such as a nucleic acid into a host cell (e.g., HEK293) or cells or organ of an organism. The transgene may or may not be integrated into genomic nucleic acid of the recipient cell.

The "nucleic acids," "polynucleotides," "heterologous nucleic acids," "transgenes" and "CpG reduced nucleic acid sequences" include full-length sequences, as well as functional subsequences, so long as the subsequence, retains some degree of functionality of the full-length sequence. Nucleic acids, polynucleotides, heterologous nucleic acids, transgenes and CpG reduced nucleic acid sequences.

The "polypeptides," "proteins" and "peptides" encoded by the "nucleic acid sequence" such as a heterologous nucleic acid sequence include full-length sequences, as with naturally occurring proteins, as well as functional subsequences, modified forms or sequence variants so long as the subsequence, modified form or variant retains some degree of functionality of the full-length protein. Such polypeptides, proteins and peptides encoded by the nucleic acid sequences can be but are not required to be identical to the endogenous protein that is defective, or whose expression is insufficient, or deficient in the treated mammal.

A "host cell" denotes, for example, microorganisms, yeast cells, insect cells, and mammalian cells, that can be, or have been, used as recipients of an AAV vector plasmid, AAV helper construct, an accessory function vector, or other transfer DNA. The term includes the progeny of the original cell which has been transfected. Thus, a "host cell" generally refers to a cell which has been transfected with an exogenous DNA sequence. It is understood that the progeny of a single parental cell may not necessarily be completely identical in morphology or in genomic or total DNA complement as the original parent, due to natural, accidental, or deliberate mutation. Exemplary host cells include human embryonic kidney (HEK) cells such as HEK293.

A "transduced cell" is a cell into which a transgene has been introduced. Accordingly, a "transduced" cell means a genetic change in a cell following incorporation of an exogenous molecule, for example, a nucleic acid (e.g., a transgene) into the cell. Thus, a "transduced" cell is a cell into which, or a progeny thereof in which an exogenous nucleic acid has been introduced. The cell(s) can be propagated (cultured) and the introduced protein expressed or nucleic acid transcribed, or vector, such as rAAV, produced by the cell. For gene therapy uses and methods, a transduced cell can comprise an organ or tissue and in turn can be in a subject.

As used herein, the term "stable" in reference to a cell, or "stably integrated" means that nucleic acid sequences, such as a selectable marker or heterologous nucleic acid sequence, or plasmid or vector has been inserted into a chromosome (e.g., by homologous recombination, non-homologous end joining, transfection, etc.) or is maintained in the recipient cell or host organism extrachromosomally, and has remained in the chromosome or is maintained extrachromosomally for a period of time.

A "cell line" refers to a population of cells capable of continuous or prolonged growth and division in vitro under appropriate culture conditions. Cell lines can, but need not be, clonal populations derived from a single progenitor cell. In cell lines, spontaneous or induced changes can occur in karyotype during storage or transfer of such clonal populations, as well as during prolonged passaging in tissue culture. Thus, progeny cells derived from the cell line may not be precisely identical to the ancestral cells or cultures. An exemplary cell line applicable to the instant invention purification methods is HEK293.

An "expression control element" refers to nucleic acid sequence(s) that influence expression of an operably linked nucleic acid. Control elements, including expression control elements as set forth herein such as promoters and enhancers. rAAV vectors can include one or more "expression control elements." Typically, such elements are included to facilitate proper heterologous polynucleotide transcription and if appropriate translation (e.g., one or more of a promoter, enhancer, splicing signal for introns, maintenance of the correct reading frame of the gene to permit in-frame translation of mRNA and, stop codons, etc.). Such elements typically act in cis, referred to as a "cis acting" element, but may also act in trans.

Expression control can be effected at the level of transcription, translation, splicing, message stability, etc. Typically, an expression control element that modulates transcription is juxtaposed near the 5' end (i.e., "upstream") of a transcribed nucleic acid. Expression control elements can also be located at the 3' end (i.e., "downstream") of the transcribed sequence or within the transcript (e.g., in an intron). Expression control elements (e.g., CpG reduced TTR, ApoE/hAAT, FGG, albumin, and SAA1 promoters as well as fusions/hybrids thereof) can be located adjacent to or at a distance away from the transcribed sequence (e.g., 1-10, 10-25, 25-50, 50-100, 100 to 500, or more nucleotides from the polynucleotide), even at considerable distances from the 5' or 3' end. Nevertheless, owing to the length limitations of rAAV vectors, expression control elements will typically be within 1 to 1000 nucleotides from the transcribed nucleic acid.

Functionally, expression of operably linked nucleic acid is at least in part controllable by the element (e.g., promoter, enhancer, etc.) such that the element modulates transcription of the nucleic acid and, as appropriate, translation of the transcript. A specific example of an expression control element is a promoter, which is usually located 5' of the transcribed sequence. A promoter typically increases expression from operably linked nucleic acid as compared to an amount (if any) expressed when no promoter exists.

Examples of promoters include TTR and ApoE/hAAT promoters, including CpG reduced versions and hybrid forms of the TTR promoter disclosed herein. Further examples of promoters include ApoE/hAAT, FGG, albumin, and SAA1 promoters including CpG reduced versions and hybrid forms thereof.

An "enhancer" as used herein can refer to a sequence that is located adjacent to the nucleic acid sequence, such as a heterologous nucleic acid sequence Enhancer elements are typically located upstream (5') of a promoter element but also function and can be located downstream (3') of or within a sequence. Hence, an enhancer element can be located upstream or downstream, e.g., within 100 base pairs, 200 base pairs, or 300 or more base pairs of the as selectable marker, and/or a heterologous nucleic acid encoding a therapeutic protein or polynucleotide sequence Enhancer elements typically increase expression of an operably linked nucleic acid above expression afforded by a promoter element.

The term "operably linked" means that the regulatory sequences necessary for expression of a nucleic acid sequence are placed in the appropriate positions relative to the sequence so as to effect expression of the nucleic acid sequence. This same definition is sometimes applied to the arrangement of nucleic acid sequences and transcription control elements (e.g. promoters, enhancers, and termination elements) in an expression vector, e.g., rAAV vector.

In the example of an expression control element in operable linkage with a nucleic acid, the relationship is such that the control element modulates expression of the nucleic acid. More specifically, for example, two DNA sequences operably linked means that the two DNAs are arranged (cis or trans) in such a relationship that at least one of the DNA sequences is able to exert a modulatory effect upon the other sequence.

Accordingly, additional elements for vectors include, without limitation, an expression control (e.g., promoter/enhancer) element, a transcription termination signal or stop codon, 5' or 3' untranslated regions (e.g., polyadenylation (polyA) sequences) which flank a sequence (e.g., heterologous sequence), such as one or more copies of an AAV ITR sequence, or an intron.

Further elements include, for example, filler or stuffer polynucleotide sequences, for example to improve packaging and reduce the presence of contaminating nucleic acid. AAV vectors typically accept inserts of DNA having a size range which is generally about 4 kb to about 5.2 kb, or slightly more. Thus, for shorter sequences, inclusion of a stuffer or filler in order to adjust the length to near or at the normal size of the virus genomic sequence acceptable for vector packaging into a rAAV particle. In certain embodiments, a filler/stuffer nucleic acid sequence is an untranslated (non-protein encoding) segment of nucleic acid. For a nucleic acid sequence less than 4.7 Kb, the filler or stuffer polynucleotide sequence has a length that when combined (e.g., inserted into a vector) with the sequence has a total length between about 3.0-5.5 Kb, or between about 4.0-5.0 Kb, or between about 4.3-4.8 Kb.

Where a wild type heterologous nucleic acid or transgene is too large to be packaged within an AAV vector particle, the heterologous nucleic acid may be provided in modified, fragmented or truncated form for packaging in and delivery by an AAV vector, such that a functional protein or nucleic acid product, such as a therapeutic protein or nucleic acid product, is ultimately provided.

In certain embodiments, the heterologous nucleic acid that encodes a protein (e.g., therapeutic protein) is provided in modified or truncated forms or the heterologous nucleic acid is provided in multiple constructs, delivered by separate and multiple AAV vectors.

In certain embodiments, the heterologous nucleic acid is provided as a truncated variant that maintains functionality of the encoded protein (e.g., therapeutic protein), including removal of portions unnecessary for function, such that the encoding heterologous polynucleotide is reduced in size for packaging in an AAV vector.

In certain embodiments the heterologous nucleic acid is provided in split AAV vectors, each providing nucleic acid encoding different portions of a protein (e.g., therapeutic protein), thus delivering multiple portions of a protein (e.g., therapeutic protein) which assemble and function in the cell.

In certain embodiments, the heterologous nucleic acid is provided by dual AAV vectors using overlapping, trans-splicing or hybrid trans-splicing dual vector technology. In certain embodiments, two overlapping AAV vectors are used which combine in the cell to generate a full expression cassette, from which a full-length protein (e.g., therapeutic protein) is expressed.

The term "identity," "homology" and grammatical variations thereof, mean that two or more referenced entities are the same, when they are "aligned" sequences. Thus, by way of example, when two polypeptide sequences are identical, they have the same amino acid sequence, at least within the referenced region or portion. Where two polynucleotide sequences are identical, they have the same polynucleotide sequence, at least within the referenced region or portion. The identity can be over a defined area (region or domain) of the sequence. An "area" or "region" of identity refers to a portion of two or more referenced entities that are the same. Thus, where two protein or nucleic acid sequences are identical over one or more sequence areas or regions they share identity within that region. An "aligned" sequence refers to multiple polynucleotide or protein (amino acid) sequences, often containing corrections for missing or additional bases or amino acids (gaps) as compared to a reference sequence.

The identity can extend over the entire length or a portion of the sequence. In certain embodiments, the length of the sequence sharing the percent identity is 2, 3, 4, 5 or more contiguous nucleic acids or amino acids, e.g., 6, 7, 8, 9, 10, 11, 12, 13, 14, 15, 16, 17, 18, 19, 20, etc. contiguous nucleic acids or amino acids. In certain embodiments, the length of the sequence sharing identity is 21 or more contiguous nucleic acids or amino acids, e.g., 21, 22, 23, 24, 25, 26, 27, 28, 29, 30, 31, 32, 33, 34, 35, 36, 37, 38, 39, 40, etc. contiguous nucleic acids or amino acids. In certain embodiments, the length of the sequence sharing identity is 41 or more contiguous nucleic acids or amino acids, e.g., 42, 43, 44, 45, 45, 47, 48, 49, 50, etc., contiguous nucleic acids or amino acids. In certain embodiments, the length of the sequence sharing identity is 50 or more contiguous nucleic acids or amino acids, e.g., 50-55, 55-60, 60-65, 65-70, 70-75, 75-80, 80-85, 85-90, 90-95, 95-100, 100-150, 150-200, 200-250, 250-300, 300-500, 500-1,000, etc. contiguous nucleic acids or amino acids.

As set forth herein, nucleic acid variants such as CpG reduced promoters including hybrid forms thereof will be distinct from wild-type but may exhibit sequence identity with wild-type promoters. In CpG reduced promoters including hybrid forms thereof, at the nucleotide sequence level, a CpG reduced promoter will typically be at least about 70% identical, more typically at least about 75% identical, even more typically about 80%-90% identical to wild-type promoter. For example, a CpG reduced promoter may have 70%-99% identity to wild-type promoter. Accordingly, a CpG reduced promoter may have 70-75%, 75-80%, 80-85%, 85-90%, 90-95%, 95-99%, 75%-99% identity to wild-type promoter.

At the amino acid sequence level, a variant such as a variant FVIII or hFVIII-BDD protein will be at least about 70% identical, more typically about 75% identical, or about 80% identical, even more typically about 85 identical, or about 90% or more identical to a reference sequence. In certain embodiments, a variant such as a variant FVIII or hFVIII-BDD BDD protein has at least about 90%, 91%, 92%, 93%, 94%, 95%, 96%, 97%, 98%, 99% or more identity to a reference sequence, e.g., wild-type FVIII protein with or without B-domain.

The terms "homologous" or "homology" mean that two or more referenced entities share at least partial identity over a given region or portion. "Areas, regions or domains" of homology or identity mean that a portion of two or more referenced entities share homology or are the same. Thus, where two sequences are identical over one or more sequence regions they share identity in these regions. "Substantial homology" means that a molecule is structurally or functionally conserved such that it has or is predicted to have at least partial structure or function of one or more of the structures or functions (e.g., a biological function or activity) of the reference molecule, or relevant/corresponding region or portion of the reference molecule to which it shares homology.

The extent of identity (homology) or "percent identity" between two sequences can be ascertained using a computer program and/or mathematical algorithm. For purposes of this invention comparisons of nucleic acid sequences are performed using the GCG Wisconsin Package version 9.1, available from the Genetics Computer Group in Madison, Wisconsin. For convenience, the default parameters (gap creation penalty=12, gap extension penalty=4) specified by that program are intended for use herein to compare sequence identity. Alternately, the Blastn 2.0 program provided by the National Center for Biotechnology Information (found on the world wide web at ncbi.nlm.nih.gov/blast/; Altschul et al., 1990, J Mol Biol 215:403-410) using a gapped alignment with default parameters, may be used to determine the level of identity and similarity between nucleic acid sequences and amino acid sequences. For polypeptide sequence comparisons, a BLASTP algorithm is typically used in combination with a scoring matrix, such as PAM100, PAM 250, BLOSUM 62 or BLOSUM 50. FASTA (e.g., FASTA2 and FASTA3) and SSEARCH sequence comparison programs are also used to quantitate extent of identity (Pearson et al., *Proc. Natl. Acad. Sci. USA* 85:2444 (1988); Pearson, *Methods Mol Biol.* 132:185 (2000); and Smith et al., *J. Mol. Biol.* 147:195 (1981)). Programs for quantitating protein structural similarity using Delaunay-based topological mapping have also been developed (Bostick et al., *Biochem Biophys Res Commun.* 304:320 (2003)).

A "therapeutic protein," in certain embodiments, is a peptide or protein that may alleviate or reduce symptoms that result from an insufficient amount, absence or defect in a protein in a cell or subject. A "therapeutic" protein encoded by a transgene can confer a benefit to a subject, e.g., to correct a genetic defect, to correct a gene (loss of expression or function) deficiency, etc.

For example, and without limitation, heterologous nucleic acids encoding gene products (e.g., therapeutic proteins) useful in accordance with the instant invention include those that may be used in the treatment of a disease or disorder including, but not limited to, "hemostasis" or blood clotting (bleeding) disorders such as hemophilia A, hemophilia A patients with inhibitory antibodies, hemophilia B, hemophilia B with inhibitory antibodies, a deficiency in any blood coagulation Factor: VII, VIII, IX, X, XI, V, XII, II, von Willebrand factor, combined FV/FVIII deficiency, thalassemia, vitamin K epoxide reductase C1 deficiency, gamma-carboxylase deficiency; anemia; bleeding associated with trauma, injury, thrombosis, thrombocytopenia, stroke, coagulopathy, disseminated intravascular coagulation (DIC); over-anticoagulation associated with heparin, low molecular weight heparin, pentasaccharide, warfarin, small molecule antithrombotics (i.e., FXa inhibitors); and platelet disorders such as, Bernard Soulier syndrome, Glanzmann thrombasthenia, and storage pool deficiency. In certain embodiments, a subject has a blood clotting disorder. In certain embodiments, a subject has hemophilia A, hemophilia A with inhibitory antibodies, hemophilia B, hemophilia B with inhibitory antibodies, a deficiency in any coagulation Factor: VII, VIII, IX, X, XI, V, XII, II, von Willebrand factor, or a combined FV/FVIII deficiency, thalassemia, vitamin K epoxide reductase C1 deficiency or gamma-carboxylase deficiency.

In certain embodiments, a subject has a disease or disorder including, for example and without limitation, a lung disease (e.g., cystic fibrosis), a bleeding disorder (e.g., hemophilia A or hemophilia B with or without inhibitors), thalassemia, a blood disorder (e.g., anemia), a neurodegenerative disorder (e.g., Alzheimer's disease, Parkinson's disease, Huntington's disease, amyotrophic lateral sclerosis (ALS)), a neurological disorder (e.g., epilepsy), a lysosomal storage disease)e.g., aspartylglucosaminuria, Batten disease, late infantile neuronal ceroid lipofuscinosis type 2 (CLN2), cystinosis, Fabry disease, Gaucher disease types I, II, and III, glycogen storage disease II (Pompe disease), glycogen storage disease III (GSDIII; Cori disease); ganglioside monosialic 2 (GM2)-gangliosidosis type I (Tay Sachs disease), GM2-gangliosidosis type II (Sandhoff disease), mucolipidosis types I (sialidosis type I and II), II (I-cell disease), III (pseudo-Hurler disease) and IV, mucopolysaccharide storage diseases (Hurler disease and variants, Hunter, Sanfilippo Types A,B,C,D, Morquio Types A and B, Maroteaux-Lamy and Sly diseases), Niemann-Pick disease types A/B, C1 and C2, and Schindler disease types I and II), an inflammatory disorder (e.g., hereditary angioedema (HAE)), a copper or iron accumulation disorder (e.g., Wilson's or Menkes disease), lysosomal acid lipase deficiency, cancer, type 1 or type 2 diabetes, adenosine deaminase deficiency, a metabolic disease or disorder (e.g., glycogen storage diseases, methylmalonic acidemia, ornithine transcarbamylase deficiency, hypophosphatsia, very-long-chain acyl-CoA dehydrogenase deficiency (VLCAD), galactosemia), an autoimmune disease (e.g., multiple sclerosis, type I diabetes, celiac disease, neuromyelitis optica (NMO), immune thrombocytopenia ((ITP); idiopathic thrombocytopenic purpura), Addison's disease, myasthenia gravis), a disease of solid organs (e.g., brain, liver, kidney, heart), or an infectious viral (e.g., hepatitis B and C, human immunodeficiency virus (HIV), etc.), bacterial or fungal disease.

In certain embodiments, a subject has a disease that affects or originates in the central nervous system (CNS). In certain embodiments, the disease is a neurodegenerative disease. In certain embodiments, the CNS or neurodegenerative disease is Alzheimer's disease, Huntington's disease, ALS, hereditary spastic hemiplegia, primary lateral sclerosis, spinal muscular atrophy, Kennedy's disease, a polyglutamine repeat disease, or Parkinson's disease. In certain embodiments, the CNS or neurodegenerative disease is a polyglutamine repeat disease. In certain embodiments, the polyglutamine repeat disease is a spinocerebellar ataxia (SCA1, SCA2, SCA3, SCA6, SCAT7, or SCA17).

Apolipoprotein E (ApoE) is a major cholesterol carrier involved in lipid transport and brain injury repair. It is suggested that human ApoE isoforms differentially affect the clearance or synthesis of amyloid-β (Aβ) in vivo. The epsilon4 (ε4) allele of ApoE is associated with increased risk of Alzheimer's disease (AD), and the presence of the ApoE ε2 allele appears to decrease AD risk, and is a protective ApoE isoform. As used herein, the term "protective ApoE isoform." refers to ApoE isoforms that decrease one or more symptoms or indications of Alzheimer's disease (e.g., physical, physiological, biochemical, histological, behavioral). A protective ApoE isoform also refers to ApoE isoforms that can reduce the risk of Alzheimer's disease by at least 5%, such as 10%, 20%, 30%, 40%, 50%, 60%, 70%, 80%, 90%, 100% or more.

In certain embodiments, the invention provides a method of delivering a protective ApoE isoform (e.g., ApoE ε2) to the CNS of a subject (e.g., mammal), by way of delivery or administration to a non-CNS cell, organ or tissue (e.g., not to cerebrospinal fluid (CSF) or brain) of the subject.

In certain embodiments, an rAAV particle comprising an AAV capsid protein and a vector comprising a nucleic acid encoding a protective ApoE isoform (e.g., ApoE ε2) inserted between a pair of AAV inverted terminal repeats (ITRs) in a manner effective to transduce non-CNS cells (e.g., liver cells) in a subject (e.g., mammal) such that the non-CNS cells (e.g., liver cells) secrete the protective ApoE isoform into the systemic circulation (vasculature or blood vessels) of the subject. The protective ApoE isoform in the circulation crosses the blood brain barrier and enters the CNS (e.g., cerebrospinal fluid (CSF) or brain, such as brain parenchyma).

In certain embodiments, the instant invention provides a vector, expression cassette or nucleic acid that encodes a protective ApoE isoform (e.g., ApoE ε2) that is expressed in the liver or in liver cells.

In certain embodiments, the heterologous nucleic acid encodes a protein selected from the group consisting of insulin, glucagon, growth hormone (GH), parathyroid hormone (PTH), growth hormone releasing factor (GRF), follicle stimulating hormone (FSH), luteinizing hormone (LH), human chorionic gonadotropin (hCG), vascular endothelial growth factor (VEGF), angiopoietins, angiostatin, granulocyte colony stimulating factor (GCSF), erythropoietin (EPO), connective tissue growth factor (CTGF), basic fibroblast growth factor (bFGF), acidic fibroblast growth factor (aFGF), epidermal growth factor (EGF), transforming growth factor α (TGFα), platelet-derived growth factor (PDGF), insulin growth factors I and II (IGF-I and IGF-II), TGFβ, activins, inhibins, bone morphogenic protein (BMP), nerve growth factor (NGF), brain-derived neurotrophic factor (BDNF), neurotrophins NT-3 and NT4/5, ciliary neurotrophic factor (CNTF), glial cell line derived neurotrophic factor (GDNF), neurturin, agrin, netrin-1 and netrin-2, hepatocyte growth factor (HGF), ephrins, noggin, sonic hedgehog and tyrosine hydroxylase.

In certain embodiments, the heterologous nucleic acid encodes a protein selected from the group consisting of thrombopoietin (TPO), interleukins (IL1 through IL-36), monocyte chemoattractant protein, leukemia inhibitory factor, granulocyte-macrophage colony stimulating factor, Fas ligand, tumor necrosis factors α and β, interferons α, β, and γ, stem cell factor, flk-2/flt3 ligand, IgG, IgM, IgA, IgD and IgE, chimeric immunoglobulins, humanized antibodies, single chain antibodies, T cell receptors, chimeric T cell receptors, single chain T cell receptors, class I and class II MHC molecules.

In certain embodiments, the heterologous nucleic acid encodes CFTR (cystic fibrosis transmembrane regulator protein), a blood coagulation (clotting) factor (Factor XIII, Factor IX, Factor VIII, Factor X, Factor VII, Factor VIIa, protein C, etc.), a gain of function blood coagulation factor, an antibody, retinal pigment epithelium-specific 65 kDa protein (RPE65), erythropoietin, LDL receptor, lipoprotein lipase, ornithine transcarbamylase, (β-globin, α-globin, spectrin, α-antitrypsin, adenosine deaminase (ADA), a metal transporter (ATP7A or ATP7), sulfamidase, an enzyme involved in lysosomal storage disease (ARSA), hypoxanthine guanine phosphoribosyl transferase, (β-25 glucocerebrosidase, sphingomyelinase, lysosomal hexosaminidase, branched-chain keto acid dehydrogenase, a hormone, a growth factor, insulin-like growth factor 1 or 2, platelet derived growth factor, epidermal growth factor, nerve growth factor, neurotrophic factor-3 and -4, brain-derived neurotrophic factor, glial derived growth factor, transforming growth factor α and β, a cytokine, α-interferon, β-interferon, interferon-γ, interleukin-2, interleukin-4, interleukin 12, granulocyte-macrophage colony stimulating factor, lymphotoxin, a suicide gene product, herpes simplex virus thymidine kinase, cytosine deaminase, diphtheria toxin, cytochrome P450, deoxycytidine kinase, tumor necrosis factor, a drug resistance protein, a tumor suppressor protein (e.g., p53, Rb, Wt-1, NF1, Von Hippel-Lindau (VHL), adenomatous polyposis coli (APC)), a peptide with immunomodulatory properties, a tolerogenic or immunogenic peptide or protein Tregitope or hCDR1, insulin, glucokinase, guanylate cyclase 2D (LCA-GUCY2D), Rab escort protein 1 (choroideremia), LCA 5 (LCA-lebercilin), ornithine ketoacid aminotransferase (gyrate atrophy), retinoschisin 1 (X-linked retinoschisis), USH1C (Usher's Syndrome 1C), X-linked retinitis pigmentosa GTPase (XLRP), MERTK (AR forms of RP: retinitis pigmentosa), DFNB1 (connexin 26 deafness), ACHM 2, 3 and 4 (achromatopsia), PKD-1 or PKD-2 (polycystic kidney disease), TPP1, CLN2, a sulfatase, N-acetylglucosamine-1-phosphate transferase, cathepsin A, GM2-AP, Niemann-Pick C1 (NPC1), VPC2, a sphingolipid activator protein, one or more zinc finger nuclease for genome editing, and one or more donor sequence used as repair templates for genome editing.

In certain embodiments, the protein encoded by the heterologous nucleic acid comprises a gene editing nuclease. In certain embodiments, the gene editing nuclease comprises a zinc finger nuclease (ZFN) or a transcription activator-like effector nuclease (TALEN). In certain embodiments, the gene editing nuclease comprises a functional Type II CRISPR-Cas9.

Other heterologous nucleic acids encoding gene products (e.g., therapeutic proteins) that may be used with the instant invention, and which may optionally be expressed in liver or liver cells (e.g., hepatocytes) and provide a benefit, include, for example and without limitation: GAA (acid alpha-glucosidase) for treatment of Pompe disease; ATP7B (copper transporting ATPase2) for treatment of Wilson's disease; alpha galactosidase (GLA) for treatment of Fabry disease; ASS1 (arginosuccinate synthase) for treatment of citrullinemia type 1; beta-glucocerebrosidase for treatment of Gaucher disease Type 1; beta-hexosaminidase A for treatment of Tay Sachs disease; SERPING1 (C1 protease inhibitor; C1 esterase inhibitor (C1EI)) for treatment of hereditary angioedema (HAE); glucose-6-phosphatase for treatment of glycogen storage disease type I (GSDI); glycogen-debranching enzyme (GDE) for treatment of glycogen storage disease type III (GSD III; cori disease); Niemann-Pick C1 protein (NPC intracellular cholesterol transporter 1; NPC1) for treatment of Niemann-Pick disease; erythropoietin (EPO) for treatment of anemia; interferon-alpha, interferon-beta, and interferon-gamma for treatment of various immune disorders, viral infections and cancer; an interleukin (IL), including any one of IL-1 through IL-36, and corresponding receptors, for treatment of various inflammatory diseases or immuno-deficiencies; a chemokine, including chemokine (C-X-C motif) ligand 5 (CXCL5) for treatment of immune disorders; granulocyte-colony stimulating factor (G-CSF) for treatment of immune disorders such as Crohn's disease; granulocyte-macrophage colony stimulating factor (GM-CSF) for treatment of various human inflammatory diseases; macrophage colony stimulating factor (M-CSF) for treatment of various human inflammatory diseases; keratinocyte growth factor (KGF) for treatment of epithelial tissue damage; chemokines such as monocyte chemoattractant protein-1 (MCP-1) for treatment of recurrent miscarriage, HIV-related complications, and insulin resistance; tumor necrosis factor (TNF) and receptors for treatment of various immune disorders; alpha1-antitrypsin for treatment of emphysema or chronic obstructive pulmonary disease (COPD); alpha-L-iduronidase for treatment of mucopolysaccharidosis I (MPS I); ornithine transcarbamoylase (OTC) for treatment of OTC deficiency; phenylalanine hydroxylase (PAH) or phenylalanine ammonia-lyase (PAL) for treatment of phenylketonuria (PKU); lipoprotein lipase for treatment of lipoprotein lipase deficiency; apolipoproteins for treatment of apolipoprotein (Apo) A-I deficiency; low-density lipoprotein receptor (LDL-R) for treatment of familial hypercholesterolemia (FH); albumin for treatment of hypoalbuminemia; lecithin cholesterol acyltransferase (LCAT); carbamoyl synthetase I; argininosuccinate synthetase; argininosuccinate lyase; arginase; fumarylacetoacetate hydrolase; porphobilinogen deaminase; cystathionine beta-synthase, for treatment of homocystinuria; branched chain ketoacid decarboxylase; isovaleryl-CoA dehydrogenase; propionyl CoA carboxylase; methylmalonyl-CoA mutase; glutaryl CoA dehydrogenase; insulin; pyruvate carboxylase; hepatic phosphorylase; phosphorylase kinase; glycine decarboxylase; H-protein; T-protein; cystic fibrosis transmembrane regulator (CFTR); ATP-binding cassette, sub-family A (ABC1), member 4 (ABCA4) for the treatment of Stargardt disease; and dystrophin.

In certain embodiments a subject has an autoimmune disease or disorder (e.g., multiple sclerosis, anti-MAG peripheral neuropathy, type 1 diabetes, Graves' disease, rheumatoid arthritis, proteoglycan induced arthritis (PGIA) or myasthenia gravis); an allergy or allergic disease.

Mature myelin oligodendrocyte glycoprotein (MOG) is associated with the bi-lipid layer. MOG is characterized by an IgV-like extracellular domain, a single-bypass transmembrane protein, a membrane-associated domain, and a cytoplasmic tail. The extracellular IgV-like domain is denoted herein as mini-MOG (mMOG). MOG is predominantly found in membranes of oligodendrocytes and contributes a small amount to the final composition of myelin. Autoimmune responses to MOG are implicated in the development and etiology of multiple sclerosis.

In certain embodiments, the therapeutic protein is a fusion protein comprising an unwanted antigen and a leader sequence for cell secretion.

In certain embodiments, the therapeutic protein is a fusion protein comprising the extracellular domain of MOG, or a fragment thereof, and a leader sequence for cell secretion.

In certain embodiments, an expression cassette comprises an regulatory element operably linked to a nucleic acid encoding a fusion protein comprising an unwanted antigen and a leader sequence for cell secretion.

In certain embodiments, the unwanted antigen comprises a self-antigen, autoantigen or protein or peptide that has structural similarity or sequence identity to the self-antigen or the autoantigen. In certain embodiments, the protein or peptide that has structural similarity or sequence identity to the self-antigen or the autoantigen is a microbial protein or peptide. In certain embodiments, the unwanted antigen comprises an allergen.

In certain embodiments, the allergen comprises a plant, insect, or animal allergen. In certain embodiments, the unwanted antigen comprises a myelin oligodendrocyte glycoprotein (MOG), myelin basic protein (MBP), proteolipid protein (PLP), or subsequence thereof.

In certain embodiments, the MOG lacks all or a part of its transmembrane domain. In certain embodiments, the MOG comprises or consists of amino acids 1-117 of mature MOG. In certain embodiments, the MOG subsequence is a subsequence of its extracellular domain or a subsequence of its transmembrane domain. In certain embodiments, the MOG comprises or consists of amino acids 35-55, 118-132, 181-195, or 186-200 of mature MOG. In certain embodiments, the MOG comprises or consists of amino acids 1-20, 11-30, 21-40, 31-50, etc. of mature MOG.

In certain embodiments, the instant invention provides methods of suppressing, reducing or inhibiting a cell-mediated or antibody mediated immune response to an unwanted antigen in a mammal. In certain embodiment, a method includes providing an expression cassette, particle or pharmaceutical composition or LNP composition as set forth herein; and administering an amount of the expression cassette, particle, pharmaceutical composition or LNP composition to the mammal, wherein the fusion protein is expressed in the mammal sufficient to suppress, reduce or inhibit a cell-mediated or antibody mediated immune response to the unwanted antigen.

In certain embodiments, the instant invention provides methods of inducing tolerance in a mammal to an unwanted antigen. In certain embodiments, a method includes providing an expression cassette, particle, or pharmaceutical composition or LNP composition as set forth herein; and administering an amount of the expression cassette, particle, pharmaceutical or LNP composition to the mammal, wherein the fusion protein is expressed in the mammal sufficient to induce tolerance to the unwanted antigen.

In certain embodiments, the instant invention provides methods of treating a subject (e.g., human) in need of a fusion protein. In certain embodiments, a method includes providing an expression cassette, particle, or pharmaceutical composition or LNP composition as set forth herein; and administering an amount of the expression cassette, particle, pharmaceutical or LNP composition to the subject (e.g., human), wherein the fusion protein is expressed in the subject (e.g., human).

In certain embodiments, the subject (e.g., human) has an autoimmune disease or disorder. In certain embodiments, the subject (e.g., human) has an allergy or allergic disease or disorder.

In certain embodiments, the subject (e.g., human) has multiple sclerosis, anti-MAG peripheral neuropathy, type 1 diabetes, Graves' disease, rheumatoid arthritis, proteoglycan induced arthritis (PGIA) or myasthenia gravis.

As used herein, an "unwanted antigen" is a self-antigen or autoantigen that is able to induce, provide, enhance and/or stimulate immune tolerance against the antigen itself or a protein that includes all or a portion of the antigen and/or that suppresses, inhibits, reduces and/or decreases an immune response directed towards the antigen itself or a protein that includes all or a portion of the antigen. An unwanted antigen as used herein also includes allergens or allergenic antigens that can induce, provide, enhance and/or stimulate immune tolerance against the allergen as well as allergens and allergenic antigens that suppress, inhibit, reduce and/or decrease an immune response directed towards the allergen or an entity that includes the allergen.

Unwanted antigens as set forth herein also include allogenic antigens or transplantation antigens or minor histocompatibility antigens that can lead to rejection of a cell, tissue or organ after their transplantation into a subject. The subject typically recognizes the transplanted cell, tissue or organ as foreign and develops an immune response against the cell, tissue or organ. Accordingly, the invention methods are directed to preventing or reducing rejection of a cell, tissue or organ after transplant into a subject.

Although not wishing to be bound by any theory or particular mechanism, it is believed that the unwanted antigen functions by binding to or activating T regulatory cells (Tregs) thereby preventing, suppressing, inhibiting, reducing, decreasing or otherwise down regulating an immune response. This binding to or activation of Tregs in turn can lead to immune tolarization against the self-antigen or autoantigen.

As used herein, a "leader" sequence is an amino acid sequence that when linked to a protein provides or facilitates secretion of the linked protein from the cell in which it is expressed. A leader sequence as used herein can also be referred to as a secretion sequence. Such leader and secretion sequences are intended to provide or facilitate cell secretion but may not always facilitate secretion if they are linked to a protein that has a signal sequence that may prevent secretion of the protein.

In certain embodiments, an unwanted antigen comprises an autoimmune disease protein or a subsequence thereof. An autoimmune disease protein includes any antigen (such as a protein, subsequence thereof, or a peptide) that contributes to initiation and/or progression of an autoimmune disease. Such autoimmune disease proteins can be derived from other organisms, such as microorganisms because the sequence or structure of the proteins from the other organisms mimic the self-antigen or autoantigen.

In certain embodiments, an autoimmune disease protein is myelin oligodendrocyte glycoprotein (MOG, e.g., for multiple sclerosis), myelin basic protein (MBP, e.g., for multiple sclerosis), proteolipid protein (PLP, e.g., for multiple sclerosis), myelin-associated glycoprotein (MAG, e.g., for anti-MAG peripheral neuropathy), insulin (e.g., for type 1 diabetes), islet-specific glucose-6-phosphatase catalytic subunit-related protein (IGRP, e.g., for type 1 diabetes), preproinsulin (e.g., for type 1 diabetes), glutamic decarboxylase (GAD, e.g., for type 1 diabetes), tyrosine phosphatase like autoantigen (e.g., for type 1 diabetes), insulinoma antigen-2 (e.g., for type 1 diabetes), islet cell antigen (e.g., for type 1 diabetes); thyroid stimulating hormone (TSH) receptor (e.g., for Graves' disease), thyrotropin receptor (e.g., for Graves' disease), chondroitin sulfate proteoglycan 1 (e.g., for rheumatoid arthritis), CD4+ T cell epitope (e.g., GRVRVNSAY (SEQ ID NO: 98)), e.g., for proteoglycan induced arthritis (PGIA) or rheumatoid arthritis), or acetylcholine receptor (e.g., for myasthenia gravis).

In certain embodiments, an autoimmune disease protein is a mammalian myelin oligodendrocyte glycoprotein (MOG), myelin basis protein (MBP), proteolipid protein (PLP), or a subsequence thereof. In some embodiments, an autoimmune disease protein is a human protein, such as human myelin basis protein (MBP), a human proteolipid protein (PLP), a human myelin oligodendrocyte glycoprotein (MOG), or a subsequence thereof.

Other heterologous nucleic acids encoding gene products useful in accordance with the instant invention include, for example and without limitation, reporters or detectable markers such as luciferase, green fluorescent protein (GFP), yellow fluorescent protein (YFP), blue fluorescent protein, cyan fluorescent protein, enhanced GFP, enhanced YFP, photoactivatable GFP, *Discosoma* species fluorescent protein (dsRed), mFruits, mCherry, TagRFPs, eqFP611, photoswitchable fluorescent proteins (for example Dronpa and EosFP), chloramphenicol acetyltransferase, Halo-tag fusion protein, alkaline phosphatase, horseradish peroxidase and beta-galactosidase.

In certain embodiments, heterologous nucleic acids comprise inhibitory DNA or encode inhibitory RNA (RNAi). Examples of inhibitory RNA include, for example and without limitation, small or short hairpin (sh)RNA, microRNA (miRNA), small or short interfering (si)RNA, trans-splicing RNA, and antisense RNA.

In certain embodiments, the heterologous nucleic acid encodes an inhibitory nucleic acid. In certain embodiments, the inhibitory nucleic acid is selected from the group consisting of a siRNA, an antisense molecule, miRNA, RNAi, a ribozyme and a shRNA. In certain embodiments, the inhibitory nucleic acid binds to a gene, a transcript of a gene, or a transcript of a gene associated with a polynucleotide repeat disease selected from the group consisting of a huntingtin (HTT) gene, a gene associated with dentatorubropallidoluysian atrophy (atrophin 1, ATN1), androgen receptor on the X chromosome in spinobulbar muscular atrophy, human Ataxin-1, -2, -3, and -7, $Ca_v2.1$ P/Q voltage-dependent calcium channel (CACNA1A), TATA-binding protein, Ataxin 8 opposite strand (ATXN8OS), Serine/threonine-protein phosphatase 2A 55 kDa regulatory subunit B beta isoform in spinocerebellar ataxia (type 1, 2, 3, 6, 7, 8, 12 17), FMR1 (fragile X mental retardation 1) in fragile X syndrome, FMR1 (fragile X mental retardation 1) in fragile X-associated tremor/ataxia syndrome, FMR1 (fragile X mental retardation 2) or AF4/FMR2 family member 2 in fragile XE mental retardation; Myotonin-protein kinase (MT-PK) in myotonic dystrophy; Frataxin in Friedreich's ataxia; a mutant of superoxide dismutase 1 (SOD1) gene in amyotrophic lateral sclerosis; a gene involved in pathogenesis of Parkinson's disease and/or Alzheimer's disease; apolipoprotein B (APOB) and proprotein convertase subtilisin/kexin type 9 (PCSK9), hypercholesterolemia; HIV Tat, human immunodeficiency virus transactivator of transcription gene, in HIV infection; HIV TAR, HIV TAR, human immunodeficiency virus transactivator response element gene, in HIV infection; C-C chemokine receptor (CCR5) in HIV infection; Rous sarcoma virus (RSV) nucleocapsid protein in RSV infection, liver-specific microRNA (miR-122) in hepatitis C virus infection; p53, acute kidney injury or delayed graft function kidney transplant or kidney injury acute renal failure; protein kinase N3 (PKN3) in advance recurrent or metastatic solid malignancies; LMP2, LMP2 also known as proteasome subunit beta-type 9 (PSMB 9), metastatic melanoma; LMP7, also known as proteasome subunit beta-type 8 (PSMB 8), metastatic melanoma; MECL1 also known as proteasome subunit beta-type 10 (PSMB 10), metastatic melanoma; vascular endothelial growth factor (VEGF) in solid tumors; kinesin spindle protein in solid tumors, apoptosis suppressor B-cell CLL/lymphoma (BCL-2) in chronic myeloid leukemia; ribonucleotide reductase M2 (RRM2) in solid tumors; Furin in solid tumors; polo-like kinase 1 (PLK1) in liver tumors, diacylglycerol acyltransferase 1 (DGAT1) in hepatitis C infection, beta-catenin in familial adenomatous polyposis; beta2 adrenergic receptor, glaucoma; RTP801/Redd1 also known as DNA damage-inducible transcript 4 protein, in diabetic macular edema (DME) or age-related macular degeneration; vascular endothelial growth factor receptor I (VEGFR1) in age-related macular degeneration or choroidal neovascularization, caspase 2 in non-arteritic ischaemic optic neuropathy; keratin 6A N17K mutant protein in pachyonychia congenital; influenza A virus genome/gene sequences in influenza infection; severe acute respiratory syndrome (SARS) coronavirus genome/gene sequences in SARS infection; respiratory syncytial virus genome/gene sequences in respiratory syncytial virus infection; Ebola filovirus genome/gene sequence in Ebola infection; hepatitis B and C virus genome/gene sequences in hepatitis B and C infection; herpes simplex virus (HSV) genome/gene sequences in HSV infection, coxsackievirus B3 genome/gene sequences in coxsackievirus B3 infection; silencing of a pathogenic allele of a gene (allele-specific silencing) like torsin A (TOR1A) in primary dystonia, pan-class I and HLA-allele specific in transplant; and mutant rhodopsin gene (RHO) in autosomal dominantly inherited retinitis pigmentosa (adRP).

Nucleic acid molecules, vectors such as cloning, expression vectors (e.g., vector genomes) and plasmids, may be prepared using recombinant DNA technology methods. The availability of nucleotide sequence information enables preparation of nucleic acid molecules by a variety of means. For example, a heterologous nucleic acid comprising a vector or plasmid can be made using various standard cloning, recombinant DNA technology, via cell expression or in vitro translation and chemical synthesis techniques. Purity of polynucleotides can be determined through sequencing, gel electrophoresis and the like. For example, nucleic acids can be isolated using hybridization or computer-based database screening techniques. Such techniques include, but are not limited to: (1) hybridization of genomic DNA or cDNA libraries with probes to detect homologous nucleotide sequences; (2) antibody screening to detect polypeptides having shared structural features, for example, using an expression library; (3) polymerase chain reaction (PCR) on genomic DNA or cDNA using primers capable of annealing to a nucleic acid sequence of interest; (4) computer searches of sequence databases for related sequences; and (5) differential screening of a subtracted nucleic acid library.

Nucleic acids of the instant invention may be maintained as DNA in any convenient cloning vector. In certain embodiments, clones are maintained in a plasmid cloning/expression vector, such as pBluescript or pBluescript II (Stratagene, La Jolla, CA), which is propagated in a suitable *E. coli* host cell. Alternatively, nucleic acids may be maintained in a vector suitable for expression in mammalian cells.

Methods that are known in the art for generating rAAV virions include, for example, transfection using AAV vector and AAV helper sequences in conjunction with coinfection with one or more AAV helper virus(es) (e.g., adenovirus, herpesvirus, or vaccinia virus) or transfection with a recombinant AAV vector, an AAV helper vector, and an accessory function vector. Methods for generating rAAV virions are described in, for example and without limitation, U.S. Pat. Nos. 6,001,650 and 6,004,797. Following recombinant rAAV vector production (i.e., vector generation in cell culture systems), rAAV virions can be obtained from the host cells and cell culture supernatant and purified as set forth herein.

Methods to determine infectious titer of rAAV vector containing a transgene are known in the art (See, e.g., Zhen et al., (2004) Hum. Gene Ther. (2004) 15:709). Methods for assaying for empty capsids and AAV vector particles with packaged genomes are known (See, e.g., Grimm et al., Gene Therapy (1999) 6:1322-1330; Sommer et al., Molec. Ther. (2003) 7:122-128).

To determine degraded/denatured capsid, purified rAAV can be subjected to SDS-polyacrylamide gel electrophoresis, consisting of any gel capable of separating the three capsid proteins, for example, a gradient gel, then running the gel until sample is separated, and blotting the gel onto nylon or nitrocellulose membranes. Anti-AAV capsid antibodies are then used as primary antibodies that bind to denatured capsid proteins (See, e.g., Wobus et al., J. Virol. (2000) 74:9281-9293). A secondary antibody that binds to the primary antibody contains a means for detecting the primary antibody. Binding between the primary and secondary antibodies is detected semi-quantitatively to determine the amount of capsids.

rAAV vectors and other compositions, agents, drugs, biologics (proteins) can be incorporated into pharmaceutical compositions. Such pharmaceutical compositions are useful for, among other things, administration and delivery to a subject in vivo or ex vivo.

The term "isolated," when used as a modifier of a composition, means that the compositions are made by the hand of man or are separated, completely or at least in part, from their naturally occurring in vivo environment. Generally, isolated compositions are substantially free of one or more materials with which they normally associate with in nature, for example, one or more protein, nucleic acid, lipid, carbohydrate, cell membrane.

With respect to protein, the term "isolated protein" or "isolated and purified protein" is sometimes used herein. This term refers primarily to a protein produced by expression of a nucleic acid molecule. Alternatively, this term may refer to a protein which has been sufficiently separated from other proteins with which it would naturally be associated, so as to exist in "substantially pure" form.

The term "isolated" does not exclude compositions herein or combinations produced by the hand of man, for example, a rAAV and/or a pharmaceutical formulation. The term "isolated" also does not exclude alternative physical forms of the composition, such as hybrids/chimeras, multimers/oligomers, modifications (e.g., phosphorylation, glycosylation, lipidation) or derivatized forms, or forms expressed in host cells produced by the hand of man.

The term "substantially pure" refers to a preparation comprising at least 50-60% by weight the compound of interest (e.g., nucleic acid, oligonucleotide, protein, etc.). The preparation can comprise at least 75% by weight, or about 90-99% by weight, of the compound of interest. Purity is measured by methods appropriate for the compound of interest (e.g., chromatographic methods, agarose or polyacrylamide gel electrophoresis, HPLC analysis, and the like).

The phrase "consisting essentially of" when referring to a particular nucleotide sequence or amino acid sequence means a sequence having the properties of a given sequence. For example, when used in reference to a nucleic acid or an amino acid sequence, the phrase includes the sequence per se and molecular modifications that would not affect the basic and novel characteristics of the sequence.

In certain embodiments, pharmaceutical compositions also contain a pharmaceutically acceptable carrier or excipient. Such excipients include any pharmaceutical agent that does not itself induce an immune response harmful to the individual receiving the composition, and which may be administered without undue toxicity.

As used herein the term "pharmaceutically acceptable" and "physiologically acceptable" mean a biologically acceptable formulation, gaseous, liquid or solid, or mixture thereof, which is suitable for one or more routes of administration, in vivo delivery or contact. A "pharmaceutically acceptable" or "physiologically acceptable" composition is a material that is not biologically or otherwise undesirable, e.g., the material may be administered to a subject without causing substantial undesirable biological effects. Thus, such a pharmaceutical composition may be used, for example in administering a nucleic acid, vector, viral particle or protein to a subject.

Pharmaceutically acceptable excipients include, but are not limited to, liquids such as water, saline, glycerol, sugars and ethanol. Pharmaceutically acceptable salts can also be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding, free base forms. In other cases, a preparation may be a lyophilized powder which may contain any or all of the following: 1-50 mM histidine, 0.1%-2% sucrose, and 2-7% mannitol, at a pH range of 4.5 to 5.5, that is combined with buffer prior to use.

Pharmaceutical compositions include solvents (aqueous or non-aqueous), solutions (aqueous or non-aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions and suspensions may include suspending agents and thickening agents. Such pharmaceutically acceptable carriers include tablets (coated or uncoated), capsules (hard or soft), microbeads, powder, granules and crystals. Supplementary active compounds (e.g., preservatives, antibacterial, antiviral and antifungal agents) can also be incorporated into the compositions.

Pharmaceutical compositions can be formulated to be compatible with a particular route of administration or delivery, as set forth herein or known to one of skill in the art. Thus, pharmaceutical compositions include carriers, diluents, or excipients suitable for administration by various routes.

Compositions suitable for parenteral administration comprise aqueous and non-aqueous solutions, suspensions or emulsions of the active compound, which preparations are typically sterile and can be isotonic with the blood of the intended recipient. Illustrative examples include, for example and without limitation, water, buffered saline, Hanks' solution, Ringer's solution, dextrose, fructose, ethanol, animal, vegetable or synthetic oils. Aqueous injection suspensions may contain substances which increase the viscosity of the suspension, such as, for example and without limitation, sodium carboxymethyl cellulose, sorbitol, or dextran.

Additionally, suspensions of the active compounds may be prepared as appropriate oil injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

Cosolvents and adjuvants may be added to the formulation, examples of which include, for example and without limitation cosolvents containing hydroxyl groups or other polar groups, for example, alcohols, such as isopropyl alcohol; glycols, such as propylene glycol, polyethyleneglycol, polypropylene glycol, glycol ether; glycerol; polyoxyethylene alcohols and polyoxyethylene fatty acid esters. Examples of adjuvants include, for example and without limitation, surfactants such as, soya lecithin and oleic acid; sorbitan esters such as sorbitan trioleate; and polyvinylpyrrolidone.

After pharmaceutical compositions have been prepared, they may be placed in an appropriate container and labeled for treatment. Such labeling could include amount, frequency, and method of administration.

Pharmaceutical compositions and delivery systems appropriate for the compositions, methods and uses of the instant invention are known in the art (see, e.g., *Remington: The Science and Practice of Pharmacy* (2003) $20^{th}$ ed., Mack Publishing Co., Easton, PA; *Remington's Pharmaceutical Sciences* (1990) $18^{th}$ ed., Mack Publishing Co., Easton, PA; *The Merck Index* (1996) $12^{th}$ ed., Merck Publishing Group, Whitehouse, NJ; *Pharmaceutical Principles of Solid Dosage Forms* (1993), Technonic Publishing Co., Inc., Lancaster, Pa.; Ansel and Stoklosa, *Pharmaceutical Calculations* (2001) $11^{th}$ ed., Lippincott Williams & Wilkins, Baltimore, MD; and Poznansky et al., *Drug Delivery Systems* (1980), R. L. Juliano, ed., Oxford, N.Y., pp. 253-315).

In certain embodiments, the nucleic acids, polynucleotides and expression cassettes of the instant invention are delivered or administered via AAV vector particles. In certain embodiments, the nucleic acids, polynucleotides and expression cassettes of the instant invention can be delivered or administered via other types of viral particles, including retroviral, adenoviral, helper-dependent adenoviral, hybrid adenoviral, herpes simplex virus, lentiviral, poxvirus, Epstein-Barr virus, vaccinia virus, and human cytomegalovirus particles.

In certain embodiments, the nucleic acids, polynucleotides and expression cassettes of the instant invention are delivered or administered with a non-viral delivery system. Non-viral delivery systems include for example, chemical methods, such as liposomes, nanoparticles, lipid nanoparticles, polymers, microparticles, microcapsules, micelles, or extracellular vesicles and physical methods, such as gene gun, electroporation, particle bombardment, ultrasound utilization and magnetofection.

In certain embodiments, the nucleic acids polynucleotides and expression cassettes of the instant invention are delivered as naked DNA, minicircles, transposons, or closed-ended linear duplex DNA.

In certain embodiments, the nucleic acids, polynucleotides and expression cassettes of the instant invention are delivered or administered in AAV vector particles, or other viral particles, that are further encapsulated or complexed with liposomes, nanoparticles, lipid nanoparticles, polymers, microparticles, microcapsules, micelles, or extracellular vesicles.

A "lipid nanoparticle" or "LNP" refers to a lipid-based vesicle useful for delivery of AAV and having dimensions on the nanoscale, i.e., from about 10 nm to about 1000 nm, or from about 50 to about 500 nm, or from about 75 to about 127 nm. Without being bound by theory, the LNP is believed to provide the nucleic acid, polynucleotides, expression cassette, or AAV vector with partial or complete shielding from the immune system. Shielding allows delivery of the nucleic acid, polynucleotide, expression cassette, or AAV vector to a tissue or cell while avoiding inducing a substantial immune response against the nucleic acid, polynucleotide, expression cassette, or AAV vector in vivo. Shielding may also allow repeated administration without inducing a substantial immune response against the nucleic acid, polynucleotide, expression vector or AAV vector in vivo (e.g., in a subject such as a human). Shielding may also improve or increase delivery efficiency in vivo.

The pI (isoelectric point) of AAV is in a range from about 6 to about 6.5. Thus, the AAV surface carries a slight negative charge. As such it may be beneficial for the LNP to comprise a cationic lipid such as, for example, an amino lipid. Exemplary amino lipids have been described in U.S. Pat. Nos. 9,352,042, 9,220,683, 9,186,325, 9,139,554, 9,126,966 9,018,187, 8,999,351, 8,722,082, 8,642,076, 8,569,256, 8,466,122, and 7,745,651 and U.S. Patent Publication Nos. 2016/0213785, 2016/0199485, 2015/0265708, 2014/0288146, 2013/0123338, 2013/0116307, 2013/0064894, 2012/0172411, and 2010/0117125.

The terms "cationic lipid" and "amino lipid" are used interchangeably herein to include those lipids and salts thereof having one, two, three, or more fatty acid or fatty alkyl chains and a pH-titratable amino group (e.g., an alkylamino or dialkylamino group). The cationic lipid is typically protonated (i.e., positively charged) at a pH below the pKa of the cationic lipid and is substantially neutral at a pH above the pKa. The cationic lipids may also be titratable cationic lipids. In certain embodiments, the cationic lipids comprise: a protonatable tertiary amine (e.g., pH-titratable) group; C18 alkyl chains, wherein each alkyl chain independently has 0 to 3 (e.g., 0, 1, 2, or 3) double bonds; and ether, ester, or ketal linkages between the head group and alkyl chains.

Cationic lipids may include, without limitation, 1,2-dilinoleyloxy-N,N-dimethylaminopropane (DLinDMA), 1,2-dilinolenyloxy-N,N-dimethylaminopropane (DLenDMA), 1,2-di-γ-linolenyloxy-N,N-dimethylaminopropane (γ-DLenDMA), 2,2-dilinoleyl-4-(2-dimethylaminoethyl)-[1,3]-dioxolane (DLin-K-C2-DMA, also known as DLin-C2K-DMA, XTC2, and C2K), 2,2-dilinoleyl-4-dimethylaminomethyl-[1,3]-dioxolane (DLin-K-DMA), dilinoleylmethyl-3-dimethylaminopropionate (DLin-M-C2-DMA, also known as MC2), (6Z,9Z,28Z,31 Z)-heptatriaconta-6,9,28,31-tetraen-19-yl 4-(dimethylamino)butanoate (DLin-M-C3-DMA, also known as MC3), salts thereof, and mixtures thereof. Other cationic lipids also include, but are not limited to, 1,2-distearyloxy-N,N-dimethyl-3-aminopropane (DSDMA), 1,2-dioleyloxy-N,N-dimethyl-3-aminopropane (DODMA), 2,2-dilinoleyl-4-(3-dimethylaminopropyl)-[1,3]-dioxolane (DLin-K-C3-DMA), 2,2-dilinoleyl-4-(3-dimethylaminobutyl)-[1,3]-dioxolane (DLin-K-C4-DMA), DLen-C2K-DMA, y-DLen-C2K-DMA, and (DLin-MP-DMA) (also known as 1-B11).

Still further cationic lipids may include, without limitation, 2,2-dilinoleyl-5-dimethylaminomethyl-[1,3]-dioxane (DLin-K6-DMA), 2,2-dilinoleyl-4-N-methylpepiazino-[1,3]-dioxolane (DLin-K-MPZ), 1,2-dilinoleylcarbamoyloxy-3-dimethylaminopropane (DLin-C-DAP), 1,2-dilinoleyoxy-3-(dimethylamino)acetoxypropane (DLin-DAC), 1,2-dilinoleyoxy-3-morpholinopropane (DLin-MA), 1,2-dilinoleoyl-3-dimethylaminopropane (DLinDAP), 1,2-dilinoleylthio-3-dimethylaminopropane (DLin-S-DMA), 1-linoleoyl-2-linoleyloxy-3-dimethylaminopropane (DLin-2-DMAP), 1,2-dilinoleyloxy-3-trimethylaminopropane chloride salt (DLin-TMA.Cl), 1,2-dilinoleoyl-3-trimethylaminopropane chloride salt (DLin-TAP.Cl), 1,2-dilinoleyloxy-3-(N-methylpiperazino)propane (DLin-MPZ), 3-(N,N-dilinoleylamino)-1,2-propanediol (DLinAP), 3-(N,N-dioleylamino)-1,2-propanedio (DOAP), 1,2-dilinoleyloxo-3-(2-N,N-dimethylamino)ethoxypropane (DLin-EG-DMA), N,N-dioleyl-N,N-dimethylammonium chloride (DODAC), N-(1-(2,3-dioleyloxy)propyl)-N,N,N-trimethylammonium chloride (DOTMA), N,N-distearyl-N,N-dimethylammonium bromide (DDAB), N-(1-(2,3-dioleoyloxy)propyl)-N,N,N-trimethylammonium chloride (DOTAP), 3-(N-(N',N'-dimethylaminoethane)-carbamoyl)cholesterol (DC-Chol), N-(1,2-dimyristyloxyprop-3-yl)-N,N-dimethyl-N-hydroxyethyl ammonium bromide (DMRIE), 2,3-dioleyloxy-N-[2(spermine-carboxamido)ethyl]-N,N-dimethyl-1-propanaminiumtrifluoroacetate (DOSPA), dioctadecylamidoglycyl spermine (DOGS), 3-dimethylamino-2-(cholest-5-en-3-beta-oxybutan-4-oxy)-1-(cis,cis-9,12-octadecadienoxy)propane (CLinDMA), 2-[5'-(cholest-5-en-3-beta-oxy)-3'-oxapentoxy)-3-dimethyl-1-(cis,cis-9', 1-2'-octadecadienoxy) propane (CpLinDMA), N,N-dimethyl-3,4-dioleyloxybenzylamine (DMOBA), 1,2-N,N'-dioleylcarbamyl-3-dimethylaminopropane (DOcarbDAP), 1,2-N,N'-dilinoleylcarbamyl-3-dimethylaminopropane (DLincarbDAP), dexamethasone-spermine (DS) and disubstituted spermine (D2S) or mixtures thereof.

A number of commercial preparations of cationic lipids can be used, such as, LIPOFECTIN® (including DOTMA and DOPE, available from GIBCO/BRL), and LIPOFECTAMINE® (comprising DOSPA and DOPE, available from GIBCO/BRL).

In certain embodiments, cationic lipid may be present in an amount from about 10% by weight of the LNP to about 85% by weight of the lipid nanoparticle, or from about 50% by weight of the LNP to about 75% by weight of the LNP.

Sterols may confer fluidity to the LNP. As used herein, "sterol" refers to any naturally occurring sterol of plant (phytosterols) or animal (zoosterols) origin as well as non-naturally occurring synthetic sterols, all of which are characterized by the presence of a hydroxyl group at the 3-position of the steroid A-ring. The sterol can be any sterol conventionally used in the field of liposome, lipid vesicle or lipid particle preparation, most commonly cholesterol. Phytosterols may include campesterol, sitosterol, and stigmasterol. Sterols also includes sterol-modified lipids, such as those described in U.S. Patent Application Publication 2011/0177156. In certain embodiments, a sterol may be present in an amount from about 5% by weight of the LNP to about 50% by weight of the lipid nanoparticle or from about 10% by weight of the LNP to about 25% by weight of the LNP.

LNP can comprise a neutral lipid. Neutral lipids may comprise any lipid species which exists either in an uncharged or neutral zwitterionic form at physiological pH. Such lipids include, without limitation, diacylphosphatidylcholine, diacylphosphatidylethanolamine, ceramide, sphingomyelin, dihydrosphingomyelin, cephalin, and cerebrosides. The selection of neutral lipids is generally guided by consideration of, inter alia, particle size and the requisite stability. In certain embodiments, the neutral lipid component may be a lipid having two acyl groups (e.g., diacylphosphatidylcholine and diacylphosphatidylethanolamine).

Lipids having a variety of acyl chain groups of varying chain length and degree of saturation are available or may be isolated or synthesized by well-known techniques. In certain embodiments, lipids containing saturated fatty acids with carbon chain lengths in the range of C14 to C22 may be used. In certain embodiments, lipids with mono or diunsaturated fatty acids with carbon chain lengths in the range of C14 to C22 are used. Additionally, lipids having mixtures of saturated and unsaturated fatty acid chains can be used. Exemplary neutral lipids include, without limitation, 1,2-dioleoyl-sn-glycero-3-phosphatidyl-ethanolamine (DOPE), 1,2-distearoyl-sn-glycero-3-phosphocholine (DSPC), 1-palmitoyl-2-oleoyl-sn-glycero-3-phosphocholine (POPC), or any related phosphatidylcholine. The neutral lipids may also be composed of sphingomyelin, dihydrosphingomyelin, or phospholipids with other head groups, such as serine and inositol.

In certain embodiments, the neutral lipid may be present in an amount from about 0.1% by weight of the lipid nanoparticle to about 75% by weight of the LNP, or from about 5% by weight of the LNP to about 15% by weight of the LNP.

LNP encapsulated nucleic acids, expression cassettes and AAV vector can be incorporated into pharmaceutical compositions, e.g., a pharmaceutically acceptable carrier or excipient. Such pharmaceutical compositions are useful for, among other things, administration and delivery of LNP encapsulated acids, expression cassettes and AAV vector to a subject in vivo or ex vivo.

Preparations of LNP can be combined with additional components, which may include, for example and without limitation, polyethylene glycol (PEG) and sterols.

The term "PEG" refers to a polyethylene glycol, a linear, water-soluble polymer of ethylene PEG repeating units with two terminal hydroxyl groups. PEGs are classified by their molecular weights; for example, PEG 2000 has an average molecular weight of about 2,000 daltons, and PEG 5000 has an average molecular weight of about 5,000 daltons. PEGs are commercially available from Sigma Chemical Co. and other companies and include, for example and without limitation, the following functional PEGs: monomethoxypolyethylene glycol (MePEG-OH), monomethoxypolyethylene glycol-succinate (MePEG-S), monomethoxypolyethylene glycol-succinimidyl succinate (MePEG-S-NHS), monomethoxypolyethylene glycol-amine (MePEG-NH2), monomethoxypolyethylene glycol-tresylate (MePEG-TRES), and monomethoxypolyethylene glycol-imidazolyl-carbonyl (MePEG-IM).

In certain embodiments, PEG may be a polyethylene glycol with an average molecular weight of about 550 to about 10,000 daltons and is optionally substituted by alkyl, alkoxy, acyl or aryl. In certain embodiments, the PEG may be substituted with methyl at the terminal hydroxyl position. In certain embodiments, the PEG may have an average molecular weight from about 750 to about 5,000 daltons, or from about 1,000 to about 5,000 daltons, or from about 1,500 to about 3,000 daltons or from about 2,000 daltons or of about 750 daltons. The PEG can be optionally substituted with alkyl, alkoxy, acyl or aryl. In certain embodiments, the terminal hydroxyl group may be substituted with a methoxy or methyl group.

PEG-modified lipids include, for example and without limitation, the PEG-dialkyloxypropyl conjugates (PEG-DAA) described in U.S. Pat. Nos. 8,936,942 and 7,803,397. PEG-modified lipids (or lipid-polyoxyethylene conjugates) that are useful may have a variety of "anchoring" lipid portions to secure the PEG portion to the surface of the lipid vesicle. Examples of suitable PEG-modified lipids include, for example and without limitation, PEG-modified phosphatidylethanolamine and phosphatidic acid, PEG-ceramide conjugates (e.g., PEG-CerC14 or PEG-CerC20) which are described in U.S. Pat. No. 5,820,873, PEG-modified dialkylamines and PEG-modified 1,2-diacyloxypropan-3-amines. In certain embodiments, the PEG-modified lipid may be PEG-modified diacylglycerols and dialkylglycerols. In certain embodiments, the PEG may be in an amount from about 0.5% by weight of the LNP to about 20% by weight of the LNP, or from about 5% by weight of the LNP to about 15% by weight of the LNP.

Furthermore, LNP can be a PEG-modified and a sterol-modified LNP. The LNPs, combined with additional components, can be the same or separate LNPs. In other words, the same LNP can be PEG modified and sterol modified or, alternatively, a first LNP can be PEG modified and a second LNP can be sterol modified. Optionally, the first and second modified LNPs can be combined.

In certain embodiments, prior to encapsulating LNPs may have a size in a range from about 10 nm to 500 nm, or from about 50 nm to about 200 nm, or from 75 nm to about 125 nm. In certain embodiments, LNP encapsulated nucleic acid, expression vector or AAV vector may have a size in a range from about 10 nm to 500 nm.

An "effective amount" or "sufficient amount" refers to an amount that provides, in single or multiple doses, alone or in combination, with one or more other compositions (therapeutic or immunosuppressive agents such as a drug like prednisone), treatments, protocols, or therapeutic regimens agents, a detectable response of any duration of time (long or short term), an expected or desired outcome in or a benefit to a subject of any measurable or detectable degree or for any duration of time (e.g., for minutes, hours, days, months, years, or cured).

Doses can vary and depend upon the type, onset, progression, severity, frequency, duration, or probability of the disease to which treatment is directed, the clinical endpoint desired, previous or simultaneous treatments, the general health, age, gender, race or immunological competency of the subject and other factors that will be appreciated by the skilled artisan. The dose amount, number, frequency or duration may be proportionally increased or reduced, as indicated by any adverse side effects, complications or other risk factors of the treatment or therapy and the status of the subject. The skilled artisan will appreciate the factors that may influence the dosage and timing required to provide an amount sufficient for providing a therapeutic or prophylactic benefit.

The dose to achieve a therapeutic effect, e.g., the dose in vector genomes/per kilogram of body weight (vg/kg), will vary based on several factors including, but not limited to: route of administration, the level of heterologous polynucleotide expression required to achieve a therapeutic effect, the specific disease treated, any host immune response to the viral vector, a host immune response to the heterologous polynucleotide or expression product (protein), and the stability of the protein expressed. One skilled in the art can determine a rAAV/vector genome dose range to treat a patient having a particular disease or disorder based on the aforementioned factors, as well as other factors.

Generally, doses will range from at least $1\times10^8$, or more, for example, $1\times10^9$, $1\times10^{10}$, $1\times10^{11}$, $1\times10^{12}$, $1\times10^{13}$ or $1\times10^{14}$, or more, vector genomes per kilogram (vg/kg) of the weight of the subject, to achieve a therapeutic effect. AAV dose in the range of $1\times10^{10}$-$1\times10^{11}$ vg/kg in mice, and $1\times10^{12}$-$1\times10^{13}$ vg/kg in dogs have been effective. Doses can be less, for example, a dose of less than $6\times10^{12}$ vector genomes per kilogram (vg/kg). More particularly, a dose from about $1\times10^{11}$ vg/kg to about $5\times10^{12}$ vg/kg, or from about $5\times10^{11}$ vg/kg to about $2\times10^{12}$ vg/kg, or from about $5\times10^{11}$ vg/kg to about $1\times10^{12}$ vg/kg.

For Pompe disease, an effective amount would be an amount of GAA that inhibits or reduces glycogen production or accumulation, enhances or increases glycogen degradation or removal, reduces lysosomal alterations in tissues of the body of a subject, or improves muscle tone and/or muscle strength and/or respiratory function in a subject, for example. Effective amounts can be determined, for example, by ascertaining the kinetics of GAA uptake by myoblasts from plasma. Myoblasts GAA uptake rates (K uptake) of about 141-147 nM may appear to be effective (see, e.g., Maga et al., J. Biol. Chem. 2012) In animal models, GAA activity levels in plasma of greater than about 1,000 nmol/hr/mL, for example, about 1,000 to about 2,000 nmol/hr/mL have been observed to be therapeutically effective.

Using hemophilia B as an example, generally speaking, it is believed that, in order to achieve a therapeutic effect, a blood coagulation factor concentration that is greater than 1% of factor concentration found in a normal individual is needed to change a severe disease phenotype to a moderate one. A severe phenotype is characterized by joint damage and life-threatening bleeds. To convert a moderate disease phenotype into a mild one, it is believed that a blood coagulation factor concentration greater than 5% of normal is needed.

Diagnosis and disease severity classification for hemophilia A and B are based on the results of factor VIII and factor IX activity assays, respectively. The two main assays used to assess factor activity are one-stage assays (OSAs), based on activated partial thromboplastin time (aPTT), and two-stage chromogenic substrate assays (CSAs), which use a factor Xa-based enzymatic chromophore substrate reaction. Such assays are well known in the art and are further described in Adcock et al., 2018, Int. J. Lab. Hem., 40:621-629.

FVIII levels in normal humans are about 150-200 ng/mL plasma, but may be less (e.g., range of about 100-150 ng/mL) or greater (e.g., range of about 200-300 ng/mL) and still considered normal, due to functional clotting as determined, for example, by an aPTT one-stage clotting assay. Thus, a therapeutic effect can be achieved by expression of FVIII or hFVIII-BDD such that the total amount of FVIII in the subject/human is greater than 1% of the FVIII present in normal subjects/humans, e.g., 1% of 100-300 ng/mL.

rAAV vector doses can be at a level, typically at the lower end of the dose spectrum, such that there is not a substantial immune response against the FVIII or AAV vector. More particularly, a dose of up to but less than $6\times10^{12}$ vg/kg, such as about $5\times10^{11}$ to about $5\times10^{12}$ vg/kg, or more particularly, about $5\times10^{11}$ vg/kg or about $1\times10^{12}$ vg/kg.

In certain embodiments, the rAAV vector dose is at a level to deliver a safe and effective amount of FVIII and provide therapeutic benefit to a subject with hemophilia A with inhibitory antibodies against FVIII (hemophilia A with inhibitors).

The doses of an "effective amount" or "sufficient amount" for treatment (e.g., to ameliorate or to provide a therapeutic benefit or improvement) typically are effective to provide a response to one, multiple or all adverse symptoms, consequences or complications of the disease, one or more adverse symptoms, disorders, illnesses, pathologies, or complications, for example, caused by or associated with the disease, to a measurable extent, although decreasing, reducing, inhibiting, suppressing, limiting or controlling progression or worsening of the disease is a satisfactory outcome.

An effective amount or a sufficient amount can but need not be provided in a single administration, may require multiple administrations, and, can but need not be, administered alone or in combination with another composition (e.g., agent), treatment, protocol or therapeutic regimen. For example, the amount may be proportionally increased as indicated by the need of the subject, type, status and severity of the disease treated or side effects (if any) of treatment. In addition, an effective amount or a sufficient amount need not be effective or sufficient if given in single or multiple doses without a second composition (e.g., another drug or agent), treatment, protocol or therapeutic regimen, since additional doses, amounts or duration above and beyond such doses, or additional compositions (e.g., drugs or agents), treatments, protocols or therapeutic regimens may be included in order to be considered effective or sufficient in a given subject. Amounts considered effective also include amounts that result in a reduction of the use of another treatment, therapeutic regimen or protocol, such as administration of recombinant clotting factor protein (e.g., FVIII) for treatment of a clotting disorder (e.g., hemophilia A or hemophilia A with inhibitory antibodies against FVIII, also known as hemophila A with inhibitors).

Accordingly, methods and uses of the instant invention also include, among other things, methods and uses that result in a reduced need or use of another compound, agent, drug, therapeutic regimen, treatment protocol, process, or remedy. For example, for a blood clotting disease, a method or use of the instant invention has a therapeutic benefit if in a given subject a less frequent or reduced dose or elimination of administration of a recombinant clotting factor protein to supplement for the deficient or defective (abnormal or mutant) endogenous clotting factor in the subject. Thus, in accordance with the instant invention, methods and uses of reducing need or use of another treatment or therapy are provided.

An effective amount or a sufficient amount need not be effective in each and every subject treated, nor a majority of treated subjects in a given group or population. An effective amount or a sufficient amount means effectiveness or sufficiency in a particular subject, not a group or the general population. As is typical for such methods, some subjects will exhibit a greater response, or less or no response to a given treatment method or use.

The term "ameliorate" means a detectable or measurable improvement in a subject's disease or symptom thereof, or an underlying cellular response. A detectable or measurable improvement includes a subjective or objective decrease, reduction, inhibition, suppression, limit or control in the occurrence, frequency, severity, progression, or duration of the disease, or complication caused by or associated with the disease, or an improvement in a symptom or an underlying cause or a consequence of the disease, or a reversal of the disease. For HemA, an effective amount would be an amount that reduces frequency or severity of acute bleeding episodes in a subject, for example, or an amount that reduces clotting time as measured by a clotting assay, for example.

Accordingly, pharmaceutical compositions of the instant invention include compositions wherein the active ingredients are contained in an effective amount to achieve the intended therapeutic purpose. Determining a therapeutically effective dose is well within the capability of a skilled medical practitioner using the techniques and guidance provided in the instant invention.

Therapeutic doses will depend on, among other factors, the age and general condition of the subject, the severity of the aberrant phenotype, and the strength of the control sequences regulating expression levels. Thus, a therapeutically effective amount in humans will fall in a relatively broad range that may be determined by a medical practitioner based on the response of an individual patient to a vector-based treatment. Such doses may be alone or in combination with an immunosuppressive agent or drug.

Compositions such as pharmaceutical compositions may be delivered to a subject, so as to allow transgene expression and optionally production of encoded protein. In certain embodiments, pharmaceutical compositions comprising sufficient genetic material to enable a recipient to produce a therapeutically effective amount of a blood-clotting factor to influence hemostasis in the subject.

The compositions may be administered alone. In certain embodiments, a recombinant AAV particle provides a therapeutic effect without an immunosuppressive agent. The therapeutic effect optionally is sustained for a period of time, e.g., 2-4, 4-6, 6-8, 8-10, 10-14, 14-20, 20-25, 25-30, or 30-50 days or more, for example, 50-75, 75-100, 100-150, 150-200 days or more without administering an immunosuppressive agent. Accordingly, in certain embodiments rAAV virus particle provides a therapeutic effect without administering an immunosuppressive agent for a period of time.

The compositions of the instant invention may be administered in combination with at least one other inert or therapeutic agent. In certain embodiments, rAAV vector is administered in conjunction with one or more immunosuppressive agents prior to, substantially at the same time or after administering a rAAV vector. In certain embodiments, e.g., 1-12, 12-24 or 24-48 hours, or 2-4, 4-6, 6-8, 8-10, 10-14, 14-20, 20-25, 25-30, 30-50, or more than 50 days following administering rAAV vector. Such administration of immunosuppressive agents after a period of time following administering rAAV vector if there is a decrease in encoded protein expression after the initial expression levels for a period of time, e.g., 20-25, 25-30, 30-50, 50-75, 75-100, 100-150, 150-200 or more than 200 days following rAAV vector.

In certain embodiments, an immunosuppressive agent is an anti-inflammatory agent. In certain embodiments, an immunosuppressive agent is a steroid. In certain embodiments, an immunosuppressive agent is prednisone, cyclosporine (e.g., cyclosporine A), mycophenolate, rituximab, rapamycin, or a derivative thereof. In certain embodiments, agents include a stabilizing compound. Other immunosuppressive agents that can be used according to the instant invention include, for example and without limitation, a B cell targeting antibody, e.g., rituximab; a proteasome inhibitor, e.g., bortezomib; a mammalian target of rapamycin (mTOR) inhibitor, e.g., rapamycin; a tyrosine kinase inhibitor, e.g., ibrutinib; an inhibitor of B-cell activating factor (BAFF); and an inhibitor of a proliferation-inducing ligand (APRIL).

Compositions may be administered in any sterile, biocompatible pharmaceutical carrier, including, but not limited to, saline, buffered saline, dextrose, and water. The compositions may be administered to a patient alone, or in combination with other agents (e.g., co-factors) which influence hemostasis.

Methods and uses of the instant invention include delivery and administration systemically, regionally or locally, or by any route, for example and without limitation, by injection or infusion. Delivery of the pharmaceutical compositions in vivo may generally be accomplished via injection using a conventional syringe, although other delivery methods such as convection-enhanced delivery are envisioned (See e.g., U.S. Pat. No. 5,720,720). For example, compositions may be delivered subcutaneously, epidermally, intradermally, intrathecally, intraorbitally, intramucosally, intraperitoneally, intravenously, intra-pleurally, intraarterially, orally, intrahepatically, via the portal vein, or intramuscularly. Other modes of administration include oral and pulmonary administration, suppositories, and transdermal applications. A clinician specializing in the treatment of patients with blood coagulation or clotting factor disorders, for example, may determine the optimal route for administration of the adenoviral-associated vectors based on a number of criteria, including, but not limited to: the condition of the patient and the purpose of the treatment (e.g., increased GAA, enhanced or reduced blood coagulation, etc.).

Methods of treatment according to the instant invention include combination therapies that include the additional use of one or more of any compound, agent, drug, treatment or other therapeutic regimen or protocol having a desired therapeutic, beneficial, additive, synergistic or complementary activity or effect. Exemplary combination compositions and treatments include, for example and without limitation, second actives, such as, biologics (proteins), agents (e.g., immunosuppressive agents) and drugs. Such biologics (proteins), agents, drugs, treatments and therapies can be administered or performed prior to, substantially contemporaneously with or following any other method of treatment according to the instant invention, for example, a therapeutic method of treating a subject for a lysosomal storage disease such as Pompe, or a therapeutic method of treating a subject for a blood clotting disease such as HemA or HemB.

The compound, agent, drug, treatment or other therapeutic regimen or protocol can be administered as a combination composition, or administered separately, such as concurrently or in series or sequentially (prior to or following) delivery or administration of a nucleic acid, vector, recombinant vector (e.g., rAAV), or recombinant virus particle. The instant invention therefore provides combinations in which a method of treatment according to the instant invention is in a combination with any compound, agent, drug, therapeutic regimen, treatment protocol, process, remedy or composition, set forth herein or known to one of skill in the art. The compound, agent, drug, therapeutic regimen, treatment protocol, process, remedy or composition can be administered or performed prior to, substantially contemporaneously with or following administration of a nucleic acid, vector, recombinant vector (e.g., rAAV), or recombinant virus particle administered to a patient or subject according to the instant invention.

The instant invention may be used in human and veterinary medical applications. Suitable subjects therefore include mammals, such as humans, as well as non-human mammals. The term "subject" refers to an animal, typically a mammal, such as humans, non-human primates (apes, gibbons, gorillas, chimpanzees, orangutans, macaques), a domestic animal (dogs and cats), a farm animal (poultry such as chickens and ducks, horses, cows, goats, sheep, pigs), and experimental animals (mouse, rat, rabbit, guinea pig). Human subjects include fetal, neonatal, infant, juvenile and adult subjects. Subjects include animal disease models, for example, mouse and other animal models of blood clotting diseases such as HemA and others known to those of skill in the art.

Subjects appropriate for treatment in accordance with the instant invention include those having or at risk of producing an insufficient amount or having a deficiency in a functional gene product (e.g., GAA or a blood clotting factor, such as FVIII or FIX), or produce an aberrant, partially functional or non-functional gene product (e.g., GAA or a blood clotting factor such as FVIII or FIX), which can lead to disease. Subjects appropriate for treatment in accordance with the instant invention also include those having or at risk of producing an aberrant, or defective (mutant) gene product (protein) that leads to a disease such that reducing amounts, expression or function of the aberrant, or defective (mutant) gene product (protein) would lead to treatment of the disease, or reduce one or more symptoms or ameliorate the disease. Target subjects, for example, include subjects having aberrant, insufficient or absent blood clotting factor production, such as hemophiliacs (e.g., hemophilia A or hemophilia B), or subjects having aberrant, insufficient or absent GAA production, such as subjects with Pompe disease.

Subjects include those with no detectable neutralizing antibodies against AAV. Subjects also include those with neutralizing antibodies against AAV. Such subjects may have low titer neutralizing antibodies against AAV.

Subjects can be tested for an immune response, e.g., antibodies against AAV. Candidate subjects (for example, hemophilia or Pompe disease subjects) can be screened prior to treatment according to a method of the instant invention. Subjects also can be tested for antibodies against AAV after treatment, and optionally monitored for a period of time after treatment. Subjects developing antibodies can be treated with an immunosuppressive agent (e.g., prednisone), or can be administered one or more additional amounts of AAV vector.

Subjects considered negative for antibodies that bind to AAV have a titer of less than 1:1. Subjects that have antibodies that bind to AAV can have a titer of greater than 1:1 but less than 1:5. Subjects may also have the same or greater than 1:5 AAV antibody titer. These antibody titers can be calculated, for example, by performing serial dilutions of a blood, plasma or serum (or other body fluid) sample from a subject, and the first dilution at which the sample inhibits AAV transduction by 50% or more, as measured by reporter activity in an in vitro cell-based assay, is reported as the antibody titer.

Strategies to reduce (overcome) or avoid humoral immunity to AAV in systemic gene transfer include, administering high vector doses, use of AAV empty capsids as decoys to adsorb anti-AAV antibodies, administration of immunosuppressive drugs to decrease, reduce, inhibit, prevent or eradicate the humoral immune response to AAV, changing the AAV capsid serotype or engineering the AAV capsid to be less susceptible to neutralizing antibodies, use of plasma exchange cycles to adsorb anti-AAV immunoglobulins, thereby reducing anti-AAV antibody titer, use of delivery techniques such as balloon catheters followed by saline flushing (Mingozzi et al., 2013, Blood, 122:23-36), and immunoadsorption (US patent application publication US 2018/0169273 A1).

Subjects appropriate for treatment in accordance with the instant invention also include those having or at risk of producing antibodies against AAV. rAAV vectors can be administered or delivered to such subjects using several techniques. For example, empty capsid AAV (i.e., AAV lacking a transgene) can be delivered to bind to the AAV antibodies in the subject thereby allowing the AAV vector bearing nucleic acid or nucleic acid variant to transform cells of the subject.

Ratio of empty capsids to the rAAV vector can be between about 2:1 to about 50:1, or between about 2:1 to about 25:1, or between about 2:1 to about 20:1, or between about 2:1 to about 15:1, or between about 2:1 to about 10:1. Ratios can also be about 2:1, 3:1, 4:1, 5:1, 6:1, 7:1, 8:1, 9:1, or 10:1.

Amounts of empty capsid AAV to administer can be calibrated based upon the amount (titer) of AAV antibodies produced in a particular subject. Empty capsid can be of any AAV serotype, for example, AAV1, AAV2, AAV3, AAV3B, AAV4, AAV5, AAV6, AAV7, AAV8, AAV9, AAV10, AAV11, AAV12, Rh10, Rh74, AAV-2i8, LK03 (SEQ ID NO:91), SPK (SEQ ID NO:92).

Alternatively, or in addition to, AAV vector can be delivered by direct intramuscular injection (e.g., one or more slow-twitch fibers of a muscle). In another alternative, a catheter introduced into the femoral artery can be used to delivery AAV vectors to liver via the hepatic artery. Non-surgical means can also be employed, such as endoscopic retrograde cholangiopancreatography (ERCP), to deliver AAV vectors directly to the liver, thereby bypassing the bloodstream and AAV antibodies. Other ductal systems, such as the ducts of the submandibular gland, can also be used as portals for delivering AAV vectors into a subject that develops or has preexisting anti-AAV antibodies.

Administration or in vivo delivery to a subject can be performed prior to development of an adverse symptom, condition, complication, etc. caused by or associated with the disease. For example, a screen (e.g., genetic) can be used to identify such subjects as candidates for invention compositions, methods and uses. Such subjects therefore include those screened positive for an insufficient amount or a deficiency in a functional gene product (e.g., blood clotting factor), or that produce an aberrant, partially functional or non-functional gene product (e.g., blood clotting factor).

Administration or in vivo delivery to a subject in accordance with the methods and uses of the instant invention as disclosed herein can be practiced within 1-2, 2-4, 4-12, 12-24 or 24-72 hours after a subject has been identified as having the disease targeted for treatment, has one or more symptoms of the disease, or has been screened and is identified as positive as set forth herein even though the subject does not have one or more symptoms of the disease. Of course, methods and uses of the instant invention can be practiced 1-7, 7-14, 14-21, 21-48 or more days, months or years after a subject has been identified as having the disease targeted for treatment, has one or more symptoms of the disease, or has been screened and is identified as positive as set forth herein.

A "unit dosage form" as used herein refers to physically discrete units suited as unitary dosages for the subject to be treated; each unit containing a predetermined quantity optionally in association with a pharmaceutical carrier (excipient, diluent, vehicle or filling agent) which, when administered in one or more doses, is calculated to produce a desired effect (e.g., prophylactic or therapeutic effect). Unit dosage forms may be within, for example, ampules and vials, which may include a liquid composition, or a composition in a freeze-dried or lyophilized state; a sterile liquid carrier, for example, can be added prior to administration or delivery in vivo. Individual unit dosage forms can be included in multi-dose kits or containers. Recombinant vector (e.g., rAAV) sequences, recombinant virus particles, and pharmaceutical compositions thereof can be packaged in single or multiple unit dosage form for ease of administration and uniformity of dosage.

Subjects can be tested for protein or activity levels of a relevant gene product (e.g., GAA or a blood clotting factor, such as FVIII or FIX) to determine if such subjects are appropriate for treatment according to a method of the instant invention. For example, candidate hemophilia A subjects can be tested for FVIII amounts or activity prior to treatment according to a method of the instant invention; candidate Pompe subjects can be tested for GAA amounts or activity prior to treatment according to the instant invention. Subjects also can be tested for amounts of FVIII or GAA protein or activity after treatment according to a method of the instant invention. Such treated subjects can be monitored after treatment for blood clotting activity (for HemA) or for GAA activity (for Pompe), periodically, e.g., every 1-4 weeks, 1-6 months, or 1, 2, 3, 4, 5 or more years.

Subjects can be tested for one or more liver enzymes for an adverse response or to determine if such subjects are appropriate for treatment according to a method of the instant invention. For examples, candidate hemophilia or Pompe subjects can be screened for amounts of one or more liver enzymes prior to treatment according to a method of the instant invention. Subjects also can be tested for amounts of one or more liver enzymes after treatment according to a method of the instant invention. Such treated subjects can be monitored after treatment for elevated liver enzymes, periodically, e.g., every 1-4 weeks or 1-6 months.

Exemplary liver enzymes include alanine aminotransferase (ALT), aspartate aminotransferase (AST), and lactate dehydrogenase (LDH), but other enzymes indicative of liver damage can also be monitored. A normal level of these enzymes in the circulation is typically defined as a range that has an upper level, above which the enzyme level is considered elevated, and therefore indicative of liver damage. A normal range depends in part on the standards used by the clinical laboratory conducting the assay.

In certain embodiments, subjects with bleeding disorders can be monitored for bleeding episodes to determine if such subjects are eligible for or responding to treatment according to the instant invention, and/or the amount or duration of responsiveness. Subjects can be monitored for bleeding episodes to determine if such subjects are in need of an additional treatment, e.g., a subsequent AAV vector administration or administration of an immunosuppressive agent, or more frequent monitoring. Hemophilia subjects can be monitored for bleeding episodes prior to and after treatment according to a method of the instant invention. Subjects also can be tested for frequency and severity of bleeding episodes during or after treatment according to a method of the instant invention.

In certain embodiments subjects with Pompe disease or in need of GAA can be monitored by a variety of tests, assays and functional assessments to demonstrate, measure and/or assess efficacy of GAA, to determine if such subjects are eligible for or responding to treatment, or are in need of additional treatment, in accordance with the instant invention.

The instant invention provides kits with packaging material and one or more components therein. A kit typically includes a label or packaging insert including a description of the components or instructions for use in vitro, in vivo, or ex vivo, of the components therein. A kit can contain a collection of such components, e.g., a nucleic acid, recombinant vector, virus (e.g., AAV) vector, or virus particle and optionally a second active, such as another compound, agent, drug or composition.

A kit refers to a physical structure housing one or more components of the kit. Packaging material can maintain the components sterilely, and can be made of material commonly used for such purposes (e.g., paper, corrugated fiber, glass, plastic, foil, ampules, vials, tubes, etc.).

Labels or inserts can include identifying information of one or more components therein, dose amounts, clinical pharmacology of the active ingredient(s) including mechanism of action, pharmacokinetics and pharmacodynamics. Labels or inserts can include information identifying manufacturer, lot numbers, manufacture location and date, expiration dates. Labels or inserts can include information identifying manufacturer information, lot numbers, manufacturer location and date. Labels or inserts can include information on a disease for which a kit component may be used. Labels or inserts can include instructions for the clinician or subject for using one or more of the kit components in a method, use, or treatment protocol or therapeutic regimen. Instructions can include dosage amounts, frequency or duration, and instructions for practicing any of the methods, uses, treatment protocols or prophylactic or therapeutic regimes described herein.

Labels or inserts can include information on any benefit that a component may provide, such as a prophylactic or therapeutic benefit. Labels or inserts can include information on potential adverse side effects, complications or reactions, such as warnings to the subject or clinician regarding situations where it would not be appropriate to use a particular composition. Adverse side effects or complications could also occur when the subject has, will be or is currently taking one or more other medications that may be incompatible with the composition, or the subject has, will be or is currently undergoing another treatment protocol or therapeutic regimen which would be incompatible with the composition and, therefore, instructions could include information regarding such incompatibilities.

Labels or inserts include "printed matter," e.g., paper or cardboard, or separate or affixed to a component, a kit or packing material (e.g., a box), or attached to an ampule, tube or vial containing a kit component. Labels or inserts can additionally include a computer readable medium, such as a bar-coded printed label, a disk, optical disk such as CD- or DVD-ROM/RAM, DVD, MP3, magnetic tape, or an electrical storage media such as RAM and ROM or hybrids of these such as magnetic/optical storage media, FLASH media or memory type cards.

Unless otherwise defined, all technical and scientific terms used herein have the same meaning as commonly understood by one of ordinary skill in the art to which the instant invention belongs. Although methods and materials similar or equivalent to those described herein can be used in the practice or testing of the present invention, suitable methods and materials are described herein.

All patents, patent applications, publications, and other references, GenBank citations and ATCC citations cited herein are incorporated by reference in their entirety. In case of conflict, the specification, including definitions, will control.

Various terms relating to the biological molecules of the instant invention are used hereinabove and also throughout the specification and claims.

All of the features disclosed herein may be combined in any combination. Each feature disclosed in the specification may be replaced by an alternative feature serving a same, equivalent, or similar purpose. Thus, unless expressly stated otherwise, disclosed features (e.g., CpG reduced) nucleic acids, vectors, plasmids, expression/recombinant vectors (e.g., rAAV) sequences, or recombinant virus particles) are an example of a genus of equivalent or similar features.

As used herein, the singular forms "a", "and," and "the" include plural referents unless the context clearly indicates otherwise. Thus, for example, reference to "a nucleic acid" includes a plurality of such nucleic acids, reference to "a vector" includes a plurality of such vectors, and reference to "a virus" or "particle" includes a plurality of such viruses/particles.

As used herein, all numerical values or numerical ranges include integers within such ranges and fractions of the values or the integers within ranges unless the context clearly indicates otherwise. Thus, to illustrate, reference to 80% or more identity, includes 81%, 82%, 83%, 84%, 85%, 86%, 87%, 88%, 89%, 90%, 91%, 92%, 93%, 94%, etc., as well as 81.1%, 81.2%, 81.3%, 81.4%, 81.5%, etc., 82.1%, 82.2%, 82.3%, 82.4%, 82.5%, etc., and so forth.

Reference to an integer with more (greater) or less than includes any number greater or less than the reference number, respectively. Thus, for example, a reference to less than 100, includes 99, 98, 97, etc. all the way down to the number one (1); and less than 10, includes 9, 8, 7, etc. all the way down to the number one (1).

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth.

Reference to a series of ranges includes ranges which combine the values of the boundaries of different ranges within the series. Thus, to illustrate reference to a series of ranges, for example, of 1-10, 10-20, 20-30, 30-40, 40-50, 50-60, 60-75, 75-100, 100-150, 150-200, 200-250, 250-300, 300-400, 400-500, 500-750, 750-850, includes ranges of 1-20, 1-30, 1-40, 1-50, 1-60, 10-30, 10-40, 10-50, 10-60, 10-70, 10-80, 20-40, 20-50, 20-60, 20-70, 20-80, 20-90, 50-75, 50-100, 50-150, 50-200, 50-250, 100-200, 100-250, 100-300, 100-350, 100-400, 100-500, 150-250, 150-300, 150-350, 150-400, 150-450, 150-500, etc.

The instant invention is generally disclosed herein using affirmative language to describe the numerous embodiments of the instant invention. The instant invention also specifically includes embodiments in which particular subject matter is excluded, in full or in part, such as substances or materials, method steps and conditions, protocols, or procedures. For example, in certain embodiments of the instant invention, materials and/or method steps are excluded. Thus, even though the instant invention is generally not expressed herein in terms of what the instant invention does not include aspects that are not expressly excluded in the instant invention are nevertheless disclosed herein.

A number of embodiments of the instant invention have been described. Nevertheless, one skilled in the art, without departing from the spirit and scope of the instant invention, can make various changes and modifications of the instant invention to adapt it to various usages and conditions. Accordingly, the following examples are intended to illustrate but not limit the scope of the instant invention claimed in any way.

EXAMPLES

Example 1: Methods hFVIII ELISA of NHP plasma: 96-well plates were coated with human-specific FVIII antibody overnight, washed, and blocked prior to incubation with diluted NHP study subject plasma samples. Standard curves were generated by incubating additional wells with a dilution series of recombinant B-domain deleted hFVIII, Xyntha® (Pfizer). Plates were washed and subsequently incubated with biotinylated human-specific FVIII detection antibody. Plates were incubated with horseradish peroxidase (HRP) conjugated streptavidin, treated with TMB substrate, and read on a microplate reader to determine absorbance at 450 nm.

hFVIII ELISA of mouse plasma: hFVIII ELISA of mouse plasma was performed essentially as described above for NHPs; however, the capture and detection antibodies utilized differed.

Cell-based assay to measure the potency of AAV vectors encoding human FVIII transgenes: Huh7 cells were plated in 48-well dishes at $5\times10^4$ cells per well overnight. Post study, remaining undiluted stock vector and vector diluted for dosing were prepared in a 10-fold dose curve (MOI ranging from $1\times10^6$-$1\times10^3$) in DMEM +10% FBS+penicillin/streptomycin/L-glutamine Existing medium was removed from Huh7 cells and replaced with virus particle containing medium. Cells were maintained at 37° C. and 5% $CO_2$ for 72 hours and supernatants were harvested and stored in low retention microtiter plates at −80° C. until assayed for hFVIII activity. Supernatants were assayed by Coatest® SP4 Factor VIII (Chromogenix) with a standard curve generated by diluting recombinant B-domain deleted hFVIII, Xyntha® (Pfizer), into cell growth medium.

Cell-based assay to measure the protein expression efficiency of plasmids encoding human FVIII transgenes: Huh7 cells were plated in 48-well dishes at $5\times10^4$ cells per well overnight in DMEM+10% FBS+penicillin/streptomycin/L-glutamine Plasmids were prepared using Plasmid Giga Kit (Qiagen) and transfected into cells at 250 ng per well using Polyethylenimine (PEI) Max. Cells were maintained at 37° C. and 5% $CO_2$ for 72 hours and supernatants were harvested and stored in low retention microtiter plates at −80° C. until assayed for hFVIII activity. Supernatants were assayed by Coatest® SP4 Factor VIII (Chromogenix) with a standard curve generated by diluting recombinant B-domain deleted hFVIII, Xyntha® (Pfizer), into cell growth medium.

Example 2

The FIX construct regulatory element unit (SEQ ID NOs:22 and 23) is composed of a 321 bp intron of the apolipoprotein E (ApoE) gene and a 397 bp promoter of the human alpha-1 antitrypsin (hAAT) gene. Overall, this unit contains 16 CpGs.

Design of CpG Reduced Promoters

Either the cytosine or the guanine of CpG sites were changed depending on the consensus sequences. If no potential transcription factor binding site was found, the cytosine (C) of the CpG dinucleotide was replaced with thymine (T). By doing so, the pyrimidine-purine structure was maintained. In some cases, the C nucleotide or the entire CpG dinucleotide was deleted, and in some cases, the guanine (G) of the CpG dinucleotide was replaced with alanine (A) or C.

Using this strategy, 22 different sequences were generated based on the ApoE/hAAT regulatory element. The sequences are illustrated, with and without 5' and 3' flanking restriction enzyme sites, in SEQ ID NOs:24-67 below.

Cloning

The different promoters were synthesized and cloned upstream of a codon-optimized sequence (SEQ ID NO:94) encoding hFIX.

Mouse Studies

The potency of the human alpha-1 antitrypsin (hAAT) gene promoter was assessed by hydrodynamic delivery of plasmid constructs in 8 weeks old male wild-type C57BL/6 mice (Jackson Laboratories). Non-fasted plasma samples were collected in heparin, 24 hours after plasmid administration, via submandibular blood collection. Plasma was placed on ice and stored at −80° C. until analyzed. All animal work was performed in accordance with institutional guidelines and approved protocols.

Potency Study

Plasma collected was used to evaluate hFIX transgene expression.

Activity levels of human FIX were measured by activated partial thromboplastin time (aPTT) assay. The aPTT assay was performed by mixing sample plasma in a 1:1:1 volume-ratio with human FIX-deficient plasma (George King Bio-Medical, Inc.) and aPTT reagent (Trinity Biotech), followed by a 180 s incubation period at 37° C. Coagulation was initiated by addition of 25 mM calcium chloride. Time to clot formation was measured using a STart 4 coagulation instrument (Diagnostica Stago). A standard curve was generated with pooled normal plasma (George King Bio-Medical, Inc.) starting at a 1:5 dilution in TBS pH 7.4 (48 μL+192 μL) followed by serial 1:2 dilutions (120 μL+120 μL). The human standard curve was used to calculate the activity of each sample at week 17 after AAV vector administration; activity in two untreated mice was also measured. FIX activity in untreated mice was averaged and then subtracted from the treated samples to calculate the extra (i.e., human) activity due to the exogenous FIX protein. The data are shown in FIG. 1.

Example 3

The FVIII construct regulatory element unit (SEQ ID NO:2 and SEQ ID NO:3) is composed of a 225 bp TTR promoter. Overall, this unit contains 4 CpGs.

Design of CpG Reduced TTR Promoters

Either the cytosine or the guanine of CpG sites were changed depending on the consensus sequences. If no potential binding site was found, the cytosine of the CpG dinucleotide was replaced with thymine. By doing so, the pyrimidine-purine structure was maintained. Using this strategy, 5 novel sequences were generated based on the TTRm (SEQ ID NO:3) regulatory element. The CpG reduced TTR sequences, with and without restriction enzyme sites, are illustrated in SEQ ID NOs:4-13.

Another set of four different short TTR hybrid promoters were designed. Five different liver-specific promoters were assessed in silico for the presence of putative transcription factor binding sites within 1000 nucleotides of the transcriptional start site (TSS) for their native genes. Subsequently, the TTR hybrid promoters were assembled by choosing specific regions from the original native promoters and assembling them in tandem. The TTR hybrid sequences, with and without restriction enzyme sites, are illustrated in SEQ ID NOs:14-21 below.

Cloning

The different promoters were synthetized and cloned upstream to a codon-optimized nucleotide sequence (SEQ ID NO:77) encodinghFVIII-BDD.

Mouse Studies

The potency of the TTR promoters was initially assessed by hydrodynamic delivery in 8 weeks old male wild-type C57BL/6 mice (Jackson laboratories). Non-fasted plasma samples were collected in heparin 24 hours after plasmid administration via submandibular blood collection. Plasma was placed on ice and stored at −80° C. until analyzed. For AAV delivery studies, the first 0.5 mL of blood was discarded, and the remaining sample was collected in EDTA, and processed to plasma. All animal work was performed in accordance with institutional guidelines and approved protocols.

hFVIII Antigen Levels in Murine Plasma

Levels of hFVIII transgene product in murine plasma were quantified using a sandwich-style ELISA as follows:

first, the wells of a microtiter plate were coated with an anti-hFVIII capture antibody (Green Mountain Antibodies, diluted to 2 μg/mL). The following day, the plate was washed four times and blocked (6% BSA, 0.2% Tween 20 in PBS) for 30 minutes at room temperature. Pooled murine plasma was spiked with a known concentration of recombinant B-domain deleted hFVIII (XYNTHA Solofuse®) and was serially diluted (1:2) to generate an 8-point standard curve ranging from 300 ng/mL to 2.34 ng/mL. The limit of quantitation of the assay is 4.8 ng/mL. Three levels of quality control samples were prepared and included on each plate to assess assay performance After addition of the samples to the wells, the plate was incubated at 37° C. for 1 hour and then washed four times. A biotinylated anti-hFVIII detection antibody (Green Mountain Antibodies, diluted to 1 μg/mL) was added to the plate for 1 hour at room temperature to bind to the captured hFVIII protein. Following washing, a peroxidase-conjugated streptavidin reagent (Thermo Fisher Scientific) at a 1:5000 dilution was added to the plate for 30 minutes at room temperature to bind to the biotinylated anti-hFVIII antibody. After washing the plate to remove unbound conjugated antibody, the peroxidase activity was revealed following a 15-minute incubation at room temperature with 3,3',5,5'-tetramethylbenzidine substrate (TMB). The reaction was stopped with TMB Stop Solution and the plate was read by an absorbance plate reader for optical density (OD). The absorbance values obtained are proportional to the concentration of hFVIII present in the plasma sample. The data are shown in FIGS. 2-5.

RNA Isolation and qPCR

Figure 6:
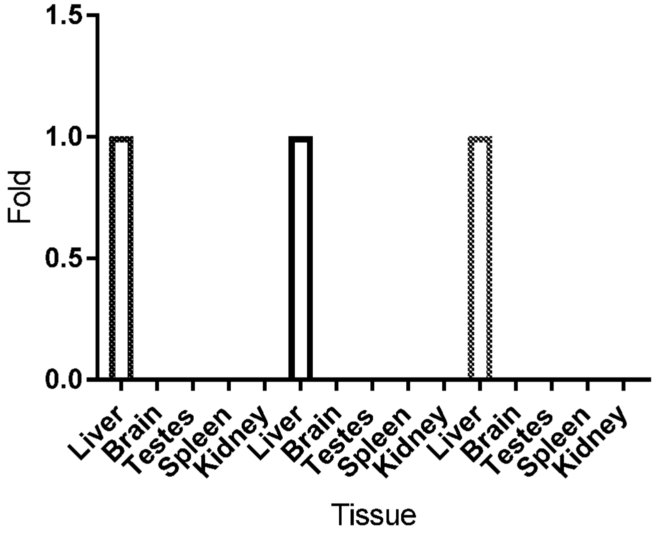
FIG. 6 shows expression of hFVIII mRNA in liver, brain, testes, spleen and kidney of mice 8 weeks following intravenous administration of AAV encapsidated non-CpG reduced (TTRm-hFVIII), Hybrid 7 and Hybrid 9 promoter-hFVIII constructs at a dose of 6.4e11 vg/kg. No hFVIII RNA was observed in any tissues other than the liver, demonstrating the liver-specific nature of the promoters. Groups of results for liver, brain, testes, spleen and kidney are shown from left to right for TTRm-hFVIII, Hybrid7-hFVIII, and Hybrid9-hFVIII, respectively.

Brain, testes, kidney, spleen, and liver mouse tissues were harvested, rinsed with DPBS, cut/mashed into multiple tiny pieces, and ~30 mg was used for RNA isolation, performed as described in the kit protocol (RNeasy plus universal mini kit, Qiagen). RNA concentrations were measured using a Nanodrop 2000 instrument, and samples were diluted to 150 ng/μL in nuclease-free. DNase treatment was done using Turbo DNA free kit (Invitrogen) as per the manufacturer's instructions. For cDNA reaction, 200 ng of RNA were used as directed in the High Capacity cDNA Reverse Transcription Kit (ABI). The cDNA samples were diluted 5-fold and 20 ng of cDNA were used in the PCR reaction. Quantitative real-time PCR was performed using forward primer: 5'-TGAGGAGGCTGAAGACTATGA-3' (SEQ ID NO:95), reverse primer: 5'-CCACAGACCTGATCTGAATGAA-3' (SEQ ID NO:96), and a probe: 5'-56-FAM-TGGATGTGG/ZEN/TGAGGTTTGATGATGACA-3IABkFQ-3' (SEQ ID NO:97). The murine actB (Integrated DNA Technologies) gene served as the housekeeping gene for normalization. The data are shown in FIG. 6.

Example 4

Figure 7:
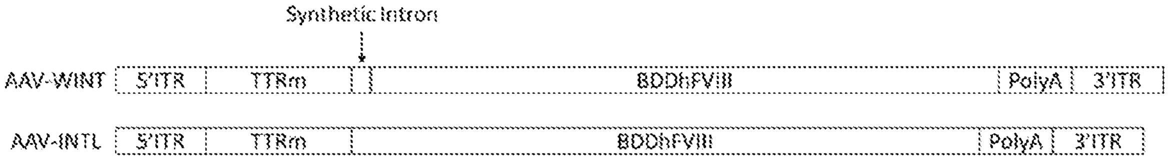
FIG. 7 shows a schematic comparison of an expression cassette with an intron, referred to as "AAV-WINT" (TTRm-intron-hFVIII-BDD) and an expression cassette without an intron, referred to as "AAV-INTL" (TTRm-hFVIII-BDD intronless; SEQ ID NO:1). AAV-WINT has a synthetic intron (SEQ ID NO:93) located between a TTRm promoter and a transgene encoding B-domain deleted human Factor VIII(hFVIII-BDD), which is not present in AAV-INTL. The codon-optimized nucleic acid sequence in these cassettes encoding hFVIII-BDD is set forth in SEQ ID NO:77.

Expression of Factor VIII was increased by altering the elements within the expression cassette that contribute to transgene expression. An intron-free version of a B-domain deleted hFVIII expressing AAV vector (AAV-INTL) was made and compared with an intron-containing version (AAV-WINT). The AAV-INTL hFVIII expression cassette (SEQ ID NO:1) contains the same elements as the AAV-WINT hFVIII expression cassette, except that AAV-WINT hFVIII has a synthetic intron (SEQ ID NO:93) positioned between a TTRm promoter and a transgene encoding B-domain deleted human Factor VIII (FIG. 7).

Example 5: Potency in Mice

Figure 8:
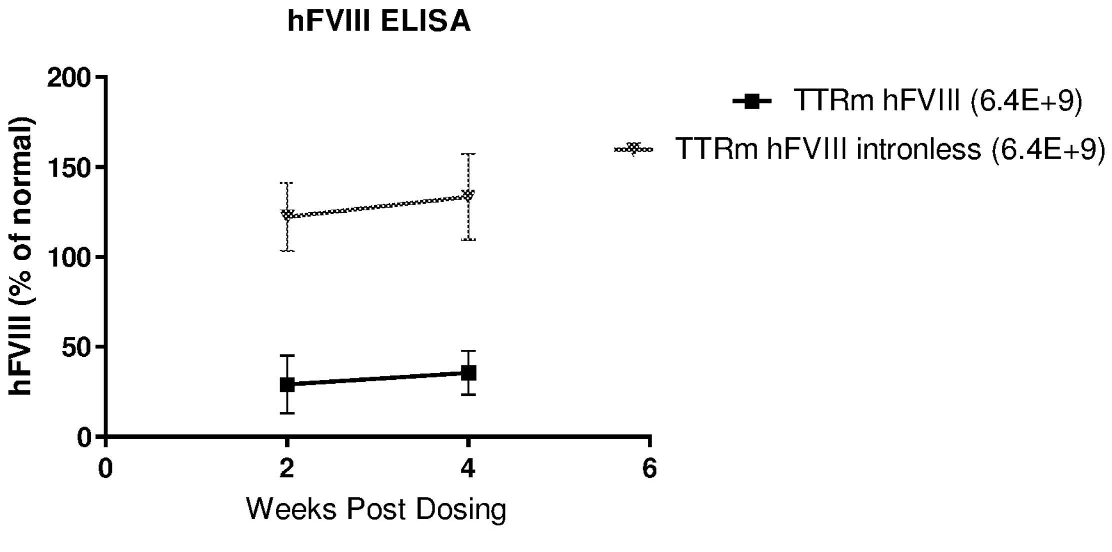
FIG. 8 shows hFVIII levels as detected by ELISA performed on mouse plasma samples for the 6.4e9 vg/mouse dosage from study #1. Results are the average of animals in each treatment group (n=5). Error bars represent standard deviation.
Figure 9:
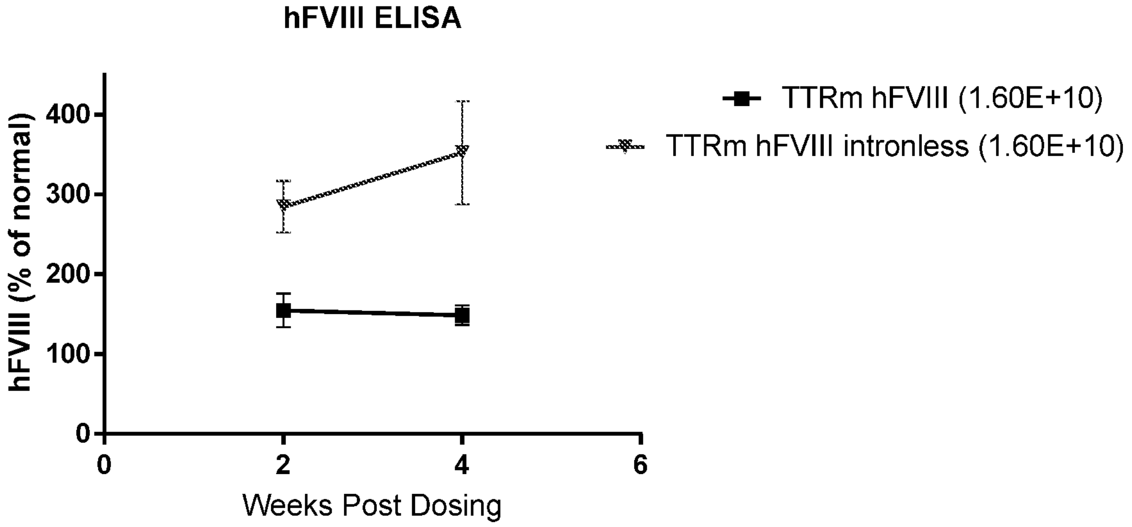
FIG. 9 shows hFVIII levels as detected by ELISA performed on mouse plasma samples for the 1.6e10 vg/mouse dosage from study #1. Results are the average of animals in each treatment group (TTRm hFVIII, n=4; TTRm hFVIII intronless, n=5). Error bars represent standard deviation.

To evaluate the potency of the intron-free cassette (TTRm hFVIII intronless; SEQ ID NO:1) versus the cassette with the intron (TTRm hFVIII) in mammals, male C57BL/6 mice (Jackson Laboratories) of approximately 8 weeks of age were injected intravenously in the lateral tail vein with AAV encapsidated cassettes at dosages of 6.4e9 or 1.6e10 vg/mouse. Plasma was collected at several time points, as indicated (FIGS. 8 and 9), and assessed for circulating hFVIII levels by hFVIII ELISA.

Figure 10:
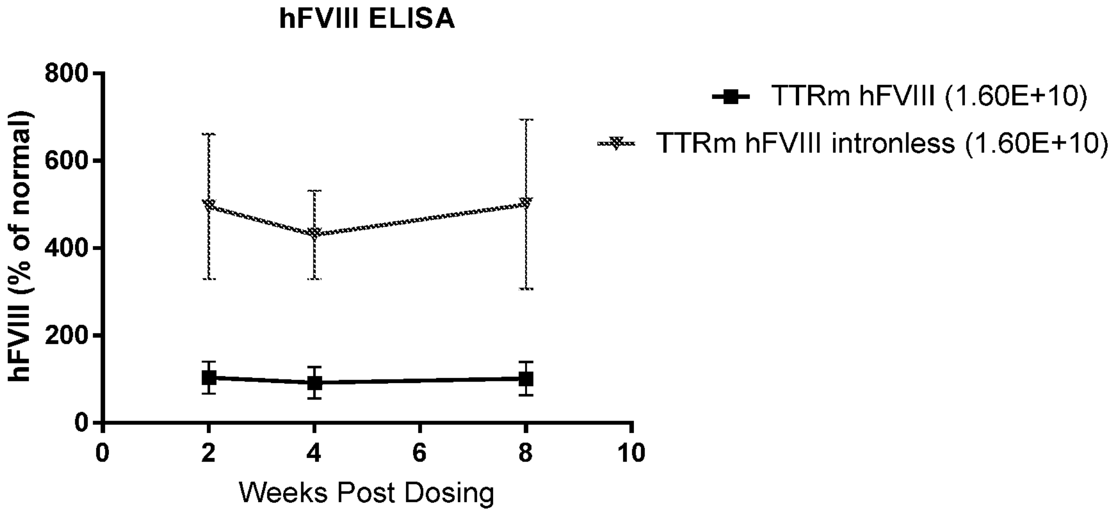
FIG. 10 shows hFVIII levels as detected by ELISA performed on mouse plasma samples from study #2. Results are the average of animals in each treatment group (n=10). Error bars represent standard deviation.

Determination of hFVIII levels showed that TTRm hFVIII intronless exhibited a significant increase in potency versus TTRm hFVIII (with the intron) (FIGS. 8 and 9), and this effect was seen at both doses and time points tested (study #1). These results were repeated in a subsequent study, study #2, with the 1.6e10 vg/mouse dose with 10 mice in each group (FIG. 10). Study #2 confirmed that TTRm hFVIII intronless (AAV-INTL) was more potent than the vector containing the synthetic intron (AAV-WINT), and that these differences were sustained for at least 8 weeks.

Example 6: Potency in NHPs, Study 1

AAV vector potencies of AAV-INTL and AAV-WINT were compared in NHPs (study #1). 12 male cynomolgus monkeys (*Macaca fascicularis*) between the ages of 24 and 50 months, with weights between 2-6 kg, and negative for AAV neutralizing antibodies, were divided into 4 randomized groups and injected intravenously with a single dose of either AAV-WINT or AAV-INTL based on the dosing groups shown in Table 1. Subsequently, plasma samples were obtained weekly to determine levels of circulating hFVIII.

TABLE 1

Group Designation and Dose Levels from NHP Study

| Group # | No. of Animals (Male) | Dose Level (vg/kg) | Dose Concentration (vg/kg) |
|---|---|---|---|
| 1 (AAV-WINT Low) | 3 | $2.0 \times 10^{12}$ | $2.0 \times 10^{11}$ |
| 2 (AAV-WINT High) | 3 | $6.0 \times 10^{12}$ | $6.0 \times 10^{11}$ |
| 3 (AAV-INTL Low) | 3 | $2.0 \times 10^{12}$ | $2.0 \times 10^{11}$ |
| 4 (AAV-INTL High) | 3 | $6.0 \times 10^{12}$ | $6.0 \times 10^{11}$ |

Figure 11:
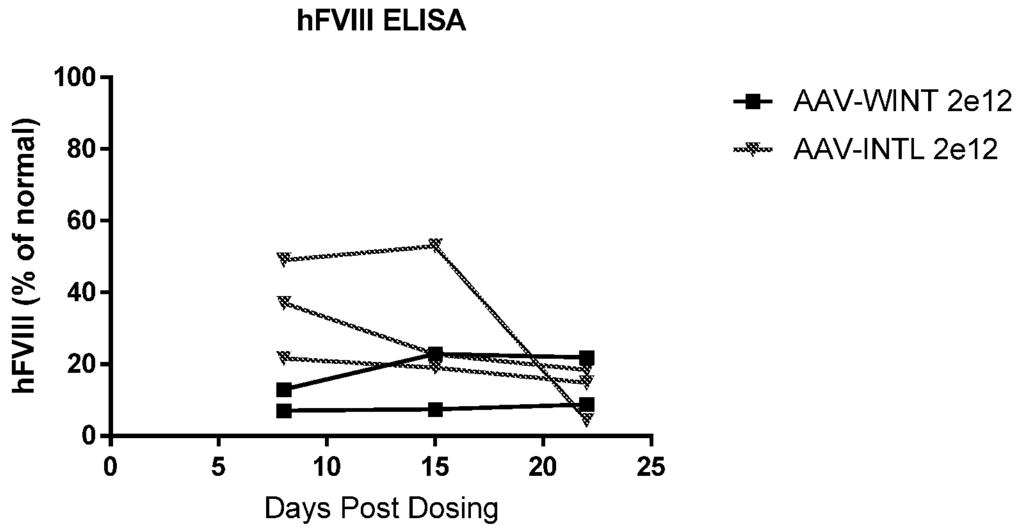
FIG. 11 shows hFVIII levels as detected by ELISA performed on non-human primate (NHP) plasma samples from study #1. Results from individual monkeys in low dose (2e12 vg/kg) group 1 (AAV-WINT, lines with boxes, n=2) and group 2 (AAV-INTL, SEQ ID NO:1, lines with triangles, n=3) are shown. One animal, P0001, from low dose AAV-WINT was removed due to positive neutralizing antibodies to AAV observed in pre-dose day −8 sample.
Figure 12:
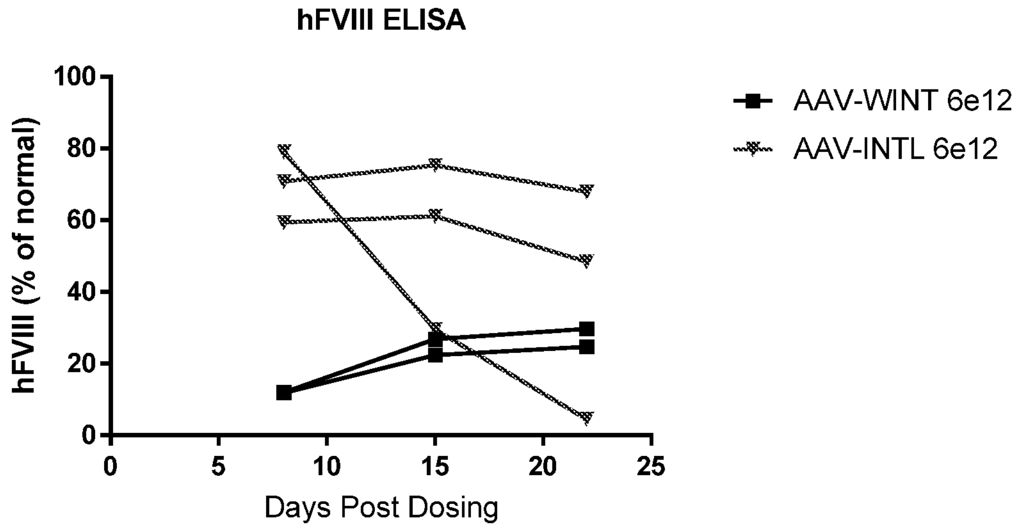
FIG. 12 shows hFVIII levels as detected by ELISA performed on NHP plasma samples from study #1. Results from individual monkeys in high dose (6e12 vg/kg) group 3 (AAV-WINT, lines with boxes, n=2) and group 4 (AAV-INTL, SEQ ID NO:1, lines with triangles, n=3) are shown. One animal, P0101, from high dose AAV-WINT was removed due to no observed hFVIII expression upon treatment.

Levels of hFVIII in plasma of monkeys dosed with either AAV-WINT or AAV-INTL were determined by ELISA at weekly intervals throughout the 8-week study. At either dose tested in this study, 2e12 vg/kg (FIG. 11) or 6e12 vg/kg (FIG. 12), an increase in the levels of circulating hFVIII of from 2- to 4-fold based on peak circulating value, regardless of time point, was observed. As expected, we observed loss of expression 2-3 weeks following treatment, indicating the development of inhibitory antibodies to BDD hFVIII. The results of the first study demonstrate that AAV-INTL displays increased potency versus AAV-WINT in NHPs.

Example 7: Potency in NHPs, Study 2

A second study (study #2) was undertaken in NHPs to confirm the increased vector potency of AAV-INTL versus AAV-WINT. Ten male cynomolgus macaques (*Macaca fascicularis*) between the ages of 24 and 50 months, with weights between 2-6 kg, and negative for AAV neutralizing antibodies, were divided into 2 randomized groups and injected intravenously with a single dose (2e12 vg/kg) of either AAV-WINT or AAV-INTL. Subsequently, plasma samples were obtained weekly to determine levels of circulating hFVIII.

Figure 13:
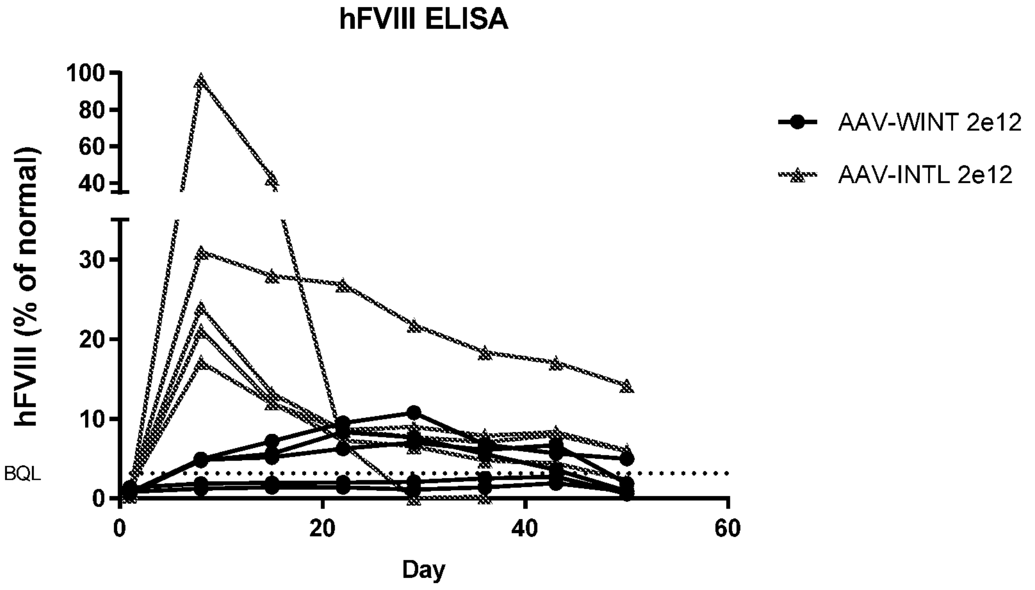
FIG. 13 shows hFVIII levels as detected by ELISA performed on plasma samples of NHPs from study #2. Results from individual monkeys at the 2e12 vg/kg dose for AAV-WINT (lines with boxes, n=5) and AAV-INTL, (SEQ ID NO:1, lines with triangles, n=5) are shown.

Levels of hFVIII in plasma of macaques dosed with either AAV-WINT or AAV-INTLwere determined by ELISA at weekly intervals throughout the 8-week study. At the dose tested in this study, 2e12 vg/kg, an increase in the levels of circulating hFVIII of from 4- to 7-fold, based on peak circulating value, regardless of time point was observed (FIG. 13). As previously seen in NHPs, loss of expression of the transgene 2-3 weeks following treatment was observed, due to the development of inhibitory antibodies to BDD hFVIII. The results of study #2 confirmed that AAV-INTL displays increased potency versus AAV-WINT in NHPs.

Example 8: Determination of Vector Potency

To confirm that the correct vector, at the proper concentration, was dosed into each group of NHPs, dosing formulation titers were determined by qPCR, and the presence or absence of the synthetic intron in stock vectors was assayed by genotyping PCR assays that allow differentiation between AAV-WINT and AAV-INTL. To directly assess vector potency of both the undiluted stock vectors and the 2e12 vg/kg dosing formulations, a cell-based potency assay was utilized.

Figure 14:
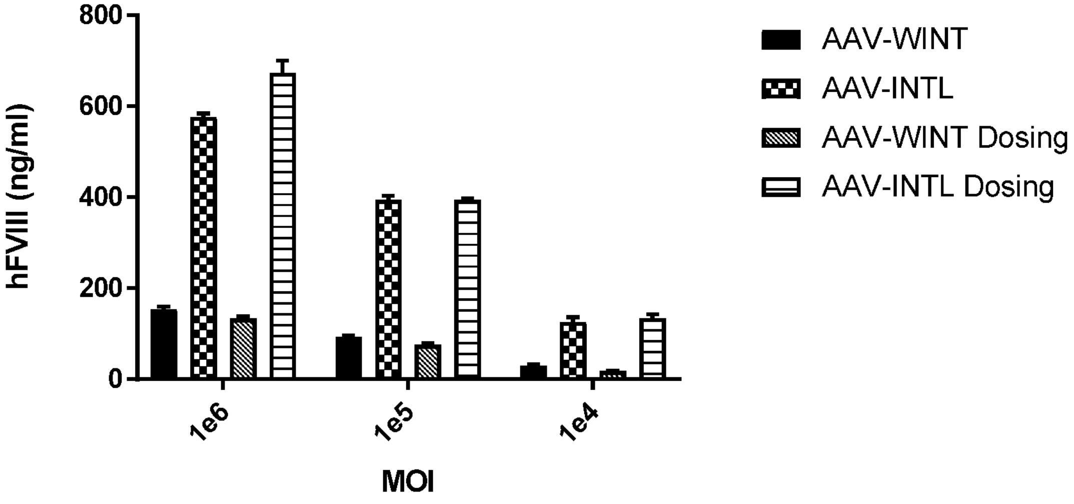
FIG. 14 shows the results of a cell-based vector potency assay at three different multiplicities of infection (MOI). Cell supernatants were assessed for hFVIII activity by Chromogenix Coatest SP4 and are the average of two biological replicates assayed in duplicate. Error bars represent standard deviation. "AAV-WINT" and "AAV-INTL" are original, undiluted stock vials of virus, whereas "AAV-WINT Dosing" and "AAV-INTL Dosing" indicate materials diluted for infusion.
Figure 15:
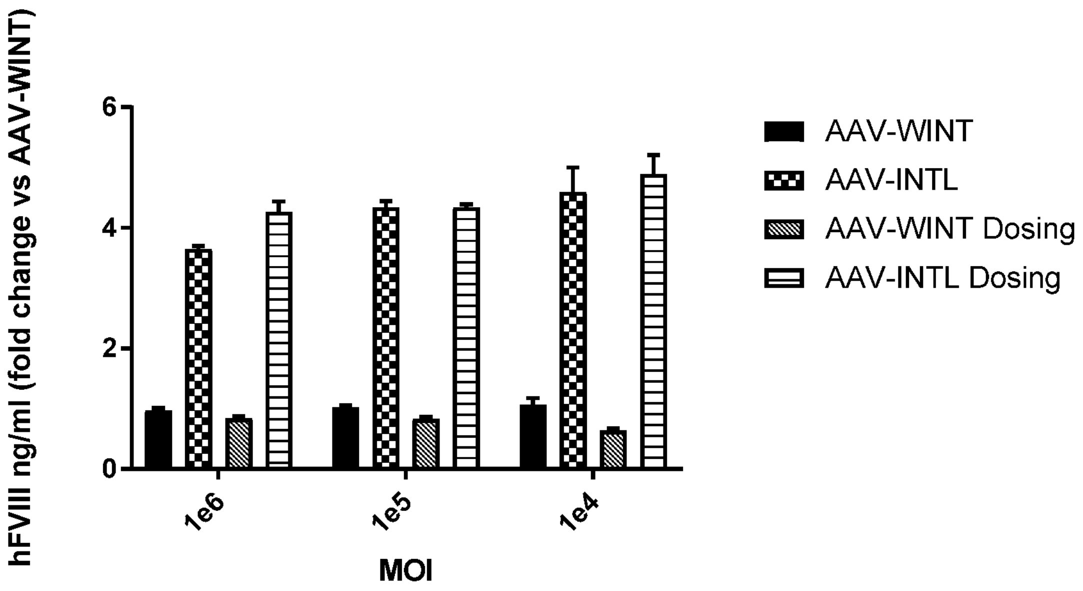
FIG. 15 shows results from FIG. 14 replotted as fold-change versus AAV-WINT for each MOI.

A human liver cell line was transduced with a dilution series of vector, and potency was determined by evaluating secreted BDD hFVIII in the supernatant by a hFVIII activity assay (Chromogenix Coatest SP4). At all MOI, AAV-INTL exhibited increased potency versus AAV-WINT (FIG. 14). Notably, stock virus and dilution formulations showed similar potency within vector groups, further confirming that the titers of the dosing formulations in the 2e12 vg/kg group were properly prepared. In addition, at each MOI, when compared to AAV-WINT, AAV-INTL displayed an approximately 4-fold increase in potency (FIG. 15). These values are in agreement with the increased potency of AAV-INTLobserved in NHP studies 1 and 2.

Example 9: Lot Comparison

Figure 16:
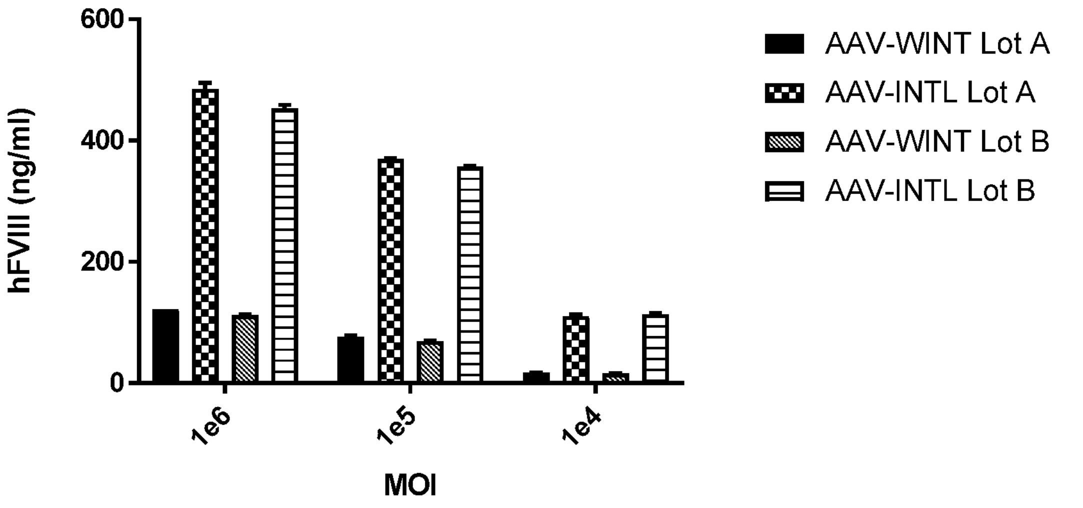
FIG. 16 shows an evaluation of vector potency in an in vitro, cell-based vector potency assay at three different MOI. Cell supernatants were assessed for hFVIII activity by Chromogenix Coatest SP4 and are the average of two biological replicates assayed in duplicate. Error bars represent standard deviation. AAV-WINT and AAV-INTL (SEQ ID NO:1) are original stock vials of virus from two different lots.

The first and second NHP studies used different lots of AAV-WINT and AAV-INTL vectors. To assess whether vector potency in the different lots was comparable, potency was measured using an in vitro assay (FIG. 16). The results of these comparisons show that batch to batch variation was minimal and that AAV-INTL remained similarly about 4- to 5-fold more potent than AAV-WINT.

Example 10: Determination of Expression Cassette Efficiency

To explore the mechanism of increased potency in vivo, the transcriptional efficiency in the absence of viral transduction was determined. A human liver cell line was transfected with plasmids containing the expression cassettes that make up AAV-WINT and AAV-INTL, TTRm-intron-BDD-hFVIII and TTRm-BDD-hFVIII intronless (SEQ ID NO:1), respectively. Supernatants from these cells were assayed for hFVIII levels by a human FVIII activity assay (Chromogenix Coatest SP4).

Figure 17:
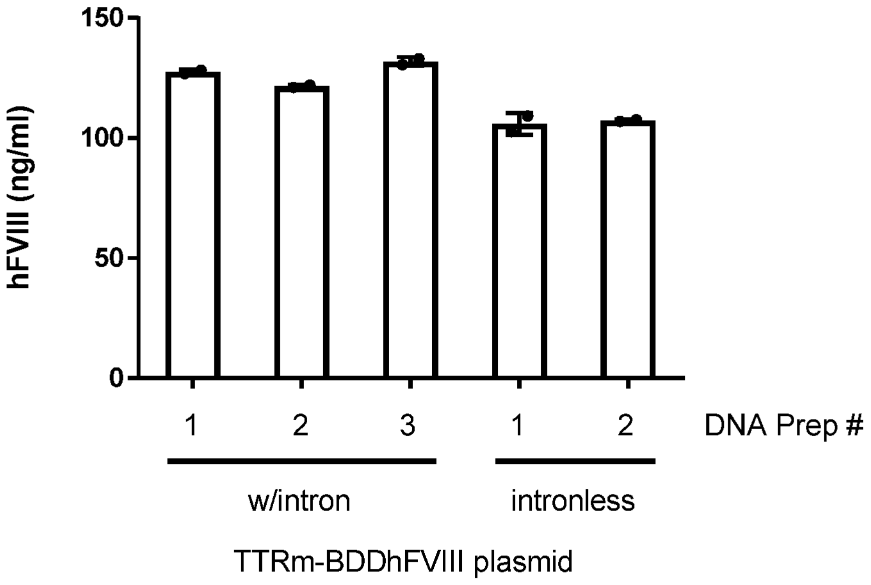
FIG. 17 shows a comparison of expression cassettes for in vitro hFVIII levels, assayed by Chromogenix Coatest SP4 from supernatants of Huh7 cells transfected with independent plasmid DNA preparations (prep) of mTTR-intron-hFVIII-BDD and mTTR-hFVIII-BDD (SEQ ID NO:1). Individual data points are shown as filled circles, with each bar representing the average of two biological replicates (n=2) assayed in duplicate. Error bars represent standard deviation.

Comparison of three independent DNA preparations of TTRm-intron-BDD-hFVIII and two independent DNA preparations of TTRm-BDD-hFVIII intronless (SEQ ID NO:1) displayed similar hFVIII levels, with a trend towards decreased expression upon intron removal (FIG. 17). Although not wishing to be bound by any theory, the data suggest a non-transcriptional mechanism is driving the increased potency of AAV-INTL over AAV-WINT.

Example 11: Discussion of Data

At equivalent doses, AAV-INTL exhibits increased potency and expression of BDD-hFVIII in cell culture, mouse and NHP models, over AAV-WINT. Mechanistically, increased potency was not apparently due to increased transcription of the FVIII transgene from the expression cassette, and is instead, perhaps, due to increased viral packaging efficiency or alternate mechanisms. These results indicate that intron-free expression cassettes may have increased potency in human clinical trials and provide benefits to patient safety and efficacy.

Example 12: Human Clinical Trial Results

A single dose study was performed in four men (N=4) with hemophila A, outlined in Table 4. All four participants received a single infusion of AAV-INTL hFVIII-BDD expression cassette (SEQ ID NO:1) encapsidated in LK03 AAV vector (SEQ ID NO:91), referred to herein as "LK03-INTL hFVIII-BDD," at a dose of $5\times10^{11}$ vg/kg.

TABLE 4

| Participant | | Age (yrs) | Weeks of Follow-up Post Infusion with Vector |
|---|---|---|---|
| 1 | 840-09-601 | 28 | 21 |
| 2 | 840-02-601 | 18 | 17 |
| 3 | 840-02-602 | 63 | 9 |
| 4 | 840-10-601 | 63 | 5 |

Figure 18:
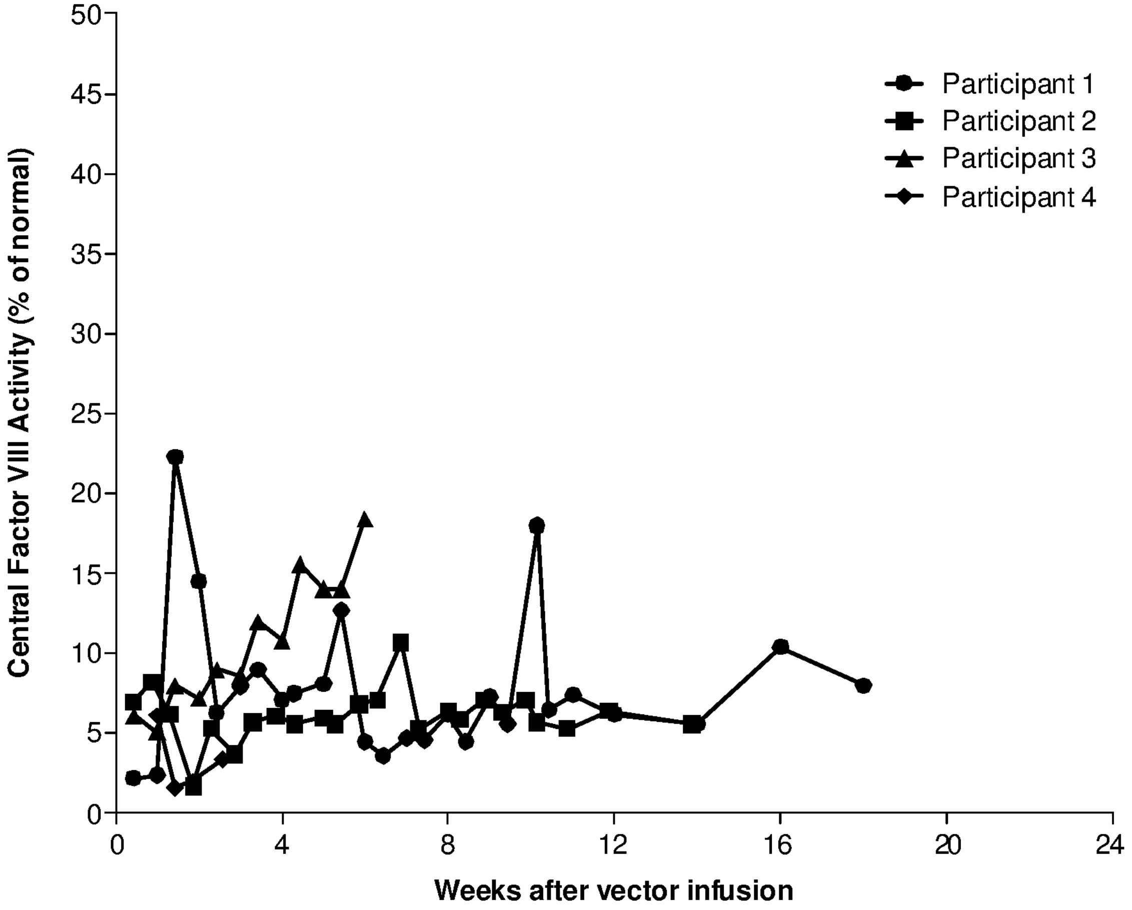
FIG. 18 shows daily FVIII activity levels in 4 human subjects (participant 1 (circle), 2 (square), 3 (triangle) and 4 (diamond)) infused with $5\times10^{11}$ vg/kg of AAV-INTL hFVIII expression cassette (SEQ ID NO:1) encapsidated in LK03 AAV vector (SEQ ID NO:91), referred to herein as LK03-INTL hFVIII-BDD.
Figure 19:
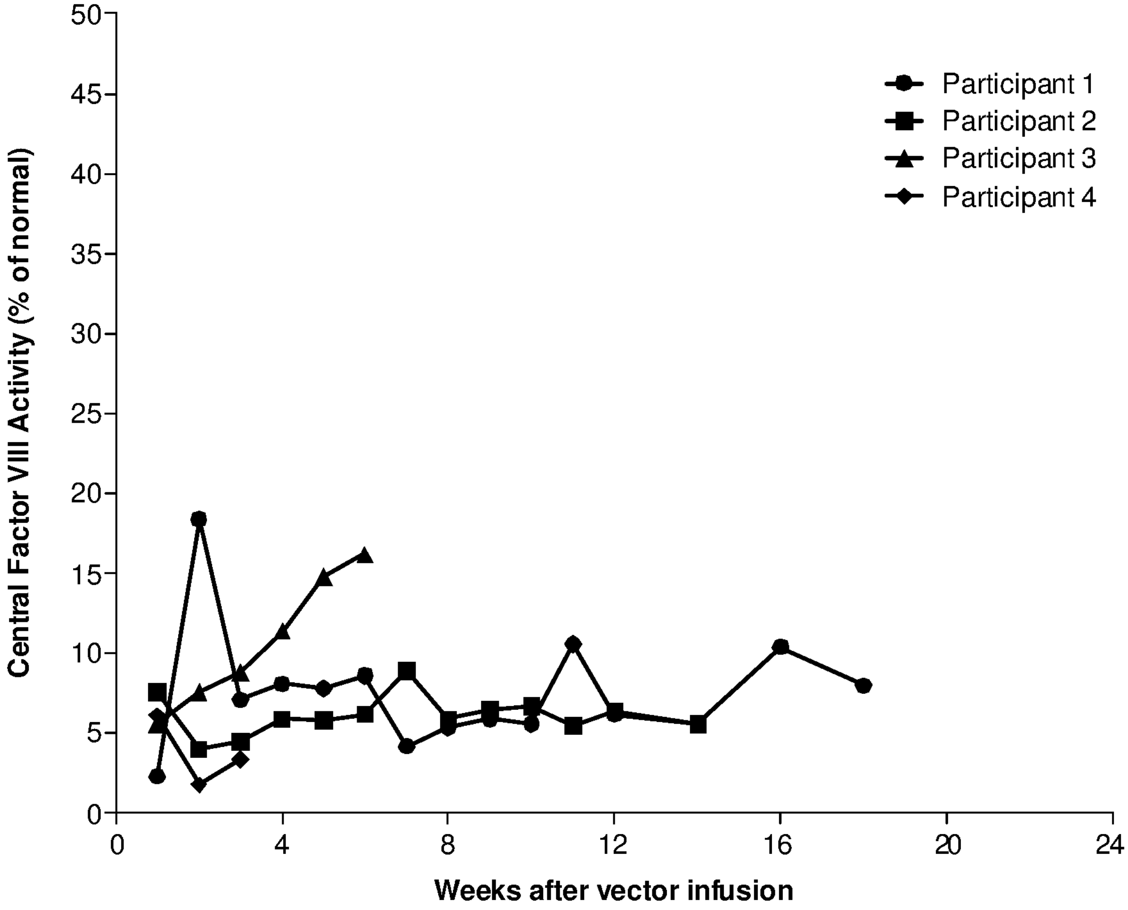
FIG. 19 shows weekly averages of FVIII activity levels in 4 human subjects (participant 1 (circle), 2 (square), 3 (triangle) and 4 (diamond)) infused with $5\times10^{11}$ vg/kg of LK03-INTL hFVIII-BDD.
Figure 20:
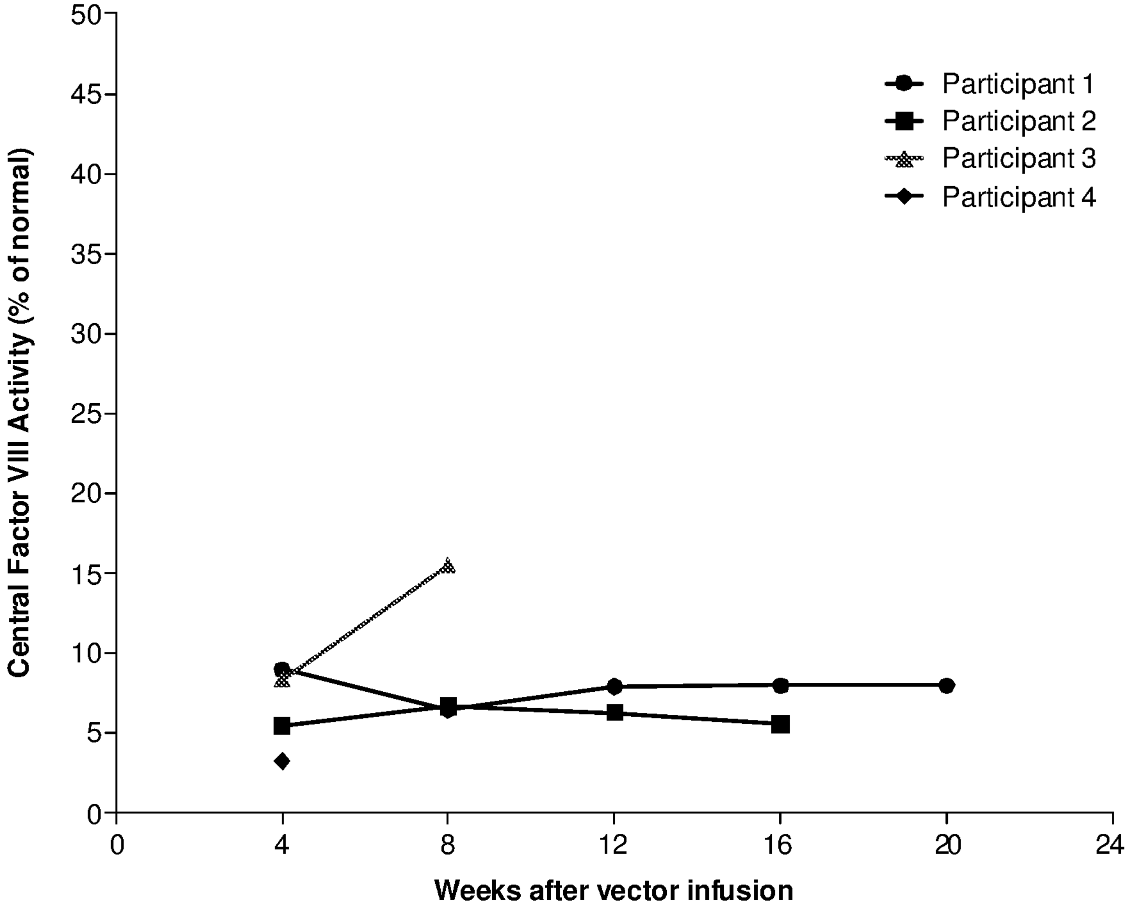
FIG. 20 shows four-week block averages of FVIII activity levels in 4 human subjects (participant 1 (circle), 2 (square), 3 (triangle) and 4 (diamond)) infused with $5\times10^{11}$ vg/kg of LK03-INTL hFVIII-BDD.

LK03-INTL hFVIII-BDD vector was seen to drive FVIII expression in all four participants (FIGS. 18-19).

Example 13: Sequences

TABLE 2

| SEQ ID NOs and descriptions | |
|---|---|
| SEQ ID NO | Description |
| SEQ ID NO: 1 | Entire nucleic acid sequence of AAV-INTL cassette (5' ITR, TTRm, hFVIII-BDD coding sequence (SEQ ID NO: 77), PolyA, and 3'ITR). |
| SEQ ID NO: 2 | Nucleic acid sequence of the wild-type TTR promoter. |
| SEQ ID NO: 3 | Nucleic acid sequence of the mutated TTR promoter "TTRm", having 4 nucleotide changes from wild-type. |
| SEQ ID NO: 4 | Nucleic acid sequence of the CpG1-TTRm promoter, where every C is changed to T for all four CpGs. |
| SEQ ID NO: 5 | Nucleic acid sequence of the CpG1-TTRm promoter, where every C is changed to T for all four CpGs with restriction enzyme sites. |

TABLE 2-continued

| SEQ ID NOs and descriptions | |
|---|---|
| SEQ ID NO | Description |
| SEQ ID NO: 6 | Nucleic acid sequence of the CpG2-TTRm promoter, where the C is changed to T in the second, third and fourth CpG. |
| SEQ ID NO: 7 | Nucleic acid sequence of the CpG2-TTRm promoter, where the C is changed to T in the second, third and fourth CpG with restriction enzyme sites. |
| SEQ ID NO: 8 | Nucleic acid sequence of the CpG3-TTRm promoter, where the C is changed to T in the first, third and fourth CpG. |
| SEQ ID NO: 9 | Nucleic acid sequence of the CpG3-TTRm promoter, where the C is changed to T in the first, third and fourth CpG with restriction enzyme sites. |
| SEQ ID NO: 10 | Nucleic acid sequence of the CpG4-TTRm promoter, where the C is changed to T in the first, second and fourth CpG. |
| SEQ ID NO: 11 | Nucleic acid sequence of the CpG4-TTRm promoter, where the C is changed to T in the first, second and fourth CpG with restriction enzyme sites. |
| SEQ ID NO: 12 | Nucleic acid sequence of the CpG5-TTRm promoter, where the C is changed to T in the first, second and third CpG. |
| SEQ ID NO: 13 | Nucleic acid sequence of the CpG5-TTRm promoter, where the C is changed to T in the first, second and third CpG with restriction enzyme sites. |
| SEQ ID NO: 14 | Nucleic acid sequence of the Hybrid6 promoter. |
| SEQ ID NO: 15 | Nucleic acid sequence of the Hybrid6 promoter with restriction enzyme sites. |
| SEQ ID NO: 16 | Nucleic acid sequence of the Hybrid7 promoter. |
| SEQ ID NO: 17 | Nucleic acid sequence of the Hybrid7 promoter with restriction enzyme sites. |
| SEQ ID NO: 18 | Nucleic acid sequence of the Hybrid8 promoter. |
| SEQ ID NO: 19 | Nucleic acid sequence of the Hybrid8 promoter with restriction enzyme sites. |
| SEQ ID NO: 20 | Nucleic acid sequence of the Hybrid9 promoter. |
| SEQ ID NO: 21 | Nucleic acid sequence of the Hybrid9 promoter with restriction enzyme sites. |
| SEQ ID NO: 22 | Nucleic acid sequence of the non-CpG reduced ApoE/hAAT regulatory element. |
| SEQ ID NO: 23 | Nucleic acid sequence of the non-CpG reduced ApoE/hAAT regulatory element with flanking restriction enzyme sites. |
| SEQ ID NO: 24 | Nucleic acid sequence of the CpG1- ApoE/hAAT promoter. |
| SEQ ID NO: 25 | Nucleic acid sequence of the CpG1- ApoE/hAAT promoter with restriction enzyme sites. |
| SEQ ID NO: 26 | Nucleic acid sequence of the CpG2- ApoE/hAAT promoter. |
| SEQ ID NO: 27 | Nucleic acid sequence of the CpG2- ApoE/hAAT promoter with restriction enzyme sites. |
| SEQ ID NO: 28 | Nucleic acid sequence of the CpG3- ApoE/hAAT promoter. |
| SEQ ID NO: 29 | Nucleic acid sequence of the CpG3- ApoE/hAAT promoter with restriction enzyme sites. |
| SEQ ID NO: 30 | Nucleic acid sequence of the CpG4- ApoE/hAAT promoter. |
| SEQ ID NO: 31 | Nucleic acid sequence of the CpG4- ApoE/hAAT promoter with restriction enzyme sites. |
| SEQ ID NO: 32 | Nucleic acid sequence of the CpG5- ApoE/hAAT promoter. |
| SEQ ID NO: 33 | Nucleic acid sequence of the CpG5- ApoE/hAAT promoter with restriction enzyme sites. |
| SEQ ID NO: 34 | Nucleic acid sequence of the CpG6- ApoE/hAAT promoter. |
| SEQ ID NO: 35 | Nucleic acid sequence of the CpG6- ApoE/hAAT with restriction enzyme sites. |
| SEQ ID NO: 36 | Nucleic acid sequence of the CpG7- ApoE/hAAT promoter. |
| SEQ ID NO: 37 | Nucleic acid sequence of the CpG7- ApoE/hAAT promoter with restriction enzyme sites. |
| SEQ ID NO: 38 | Nucleic acid sequence of the CpG8- ApoE/hAAT promoter. |
| SEQ ID NO: 39 | Nucleic acid sequence of the CpG8- ApoE/hAAT promoter with restriction enzyme sites. |
| SEQ ID NO: 40 | Nucleic acid sequence of the CpG9- ApoE/hAAT promoter. |
| SEQ ID NO: 41 | Nucleic acid sequence of the CpG9- ApoE/hAAT promoter with restriction enzyme sites |
| SEQ ID NO: 42 | Nucleic acid sequence of the CpG10- ApoE/hAAT promoter. |
| SEQ ID NO: 43 | Nucleic acid sequence of the CpG10- ApoE/hAAT promoter with restriction enzyme sites |
| SEQ ID NO: 44 | Nucleic acid sequence of the CpG11- ApoE/hAAT promoter. |
| SEQ ID NO: 45 | Nucleic acid sequence of the CpG11- ApoE/hAAT promoter with restriction enzyme sites. |
| SEQ ID NO: 46 | Nucleic acid sequence of the CpG12- ApoE/hAAT promoter. |
| SEQ ID NO: 47 | Nucleic acid sequence of the CpG12- ApoE/hAAT promoter with restriction enzyme sites. |
| SEQ ID NO: 48 | Nucleic acid sequence of the CpG13- ApoE/hAAT promoter. |
| SEQ ID NO: 49 | Nucleic acid sequence of the CpG13- ApoE/hAAT promoter with restriction enzyme sites. |

TABLE 2-continued

| SEQ ID NOs and descriptions | |
|---|---|
| SEQ ID NO | Description |
| SEQ ID NO: 50 | Nucleic acid sequence of the CpG14- ApoE/hAAT promoter. |
| SEQ ID NO: 51 | Nucleic acid sequence of the CpG14- ApoE/hAAT promoter with restriction enzyme sites. |
| SEQ ID NO: 52 | Nucleic acid sequence of the CpG15- ApoE/hAAT promoter. |
| SEQ ID NO: 53 | Nucleic acid sequence of the CpG15- ApoE/hAAT promoter with restriction enzyme sites. |
| SEQ ID NO: 54 | Nucleic acid sequence of the CpG16- ApoE/hAAT promoter. |
| SEQ ID NO: 55 | Nucleic acid sequence of the CpG16- ApoE/hAAT promoter with restriction enzyme sites. |
| SEQ ID NO: 56 | Nucleic acid sequence of the CpG17- ApoE/hAAT promoter. |
| SEQ ID NO: 57 | Nucleic acid sequence of the CpG17- ApoE/hAAT promoter with restriction enzyme sites. |
| SEQ ID NO: 58 | Nucleic acid sequence of the CpG18- ApoE/hAAT promoter. |
| SEQ ID NO: 59 | Nucleic acid sequence of the CpG18- ApoE/hAAT promoter with restriction enzyme sites. |
| SEQ ID NO: 60 | Nucleic acid sequence of the CpG19- ApoE/hAAT promoter. |
| SEQ ID NO: 61 | Nucleic acid sequence of the CpG19- ApoE/hAAT promoter with restriction enzyme sites. |
| SEQ ID NO: 62 | Nucleic acid sequence of the CpG20- ApoE/hAAT promoter. |
| SEQ ID NO: 63 | Nucleic acid sequence of the CpG20- ApoE/hAAT promoter with restriction enzyme sites. |
| SEQ ID NO: 64 | Nucleic acid sequence of the CpG21- ApoE/hAAT promoter. |
| SEQ ID NO: 65 | Nucleic acid sequence of the CpG21- ApoE/hAAT promoter with restriction enzyme sites. |
| SEQ ID NO: 66 | Nucleic acid sequence of the CpG22- ApoE/hAAT promoter. |
| SEQ ID NO: 67 | Nucleic acid sequence of the CpG22- ApoE/hAAT promoter with restriction enzyme sites. |
| SEQ ID NO: 68 | The amino acid sequence of FVIII-BDD. |
| SEQ ID NO: 69 | The amino acid sequence of SFSQNPPVLKRHQR (SEQ ID NO: 69) ("SQ sequence"). |
| SEQ ID NO: 70 | The wild-type nucleic acid sequence encoding FVIII-BDD. |
| SEQ ID NO: 71 | Nucleic acid sequence encoding FVIII-BDD. |
| SEQ ID NO: 72 | Nucleic acid sequence encoding FVIII-BDD. |
| SEQ ID NO: 73 | Nucleic acid sequence encoding FVIII-BDD. |
| SEQ ID NO: 74 | Nucleic acid sequence encoding FVIII-BDD. |
| SEQ ID NO: 75 | Nucleic acid sequence encoding FVIII-BDD. |
| SEQ ID NO: 76 | Nucleic acid sequence encoding FVIII-BDD. |
| SEQ ID NO: 77 | Nucleic acid sequence encoding FVIII-BDD. |
| SEQ ID NO: 78 | Nucleic acid sequence encoding FVIII-BDD. |
| SEQ ID NO: 79 | Nucleic acid sequence encoding FVIII-BDD. |
| SEQ ID NO: 80 | Nucleic acid sequence encoding FVIII-BDD. |
| SEQ ID NO: 81 | Nucleic acid sequence encoding FVIII-BDD. |
| SEQ ID NO: 82 | Nucleic acid sequence encoding FVIII-BDD. |
| SEQ ID NO: 83 | Nucleic acid sequence encoding FVIII-BDD. |
| SEQ ID NO: 84 | Nucleic acid sequence encoding FVIII-BDD. |
| SEQ ID NO: 85 | Nucleic acid sequence encoding FVIII-BDD. |
| SEQ ID NO: 86 | Nucleic acid sequence encoding FVIII-BDD. |
| SEQ ID NO: 87 | Nucleic acid sequence encoding FVIII-BDD. |
| SEQ ID NO: 88 | Nucleic acid sequence encoding FVIII-BDD. |
| SEQ ID NO: 89 | cDNA encoding FVIII-V3 |
| SEQ ID NO: 90 | cDNA encoding FVIII-CO3 |
| SEQ ID NO: 91 | LK03 capsid protein |
| SEQ ID NO: 92 | SPK capsid protein |
| SEQ ID NO: 93 | Nucleic acid sequence of intron in AAV-WINT cassette. |
| SEQ ID NO: 94 | Nucleic acid encoding human FIX |
| SEQ ID NO: 95 | Forward primer |
| SEQ ID NO: 96 | Reverse primer |
| SEQ ID NO: 97 | Probe |

Entire nucleic acid sequence of AAV-INTL expression cassette (5' ITR, TTRm, hFVIII-BDD, PolyA, and 3'ITR) (SEQ ID NO:1) and legend (Table 3):

```
cctgcaggcagctgcgcgctcgctcgctcactgaggccgcccgggcaaagcccgggcgtcgg

gcgacctttggtcgcccggcctcagtgagcgagcgagcgcgcagagagggagtggccaactc

catcactaggggttcctgtcgacgtgtctgtctgcacatttcgtagagcgagtgttccgata

ctctaatctccctaggcaaggttcatattgacttaggttacttattctccttttgttgacta

agtcaataatcagaatcagcaggtttggagtcagcttggcagggatcagcagcctgggttgg
```

-continued aaggagggggtataaaagccccttcaccaggagaagccgtcacacagatccacaagctcctg ctagcgtttaaacgccaccatgcagattgagctgagcacctgcttcttcctgtgtctgctga ggttctgcttctctgccaccaggaggtattacctgggggctgtggagctgagctgggactat atgcagtctgacctgggggagctgcctgtggatgctaggttcccccccagggtgcccaagag cttcccctttaacacttctgtggtgtacaagaagaccctgtttgtggagttcactgaccacc tgttcaacattgccaagcccaggccccccctggatggggctgctggggcccaccatccaggct gaggtgtatgacactgtggtgatcaccctgaagaacatggccagccaccctgtgagcctgca tgctgtgggggtgagctactggaaggcttctgagggggctgagtatgatgaccagactagcc agagggagaaggaggatgacaaggtgtttcctgggggcagccatacctatgtgtggcaggtg ctgaaggagaatggccccatggcctctgacccccctgtgcctgacctacagctacctgtctca tgtggacctggtgaaggacctgaactctggcctgattggggctctgctggtgtgtagggagg gcagcctggctaaggaaaagacccagaccctgcataagtttatcctgctgtttgctgtgttt gatgagggcaagagctggcactctgagaccaagaacagcctgatgcaggatagggatgctgc ctctgccagggcttggcctaagatgcacactgtgaatgggtatgtgaataggagcctgcctg gcctgattggctgccacaggaagtctgtgtactggcatgtgattgggatgggcaccacccct gaggtccatagcatcttcctggagggccacactttcctggtgaggaaccacagacaggcctc tctggagatctctcccatcaccttcctgactgctcagactctgctgatggacctgggccagt tcctgctgttttgccatattagcagccaccagcatgatgggatggaggcctatgtgaaggtg gatagctgccctgaggagcctcagctgaggatgaagaacaatgaggaggctgaagactatga tgatgacctgactgattctgagatggatgtggtgaggtttgatgatgacaatagccccagct tcattcagatcaggtctgtggccaagaaacaccccaagacctgggtgcactacattgctgct gaggaagaggactgggactatgctcccctggtgctggcccctgatgataggtcttataagag ccagtacctgaacaatgggccccagaggattggcaggaagtacaagaaggtgaggttcatgg cctacactgatgaaaccttcaaaaccagggaggccattcagcatgagtctggcatcctgggc cctctgctgtatggggaggtgggggacaccctgctgatcatcttcaagaaccaggccagcag gccctacaacatctatcctcatggcatcactgatgtgaggcccctgtacagcaggaggctgc ccaaggggggtgaagcacctgaaagacttccccatcctgcctggggagatctttaagtataag tggactgtgactgtggaggatggccctaccaagtctgaccccaggtgtctgaccaggtacta ttctagctttgtgaacatggagagggacctggcctctggcctgattgggcccctgctgatct gctacaaggagtctgtggaccagaggggcaaccagatcatgtctgacaagaggaatgtgatc ctgttttctgtgtttgatgagaataggagctggtacctgactgagaacatccagaggtttct gcccaatcctgctggggtgcagctggaggatcctgagttccaggccagcaatatcatgcata gcatcaatggctatgtgtttgacagcctgcagctgtctgtgtgcctgcatgaggtggcctac tggtacatcctgagcattggggcccagactgactttctgtctgtgttcttttctggctatac cttcaagcacaagatggtgtatgaggataccctgaccctgttccccttctctggggagactg tgttcatgagcatggagaatcctgggctgtggatcctggggtgccacaactctgattttagg aacaggggggatgactgccctgctgaaggtgtctagctgtgataagaacactggggactacta tgaggacagctatgaggacatttctgcttatctgctgtctaagaataatgccattgagccca gaagcttcagccagaatccccctgtgctgaagagacatcagagggagatcaccagaactacc ctgcagtctgatcaggaggagattgactatgatgacactatctctgtggagatgaagaagga -continued ggactttgacatctatgatgaggatgagaatcagtctcccaggagctttcagaagaagacca gacattacttcattgctgctgtggagaggctgtgggactatggcatgagctctagccctcat gtgctgaggaacagggcccagtctggctctgtgccccagttcaagaaggtggtgttccagga attcactgatggcagcttcacccagcccctgtacagggggggagctgaatgagcacctgggcc tgctggggccttatatcagggctgaggtggaggataatattatggtgactttcaggaaccag gccagcaggccctactctttctatagcagcctgatctcttatgaggaggatcagaggcaggg ggctgagcctaggaagaactttgtgaagcccaatgagactaagacctacttctggaaggtcc agcaccacatggcccctaccaaggatgagtttgactgcaaggcctgggcctatttctctgat gtggatctggagaaggatgtccattctgggctgattggcccccctgctggtgtgccacactaa cactctgaatcctgcccatggcaggcaggtgactgtccaggagtttgccctgttcttcacta tctttgatgagaccaagagctggtactttactgagaacatggagaggaactgcagagctcct tgcaatattcagatggaggaccccaccttcaaggagaattacaggttccatgccattaatgg gtacatcatggacaccctgcctggcctggtgatggctcaggaccagaggatcaggtggtacc tgctgagcatgggctctaatgagaatatccacagcatccacttctctgggcatgtgttcact gtgaggaagaaggaggagtacaagatggctctgtataatctgtaccctggggtgtttgaaac tgtggagatgctgccctctaaggctggcatctggagggtggagtgcctgattggggagcacc tgcatgctggcatgagcaccctgttcctggtgtacagcaacaagtgccagacccccctgggc atggcctctggccacatcagggacttccagatcactgcctctggccagtatggccagtgggc ccccaagctggccaggctgcactattctggcagcatcaatgcctggagcaccaaggagccct tcagctggatcaaggtggacctgctggcccccatgatcattcatggcatcaagacccagggg gccaggcagaagttcagctctctgtacatctctcagttcatcatcatgtactctctggatgg gaagaagtggcagacctacaggggcaacagcactggcaccctgatggtgttctttgggaatg tggactcttctggcatcaagcacaacatcttcaatcccccatcattgctaggtatattagg ctgcatcccacccactacagcatcaggtctaccctgaggatggagctgatgggctgtgacct gaactcttgcagcatgcccctgggcatggagtctaaggccatctctgatgcccagattactg ccagcagctacttcaccaacatgtttgccacctggagcccctctaaggccaggctgcatctg caggggaggagcaatgcctggaggcctcaggtgaacaaccccaaggagtggctgcaggtgga tttccagaagaccatgaaggtgactggggtgaccacccaggggggtcaagagcctgctgacca gcatgtatgtgaaggagttcctgatcagcagcagccaggatggccaccagtggactctgttc tttcagaatgggaaggtgaaggtgtttcagggcaatcaggactctttcacccctgtggtgaa cagcctggacccccccctgctgaccagatacctgaggatccacccccagtcttgggtgcatc agattgccctgaggatggaggtgctgggctgtgaggctcaggatctgtactgagcggccgca ataaaagatcagagctctagagatctgtgtgttggtttttgtgtaggaacccctagtgatg gagttggccactccctctctgcgcgctcgctcgctcactgaggccgggcgaccaaaggtcgc ccgacgcccgggctttgcccgggcggcctcagtgagcgagcgagcgcgcagctgcctgcagg

TABLE 3

| Features of SEQ ID NO: 1 | | | |
|---|---|---|---|
| Name | Type | Start | End |
| AAV2 5' ITR | repeat region | 1 | 141 |
| TTRm promoter | promoter | 148 | 372 |
| B-domain deleted, codon-optimized hFVIII | coding sequence | 392 | 4,765 |
| Rabbit beta-globin polyA | poly A signal | 4,774 | 4,819 |
| AAV2 3' ITR | repeat region | 4,820 | 4,960 |

Wild-type TTR promoter (SEQ ID NO:2). The 4 underlined nucleotides are altered in mutated TTR promoter (SEQ ID NO:3), below.

gtgtctgtctgcacatttcgtagagcgagtgttccgatactctaatctccc taggcaaggttcatatttgtgtaggttacttattctccttttgttgactaa gtcaataatcagaatcagcaggtttggagtcagcttggcagggatcagcag cctgggttggaaggagggggtataaaagccccttcaccaggagaagccgtc acacagatccacaagctcctg Mutated TTR promoter (4 nucleotide changes; underlined) "TTRm" (SEQ ID NO:3):

gtgtctgtctgcacatttcgtagagcgagtgttccgatactctaatctccc taggcaaggttcatattgacttaggttacttattctccttttgttgactaa gtcaataatcagaatcagcaggtttggagtcagcttggcagggatcagcag cctgggttggaaggagggggtataaaagccccttcaccaggagaagccgtc acacagatccacaagctcctg Nucleic acid sequence of CpG1-TTRm (SEQ ID NO:4). In CpG1, every C is changed to T for all four CpGs (double underlined). M1uI (acgcgt) and PmeI (gtttaaac) restriction sites are at the 5' and 3' ends, respectively, when the sequence was cloned into the FVIII expression cassette. SEQ ID NO:5 is CpG1-TTRm with these restriction enzyme sites (underlined).

SEQ ID NO:4:

gtgtctgtctgcacattttgtagagtgagtgttctgatactctaatctccc taggcaaggttcatattgacttaggttacttattctccttttgttgactaa gtcaataatcagaatcagcaggtttggagtcagcttggcagggatcagcag cctgggttggaaggagggggtataaaagccccttcaccaggagaagctgtc acacagatccacaagctcctg

SEQ ID NO:5:

acgcgtgtctgtctgcacattttgtagagtgagtgttctgatactctaat ctccctaggcaaggttcatattgacttaggttacttattctccttttgtt gactaagtcaataatcagaatcagcaggtttggagtcagcttggcaggga tcagcagcctgggttggaaggagggggtataaaagccccttcaccaggag aagctgtcacacagatccacaagctcctgtttaaac Nucleic acid sequence of CpG2-TTRm (SEQ ID NO:6). In CpG2, the C is changed to T in the second, third and fourth CpG (double underlined). M1uI (acgcgt) and PmeI (gtttaaac) restriction sites are at the 5' and 3' ends, respectively, when the sequence was cloned into the FVIII expression cassette. SEQ ID NO:7 is CpG2-TTRm with these restriction enzyme sites (underlined).

SEQ ID NO:6:

gtgtctgtctgcacatttcgtagagtgagtgttctgatactctaatctccc taggcaaggttcatattgacttaggttacttattctccttttgttgactaa gtcaataatcagaatcagcaggtttggagtcagcttggcagggatcagcag cctgggttggaaggagggggtataaaagccccttcaccaggagaagctgtc acacagatccacaagctcctg

SEQ ID NO:7:

acgcgtgtctgtctgcacatttcgtagagtgagtgttctgatactctaat ctccctaggcaaggttcatattgacttaggttacttattctccttttgtt gactaagtcaataatcagaatcagcaggtttggagtcagcttggcaggga tcagcagcctgggttggaaggagggggtataaaagccccttcaccaggag aagctgtcacacagatccacaagctcctgtttaaac Nucleic acid sequence of CpG3-TTRm (SEQ ID NO:8). In CpG3, the C is changed to T in the first, third and fourth CpG (double underlined). M1uI (acgcgt) and PmeI (gtttaaac) restriction sites are at the 5' and 3' ends, respectively, when the sequence was cloned into the FVIII expression cassette. SEQ ID NO:9 is CpG3-TTRm with these restriction enzyme sites (underlined).

SEQ ID NO:8:

gtgtctgtctgcacattttgtagagcgagtgttctgatactctaatctccc taggcaaggttcatattgacttaggttacttattctccttttgttgactaa gtcaataatcagaatcagcaggtttggagtcagcttggcagggatcagcag cctgggttggaaggagggggtataaaagccccttcaccaggagaagctgtc acacagatccacaagctcctg

SEQ ID NO:9:

acgcgtgtctgtctgcacattttgtagagcgagtgttctgatactctaat ctccctaggcaaggttcatattgacttaggttacttattctccttttgtt gactaagtcaataatcagaatcagcaggtttggagtcagcttggcaggga tcagcagcctgggttggaaggagggggtataaaagccccttcaccaggag aagctgtcacacagatccacaagctcctgtttaaac Nucleic acid sequence of CpG4-TTRm (SEQ ID NO:10). In CpG4, the C is changed to T in the first, second and fourth CpG (double underlined). M1uI (acgcgt) and PmeI (gtttaaac) restriction sites are at the 5' and 3' ends, respectively, when the sequence was cloned into the FVIII expression cassette. SEQ ID NO:11 is CpG4-TTRm with these restriction enzyme sites (underlined).

SEQ ID NO:10:

gtgtctgtctgcacattttgtagagtgagtgttccgatactctaatctccc
taggcaaggttcatattgacttaggttacttattctccttttgttgactaa
gtcaataatcagaatcagcaggtttggagtcagcttggcagggatcagcag
cctgggttggaaggagggggtataaaagccccttcaccaggagaagctgtc
acacagatccacaagctcctg

SEQ ID NO:11:

acgcgtgtctgtctgcacattttgtagagtgagtgttccgatactctaat
ctccctaggcaaggttcatattgacttaggttacttattctccttttgtt
gactaagtcaataatcagaatcagcaggtttggagtcagcttggcaggga
tcagcagcctgggttggaaggagggggtataaaagccccttcaccaggag
aagctgtcacacagatccacaagctcctgtttaaac Nucleic acid sequence of CpG5-TTRm (SEQ ID NO:12). In CpG5, the C is changed to T in the first, second and third CpG (double underlined). M1uI (acgcgt) and PmeI (gtttaaac) restriction sites are at the 5' and 3' ends, respectively, when the sequence was cloned into the FVIII expression cassette. SEQ ID NO:13 is CpG5-TTRm with these restriction enzyme sites (underlined).

SEQ ID NO:12:

gtgtctgtctgcacattttgtagagtgagtgttctgatactctaatctccc
taggcaaggttcatattgacttaggttacttattctccttttgttgactaa
gtcaataatcagaatcagcaggtttggagtcagcttggcagggatcagcag
cctgggttggaaggagggggtataaaagccccttcaccaggagaagccgtc
acacagatccacaagctcctg

SEQ ID NO:13:

acgcgtgtctgtctgcacattttgtagagtgagtgttctgatactctaat
ctccctaggcaaggttcatattgacttaggttacttattctccttttgtt
gactaagtcaataatcagaatcagcaggtttggagtcagcttggcaggga
tcagcagcctgggttggaaggagggggtataaaagccccttcaccaggag
aagccgtcacacagatccacaagctcctgtttaaac Nucleic acid sequence of Hybrid6 promoter (TTR/hAAT/albumin hybrid) (SEQ ID NO:14). The G is changed to A in the single CpG dinucleotide (double underlined). M1uI (acgcg) and PmeI (gtttaaac) restriction sites are at the 5' and 3' ends, respectively, when the sequence was cloned into the FVIII expression cassette. (Italics=TTR, Underline=albumin, Bold=hAAT.) SEQ ID NO:15 is Hybrid6 promoter with these restriction enzyme sites.

TAGGCAAGGTTCATATTGACTTAGGTTACTTATTCTCCTTTTGCCTGCTGA
CCTTGGAGCTGGGGCAGAGGTCAGAGGAGTCAGCTTGGCAGGGATCAGCAG
ATGAATTTTGTAATCAGTTCCCTTGAGTCATTAAAAAATATAAAACAAAGA
TGAGTCTAGTTAATAATCTACAAT

Nucleic acid sequence of Hybrid7 promoter (TTR/hAAT hybrid) (SEQ ID NO:16). The C is changed to T in both CpG dinucleotides (double underlined). M1uI (acgcg) and PmeI (gtttaaac) restriction sites are at the 5' and 3' ends, respectively, when the sequence was cloned into the FVIII expression cassette. (Italics=TTR, Bold=hAAT.) SEQ ID NO:17 is Hybrid7 promoter with these restriction enzyme sites.

TAGGCAAGGTTCATATTGACTTAGGTTACTTATTCTCCTTTTGATAACTGG
GGTGACCTTGGTTAATATTCACCAGCAGAGTCAGCTTGGCAGGGATCAGCA
GCCTGGGTTGGAAGGAGGGGGTATAAAATGATAACTGGGGTGACCTTGGTT
AATATTCACCAGCA

Nucleic acid sequence of Hybrid8 promoter (TTR/FGG (fribrinogen gamma chain gene promoter)/albumin promoter hybrid) (SEQ ID NO:18). The G is changed to A in the single CpG dinucleotide (double underlined). M1uI (acgcgt) and PmeI (gtttaaac) restriction sites are at the 5' and 3' ends, respectively, when the sequence was cloned into the FVIII expression cassette. (Underline=albumin, Underline italics=FGG, Italics=TTR.) SEQ ID NO:19 is Hybrid8 promoter with these restriction enzyme sites.

ACTCCCTTGAGTCATTAAAAAAATATATTTGGTAATTCATAAACCTTACAA
ACATTTACTTAACACTTACCATGAATTGGGTAATGTGCTCAATTGACTTAG
GTTACTTATTCTCCTTTTGAATTTTTTGGCAAGAATATTATGAATTTTGTA
ATCAGTTATAAAGGCAGCCAATGAAATACAAAGATGAGTCTAGTTAATAAT
CTACAAT

Nucleic acid sequence of Hybrid9 promoter (TTR/FGG/hAAT/SAA1 hybrid) (SEQ ID NO:20). The C is changed to T in all three CpG dinucleotides (double underlined). M1uI (acgcgt) and PmeI (tttaaac) restriction sites at the 5' and 3' ends, respectively, when the sequence was cloned into the FVIII expression cassette. (Italics=TTR, Bold=hAAT, Underline italics=FGG, Underline bold=SAA1.) SEQ ID NO:21 is Hybrid9 promoter with these restriction enzyme sites.

TAGGCAAGGTTCATATTGACTTAGGTTACTTATTCTCCTTTGGGTGACTCA
GATCCCAGCCAGTGGACTTAGCCCCTGTTTGCTCCTCTGATAACTGGGGTG
ACCTTGGTTAATATTCACCAGCATTTTTGAGTCAATAATAATGTTAACTGA
TCCCTAGGCTATAAAATAATAGTGTTAACTGATCCCTGTGCAGTGGTGTGA
TTATAG

Nucleic acid sequence of non-CpG reduced ApoE/hAAT regulatory element (SEQ ID NO:22). The sequence contains a total of CpGs (double underlined). The C/EBP (CCAAT/enhancer-binding protein) site is underlined.

atgccacctccaacatccactcgaccccttggaatttcggtggagaggagc
agaggttgtcctggcgtggtttaggtagtgtgagaggggtacccggggatc
ttgctaccagtggaacagccactaaggattctgcagtgagagcagagggcc
agctaagtggtactctcccagagactgtctgactcacgccaccccctccac
cttggacacaggacgctgtggtttctgagccaggtacaatgactcctttcg -continued gtaagtgcagtggaagctgtacactgcccaggcaaagcgtccgggcagcgt
aggcgggcgactcagatcccagccagtggacttagcccctgtttgctcctc
cgataactggggtgaccttggttaatattcaccagcagcctcccccgttgc
ccctctggatccactgcttaaatacggacgaggaca Nucleic acid sequence of non-CpG reduced ApoE/hAAT regulatory unit flanked at the 5' and 3' ends by ApaI restriction sites (SEQ ID NO:23). The sequence contains a total of 16 CpGs (double underlined). The ApaI restriction sites were used when the sequence was cloned into the FIX expression cassette.

gggcccatgccacctccaacatccactcgaccccttggaatttcggtggag
aggagcagaggttgtcctggcgtggtttaggtagtgtgagaggggtacccg
gggatcttgctaccagtggaacagccactaaggattctgcagtgagagcag
agggccagctaagtggtactctcccagagactgtctgactcacgccacccc
ctccaccttggacacaggacgctgtggtttctgagccaggtacaatgactc
ctttcggtaagtgcagtggaagctgtacactgcccaggcaaagcgtccggg
cagcgtaggcgggcgactcagatcccagccagtggacttagcccctgtttg
ctcctccgataactggggtgaccttggttaatattcaccagcagcctcccc
cgttgcccctctggatccactgcttaaatacggacgaggacagggccc Nucleic acid sequence of CpG1-ApoE/hAAT (SEQ ID NO:24). Every C changed to T, except in the seventh CpG, where G is changed to A. ApaI restriction sites are at the 5' and 3' ends when the sequence was cloned into the FIX expression cassette. SEQ ID NO:25 is CpG1-ApoE/hAAT with these restriction enzyme sites (underlined).

gggcccatgccacctccaacatccacttgaccccttggaattttggtggag
aggagcagaggttgtcctggtgtggtttaggtagtgtgagaggggtacctg
gggatcttgctaccagtggaacagccactaaggattctgcagtgagagcag
agggccagctaagtggtactctcccagagactgtctgactcatgccacccc
ctccaccttggacacaggatgctgtggtttctgagccaggtacaatgactc
ctttcagtaagtgcagtggaagctgtacactgcccaggcaaagtgtctggg
cagtgtaggtgggtgactcagatcccagccagtggacttagcccctgtttg
ctcctctgataactggggtgaccttggttaatattcaccagcagcctcccc
tgttgcccctctggatccactgcttaaatatggatgaggacagggccc Nucleic acid sequence of CpG2-ApoE/hAAT (SEQ ID NO:26). Every C changed to T, except leave first CpG with no change, and G changed to A in the seventh CpG. The unchanged "c" is in bold. ApaI restriction sites are at the 5' and 3' ends, respectively, when the sequence was cloned into the FIX expression cassette. SEQ ID NO:27 is CpG2-ApoE/hAAT with these restriction enzyme sites (underlined).

gggcccatgccacctccaacatccactcgaccccttggaattttggtgga
gaggagcagaggttgtcctggtgtggtttaggtagtgtgagaggggtacc
tggggatcttgctaccagtggaacagccactaaggattctgcagtgagag
cagagggccagctaagtggtactctcccagagactgtctgactcatgcca
ccccctccaccttggacacaggatgctgtggtttctgagccaggtacaat
gactcctttcagtaagtgcagtggaagctgtacactgcccaggcaaagtg
tctgggcagtgtaggtgggtgactcagatcccagccagtggacttagccc
ctgtttgctcctctgataactggggtgaccttggttaatattcaccagca
gcctcccctgttgcccctctggatccactgcttaaatatggatgaggaca
gggccc Nucleic acid sequence of CpG3-ApoE/hAAT (SEQ ID NO:28). Every C changed to T, except leave second CpG with no change, and G changed to A in the seventh CpG. The unchanged "c" is in bold. ApaI restriction sites are at the 5' and 3' ends when the sequence was cloned into the FIX expression cassette. SEQ ID NO:29 is CpG3-ApoE/hAAT with these restriction enzyme sites (underlined).

gggcccatgccacctccaacatccacttgaccccttggaatttcggtgga
gaggagcagaggttgtcctggtgtggtttaggtagtgtgagaggggtacc
tggggatcttgctaccagtggaacagccactaaggattctgcagtgagag
cagagggccagctaagtggtactctcccagagactgtctgactcatgcca
ccccctccaccttggacacaggatgctgtggtttctgagccaggtacaat
gactcctttcagtaagtgcagtggaagctgtacactgcccaggcaaagtg
tctgggcagtgtaggtgggtgactcagatcccagccagtggacttagccc
ctgtttgctcctctgataactggggtgaccttggttaatattcaccagca
gcctcccctgttgcccctctggatccactgcttaaatatggatgaggaca
gggccc Nucleic acid sequence of CpG4-ApoE/hAAT (SEQ ID NO:30). Every C changed to T, except leave third CpG with no change, and G changed to A in the seventh CpG. The unchanged "c" is in bold. ApaI restriction sites are at the 5' and 3' ends when the sequence was cloned into the FIX expression cassette. SEQ ID NO:31 is CpG4-ApoE/hAAT with these restriction enzyme sites (underlined).

gggcccatgccacctccaacatccacttgaccccttggaattttggtgga
gaggagcagaggttgtcctggcgtggtttaggtagtgtgagaggggtacc
tggggatcttgctaccagtggaacagccactaaggattctgcagtgagag
cagagggccagctaagtggtactctcccagagactgtctgactcatgcca
ccccctccaccttggacacaggatgctgtggtttctgagccaggtacaat
gactcctttcagtaagtgcagtggaagctgtacactgcccaggcaaagtg
tctgggcagtgtaggtgggtgactcagatcccagccagtggacttagccc
ctgtttgctcctctgataactggggtgaccttggttaatattcaccagca
gcctcccctgttgcccctctggatccactgcttaaatatggatgaggaca
gggccc Nucleic acid sequence of CpG5-ApoE/hAAT (SEQ ID NO:32). Every C changed to T, except leave fourth CpG with no change, and G changed to A in the seventh CpG. The unchanged CpG (the fourth) is in bold. ApaI restriction sites are at the 5' and 3' ends when the sequence was cloned into the FIX expression cassette. SEQ ID NO:33 is CpG5-ApoE/hAAT with these restriction enzyme sites (underlined).

gggcccatgccacctccaacatccacttgaccccttggaattttggtgga
gaggagcagaggttgtcctggtgtggtttaggtagtgtgagaggggtacc
cggggatcttgctaccagtggaacagccactaaggattctgcagtgagag
cagagggccagctaagtggtactctcccagagactgtctgactcatgcca
ccccctccaccttggacacaggatgctgtggtttctgagccaggtacaat
gactcctttcagtaagtgcagtggaagctgtacactgcccaggcaaagtg
tctggcagtgtaggtgggtgactcagatcccagccagtggacttagccc
ctgtttgctcctctgataactggggtgaccttggttaatattcaccagca
gcctcccctgttgcccctctggatccactgcttaaatatggatgaggaca
gggccc Nucleic acid sequence of CpG6-ApoE/hAAT (SEQ ID NO:34). Every C changed to T, except leave fifth CpG with no change, and G changed to A in the seventh CpG. The unchanged CpG (the fifth) is in bold. ApaI restriction sites are at the 5' and 3' ends when the sequence was cloned into the FIX expression cassette. SEQ ID NO:35 is CpG6-ApoE/hAAT with these restriction enzyme sites (underlined).

gggcccatgccacctccaacatccacttgaccccttggaattttggtgga
gaggagcagaggttgtcctggtgtggtttaggtagtgtgagaggggtacc
tggggatcttgctaccagtggaacagccactaaggattctgcagtgagag
cagagggccagctaagtggtactctcccagagactgtctgactcacgcca
ccccctccaccttggacacaggatgctgtggtttctgagccaggtacaat
gactcctttcagtaagtgcagtggaagctgtacactgcccaggcaaagtg
tctggcagtgtaggtgggtgactcagatcccagccagtggacttagccc
ctgtttgctcctctgataactggggtgaccttggttaatattcaccagca
gcctcccctgttgcccctctggatccactgcttaaatatggatgaggaca
gggccc Nucleic acid sequence of CpG7-ApoE/hAAT (SEQ ID NO:36). Every C changed to T, except leave sixth CpG with no change, and G changed to A in the seventh CpG. The unchanged CpG (the sixth) is in bold. ApaI restriction sites are at the 5' and 3' ends when the sequence was cloned into the FIX expression cassette. SEQ ID NO:37 is CpG7-ApoE/hAAT with these restriction enzyme sites (underlined).

gggcccatgccacctccaacatccacttgaccccttggaattttggtgga
gaggagcagaggttgtcctggtgtggtttaggtagtgtgagaggggtacc
tggggatcttgctaccagtggaacagccactaaggattctgcagtgagag
cagagggccagctaagtggtactctcccagagactgtctgactcatgcca
ccccctccaccttggacacaggacgctgtggtttctgagccaggtacaat
gactcctttcagtaagtgcagtggaagctgtacactgcccaggcaaagtg
tctggcagtgtaggtgggtgactcagatcccagccagtggacttagccc -continued ctgtttgctcctctgataactggggtgaccttggttaatattcaccagca
gcctcccctgttgcccctctggatccactgcttaaatatggatgaggaca
gggccc Nucleic acid sequence of CpG8-ApoE/hAAT (SEQ ID NO:38). Every C changed to T, except leave seventh site with no change. The unchanged CpG (the seventh) is in bold. ApaI restriction sites are at the 5' and 3' ends when the sequence was cloned into the FIX expression cassette. SEQ ID NO:39 is CpG8-ApoE/hAAT with these restriction enzyme sites (underlined).

gggcccatgccacctccaacatccacttgaccccttggaattttggtgga
gaggagcagaggttgtcctggtgtggtttaggtagtgtgagaggggtacc
tggggatcttgctaccagtggaacagccactaaggattctgcagtgagag
cagagggccagctaagtggtactctcccagagactgtctgactcatgcca
ccccctccaccttggacacaggatgctgtggtttctgagccaggtacaat
gactcctttcggtaagtgcagtggaagctgtacactgcccaggcaaagtg
tctggcagtgtaggtgggtgactcagatcccagccagtggacttagccc
ctgtttgctcctctgataactggggtgaccttggttaatattcaccagca
gcctcccctgttgcccctctggatccactgcttaaatatggatgaggaca
gggccc Nucleic acid sequence of CpG9-ApoE/hAAT (SEQ ID NO:40). Every C changed to T, except leave eighth CpG with no change, and G changed to A in the seventh CpG. The unchanged CpG (the eighth) is in bold. ApaI restriction sites are at the 5' and 3' ends when the sequence was cloned into the FIX expression cassette. SEQ ID NO:41 is CpG9-ApoE/hAAT with these restriction enzyme sites (underlined).

gggcccatgccacctccaacatccacttgaccccttggaattttggtgga
gaggagcagaggttgtcctggtgtggtttaggtagtgtgagaggggtacc
tggggatcttgctaccagtggaacagccactaaggattctgcagtgagag
cagagggccagctaagtggtactctcccagagactgtctgactcatgcca
ccccctccaccttggacacaggatgctgtggtttctgagccaggtacaat
gactcctttcagtaagtgcagtggaagctgtacactgcccaggcaaagcg
tctggcagtgtaggtgggtgactcagatcccagccagtggacttagccc
ctgtttgctcctctgataactggggtgaccttggttaatattcaccagca
gcctcccctgttgcccctctggatccactgcttaaatatggatgaggaca
gggccc Nucleic acid sequence of CpG10-ApoE/hAAT (SEQ ID NO:42). Every C changed to T, except leave ninth SpG with no change, and G changed to A in the seventh CpG. The unchanged CpG (the ninth) is in bold. ApaI restriction sites are at the 5' and 3' ends when the sequence was cloned into the FIX expression cassette. SEQ ID NO:43 is CpG10-ApoE/hAAT with these restriction enzyme sites (underlined).

-continued gggcccatgccacctccaacatccacttgaccccttggaatttggtgga
gaggagcagaggttgtcctggtgtggtttaggtagtgtgagaggggtacc
tggggatcttgctaccagtggaacagccactaaggattctgcagtgagag
cagagggccagctaagtggtactctcccagagactgtctgactcatgcca
cccctccaccttggacacaggatgctgtggtttctgagccaggtacaat
gactcctttcagtaagtgcagtggaagctgtacactgcccaggcaaagtg
tccgggcagtgtaggtgggtgactcagatcccagccagtggacttagccc
ctgtttgctcctctgataactggggtgaccttggttaatattcaccagca
gcctcccctgttgcccctctggatccactgcttaaatatg
gatgaggacagggccc Nucleic acid sequence of CpG11-ApoE/hAAT (SEQ ID NO:44). Every C changed to T, except leave tenth CpG with no change, and G changed to A in the seventh CpG. The unchanged CpG (the tenth) is in bold. ApaI restriction sites are at the 5' and 3' ends when the sequence was cloned into the FIX expression cassette. SEQ ID NO:45 is CpG11-ApoE/hAAT with these restriction enzyme sites (underlined).

gggcccatgccacctccaacatccacttgaccccttggaatttggtgga
gaggagcagaggttgtcctggtgtggtttaggtagtgtgagaggggtacc
tggggatcttgctaccagtggaacagccactaaggattctgcagtgagag
cagagggccagctaagtggtactctcccagagactgtctgactcatgcca
cccctccaccttggacacaggatgctgtggtttctgagccaggtacaat
gactcctttcagtaagtgcagtggaagctgtacactgcccaggcaaagtg
tctgggcagcgtaggtgggtgactcagatcccagccagtggacttagccc
ctgtttgctcctctgataactggggtgaccttggttaatattcaccagca
gcctcccctgttgcccctctggatccactgcttaaatatggatgaggaca
gggccc Nucleic acid sequence of CpG12-ApoE/hAAT (SEQ ID NO:46). Every C changed to T, except leave eleventh CpG with no change, and G changed to A in the seventh CpG. The unchanged CpG (the eleventh) is in bold. ApaI restriction sites are at the 5' and 3' ends when the sequence was cloned into the FIX expression cassette. SEQ ID NO:47 is CpG12-ApoE/hAAT with these restriction enzyme sites (underlined).

gggcccatgccacctccaacatccacttgaccccttggaatttggtgga
gaggagcagaggttgtcctggtgtggtttaggtagtgtgagaggggtacc
tggggatcttgctaccagtggaacagccactaaggattctgcagtgagag
cagagggccagctaagtggtactctcccagagactgtctgactcatgcca
cccctccaccttggacacaggatgctgtggtttctgagccaggtacaat
gactcctttcagtaagtgcagtggaagctgtacactgcccaggcaaagtg
tctgggcagtgtaggcgggtgactcagatcccagccagtggacttagccc
ctgtttgctcctctgataactggggtgaccttggttaatattcaccagca
gcctcccctgttgcccctctggatccactgcttaaatatggatgaggaca
gggccc Nucleic acid sequence of CpG13-ApoE/hAAT (SEQ ID NO:48). Every C changed to T, except leave twelfth CpG with no change, and G changed to A in the seventh CpG. The unchanged CpG (the twelfth) is in bold. ApaI restriction sites are at the 5' and 3' ends when the sequence was cloned into the FIX expression cassette. SEQ ID NO:49 is CpG13-ApoE/hAAT with these restriction enzyme sites (underlined).

gggcccatgccacctccaacatccacttgaccccttggaatttggtgga
gaggagcagaggttgtcctggtgtggtttaggtagtgtgagaggggtacc
tggggatcttgctaccagtggaacagccactaaggattctgcagtgagag
cagagggccagctaagtggtactctcccagagactgtctgactcatgcca
cccctccaccttggacacaggatgctgtggtttctgagccaggtacaat
gactcctttcagtaagtgcagtggaagctgtacactgcccaggcaaagtg
tctgggcagtgtaggtgggcgactcagatcccagccagtggacttagccc
ctgtttgctcctctgataactggggtgaccttggttaatattcaccagca
gcctcccctgttgcccctctggatccactgcttaaatatg
gatgaggacagggccc Nucleic acid sequence of CpG14-ApoE/hAAT (SEQ ID NO:50). Every C changed to T, except leave thirteenth CpG with no change, and G changed to A in the seventh CpG. The unchanged CpG (the thirteenth) is in bold. ApaI restriction sites are at the 5' and 3' ends when the sequence was cloned into the FIX expression cassette. SEQ ID NO:51 is CpG14-ApoE/hAAT with these restriction enzyme sites (underlined).

gggcccatgccacctccaacatccacttgaccccttggaatttggtgga
gaggagcagaggttgtcctggtgtggtttaggtagtgtgagaggggtacc
tggggatcttgctaccagtggaacagccactaaggattctgcagtgagag
cagagggccagctaagtggtactctcccagagactgtctgactcatgcca
cccctccaccttggacacaggatgctgtggtttctgagccaggtacaat
gactcctttcagtaagtgcagtggaagctgtacactgcccaggcaaagtg
tctgggcagtgtaggtgggtgactcagatcccagccagtggacttagccc
ctgtttgctcctccgataactggggtgaccttggttaatattcaccagca
gcctcccctgttgcccctctggatccactgcttaaatatggatgaggaca
gggccc Nucleic acid sequence of CpG15-ApoE/hAAT (SEQ ID NO:52). Every C changed to T, except leave fourteenth CpG with no change, and G changed to A in the seventh CpG. The unchanged CpG (the fourteenth) is in bold. ApaI restriction sites are at the 5' and 3' ends when the sequence was cloned into the FIX expression cassette. SEQ ID NO:53 is CpG15-ApoE/hAAT with these restriction enzyme sites (underlined).

gggcccatgccacctccaacatccacttgaccccttggaatttggtgga
gaggagcagaggttgtcctggtgtggtttaggtagtgtgagaggggtacc
tggggatcttgctaccagtggaacagccactaaggattctgcagtgagag
cagagggccagctaagtggtactctcccagagactgtctgactcatgcca
cccctccaccttggacacaggatgctgtggtttctgagccaggtacaat
gactcctttcagtaagtgcagtggaagctgtacactgcccaggcaaagtg
tctgggcagtgtaggtgggtgactcagatcccagccagtggacttagccc
ctgtttgctcctctgataactggggtgaccttggttaatattcaccagca
gcctcccccgttgcccctctggatccactgcttaaatatggatgaggaca
gggccc Nucleic acid sequence of CpG16-ApoE/hAAT (SEQ ID NO:54). Every C changed to T, except leave fifteenth CpG with no change, and G changed to A in the seventh CpG. The unchanged CpG (the fifteenth) is in bold. ApaI restriction sites are at the 5' and 3' ends when the sequence was cloned into the FIX expression cassette. SEQ ID NO:55 is CpG16-ApoE/hAAT with these restriction enzyme sites (underlined).

gggcccatgccacctccaacatccacttgaccccttggaatttggtgga
gaggagcagaggttgtcctggtgtggtttaggtagtgtgagaggggtacc
tggggatcttgctaccagtggaacagccactaaggattctgcagtgagag
cagagggccagctaagtggtactctcccagagactgtctgactcatgcca
cccctccaccttggacacaggatgctgtggtttctgagccaggtacaat
gactcctttcagtaagtgcagtggaagctgtacactgcccaggcaaagtg
tctgggcagtgtaggtgggtgactcagatcccagccagtggacttagccc
ctgtttgctcctctgataactggggtgaccttggttaatattcaccagca
gcctcccctgttgcccctctggatccactgcttaaatacggatgaggaca
gggccc Nucleic acid sequence of CpG17-ApoE/hAAT (SEQ ID NO:56). Every C changed to T, except leave the sixteenth CpG with no change, and G changed to A in the seventh CpG. The unchanged CpG (the sixteenth) is in bold. ApaI restriction sites are at the 5' and 3' ends when the sequence was cloned into the FIX expression cassette. SEQ ID NO:57 is CpG17-ApoE/hAAT with these restriction enzyme sites (underlined).

gggcccatgccacctccaacatccacttgaccccttggaa
tttggtggagaggagcagaggttgtcctggtgtggttta
ggtagtgtgagaggggtacctggggatcttgctaccagtg
gaacagccactaaggattctgcagtgagagcagagggcca
gctaagtggtactctcccagagactgtctgactcatgcca
cccctccaccttggacacaggatgctgtggtttctgagc
caggtacaatgactcctttcagtaagtgcagtggaagctg
tacactgcccaggcaaagtgtctgggcagtgtaggtggg -continued tgactcagatcccagccagtggacttagcccctgtttgc
tcctctgataactggggtgaccttggttaatattcacca
gcagcctcccctgttgcccctctggatccactgcttaaa
tatggacgaggacagggccc Nucleic acid sequence of CpG18-ApoE/hAAT (SEQ ID NO:58). The C of the fifth, seventh, eighth, tenth and eleventh CpG is removed, and C is changed to T for the remaining CpGs. ApaI restriction sites are at the 5' and 3' ends when the sequence was cloned into the FIX expression cassette. SEQ ID NO:59 is CpG18-ApoE/hAAT with these restriction enzyme sites (underlined).

gggcccatgccacctccaacatccacttgaccccttggaatttggtgga
gaggagcagaggttgtcctggtgtggtttaggtagtgtgagaggggtacc
tggggatcttgctaccagtggaacagccactaaggattctgcagtgagag
cagagggccagctaagtggtactctcccagagactgtctgactcagccac
ccctccaccttggacacaggatgctgtggtttctgagccaggtacaatg
actcctttggtaagtgcagtggaagctgtacactgcccaggcaaaggtc
tgggcaggtagggggtgactcagatcccagccagtggacttagcccctgt
ttgctcctctgataactggggtgaccttggttaatattcaccagcagcct
cccctgttgcccctctggatccactgcttaaatatggatgaggaca
gggccc Nucleic acid sequence of CpG19-ApoE/hAAT (SEQ ID NO:60). C changed to T in the first through fifth and eighth through eleventh CpG, and the C of the seventh CpG is removed. All remaining CpGs (sixth and twelfth through sixteenth) are unchanged (bold). ApaI restriction sites are at the 5' and 3' ends when the sequence was cloned into the FIX expression cassette. SEQ ID NO:61 is CpG19-ApoE/hAAT with these restriction enzyme sites (underlined).

gggcccatgccacctccaacatccacttgaccccttggaatttggtgga
gaggagcagaggttgtcctggtgtggtttaggtagtgtgagaggggtacc
tggggatcttgctaccagtggaacagccactaaggattctgcagtgagag
cagagggccagctaagtggtactctcccagagactgtctgactcatgcca
cccctccaccttggacacaggacgctgtggtttctgagccaggtacaat
gactcctttggtaagtgcagtggaagctgtacactgcccaggcaaagtgt
ctgggcagtgtaggtgggcgactcagatcccagccagtggacttagcccc
tgtttgctcctccgataactggggtgaccttggttaatattcaccagcag
cctcccccgttgcccctctggatccactgcttaaatacggacgaggaca
gggccc Nucleic acid sequence of CpG20-ApoE/hAAT (SEQ ID NO:62). Result of multiple deletions of regions without putative transcription factor binding sites. G changed to A in the only remaining CpG (the seventh CpG of SEQ ID NO:22). ApaI restriction sites are at the 5' and 3' ends when the sequence was cloned into the FIX expression cassette. SEQ ID NO:63 is CpG20-ApoE/hAAT with these restriction enzyme sites (underlined).

gggcccatgccacctccaaggagcagaggtgatcttgctaccagtggaga gcagagggccagctctcccagagactgtctgactcagccacccccctccac cttggacacaggaggtttctgagccatcctttcagtaagtgcatgtacac tgcccagctgggcagctcagatcccagccagtggacttagcccctgtttg ctcctctgataactggggtgaccttggttaatattcaccagcagcctgtt gcccctctggatccactgcttaaagggccc Nucleic acid sequence of CpG21-ApoE/hAAT (SEQ ID NO:64). C changed to T in all CpGs, except the fifth and sixth CpGs, where G is changed to C and A, respectively. ApaI restriction sites are at the 5' and 3' ends when the sequence was cloned into the FIX expression cassette. SEQ ID NO:65 is CpG21-ApoE/hAAT with these restriction enzyme sites (underlined).

gggcccatgccacctccaacatccacttgaccccttggaatttggtgga gaggagcagaggttgtcctggtgtggtttaggtagtgtgagaggggtacc tggggatcttgctaccagtggaacagccactaaggattctgcagtgagag cagagggccagctaagtggtactctcccagagactgtctgactcaccccca cccctccaccttggacacaggacactgtggtttctgagccaggtacaat gactccttttggtaagtgcagtggaagctgtacactgcccaggcaaagtg tctggcagtgtaggtgggtgactcagatcccagccagtggacttagccc ctgtttgctcctctgataactggggtgaccttggttaatattcaccagca gcctccccctgttgcccctctggatccactgcttaaatatggatgaggaca gggccc Nucleic acid sequence of CpG22-ApoE/hAAT (SEQ ID NO:66). C changed to T in all CpGs, except leave fifth CpG with no change (bold), and change G to A in the sixth CpG. ApaI restriction sites are at the 5' and 3' ends when the sequence was cloned into the FIX expression cassette. SEQ ID NO:67 is CpG22-ApoE/hAAT with these restriction enzyme sites (underlined).

gggcccatgccacctccaacatccacttgaccccttggaatttggtgga gaggagcagaggttgtcctggtgtggtttaggtagtgtgagaggggtacc tggggatcttgctaccagtggaacagccactaaggattctgcagtgagag cagagggccagctaagtggtactctcccagagactgtctgactcacgcca cccctccaccttggacacaggacactgtggtttctgagccaggtacaat gactccttttggtaagtgcagtggaagctgtacactgcccaggcaaagtg tctggcagtgtaggtgggtgactcagatcccagccagtggacttagccc ctgtttgctcctctgataactggggtgaccttggttaatattcaccagca -continued gcctccccctgttgcccctctggatccactgcttaaatatggatgaggaca gggccc Amino Acid Sequence of FVIII-BDD (SQ Sequence Bold/Underlined) (SEQ ID NO:68).

MQIELSTCFFLCLLRFCFSATRRYYLGAVELSWDYMQSDLGELPVDARFP

PRVPKSFPFNTSVVYKKTLFVEFTDHLFNIAKPRPPWMGLLGPTIQAEVY

DTVVITLKNMASHPVSLHAVGVSYWKASEGAEYDDQTSQREKEDDKVFPG

GSHTYVWQVLKENGPMASDPLCLTYSYLSHVDLVKDLNSGLIGALLVCRE

GSLAKEKTQTLHKFILLFAVFDEGKSWHSETKNSLMQDRDAASARAWPKM

HTVNGYVNRSLPGLIGCHRKSVYWHVIGMGTTPEVHSIFLEGHTFLVRNH

RQASLEISPITFLTAQTLLMDLGQFLLFCHISSHQHDGMEAYVKVDSCPE

EPQLRMKNNEEAEDYDDDLTDSEMDVVRFDDDNSPSFIQIRSVAKKHPKT

WVHYIAAEEEDWDYAPLVLAPDDRSYKSQYLNNGPQRIGRKYKKVRFMAY

TDETFKTREAIQHESGILGPLLYGEVGDTLLIIFKNQASRPYNIYPHGIT

DVRPLYSRRLPKGVKHLKDFPILPGEIFKYKWTVTVEDGPTKSDPRCLTR

YYSSFVNMERDLASGLIGPLLICYKESVDQRGNQIMSDKRNVILFSVFDE

NRSWYLTENIQRFLPNPAGVQLEDPEFQASNIMHSINGYVFDSLQLSVCL

HEVAYWYILSIGAQTDFLSVFFSGYTFKHKMVYEDTLTLFPFSGETVFMS

MENPGLWILGCHNSDFRNRGMTALLKVSSCDKNTGDYYEDSYEDISAYLL

SKNNAIEPRSFSQNPPVLKRHQREITRTTLQSDQEEIDYDDTISVEMKKE

DFDIYDEDENQSPRSFQKKTRHYFIAAVERLWDYGMSSSPHVLRNRAQSG

SVPQFKKVVFQEFTDGSFTQPLYRGELNEHLGLLGPYIRAEVEDNIMVTF

RNQASRPYSFYSSLISYEEDQRQGAEPRKNFVKPNETKTYFWKVQHHMAP

TKDEFDCKAWAYFSDVDLEKDVHSGLIGPLLVCHTNTLNPAHGRQVTVQE

FALFFTIFDETKSWYFTENMERNCRAPCNIQMEDPTFKENYRFHAINGYI

MDTLPGLVMAQDQRIRWYLLSMGSNENIHSIHFSGHVFTVRKKEEYKMAL

YNLYPGVFETVEMLPSKAGIWRVECLIGEHLHAGMSTLFLVYSNKCQTPL

GMASGHIRDFQITASGQYGQWAPKLARLHYSGSINAWSTKEPFSWIKVDL

LAPMIIHGIKTQGARQKFSSLYISQFIIMYSLDGKKWQTYRGNSTGTLMV

FFGNVDSSGIKHNIFNPPIIARYIRLHPTHYSIRSTLRMELMGCDLNSCS

MPLGMESKAISDAQITASSYFTNMFATWSPSKARLHLQGRSNAWRPQVNN

PKEWLQVDFQKTMKVTGVTTQGVKSLLTSMYVKEFLISSSQDGHQWTLFF

QNGKVKVFQGNQDSFTPVVNSLDPPLLTRYLRIHPQSWVHQIALRMEVLG

CEAQDLY

SQ Sequence (SEQ ID NO:69).

SFSQNPPVLKRHQR

Wild-Type FVIII-BDD cDNA (SEQ ID NO:70).

atgcaaatagagctctccacctgcttctttctgtgccttttgcgattctgctttagtgccac cagaagatactacctgggtgcagtggaactgtcatgggactatatgcaaagtgatctcggtg -continued agctgcctgtggacgcaagatttcctcctagagtgccaaaatcttttccattcaacacctca gtcgtgtacaaaaagactctgtttgtagaattcacggatcaccttttcaacatcgctaagcc aaggccaccctggatgggtctgctaggtcctaccatccaggctgaggtttatgatacagtgg tcattacacttaagaacatggcttcccatcctgtcagtcttcatgctgttggtgtatcctac tggaaagcttctgagggagctgaatatgatgatcagaccagtcaaagggagaaagaagatga taaagtcttccctggtggaagccatacatatgtctggcaggtcctgaaagagaatggtccaa tggcctctgacccactgtgccttacctactcatatctttctcatgtggacctggtaaaagac ttgaattcaggcctcattggagccctactagtatgtagagaagggagtctggccaaggaaaa gacacagaccttgcacaaatttatactacttttttgctgtatttgatgaagggaaaagttggc actcagaaacaaagaactccttgatgcaggatagggatgctgcatctgctcgggcctggcct aaaatgcacacagtcaatggttatgtaaacaggtctctgccaggtctgattggatgccacag gaaatcagtctattggcatgtgattggaatgggcaccactcctgaagtgcactcaatattcc tcgaaggtcacacatttcttgtgaggaaccatcgccaggcgtccttggaaatctcgccaata actttccttactgctcaaacactcttgatggaccttggacagtttctactgttttgtcatat ctcttcccaccaacatgatggcatggaagcttatgtcaaagtagacagctgtccagaggaac cccaactacgaatgaaaaataatgaagaagcggaagactatgatgatgatcttactgattct gaaatggatgtggtcaggtttgatgatgacaactctccttcctttatccaaattcgctcagt tgccaagaagcatcctaaaacttgggtacattacattgctgctgaagaggaggactgggact atgctcccttagtcctcgcccccgatgacagaagttataaaagtcaatatttgaacaatggc cctcagcggattggtaggaagtacaaaaaagtccgatttatggcatacacagatgaaacctt taagactcgtgaagctattcagcatgaatcaggaatcttgggacctttactttatggggaag ttggagacacactgttgattatatttaagaatcaagcaagcagaccatataacatctaccct cacggaatcactgatgtccgtcctttgtattcaaggagattaccaaaaggtgtaaaacattt gaaggattttccaattctgccaggagaaatattcaaatataaatggacagtgactgtagaag atgggccaactaaatcagatcctcggtgcctgacccgctattactctagtttcgttaatatg gagagagatctagcttcaggactcattggccctctcctcatctgctacaaagaatctgtaga tcaaagaggaaaccagataatgtcagacaagaggaatgtcatcctgttttctgtatttgatg agaaccgaagctggtacctcacagagaatatacaacgctttctccccaatccagctggagtg cagcttgaggatccagagttccaagcctccaacatcatgcacagcatcaatggctatgtttt tgatagtttgcagttgtcagtttgtttgcatgaggtggcatactggtacattctaagcattg gagcacagactgacttcctttctgtcttcttctctggatataccttcaaacacaaaatggtc tatgaagacacactcaccctattcccattctcaggagaaactgtcttcatgtcgatggaaaa cccaggtctatggattctggggtgccacaactcagactttcggaacagaggcatgaccgcct tactgaaggtttctagttgtgacaagaacactggtgattattacgaggacagttatgaagat atttcagcatacttgctgagtaaaaacaatgccattgaaccaagaagcttctcccaaaaccc accagtcttgaaacgccatcaacgggaaataactcgtactactcttcagtcagatcaagagg aaattgactatgatgataccatatcagttgaaatgaagaaggaagattttgacatttatgat gaggatgaaaatcagagcccccgcagctttcaaaagaaaacacgacactattttattgctgc agtggagaggctctgggattatgggatgagtagctccccacatgttctaagaaacagggctc agagtggcagtgtccctcagttcaagaaagttgttttccaggaatttactgatggctccttt actcagcccttataccgtggagaactaaatgaacatttgggactcctggggccatatataag -continued agcagaagttgaagataatatcatggtaactttcagaaatcaggcctctcgtccctattcct tctattctagccttatttcttatgaggaagatcagaggcaaggagcagaacctagaaaaaac tttgtcaagcctaatgaaaccaaaacttacttttggaaagtgcaacatcatatggcacccac taaagatgagtttgactgcaaagcctgggcttatttctctgatgttgacctggaaaaagatg tgcactcaggcctgattggaccccttctggtctgccacactaacacactgaaccctgctcat gggagacaagtgacagtacaggaatttgctctgtttttcaccatctttgatgagaccaaaag ctggtacttcactgaaaatatggaaagaaactgcagggctccctgcaatatccagatggaag atcccacttttaaagagaattatcgcttccatgcaatcaatggctacataatggatacacta cctggcttagtaatggctcaggatcaaaggattcgatggtatctgctcagcatgggcagcaa tgaaaacatccattctattcatttcagtggacatgtgttcaccgtacgaaaaaaagaggagt ataaaatggcactgtacaatctctatccaggtgtttttgagacagtggaaatgttaccatcc aaagctggaatttggcgggtggaatgccttattggcgagcatctacatgctgggatgagcac actttttctggtgtacagcaataagtgtcagactcccctgggaatggcttctggacacatta gagattttcagattacagcttcaggacaatatggacagtgggccccaaagctggccagactt cattattccggatcaatcaatgcctggagcaccaaggagcccttttcttggatcaaggtgga tctgttggcaccaatgattattcacggcatcaagacccagggtgcccgtcagaagttctcca gcctctacatctctcagtttatcatcatgtatagtcttgatgggaagaagtggcagacttat cgaggaaattccactggaaccttaatggtcttctttggcaatgtggattcatctgggataaa acacaatatttttaaccctccaattattgctcgatacatccgtttgcacccaactcattata gcattcgcagcactcttcgcatggagttgatgggctgtgatttaaatagttgcagcatgcca ttgggaatggagagtaaagcaatatcagatgcacagattactgcttcatcctactttaccaa tatgtttgccacctggtctccttcaaaagctcgacttcacctccaagggaggagtaatgcct ggagacctcaggtgaataatccaaaagagtggctgcaagtggacttccagaagacaatgaaa gtcacaggagtaactactcagggagtaaaatctctgcttaccagcatgtatgtgaaggagtt cctcatctccagcagtcaagatggccatcagtggactctcttttttcagaatggcaaagtaa aggtttttcagggaaatcaagactccttcacacctgtggtgaactctctagacccaccgtta ctgactcgctaccttcgaattcacccccagagttgggtgcaccagattgccctgaggatgga ggttctgggctgcgaggcacaggacctctactga FVIII-BDD Encoding CpG Reduced Nucleic Acid Variant (SEQ ID NO:71)

atgcagattgagctgtctacctgcttcttcctgtgcctgctgaggttctgcttctctgct accaggaggtactacctgggggctgtggagctgagctgggattacatgcagtctgacctg gggggagctgcctgtggatgccaggtttccccccagggtgcccaagagcttccccttcaat acctctgtggtgtataagaagaccctgtttgtggagttcactgatcatctgttcaacatt gctaaacccaggccccccctggatggggctgctgggccctaccatccaggctgaggtgtat gacactgtggtgatcactctgaagaacatggctagccatcctgtgtctctgcatgctgtg ggggtgagctactggaaggcttctgaggggggctgagtatgatgatcagactagccagagg gagaaggaggatgacaaggtgttccctgggggctctcacacctatgtctggcaggtgctg aaggagaatggccccatggcctctgatcctctgtgtctgacctatagctacctgagccat -continued gtggacctggtgaaggacctgaactctggcctgattggggccctgctggtgtgtagggag gggagcctggccaaggagaagacccagaccctgcacaagttcattctgctgtttgctgtg tttgatgagggcaagagctggcattctgaaaccaagaacagcctgatgcaggacagggat gctgcctctgctagggcctggcccaagatgcacactgtgaatgggtatgtcaataggtct ctgcctggcctgattggctgccacaggaagtctgtgtactggcatgtgattgggatgggc accacccctgaggtgcacagcatctttctggagggccacaccttcctggtgaggaatcac agacaggccagcctggagatcagccccatcaccttcctgactgcccagaccctgctgatg gacctgggccagtttctgctgttctgccacatctctagccaccagcatgatggcatggag gcctatgtgaaggtggactcctgccctgaggagccccagctgaggatgaagaataatgag gaggctgaggactatgatgatgacctgactgactctgagatggatgtggtgagatttgat gatgacaattctcccagcttcattcagatcaggtctgtggccaagaagcatcccaagacc tgggtgcactacattgctgctgaggaggaggactgggactatgccccccctggtgctggcc cctgatgacaggagctataagagccagtacctgaataatggcccccagaggattgggagg aagtataagaaggtgaggttcatggcctatactgatgaaaccttcaagaccagagaggcc atccagcatgagtctgggatcctggggcccctgctgtatggggaggtgggggacaccctg ctgatcatcttcaagaaccaggccagcaggccctacaacatctaccctcatggcatcact gatgtgaggcctctgtacagcagaaggctgcccaaggggggtgaagcatctgaaggacttc cccattctgcctggggagattttcaagtacaagtggactgtgactgtggaggatggccca accaagtctgaccctaggtgcctgactaggtactacagcagctttgtgaatatggagagg gacctggcctctggcctgattggccccctgctgatctgctacaaggagtctgtggatcag aggggcaaccagatcatgtctgacaagaggaatgtgatcctgttctctgtgtttgatgag aacaggagctggtacctgactgagaacattcagaggtttctgcccaaccctgctggggtg cagctggaggaccctgaattccaggcctctaacatcatgcacagcattaatggctatgtg tttgacagcctgcagctgtctgtgtgcctgcatgaggtggcctactggtacattctgagc attggggcccagactgacttcctgtctgtgttcttctctggctacacctttaagcacaag atggtgtatgaggataccctgaccctgtttcctttctctggggagactgtgttcatgagc atggagaaccctggcctgtggatcctgggctgccacaactctgacttcaggaacaggggg atgactgctctgctgaaggtgagcagctgtgataagaacactggggactactatgaggac agctatgaggacatctctgcctatctgctgagcaagaataatgctattgagcccaggagc ttctctcagaacccccctgtgctgaagaggcaccagagggagatcaccagaactactctg cagtctgaccaggaggagattgactatgatgacaccatctctgtggagatgaagaaggag gattttgatatttatgatgaggatgaaaaccagagccccaggagctttcagaagaagact aggcactatttcattgctgctgtggagaggctgtgggactatggcatgtcttctagcccc catgtgctgaggaacagggcccagtctggctctgtgccccagttcaagaaggtggtgttc caggagttcactgatggcagcttcactcagcccctgtacaggggggagctgaatgagcac ctggggctgctgggcccttatatcagggctgaggtggaggataacatcatggtgaccttc aggaaccaggccagcaggccctacagcttctactctagcctgatcagctatgaggaggac cagaggcaggggggctgagcccaggaagaactttgtgaagcccaatgagaccaagacttat ttctggaaggtgcagcaccatatggcccccaccaaggatgagtttgattgcaaagcctgg gcctacttctctgatgtggacctggagaaggatgtgcactctgggctgattggccccctg ctggtgtgccacaccaacactctgaaccctgcccatggcaggcaggtgactgtgcaggag -continued tttgccctgttcttcaccatctttgatgagactaagagctggtacttcactgagaacatg gagaggaactgcagggccccctgcaatatccagatggaggaccccacctttaaggaaaat tataggtttcatgccattaatggctacatcatggacaccctgcctggcctggtgatggcc caggaccagaggatcaggtggtacctgctgagcatgggcagcaatgagaacattcacagc atccacttctctggccatgtgttcactgtgaggaagaaggaggagtacaagatggccctg tataatctgtaccctggggtgtttgagactgtggagatgctgcccagcaaggctggcatc tggagggtggagtgcctgattggggagcacctgcatgctggcatgagcaccctgttcctg gtgtattctaacaagtgtcagacccccctgggcatggcctctggccatatcagggacttc cagatcactgcctctggccagtatgggcagtgggcccccaagctggccaggctgcattac tctggcagcatcaatgcctggagcaccaaggagccattcagctggattaaggtggacctg ctggctccaatgattatccatggcatcaagacccaggggggccaggcagaagtttagcagc ctgtacatctctcagtttatcatcatgtactctctggatggcaaaaagtggcagacctac aggggcaattctactggcactctgatggtgttctttggcaatgtggacagctctgggatc aagcacaacatctttaacccccctatcattgccaggtacattaggctgcaccccacccat tacagcatcaggagcaccctgaggatggagctgatgggctgtgatctgaacagctgcagc atgcccctgggcatggagagcaaggctatctctgatgcccagattactgccagcagctac ttcaccaatatgtttgccacctggagccccagcaaggccaggctgcacctgcagggcagg tctaatgcctggaggccccaggtgaacaaccccaaggagtggctgcaggtggacttccag aagaccatgaaggtgactggggtgaccacccaggggggtgaagagcctgctgactagcatg tatgtgaaggagttcctgatcagcagcagccaggatggccatcagtggaccctgttcttc cagaatggcaaggtgaaggtgttccagggcaatcaggacagcttcacccctgtggtgaac agcctggaccccccccctgctgaccagatacctgaggatccacccccagagctgggtgcat cagattgccctgaggatggaggtgctggggtgtgaggcccaggacctgtactga FVIII-BDD Encoding CpG Reduced Nucleic Acid Variant
(SEQ ID NO:72)

atgcagattgagctgtctacctgcttttttcctgtgtctgctgaggttctgcttctctgcc actaggaggtactacctgggggctgtggagctgtcttgggattacatgcagtctgatctg gggggagctgcctgtggatgccaggtttcctcccagggtgcccaagtctttccccttcaat acctctgtggtgtataagaagaccctgtttgtggagtttactgatcacctgttcaacatt gccaagcccaggccccccttggatgggcctgctggggcccaccatccaggctgaggtgtat gacactgtggtgatcaccctgaagaacatggcctctcaccctgtgagcctgcatgctgtg ggggtgagctactggaaggcctctgaggggggctgagtatgatgaccagaccagccagagg gagaaggaggatgataaggtgttccctgggggggagccacacttatgtgtggcaggtgctg aaggagaatggcccaatggcctctgatcccctgtgcctgacctattcttacctgagccat gtggacctggtgaaggacctgaactctggcctgattggggccctgctggtgtgcagggag ggctctctggctaaggagaagacccagaccctgcacaagttcatcctgctgtttgctgtg tttgatgaggggaagagctggcactctgagaccaagaacagcctgatgcaggacagggat gctgcctctgccagggcctggcccaaaatgcacactgtgaatggctatgtgaataggagc ctgcctggcctgattggctgccacaggaagtctgtgtattggcatgtgattggcatgggc -continued accacccctgaggtgcactctatcttcctggagggccatactttcctggtgaggaatcat aggcaggccagcctggagattagccccattacctttctgactgcccagaccctgctgatg gacctgggccagttcctgctgttttgccacatcagctctcaccagcatgatggcatggag gcctatgtgaaggtggatagctgccctgaggagccccagctgaggatgaagaacaatgag gaggctgaggattatgatgatgatctgactgattctgaaatggatgtggtgaggtttgat gatgacaatagcccctctttcatccagatcaggtctgtggccaagaagcatcctaagacc tgggtgcactacattgctgctgaggaggaggactgggactatgctcccctggtgctggcc cctgatgacaggtcttacaagagccagtacctgaacaatggcccccagagaattgggagg aagtataagaaggtgagattcatggcttacactgatgagaccttcaagactagggaggcc atccagcatgagtctggcattctgggcccccctgctgtatggggaggtgggggacaccctg ctgatcatcttcaagaaccaggcctctaggccctacaatatttacccccatgggatcact gatgtgaggcccctgtacagcaggaggctgcctaagggggtgaagcatctgaaggacttc cccatcctgcctggggagatcttcaagtataagtggactgtgactgtggaagatggcccc accaagtctgaccctaggtgcctgaccaggtactactcttcttttgtgaacatggagagg gacctggcctctggcctgattggcccccctgctgatctgctacaaggagtctgtggaccag agggggaaccagattatgtctgacaagaggaatgtgattctgttctctgtgtttgatgag aacaggagctggtatctgactgagaacatccagaggttcctgcccaatcctgctggggtg cagctggaggaccctgagttccaggccagcaacatcatgcacagcatcaatgggtatgtg tttgattctctgcagctgtctgtgtgcctgcatgaggtggcctactggtacatcctgagc attggggctcagactgatttcctgtctgtgttcttttctggctacacctttaagcataag atggtgtatgaggacactctgaccctgtttcccttctctggggagactgtgtttatgagc atggagaaccctggcctgtggatcctgggctgccacaactctgatttcaggaacaggggc atgactgctctgctgaaggtgtcttcttgtgacaagaacactggggactattatgaggac agctatgaggacatctctgcctacctgctgagcaagaacaatgctattgagcccagatct ttcagccagaacccccctgtgctgaagaggcaccagagggagatcactaggaccaccctg cagtctgaccaggaggagattgactatgatgacactatctctgtggagatgaagaaggag gactttgatatctatgatgaggatgagaaccagtctcccaggagcttccagaaaaagacc aggcactacttcattgctgctgtggagaggctgtgggactatggcatgtcttctagcccc catgtgctgaggaacagggcccagtctgggtctgtgccccagttcaagaaggtggtgttc caggagttcactgatgggagcttcacccagcctctgtacagggggggagctgaatgagcac ctggggctgctgggcccttatattagggctgaggtggaggacaacatcatggtgactttc aggaatcaggcctctaggccctatagcttctacagctctctgatcagctatgaggaggat cagaggcaggggggctgagcccaggaagaactttgtgaagcccaatgagaccaagacctac ttctggaaggtgcagcaccacatggctcctaccaaggatgagtttgactgcaaggcctgg gcctacttttctgatgtggacctggagaaggatgtgcactctggcctgattggcccccctg ctggtgtgtcataccaacaccctgaaccctgcccatggcaggcaggtgactgtgcaggag tttgccctgttcttcaccatctttgatgagaccaagagctggtactttactgagaacatg gagaggaattgcagagccccttgcaacatccagatggaggacccaaccttcaaagagaac tacaggttccatgccatcaatgggtacatcatggacaccctgcctggcctggtgatggct caggaccagaggatcaggtggtatctgctgagcatgggcagcaatgagaatatccatagc attcacttctctggccatgtgttcactgtgaggaagaaggaggagtacaagatggccctg -continued

```
tataacctgtaccctggggtgtttgagactgtggagatgctgccaagcaaggctgggatt
tggagggtggagtgcctgattggggagcacctgcatgctggcatgtctaccctgttcctg
gtgtactccaataagtgccagacccccctgggcatggcctctggccacatcagggacttc
cagatcactgcctctggccagtatgggcagtgggccccaaagctggccaggctgcactat
tctgggagcatcaatgcttggagcaccaaggagcctttcagctggattaaggtggatctg
ctggcccccatgatcattcatggcatcaaaacccaggggggctagacagaagttttctagc
ctgtacatcagccagttcatcatcatgtacagcctggatggcaagaagtggcagacttac
aggggcaatagcactggcaccctgatggtgtttttggcaatgtggacagctctggcatc
aagcacaacatctttaaccccccattattgccaggtatatcaggctgcatcccacccac
tattctattaggtctactctgagaatggagctgatgggctgtgacctgaacagctgtagc
atgcccctggggatggagagcaaggctatctctgatgcccagatcactgccagctcttat
ttcaccaatatgtttgccacctggtctccctctaaggccaggctgcacctgcagggcagg
agcaatgcttggaggccccaggtgaataaccccaaggagtggctgcaggtggacttccag
aagaccatgaaggtgactggggtgactacccaggggggtgaagtctctgctgactagcatg
tatgtgaaggagttcctgatcagcagcagccaggatgggcatcagtggactctgttcttc
cagaatggcaaggtgaaggtcttccaggggaaccaggatagcttcactcctgtggtgaac
tctctggaccccccccctgctgactaggtatctgaggatccacccccagagctgggtgcac
cagattgccctgaggatggaggtgctgggctgtgaggcccaggacctgtattga
```

FVIII-BDD Encoding CpG Reduced Nucleic Acid Variant
(SEQ ID NO:73)

```
atgcagattgaactgtctacttgtttcttcctgtgcctgctgaggttttgcttctctgct
actaggaggtactatctgggggctgtggagctgtcttgggactatatgcagtctgacctg
gggggagctgcctgtggatgctaggtttcccccccagggtgcccaagagcttcccctttaac
acctctgtggtgtataagaagactctgtttgtggagttcactgaccatctgttcaacatt
gccaagccaaggcccccctggatgggcctgctgggccccaccatccaggctgaggtgtat
gacactgtggtgattactctgaagaacatggccagccatcctgtgagcctgcatgctgtg
gggtgtcttactggaaggcctctgagggggctgagtatgatgaccagacctctcagagg
gagaaggaggatgacaaggtgttccctgggggctctcatacctatgtgtggcaggtcctg
aaggagaatgggcccatggcctctgacccccctgtgcctgacctactcttatctgtctcat
gtggacctggtgaaggacctgaactctggcctgattggggccctgctggtgtgcagggag
ggcagcctggctaaggagaagacccagactctgcacaagttcatcctgctgtttgctgtg
tttgatgagggcaagagctggcactctgagaccaagaacagcctgatgcaggacagggat
gctgcctctgctagggcctggcccaagatgcacactgtgaatgggtatgtgaacaggagc
ctgccaggcctgattggctgccataggaagtctgtgtattggcatgtgattgggatgggg
actacccctgaggtccacagcattttcctggaggggcatacctttctggtgaggaaccac
aggcaggcctctctggagatctctcccattactttcctgactgcccagaccctgctgatg
gacctgggccagttcctgctgttctgccacatcagcagccaccagcatgatggcatggag
gcctatgtgaaggtggatagctgccctgaggagccccagctgaggatgaaaaacaatgag
gaggctgaggattatgatgatgacctgactgattctgagatggatgtggtgaggtttgat
```

-continued gatgataacagccccagcttcatccagattaggtctgtggccaagaagcatcccaagacc tgggtgcactacattgctgctgaggaggaggattgggactatgctcctctggtgctggcc cctgatgacaggagctacaagagccagtacctgaataatggcccccagaggattggcagg aagtataagaaggtgaggttcatggcctacactgatgagacctttaagaccagggaggcc atccagcatgaatctgggatcctgggccccctgctgtatggggaggtgggggacaccctg ctgattatctttaagaaccaggctagcaggccctacaacatttacccccatggcattact gatgtgaggcccctgtacagcaggaggctgcccaaggggggtgaagcacctgaaggatttc cccattctgcctggggagatctttaagtacaaatggactgtgactgtggaggatggccct actaagtctgatcccaggtgtctgaccagatactacagcagctttgtgaatatggagagg gacctggcttctggcctgattggcccccctgctgatctgctacaaggagtctgtggaccag aggggcaatcagattatgtctgacaagaggaatgtgatcctgttctctgtgtttgatgag aacagaagctggtacctgactgagaacatccagaggttcctgcccaaccctgctggggtg cagctggaggaccctgagttccaggctagcaatatcatgcacagcattaatggctatgtg tttgacagcctgcagctgtctgtgtgcctgcatgaggtggcctattggtacattctgagc attggggcccagactgatttcctgtctgtgttcttttctggctacaccttcaagcacaag atggtgtatgaggatactctgaccctgtttcccttctctggggagactgtgttcatgagc atggagaaccctggcctgtggatcctgggctgtcacaactctgacttcaggaacaggggc atgactgccctgctgaaggtgagctcttgtgataagaacactggggactactatgaggac tcttatgaggacatctctgcctacctgctgagcaagaacaatgctattgagcccaggagc ttctctcagaatccccctgtgctgaagaggcatcagagggagatcactaggactaccctg cagtctgaccaggaagagattgactatgatgacaccatctctgtggaaatgaagaaggag gactttgatatctatgatgaggatgaaaaccagagccccaggagcttccagaagaagacc aggcattacttcattgctgctgtggagaggctgtgggactatgggatgagctcttctccc catgtgctgaggaatagggctcagtctggctctgtcccacagttcaagaaggtggtgttt caggagttcactgatggcagcttcactcagcccctgtacaggggggagctgaatgagcat ctgggcctgctggggccctacatcagggctgaggtggaggataacattatggtgactttc aggaaccaggcctctaggccctacagcttctacagcagcctgatcagctatgaggaggac cagaggcaggggggctgagcccaggaagaactttgtgaagcccaatgagactaagacctat ttctggaaggtgcagcatcacatggctcccactaaagatgagtttgactgcaaggcctgg gcctacttctctgatgtggatctggagaaggatgtgcattctgggctgattggccctctg ctggtctgccatactaacaccctgaatcctgcccatggcaggcaggtgactgtgcaggag tttgccctgttctttaccatctttgatgagaccaagtcttggtacttcactgagaacatg gagaggaactgcagggcccccctgtaacatccagatggaggaccccacctttaaggagaac tacaggttccatgccatcaatggctacatcatggacactctgcctggcctggtgatggcc caggaccagaggatcaggtggtacctgctgtctatgggctctaatgagaacattcattct atccacttctctggccatgtgtttactgtgaggaagaaggaggagtacaagatggccctg tacaatctgtaccctggggtgtttgaaactgtggagatgctgccctctaaggctggcatc tggagggtggagtgcctgattggggaacacctgcatgctggcatgagcaccctgttcctg gtctatagcaataagtgccagacccccctggggatggcctctgggcatatcagagacttc cagatcactgcctctggccagtatggccagtgggcccccaagctggccaggctgcactac tctggcagcattaatgcctggagcaccaaggagcccttctcttggatcaaggtggacctg -continued ctggctcccatgatcatccatgggatcaagacccagggggccaggcagaagttcagcagc ctgtacatctctcagttcatcatcatgtactctctggatggcaagaagtggcagacctac aggggcaatagcactgggaccctgatggtgttctttgggaatgtggacagctctggcatc aagcacaatatcttcaaccccccccatcattgccaggtacatcagactgcaccccactcat tacagcatcaggagcactctgaggatggagctgatgggctgtgacctgaatagctgctct atgcccctgggcatggagagcaaggccatttctgatgcccagattactgcctcttcttac ttcactaatatgtttgccacctggagccccagcaaggccaggctgcatctgcaggggagg agcaatgcctggaggccccaggtgaacaaccccaaggagtggctgcaggtggacttccag aagactatgaaggtgactggggtgaccactcaggggtgaagagcctgctgaccagcatg tatgtgaaggagttcctgatctcttctagccaggatgggcaccagtggaccctgtttttc cagaatgggaaggtgaaggtgtttcagggcaatcaggacagctttactcctgtggtgaac agcctggacccccccctgctgactaggtacctgaggattcacccccagagctgggtgcac cagattgccctgaggatggaggtgctgggctgtgaggcccaggatctgtactga FVIII-BDD encoding CpG reduced nucleic acid variant
(SEQ ID NO:74)

atgcagattgagctgtctacctgcttctttctgtgcctgctgaggttctgtttctctgcc actaggaggtattatctgggggctgtggagctgtcctgggactacatgcagtctgatctg gggagctgcctgtggatgccaggttccctcccagggtgcccaagtctttccctttcaat acctctgtggtgtacaagaagactctgtttgtggagtttactgatcacctgtttaacatt gccaagcccaggccccccctggatggggctgctgggccccaccatccaggctgaggtgtat gacactgtggtgattactctgaagaatatggcttctcaccctgtgagcctgcatgctgtg ggggtgagctactggaaggcctctgagggggctgagtatgatgaccagaccagccagagg gagaaggaggatgacaaggtgttccctgggggcagccacacttatgtgtggcaggtgctg aaggagaatggcccaatggcctctgacccccctgtgcctgacctacagctatctgagccat gtggatctggtgaaggatctgaactctggcctgattggggccctgctggtgtgcagggag ggctctctggccaaggagaagactcagactctgcacaagttcatcctgctgtttgctgtg tttgatgagggcaagagctggcactctgagaccaagaactctctgatgcaggatagggat gctgcttctgccagggcctggcccaagatgcacactgtgaatgggtatgtgaataggagc ctgcctgggctgattgggtgtcacaggaagtctgtgtactggcatgtgattggcatgggc accactcctgaggtgcacagcatctttctggagggccacacttttctggtgaggaatcac aggcaggccagcctggagatcagccccatcaccttcctgactgcccagaccctgctgatg gatctgggccagttcctgctgttttgccatatcagcagccatcagcatgatgggatggag gcttatgtgaaggtggactcttgccctgaggagcctcagctgaggatgaagaataatgaa gaggctgaggactatgatgatgatctgactgactctgagatggatgtggtgaggtttgat gatgacaacagccccagctttatccagattaggtctgtggccaagaagcaccccaagacc tgggtgcattacattgctgctgaggaagaggattgggactatgccccccctggtgctggcc cctgatgacaggagctacaagtctcagtacctgaacaatggccctcagaggattggcagg aagtacaagaaggtgaggttcatggcttacactgatgagaccttcaagaccagggaggcc attcagcatgaatctgggatcctgggcccccctgctgtatggggaggtgggggacaccctg -continued ctgattattttcaagaaccaggccagcaggccctacaacatttatcctcatggcattact gatgtgagacccctgtacagcaggaggctgcctaagggggtgaagcacctgaaggacttc cccatcctgcctggggagatcttcaagtacaagtggactgtgactgtggaggatggcccc actaagtctgaccccaggtgcctgactaggtactactccagctttgtgaacatggagagg gacctggcctctggcctgattggcccctgctgatctgctacaaggagtctgtggatcag aggggcaaccagatcatgtctgacaagagaaatgtgatcctgttctctgtgtttgatgag aataggtcttggtacctgactgagaacatccagaggtttctgcctaatcctgctggggtg cagctggaggatcctgagttccaggcctctaacattatgcacagcatcaatgggtatgtg tttgacagcctgcagctgtctgtgtgcctgcatgaggtggcctactggtacatcctgagc attggggcccagactgactttctgtctgtgttcttctctggctacacctttaagcataag atggtgtatgaggacaccctgactctgttccccttctctggggagactgtgttcatgagc atggagaacccaggcctgtggatcctgggctgccacaactctgatttcaggaataggggc atgactgccctgctgaaggtgagcagctgtgataagaacactggggactattatgaggat agctatgaggacatctctgcctacctgctgagcaagaacaatgccattgagcccaggagc ttcagccagaatcctcctgtgctgaagaggcaccagagggagatcaccaggaccaccctg cagtctgatcaggaggagattgactatgatgacactatctctgtggagatgaagaaggag gactttgacatctatgatgaggatgagaatcagagccccaggagcttccagaagaagact agacactactttattgctgctgtggagaggctgtgggactatggcatgagctcttctccc catgtgctgagaaacagggcccagtctggctctgtgccccagttcaagaaggtggtcttc caggagttcactgatggctctttcacccagcctctgtatagaggggagctgaatgagcac ctgggcctgctgggcccttacatcagggctgaggtggaggacaatatcatggtgaccttc aggaaccaggctagcaggccctactctttctacagcagcctgatcagctatgaggaggac cagaggcaggggggctgagcctaggaagaattttgtgaagcccaatgagaccaagacctac ttctggaaggtgcagcaccacatggctcccactaaggatgagtttgactgcaaggcctgg gcctacttttctgatgtggacctggagaaggatgtgcattctggcctgattggcccctg ctggtctgccacaccaatactctgaaccctgctcatgggagacaggtgactgtgcaggag tttgccctgttcttcaccatctttgatgagaccaagtcctggtactttactgagaacatg gagaggaattgcagggccccttgcaacatccagatggaggaccccaccttcaaggaaaat tataggttccatgccatcaatggctacatcatggacaccctgcctggcctggtgatggcc caggaccagaggatcaggtggtatctgctgtctatgggctctaatgagaacatccacagc atccatttctctggccatgtgttcactgtgaggaagaaggaggagtataagatggctctg tacaacctgtaccctggggtctttgagactgtggagatgctgcccagcaaggctggcatt tggagggtggagtgcctgattggggaacacctgcatgctgggatgagcaccctgttcctg gtgtactctaacaagtgccagaccccactgggcatggcttctggccacatcagggatttc cagattactgcctctggccagtatggccagtgggctcccaagctggctaggctgcactac tctgggagcatcaatgcctggtctactaaggagcctttctcttggatcaaagtggacctg ctggcccctatgatcatccatgggatcaagactcaggggggccaggcagaagttcagcagc ctgtacatctctcagttcatcattatgtacagcctggatggcaagaagtggcagacctac aggggcaacagcactggcaccctgatggtgttctttgggaatgtggacagctctgggatt aagcacaacatctttaacccccccatcattgccaggtatatcaggctgcaccctacccac tacagcattaggagcaccctgaggatggagctgatgggctgtgacctgaacagctgcagc -continued atgcccctggggatggagagcaaggccatttctgatgctcagatcactgcttctagctac ttcactaacatgtttgccacctggtctcccagcaaggctagactgcacctgcaggggagg agcaatgcctggaggccccaggtgaataatcccaaggagtggctgcaggtggatttccag aaaaccatgaaggtgactggggtgactacccaggggtgaagtctctgctgaccagcatg tatgtgaaggagttcctgatcagcagcagccaggatgggcatcagtggaccctgttcttt cagaatgggaaggtgaaggtgtttcagggcaatcaggacagcttcacccctgtggtgaac agcctggaccccccctgctgaccaggtacctgaggatccacccccagagctgggtgcat cagattgccctgaggatggaggtgctgggctgtgaggcccaggacctgtactga FVIII-BDD Encoding CpG Reduced Nucleic Acid Variant (SEQ ID NO:75)

atgcagattgagctgtctacttgcttcttcctgtgcctgctgaggttctgcttctctgcc actaggaggtattacctgggggctgtggagctgagctgggactatatgcagtctgacctg gggggagctgcctgtggatgccaggtttcctcccagggtgcctaagagcttccccttcaac acctctgtggtgtacaagaagactctgtttgtggagtttactgatcatctgttcaacatt gccaagcccaggcctccttggatggggctgctgggccccaccatccaggctgaggtgtat gacactgtggtgattaccctgaagaatatggccagccatcctgtgagcctgcatgctgtg ggggtgagctattggaaggcctctgaggggctgagtatgatgatcagactagccagagg gagaaggaggatgacaaggtgttccctgggggagccatacctatgtgtggcaggtgctg aaggagaatggccccatggcctctgaccctctgtgcctgacttatagctacctgagccat gtggatctggtgaaggacctgaactctggcctgattggggccctgctggtgtgcagggag ggcagcctggccaaggagaagactcagaccctgcacaagttcatcctgctgtttgctgtg tttgatgaggggaagtcctggcactctgagactaagaacagcctgatgcaggatagggat gctgcttctgccagggcctggcctaagatgcacactgtgaatggctatgtgaataggagc ctgcctggcctgattggctgccataggaagtctgtgtactggcatgtgattgggatgggc accacccctgaggtgcactctattttcctggagggccatactttcctggtgaggaaccat aggcaggccagcctggagatcagccccatcactttcctgactgcccagactctgctgatg gacctgggccagttcctgctgttctgccacatcagcagccatcagcatgatggcatggag gcttatgtgaaggtggacagctgccctgaggagcctcagctgaggatgaagaataatgag gaggctgaggactatgatgatgacctgactgactctgagatggatgtggtgaggtttgat gatgacaactctccctctttcatccagatcaggtctgtggccaagaagcaccctaagacc tgggtgcactacattgctgctgaggaggaggattgggactatgccccctggtgctggcc ccagatgacaggagctacaagtcccagtacctgaacaatggcccccagaggattggcagg aagtacaagaaggtgaggttcatggcttatactgatgagactttcaagaccagggaggcc atccagcatgagtctggcatcctgggccctctgctgtatggggaggtgggggacaccctg ctgattatcttcaagaaccaggcttctaggccctacaatatctaccctcatggcatcact gatgtgaggcccctgtacagcaggaggctgcccaagggggtgaagcatctgaaggatttc cccatcctgcctggggagatctttaagtataagtggactgtgactgtggaggatggcccc actaagtctgaccccaggtgcctgaccaggtattacagcagctttgtgaacatggagagg gatctggcttctgggctgattggcccctgctgatctgctacaaggagtctgtggaccag -continued aggggcaaccagatcatgtctgacaagaggaatgtgatcctgttctctgtgtttgatgag aataggagctggtacctgactgagaacatccagaggtttctgcccaatcctgctggggtg cagctggaggatcctgagtttcaggcctctaatatcatgcacagcatcaatggctatgtg tttgactctctgcagctgtctgtgtgcctgcatgaggtggcctattggtacatcctgagc attggggcccagactgactttctgtctgtgtttttttctggctacaccttcaagcacaag atggtgtatgaggatactctgactctgttcccttttttctggggagactgtgttcatgtct atggagaaccctgggctgtggattctgggctgccacaattctgacttcaggaacagaggc atgactgctctgctgaaggtgagcagctgtgacaagaacactggggactactatgaggac tcttatgaggacatttctgcctacctgctgagcaagaacaatgccattgagcccagaagc ttttctcagaaccccccctgtgctgaagaggcaccagagggagatcaccaggaccaccctg cagtctgaccaggaggagattgactatgatgatactatttctgtggagatgaagaaggag gactttgacatctatgatgaggatgagaaccagagccccaggtctttccagaagaagact aggcactactttattgctgctgtggagaggctgtgggactatgggatgtctagctctcct catgtgctgaggaacagggcccagtctggctctgtgccccagtttaaaaaggtggtgttc caggaattcactgatggcagctttacccagcctctgtacagggggggagctgaatgagcac ctggggctgctggggccttacattagggctgaggtggaggacaacatcatggtgaccttc aggaatcaggccagcaggccctactctttctacagcagcctgatctcttatgaggaggac cagaggcagggggctgaacccaggaagaactttgtgaagcccaatgagaccaagacctac ttctggaaggtgcagcaccacatggctcccaccaaggatgagtttgattgcaaggcctgg gcttacttctctgatgtggatctggagaaggatgtgcactctgggctgattggcccccctg ctggtgtgccacaccaacactctgaaccctgcccatggcagacaggtgactgtgcaggag tttgccctgttcttcactatctttgatgagactaagagctggtacttcactgagaacatg gagaggaattgcagggccccttgcaacatccagatggaggaccccacctttaaggagaac tacaggtttcatgccattaatggctacatcatggacaccctgcctggcctggtgatggcc caggaccagaggatcaggtggtacctgctgtctatggggagcaatgagaacatccacagc attcacttctctggccatgtgttcactgtgaggaagaaggaggagtacaagatggccctg tacaacctgtaccctggggtgtttgagactgtggagatgctgcccagcaaggctgggatc tggagggtggagtgcctgattggggagcacctgcatgctgggatgagcaccctgttcctg gtgtatagcaacaagtgccagacccccctgggcatggcctctggccacatcagagacttt cagattactgcctctggccagtatgggcagtgggcccccaagctggccaggctgcactat tctggctctattaatgcctggagcactaaggagcccttcagctggattaaggtggacctg ctggctcccatgatcatccatggcatcaagactcagggggccaggcagaagttctcttct ctgtacatcagccagttcattatcatgtactccctggatggcaagaagtggcagacctat aggggcaacagcactggcaccctgatggtgttctttgggaatgtggacagctctggcatc aagcataatatcttcaatcccccatcattgctaggtacatcaggctgcaccccacccac tactctattaggtctaccctgaggatggagctgatgggctgtgacctgaacagctgcagc atgcctctgggcatggagagcaaagccatctctgatgcccagatcactgccagcagctac tttaccaacatgtttgctacttggagccccagcaaggccaggctgcacctgcaggggagg tctaatgcctggaggccccaggtgaacaaccccaaggagtggctgcaggtggacttccag aagactatgaaggtgactggggtgaccacccaggggtgaagagcctgctgacctctatg tatgtgaaggagttcctgattagcagcagccaggatggccaccagtggaccctgtttttc -continued cagaatgggaaggtgaaggtgtttcaggggaaccaggacagcttcactcctgtggtgaac tctctggacccccccctgctgaccaggtatctgaggatccaccctcagagctgggtgcac cagattgccctgaggatggaggtgctgggctgtgaggcccaggacctgtactga FVIII-BDD encoding CpG reduced nucleic acid variant (SEQ ID NO:76)

atgcagattgagctgagcacctgcttcttcctgtgcctgctgaggttttgcttctctgccac caggaggtactacctgggggctgtggagctgagctgggattacatgcagtctgacctgggg agctgcctgtggatgccaggttccctcccagggtgcccaagtctttccccttcaacacttct gtggtgtacaagaagaccctgtttgtggagtttactgaccacctgttcaacattgccaagcc caggcctccctggatgggcctgctgggccccaccattcaggctgaggtgtatgacactgtgg tcatcaccctgaaaaatatggctagccaccctgtgtctctgcatgctgtgggggtgagctac tggaaggcctctgagggggctgagtatgatgaccagactagccagagggagaaggaggatga caaggtgttccctgggggcagccacacttatgtgtggcaggtgctgaaagagaatggcccca tggcttctgatcccctgtgtctgacctatagctacctgagccatgtggatctggtgaaggac ctgaactctggcctgattggggccctgctggtgtgcagggagggcagcctggctaaggagaa gacccagaccctgcataagttcatcctgctgtttgctgtgtttgatgagggcaagagctggc actctgagactaagaacagcctgatgcaggatagggatgctgcttctgccagggcctggccc aagatgcacactgtgaatgggtatgtgaacaggagcctgcctggcctgattggctgccatag gaagtctgtctattggcatgtgattggcatgggcactactcctgaggtgcacagcatctttc tggagggccacaccttcctggtgaggaaccacaggcaggccagcctggagatctctcccatc actttcctgactgctcagaccctgctgatggacctgggccagttcctgctgttctgtcacat ctctagccaccagcatgatggcatggaggcctatgtgaaggtggatagctgccctgaggaac cccagctgaggatgaagaacaatgaggaggctgaggattatgatgatgatctgactgattct gagatggatgtggtgaggtttgatgatgacaattctcctagcttcattcagatcagatctgt ggccaaaaagcatcctaagacttgggtgcattatattgctgctgaggaggaggattgggatt atgccccccctggtgctggctcctgatgataggagctacaagtctcagtacctgaataatggg ccccagaggattggcaggaagtacaagaaggtgaggttcatggcctacactgatgagacctt caagaccagggaggccattcagcatgagtctgggattctggggcccctgctgtatggggagg tgggggataccctgctgatcattttcaagaaccaggccagcaggccctacaacatctacccc catgggattactgatgtgaggcccctgtactctaggaggctgcctaagggggtgaagcacct gaaggattttcctatcctgcctggggaaatcttcaagtacaagtggactgtgactgtggagg atggccccactaagtctgatcccaggtgtctgaccaggtattatagctcttttgtgaacatg gagagggatctggcctctgggctgattggccctctgctgatctgctacaaggagtctgtgga ccagaggggcaaccagatcatgtctgacaagaggaatgtgatcctgttctctgtgtttgatg agaacaggagctggtatctgactgagaacatccagaggtttctgcccaatcctgctggggtg cagctggaggatcctgagttccaggctagcaacatcatgcacagcatcaatgggtatgtgtt tgacagcctgcagctgtctgtgtgtctgcatgaggtggcctactggtatatcctgtctattg gggcccagactgacttcctgtctgtgtttttttctgggtatacttttaagcacaagatggtg tatgaggacaccctgactctgttccccttctctggggagactgtgtttatgagcatggagaa -continued ccctggcctgtggatcctgggctgccacaattctgacttcaggaataggggatgactgccc tgctgaaggtgagcagctgtgataagaatactggggactactatgaggactcttatgaggac atttctgcctatctgctgtctaagaacaatgccattgaacccaggagcttctctcagaaccc ccctgtgctgaagaggcaccagagggaaatcaccagaactactctgcagtctgatcaggagg aaattgactatgatgacactatttctgtggagatgaagaaggaggactttgacatctatgat gaggatgagaaccagagcccaaggagcttccagaagaagactaggcactacttcattgctgc tgtggagaggctgtgggactatggcatgagcagcagccccatgtgctgagaaacagggccc agtctgggtctgtgccccagttcaagaaggtggtgttccaggagttcactgatgggagcttc acccagcccctgtatagggggagctgaatgagcacctgggcctgctgggcccctatattag ggctgaggtggaggacaacatcatggtgaccttcaggaatcaggcctctaggccctacagct tctacagcagcctgattagctatgaggaggatcagaggcagggggctgaacccaggaagaac tttgtgaagcccaatgagaccaagacctatttctggaaggtgcagcatcacatggcccccac caaggatgagtttgactgcaaggcctgggcctacttctctgatgtggatctggagaaggatg tgcactctggcctgattggcccctgctggtgtgccacaccaacaccctgaaccctgctcat ggcaggcaggtgactgtgcaggagtttgccctgttcttcaccatctttgatgagactaagtc ttggtacttcactgagaatatggagaggaattgcagggcccccctgcaatattcagatggaag accccaccttcaaggagaattacaggttccatgccattaatggctacatcatggataccctg cctggcctggtgatggcccaggatcagaggatcaggtggtacctgctgagcatgggcagcaa tgagaacatccactctatccacttctctggccatgtgtttactgtgaggaagaaggaggagt ataagatggccctgtacaacctgtaccctggggtctttgagactgtggagatgctgccttct aaggctggcatttggagggtggagtgcctgattggggaacacctgcatgctggcatgtctac cctgttcctggtgtacagcaataagtgccagacccccctgggcatggcctctgggcatatca gggatttccagatcactgcctctggccagtatggccagtgggccccaaagctggctaggctg cactactctgggagcatcaatgcctggagcactaaggagcccttcagctggatcaaggtgga cctgctggcccccatgattatccatgggattaagactcagggggccaggcagaagttcagca gcctgtacatcagccagttcattatcatgtacagcctggatggcaagaagtggcagacctat aggggcaactctactgggaccctgatggtgttctttgggaatgtggatagctctgggatcaa gcacaatatcttcaacccccccatcattgccaggtatatcaggctgcaccccacccactaca gcattaggtctaccctgaggatggagctgatgggctgtgatctgaacagctgtagcatgcct ctgggcatggagtctaaggccatttctgatgcccagattactgctagcagctacttcaccaa catgtttgccacctggtctcccagcaaggccaggctgcatctgcagggcaggtctaatgctt ggaggccccaggtgaacaacccaaaggagtggctgcaggtggatttccagaagactatgaag gtgactggggtgaccactcagggggtgaagtctctgctgacctctatgtatgtgaaggagtt cctgatctctagcagccaggatggccatcagtggaccctgttcttccagaatggcaaggtga aagtgttccagggcaatcaggatagcttcactccagtggtgaacagcctggatcccccctctg ctgactaggtacctgaggatccacccccagagctgggtgcaccagattgccctgaggatgga ggtgctgggctgtgaggcccaggacctgtactga FVIII-BDD Encoding CpG Reduced Nucleic Acid Variant (SEQ ID NO:77).

```
atgcagattgagctgagcacctgcttcttcctgtgtctgctgaggttctgcttctctgccac
caggaggtattacctggggggctgtggagctgagctgggactatatgcagtctgacctggggg
agctgcctgtggatgctaggttccccccccagggtgcccaagagcttcccctttaacacttct
gtggtgtacaagaagaccctgtttgtggagttcactgaccacctgttcaacattgccaagcc
caggccccccctggatggggctgctggggcccaccatccaggctgaggtgtatgacactgtgg
tgatcaccctgaagaacatggccagccaccctgtgagcctgcatgctgtgggggtgagctac
tggaaggcttctgagggggctgagtatgatgaccagactagccagagggagaaggaggatga
caaggtgtttcctgggggcagccatacctatgtgtggcaggtgctgaaggagaatggcccca
tggcctctgacccccctgtgcctgacctacagctacctgtctcatgtggacctggtgaaggac
ctgaactctggcctgattggggctctgctggtgtgtagggagggcagcctggctaaggaaaa
gacccagaccctgcataagtttatcctgctgtttgctgtgtttgatgagggcaagagctggc
actctgagaccaagaacagcctgatgcaggatagggatgctgcctctgccagggcttggcct
aagatgcacactgtgaatgggtatgtgaataggagcctgcctggcctgattggctgccacag
gaagtctgtgtactggcatgtgattgggatgggcaccacccctgaggtccatagcatcttcc
tggagggccacactttcctggtgaggaaccacagacaggcctctctggagatctctcccatc
accttcctgactgctcagactctgctgatggacctgggccagttcctgctgttttgccatat
tagcagccaccagcatgatgggatggaggcctatgtgaaggtggatagctgccctgaggagc
ctcagctgaggatgaagaacaatgaggaggctgaagactatgatgatgacctgactgattct
gagatggatgtggtgaggtttgatgatgacaatagccccagcttcattcagatcaggtctgt
ggccaagaaacaccccaagacctgggtgcactacattgctgctgaggaagaggactgggact
atgctcccctggtgctggcccctgatgataggtcttataagagccagtacctgaacaatggg
ccccagaggattggcaggaagtacaagaaggtgaggttcatggcctacactgatgaaacctt
caaaaccagggaggccattcagcatgagtctggcatcctgggccctctgctgtatggggagg
tgggggacaccctgctgatcatcttcaagaaccaggccagcaggccctacaacatctatcct
catggcatcactgatgtgaggcccctgtacagcaggaggctgcccaagggggtgaagcacct
gaaagacttccccatcctgcctggggagatctttaagtataagtggactgtgactgtggagg
atggccctaccaagtctgaccccaggtgtctgaccaggtactattctagctttgtgaacatg
gagagggacctggcctctggcctgattgggcccctgctgatctgctacaaggagtctgtgga
ccagaggggcaaccagatcatgtctgacaagaggaatgtgatcctgttttctgtgtttgatg
agaataggagctggtacctgactgagaacatccagaggtttctgcccaatcctgctggggtg
cagctggaggatcctgagttccaggccagcaatatcatgcatagcatcaatggctatgtgtt
tgacagcctgcagctgtctgtgtgcctgcatgaggtggcctactggtacatcctgagcattg
ggcccagactgactttctgtctgtgttcttttctggctataccttcaagcacaagatggtg
tatgaggataccctgaccctgttccccttctctggggagactgtgttcatgagcatggagaa
tcctgggctgtggatcctggggtgccacaactctgattttaggaacaggggggatgactgccc
tgctgaaggtgtctagctgtgataagaacactggggactactatgaggacagctatgaggac
atttctgcttatctgctgtctaagaataatgccattgagcccagaagcttcagccagaatcc
ccctgtgctgaagagacatcagagggagatcaccagaactaccctgcagtctgatcaggagg
agattgactatgatgacactatctctgtggagatgaagaaggaggactttgacatctatgat
```

-continued gaggatgagaatcagtctcccaggagctttcagaagaagaccagacattacttcattgctgc tgtggagaggctgtgggactatggcatgagctctagccctcatgtgctgaggaacagggccc agtctggctctgtgccccagttcaagaaggtggtgttccaggaattcactgatggcagcttc acccagcccctgtacagggggggagctgaatgagcacctgggcctgctggggccttatatcag ggctgaggtggaggataatattatggtgactttcaggaaccaggccagcaggccctactctt tctatagcagcctgatctcttatgaggaggatcagaggcaggggggctgagcctaggaagaac tttgtgaagcccaatgagactaagacctacttctggaaggtccagcaccacatggcccctac caaggatgagtttgactgcaaggcctgggcctatttctctgatgtggatctggagaaggatg tccattctgggctgattggcccccctgctggtgtgccacactaacactctgaatcctgcccat ggcaggcaggtgactgtccaggagtttgccctgttcttcactatctttgatgagaccaagag ctggtactttactgagaacatggagaggaactgcagagctccttgcaatattcagatggagg accccaccttcaaggagaattacaggttccatgccattaatgggtacatcatggacaccctg cctggcctggtgatggctcaggaccagaggatcaggtggtacctgctgagcatgggctctaa tgagaatatccacagcatccacttctctgggcatgtgttcactgtgaggaagaaggaggagt acaagatggctctgtataatctgtaccctggggtgtttgaaactgtggagatgctgccctct aaggctggcatctggagggtggagtgcctgattggggagcacctgcatgctggcatgagcac cctgttcctggtgtacagcaacaagtgccagacccccctgggcatggcctctggccacatca gggacttccagatcactgcctctggccagtatggccagtgggcccccaagctggccaggctg cactattctggcagcatcaatgcctggagcaccaaggagcccttcagctggatcaaggtgga cctgctggcccccatgatcattcatggcatcaagacccaggggggccaggcagaagttcagct ctctgtacatctctcagttcatcatcatgtactctctggatgggaagaagtggcagacctac aggggcaacagcactggcaccctgatggtgttctttgggaatgtggactcttctggcatcaa gcacaacatcttcaatcccccccatcattgctaggtatattaggctgcatcccacccactaca gcatcaggtctaccctgaggatggagctgatgggctgtgacctgaactcttgcagcatgccc ctgggcatggagtctaaggccatctctgatgcccagattactgccagcagctacttcaccaa catgtttgccacctggagcccctctaaggccaggctgcatctgcaggggaggagcaatgcct ggaggcctcaggtgaacaaccccaaggagtggctgcaggtggatttccagaagaccatgaag gtgactggggtgaccacccaggggggtcaagagcctgctgaccagcatgtatgtgaaggagtt cctgatcagcagcagccaggatggccaccagtggactctgttctttcagaatgggaaggtga aggtgtttcagggcaatcaggactctttcacccctgtggtgaacagcctggacccccccctg ctgaccagatacctgaggatccacccccagtcttgggtgcatcagattgccctgaggatgga ggtgctgggctgtgaggctcaggatctgtactga FVIII-BDD encoding CpG reduced nucleic acid variant (SEQ ID NO:78)

atgcagattgagctgagcacttgctttttttctgtgcctgctgaggttttgtttttctgccac caggaggtactacctgggggctgtggagctgagctgggactatatgcagtctgatctggggg agctgcctgtggatgccaggttcccccccagggtgcccaagtcttttcccttcaacacctct gtggtgtataagaagaccctgtttgtggagttcactgaccacctgttcaacattgctaagcc taggccccccctggatgggcctgctgggccctaccattcaggctgaggtgtatgacactgtgg tgatcaccctgaagaacatggccagccatcctgtgagcctgcatgctgtgggggtctcttac -continued tggaaggcctctgagggggctgagtatgatgaccagaccagccagagagagaaggaggatga caaggtcttccctgggggctctcacacctatgtgtggcaggtgctgaaggaaaatggcccca tggcctctgacccccctgtgcctgacctacagctatctgagccatgtggatctggtgaaggac ctgaattctggcctgattggggccctgctggtgtgcagggagggcagcctggccaaggagaa gacccagaccctgcacaagtttatcctgctgtttgctgtgtttgatgagggcaagtcttggc actctgagactaagaacagcctgatgcaggacagggatgctgcctctgccagggcctggccc aagatgcacactgtgaatggctatgtgaacaggagcctgcctgggctgattggctgccacag gaagtctgtgtactggcatgtgattggcatgggcaccacccctgaggtgcacagcatcttcc tggaaggccacactttcctggtgaggaaccataggcaggccagcctggagatcagccctatc accttcctgactgcccagaccctgctgatggatctggggcagttcctgctgttctgccacat ctctagccaccagcatgatgggatggaggcctatgtgaaggtggacagctgcccagaggagc ctcagctgaggatgaaaaacaatgaagaggctgaggattatgatgatgatctgactgactct gagatggatgtggtgagatttgatgatgacaatagccctagctttattcagatcaggtctgt ggctaagaagcaccccaagacctgggtgcattacattgctgctgaggaggaggactgggatt atgctcctctggtgctggcccctgatgataggagctacaagagccagtacctgaataatggc cctcagaggattggcaggaagtacaagaaggtgaggttcatggcttacactgatgagacctt caagactagggaggccatccagcatgagtctgggatcctggggcccctgctgtatggggagg tgggggacaccctgctgatcatcttcaagaaccaggctagcaggccttacaacatctatccc catgggatcactgatgtgagacctctgtacagcaggaggctgcccaaggggggtcaagcatct gaaagacttccccatcctgcctggggagatctttaagtataagtggactgtgactgtggagg atgggcccaccaagtctgaccccaggtgcctgaccaggtattacagcagctttgtgaacatg gagagggatctggcctctgggctgattggcccccctgctgatctgttacaaggaatctgtgga tcagaggggcaatcagatcatgtctgacaagaggaatgtgatcctgttctctgtgtttgatg agaataggtcttggtacctgactgaaaacatccagaggttcctgcccaaccctgctggggtc cagctggaggatcctgagttccaggctagcaacatcatgcacagcatcaatgggtatgtgtt tgatagcctgcagctgtctgtgtgcctgcatgaggtggcctactggtacatcctgtctattg ggcccagactgacttcctgtctgtgttcttttctggctacaccttcaagcacaagatggtg tatgaggacaccctgaccctgttccccttctctggggagactgtctttatgagcatggagaa ccctgggctgtggatcctgggctgccacaactctgatttcaggaataggggcatgactgctc tgctgaaggtgagctcttgtgacaagaacactggggattactatgaggacagctatgaggac atttctgcctacctgctgagcaagaacaatgccattgagcctaggagctttagccagaatcc tcctgtcctgaagaggcaccagagggagatcaccaggaccaccctgcagtctgaccaggagg agattgactatgatgataccatctctgtggagatgaagaaggaggactttgacatctatgat gaggatgagaatcagtctcccaggagcttccagaagaagaccaggcactatttcattgctgc tgtggagaggctgtgggactatggcatgagcagctctcctcatgtgctgaggaatagggctc agtctggctctgtgccccagttcaagaaagtggtgtttcaggagttcactgatggctctttc acccagcctctgtatagggggggagctgaatgagcacctggggctgctgggcccctatatcag ggctgaggtggaggataacatcatggtgaccttcaggaaccaggcctctaggccctacagct tctatagcagcctgatcagctatgaggaggaccagaggcaggggggctgagcccaggaagaac tttgtgaagcccaatgagaccaagacttacttctggaaggtgcagcatcacatggcccccac -continued caaggatgagtttgactgtaaggcctgggcctacttctctgatgtggatctggagaaggatg tgcactctggcctgattggcccctgctggtgtgccataccaatactctgaaccctgctcat ggcaggcaggtgactgtgcaggagtttgctctgttcttcactatctttgatgagaccaagtc ttggtatttcactgagaatatggagaggaactgcagggcccctgcaacatccagatggagg accccacctttaaggagaactataggtttcatgccatcaatggctacatcatggacaccctg cctggcctggtgatggcccaggatcagaggatcaggtggtacctgctgagcatggggtctaa tgagaacatccacagcatccacttctctggccatgtgtttactgtgagaaagaaggaggagt acaagatggctctgtacaatctgtaccctggggtctttgagactgtggagatgctgcctagc aaggctgggatctggagggtggagtgcctgattggggaacatctgcatgctgggatgtctac tctgttcctggtgtacagcaacaagtgccagacccccctgggcatggcttctggccatatca gggactttcagattactgcctctgggcagtatggccagtgggcccccaagctggctaggctg cattattctggcagcatcaatgcctggtctactaaggagcccttcagctggatcaaggtgga tctgctggcccccatgatcatccatggcatcaagacccaggggccaggcagaagtttagct ctctgtacattagccagttcatcatcatgtacagcctggatgggaagaagtggcagacctac aggggcaattctactggcaccctgatggtgttctttggcaatgtggacagctctggcatcaa gcacaacatctttaacccccctatcattgctaggtacatcaggctgcatcccacccattaca gcatcaggagcaccctgaggatggagctgatgggctgtgacctgaactcttgcagcatgccc ctgggcatggagagcaaggccatttctgatgcccagattactgccagcagctacttcactaa catgtttgccacctggtctcccagcaaggccaggctgcacctgcagggcaggagcaatgcct ggaggccccaggtgaacaaccccaaggagtggctgcaggtggatttccagaagaccatgaag gtgactggggtgaccacccaggggtgaagagcctgctgactagcatgtatgtgaaggagtt cctgatcagctctagccaggatggccaccagtggactctgtttttccagaatggcaaggtga aggtgttccagggcaaccaggactctttcactcctgtggtgaacagcctggaccccccctg ctgaccaggtatctgaggattcacccccagtcttgggtgcatcagattgccctgaggatgga ggtgctgggctgtgaggcccaggatctgtactga FVIII-BDD Encoding CpG Reduced Nucleic Acid Variant
(SEQ ID NO:79)

atgcagattgagctgagcacctgcttcttcctgtgtctgctgagattttgcttttctgccac taggaggtattacctgggggctgtggagctgtcttgggactacatgcagtctgatctggggg agctgcctgtggatgccaggttcccacctagggtgcctaagagctttcccttcaatacctct gtggtgtacaagaagaccctgtttgtggagttcactgaccacctgttcaacattgccaagcc taggccccccctggatgggcctgctgggccctaccatccaggctgaagtgtatgacactgtgg tgatcaccctgaagaacatggccagccaccctgtgagcctgcatgctgtgggggtgtcttac tggaaggcctctgagggggctgagtatgatgatcagaccagccagagggagaaggaagatga caaggtgttccctgggggcagccacacctatgtctggcaggtgctgaaggagaatggcccca tggcctctgatcccctgtgcctgacctactcttacctgagccatgtggacctggtgaaggat ctgaattctggcctgattggggccctgctggtgtgcagggagggcagcctggccaaggagaa gacccagaccctgcataagttcatcctgctgtttgctgtgtttgatgaagggaagagctggc actctgagactaagaacagcctgatgcaggacagggatgctgcttctgccagggcctggccc aagatgcacactgtgaatggctatgtgaatagaagcctgcctggcctgattgggtgccacag -continued gaagtctgtgtactggcatgtgattgggatgggcactacccctgaggtgcatagcatcttcc tggaaggccataccttcctggtgaggaatcataggcaggcttctctggaaatttctcccatc actttcctgactgctcagaccctgctgatggacctgggccagttcctgctgttctgccacat cagctctcaccagcatgatgggatggaggcctatgtgaaggtggacagctgtcctgaggagc cccagctgaggatgaagaacaatgaggaggctgaggactatgatgatgacctgactgactct gagatggatgtggtcaggtttgatgatgacaatagcccctctttcatccagatcaggtctgt ggccaagaagcaccccaagacttgggtgcactacattgctgctgaggaggaggattgggatt atgcccctctggtgctggcccctgatgacaggagctataagtctcagtacctgaataatggc ccccagaggattgggaggaagtataagaaggtgaggtttatggcctacactgatgagacctt caagaccagggaggccatccagcatgagtctggcatcctgggcccccctgctgtatggggagg tgggggataccctgctgatcatcttcaagaaccaggcctctaggccctacaatatctaccct catggcatcactgatgtgagacccctgtatagcaggaggctgcctaaggggggtgaagcacct gaaggacttccccatcctgcctggggagatcttcaagtataagtggactgtgactgtggagg atggccccaccaagtctgaccccaggtgcctgaccaggtattacagctcttttgtgaacatg gagagggatctggcctctgggctgattggcccactgctgatctgctacaaggagtctgtgga tcagaggggcaatcagatcatgtctgacaagaggaatgtgatcctgttttctgtgtttgatg aaaataggtcttggtatctgactgagaacatccagaggtttctgcccaatcctgctggggtg cagctggaggatcctgagtttcaggcctctaatatcatgcattctatcaatggctatgtgtt tgacagcctgcagctgtctgtgtgcctgcatgaggtggcctactggtacatcctgagcattg gggctcagactgacttcctgtctgtgttcttttctggctatactttcaagcacaagatggtg tatgaggacactctgaccctgttccccttctctggggagactgtgttcatgtctatggaaaa tcctgggctgtggattctgggctgccacaattctgacttcaggaatagggggatgactgccc tgctgaaggtgtctagctgtgataagaacactggggattactatgaggactcttatgaagat atctctgcctatctgctgagcaagaacaatgccattgagcccaggagcttcagccagaaccc ccctgtgctgaagaggcaccagagggagatcaccaggaccactctgcagtctgatcaggagg agattgactatgatgacactatctctgtggagatgaagaaggaggattttgacatttatgat gaggatgagaaccagtctcccaggagcttccagaagaagaccaggcattactttattgctgc tgtggagaggctgtgggactatgggatgagcagctctcctcatgtgctgaggaacagggccc agtctgggtctgtgccccagttcaagaaggtggtgttccaggagttcactgatgggagcttc acccagcccctgtatagggggggagctgaatgagcacctgggcctgctgggcccctacatcag ggctgaggtggaggataatatcatggtgaccttcaggaaccaggctagcaggccttacagct tttacagcagcctgatctcttatgaagaagaccagaggcaggggggctgagcccaggaagaat tttgtgaagcctaatgagaccaagacttatttttggaaggtgcagcatcacatggctcctac caaggatgagtttgactgcaaggcctgggcctacttttctgatgtggatctggagaaggatg tgcactctggcctgattggccctctgctggtgtgccatactaacactctgaaccctgcccat gggaggcaggtgactgtgcaggagtttgccctgttcttcactatttttgatgagaccaagtc ttggtatttcactgagaacatggagaggaactgcagggctccctgcaacatccagatggaag accccaccttcaaggagaactataggttccatgccatcaatgggtacatcatggataccctg cctggcctggtgatggcccaggatcagaggattaggtggtatctgctgagcatgggctctaa tgagaacatccacagcatccatttctctggccatgtgttcactgtgaggaagaaggaggagt -continued acaagatggctctgtacaacctgtatcctggggtgtttgagactgtggagatgctgcccagc aaggctggcatctggagggtggaatgcctgattggggagcacctgcatgctggcatgagcac tctgttcctggtgtatagcaacaagtgccagacccccctgggcatggcctctggccatatca gggatttccagatcactgcttctggccagtatggccagtgggcccccaagctggccaggctg cactattctggcagcatcaatgcctggagcactaaggagcctttttcttggatcaaggtgga cctgctggcccctatgattattcatggcatcaagacccaggggggccaggcagaagttctcta gcctgtacatctctcagttcatcattatgtatagcctggatggcaagaagtggcagacctac aggggcaatagcactggcaccctgatggtgtttttgggaatgtggactcttctgggatcaa gcacaacatctttaacccccccatcattgccaggtatattaggctgcaccccacccactaca gcatcaggagcaccctgaggatggagctgatgggctgtgatctgaattcttgctctatgccc ctgggcatggagagcaaggccatctctgatgcccagatcactgccagctcttacttcaccaa catgtttgccacctggtctcctagcaaggccaggctgcatctgcagggcaggagcaatgcct ggaggccccaggtgaacaaccccaaggagtggctgcaggtggacttccagaagaccatgaag gtgactggggtgaccactcaggggggtgaagagcctgctgacctctatgtatgtgaaggagtt cctgatcagcagcagccaggatggccaccagtggactctgttcttccagaatgggaaggtga aggtgttccagggcaaccaggatagctttacccctgtggtgaacagcctggaccctcctctg ctgaccagatacctgaggatccatcctcagagctgggtgcaccagattgccctgaggatgga ggtgctgggctgtgaggcccaggatctgtactga FVIII-BDD encoding CpG reduced nucleic acid variant (SEQ ID NO:80)

atgcagattgagctgagcacttgcttcttcctgtgcctgctgaggttctgcttttctgctac taggaggtactacctgggggctgtggagctgagctgggattacatgcagtctgacctggggg agctgccagtggatgccaggttcccccccagggtgcccaagtcttttcctttcaacacctct gtggtgtacaagaagaccctgtttgtggagttcactgaccacctgttcaacattgccaagcc caggccccccctggatggggctgctggggcccaccatccaggctgaggtgtatgacactgtgg tgattaccctgaagaacatggctagccaccctgtgagcctgcatgctgtgggggtgagctat tggaaggcctctgaggggggctgagtatgatgatcagaccagccagagggaaaaggaggatga caaggtgttccctgggggcagccatacttatgtgtggcaggtgctgaaggagaatgggccca tggcctctgacccccctgtgcctgacttacagctatctgagccatgtggacctggtgaaggat ctgaactctggcctgattggggctctgctggtgtgcagggagggcagcctggctaaggagaa gactcagactctgcataagttcatcctgctgtttgctgtgtttgatgaaggcaagagctggc actctgagaccaagaactctctgatgcaggatagggatgctgcctctgccagggcttggccc aagatgcacactgtgaatggctatgtgaacaggagcctgcctggcctgattgggtgccacag gaagtctgtgtactggcatgtgattggcatgggcaccacccctgaggtgcacagcattttcc tggagggccacaccttcctggtgaggaatcacaggcaggccagcctggagatcagccccatc accttcctgactgcccagaccctgctgatggacctggggcagtttctgctgttctgccacat cagcagccatcagcatgatggcatggaggcctatgtgaaggtggactcttgccctgaggagc cccagctgaggatgaagaacaatgaggaggctgaggattatgatgatgacctgactgactct gagatggatgtggtgaggtttgatgatgacaatagccccagcttcatccagattaggtctgt ggccaagaagcaccctaagacctgggtgcactacattgctgctgaggaggaggattgggatt -continued atgccccccctggtgctggctcctgatgacaggtcttataagagccagtacctgaacaatggg
ccccagaggattggcaggaagtacaagaaggtgaggttcatggcttacactgatgagacctt
caagactagggaggccatccagcatgagtctggcatcctgggccccctgctgtatggggagg
tgggggataccctgctgatcatcttcaagaaccaggccagcaggccctacaacatttaccct
catggcatcactgatgtgaggcccctgtacagcaggagactgcccaaggggggtgaagcacct
gaaggattttcccattctgcctggggagatcttcaagtacaagtggactgtgactgtggagg
atggccccaccaagtctgatcccaggtgcctgactaggtactactcttcttttgtgaatatg
gagagggatctggcctctggcctgattggcccccctgctgatctgctacaaggagtctgtgga
ccagaggggcaaccagatcatgtctgacaagaggaatgtgatcctgttctctgtgtttgatg
agaataggagctggtacctgactgagaatatccagaggttcctgcctaatcctgctggggtc
cagctggaggatcctgagttccaggctagcaacattatgcacagcatcaatggctatgtgtt
tgattctctgcagctgtctgtgtgcctgcatgaggtggcttactggtacatcctgtctattg
ggcccagactgatttcctgtctgtgttcttctctggctacactttcaagcataagatggtg
tatgaggataccctgaccctgttccccttctctggggagactgtgttcatgtctatggagaa
ccctggcctgtggatcctgggctgtcataactctgacttcagaaacaggggcatgactgccc
tgctgaaggtgagcagctgtgacaagaacactggggactactatgaggacagctatgaggat
atctctgcttatctgctgagcaagaataatgccattgagcccaggagcttcagccagaaccc
ccctgtgctgaagaggcaccagagggagatcactaggactaccctgcagtctgatcaggagg
agattgactatgatgacaccatctctgtggagatgaagaaggaggactttgacatctatgat
gaggatgagaaccagtcccccaggtctttccagaagaagaccaggcactacttcattgctgc
tgtggagaggctgtgggactatggcatgagctctagcccccatgtgctgaggaacagggctc
agtctggctctgtgccccagttcaagaaggtggtcttccaggagttcactgatggctctttt
acccagcctctgtacagaggggagctgaatgagcacctgggcctgctgggcccctacatcag
ggctgaggtggaggataatatcatggtgaccttcagaaaccaggcctctaggccctacagct
tctacagcagcctgatctcttatgaggaggatcagaggcaggggggctgagcccaggaagaac
tttgtgaagcccaatgagaccaagacctacttctggaaggtgcagcaccatatggcccctac
taaggatgagtttgactgcaaggcctgggcttatttttctgatgtggacctggagaaggatg
tgcactctgggctgattggcccccctgctggtgtgccacaccaacaccctgaaccctgcccat
ggcaggcaggtgactgtgcaggagtttgccctgttcttcactatctttgatgagaccaagag
ctggtacttcactgagaacatggagagaaattgtagggctccctgcaatatccagatggagg
accccaccttcaaagaaaattacagattccatgccatcaatgggtacatcatggataccctg
cctgggctggtgatggctcaggaccagaggatcaggtggtacctgctgagcatggggtctaa
tgagaacatccactctatccatttctctggccatgtgttcactgtgagaaagaaggaggagt
ataagatggctctgtacaacctgtacccaggggtgtttgagactgtggaaatgctgcccagc
aaagctgggatctggagggtggagtgcctgattggggagcacctgcatgctggcatgtctac
cctgttcctggtgtacagcaacaagtgccagactcccctgggcatggcctctgggcacatca
gggattttcagatcactgcctctggccagtatggccagtgggcccccaagctggccaggctg
cactactctggcagcattaatgcttggagcactaaggagcccttcagctggatcaaggtgga
tctgctggcccccatgatcatccatggcatcaagacccagggggccaggcagaagttctcta
gcctgtacatttctcagttcatcatcatgtacagcctggatgggaagaagtggcagacctac -continued agggggaacagcactgggaccctgatggtgttctttggcaatgtggatagctctggcatcaa gcacaatatcttcaatcccccattattgccaggtacattaggctgcatcctactcactact ctattaggagcaccctgaggatggagctgatggggtgtgacctgaacagctgttctatgccc ctgggcatggagtctaaggctatctctgatgcccagatcactgccagcagctacttcactaa tatgtttgccacctggagccctagcaaggccagactgcacctgcagggcaggagcaatgcct ggaggccccaggtgaacaaccccaaggagtggctgcaggtggacttccagaagaccatgaag gtgactggggtgaccactcaggggtgaagagcctgctgaccagcatgtatgtgaaggagtt cctgatcagcagcagccaggatggccaccagtggaccctgttcttccagaatgggaaggtga aggtgttccagggcaaccaggactctttcacccctgtggtgaacagcctggatcctcccctg ctgaccaggtacctgaggatccacccccagagctgggtgcaccagattgctctgaggatgga agtgctgggctgtgaggcccaggatctgtactga FVIII-BDD Encoding CpG Reduced Nucleic Acid Variant
(SEQ ID NO:81)

atgcagattgagctgagcacctgcttcttcctgtgcctgctgaggttttgcttctctgctac caggaggtactacctgggggctgtggagctgagctgggactatatgcagtctgacctggggg agctgcctgtggatgctaggttccctcccagggtgcccaagagcttcccctttaatacctct gtggtgtacaagaaaaccctgtttgtggagttcactgaccatctgttcaacattgccaagcc caggccccccttggatgggcctgctgggccccaccattcaggctgaggtgtatgacactgtgg tcattaccctgaagaacatggcttctcaccctgtgagcctgcatgctgtgggggtgagctac tggaaggcctctgagggggctgagtatgatgaccagaccagccagagggagaaggaggatga taaggtgttccctgggggcagccacacctatgtgtggcaggtgctgaaggagaatggcccca tggcctctgatcccctgtgcctgacctactcttatctgtctcatgtggacctggtgaaggac ctgaactctggcctgattggggctctgctggtgtgcagggagggctctctggccaaggagaa gacccagaccctgcacaagtttattctgctgtttgctgtctttgatgagggcaagagctggc attctgagaccaagaacagcctgatgcaggacagggatgctgcctctgccagggcctggccc aaaatgcacactgtgaatggctatgtgaacaggagcctgcctggcctgattggctgccacag gaagtctgtgtactggcatgtgattggcatgggcaccacccctgaggtgcacagcatcttcc tggagggccacacctttctggtgaggaatcacaggcaggccagcctggagattagccccatc accttcctgactgcccagaccctgctgatggacctgggccagttcctgctgttctgccacat cagcagccaccagcatgatggcatggaggcctatgtgaaggtggatagctgccctgaggagc cccagctgaggatgaaaaacaatgaggaggctgaggattatgatgatgacctgactgactct gagatggatgtggtgaggtttgatgatgacaatagccccagctttattcagattaggtctgt ggctaagaagcaccccaagacttgggtgcactacattgctgctgaggaggaggattgggact atgcccctctggtcctggcccctgatgataggtcttacaagagccagtatctgaacaatggc cccagaggattggcaggaagtacaagaaggtgaggttcatggcctacactgatgagacctt taagaccagggaggccattcagcatgagtctgggatcctgggcccccctgctgtatggggagg tgggggacactctgctgatcatcttcaagaaccaggccagcaggccttataacatctaccct catgggatcactgatgtgaggcccctgtactctagaaggctgcccaagggggtcaagcacct gaaggattttcccatcctgcctggggagattttcaagtacaagtggactgtgactgtggagg atggccccaccaagtctgaccctaggtgcctgaccaggtactacagctcttttgtgaacatg -continued gagagggacctggcctctggcctgattggccctctgctgatttgctacaaggagtctgtgga ccagaggggcaaccagatcatgtctgacaagaggaatgtgatcctgttttctgtgtttgatg agaacaggtcttggtacctgactgagaacatccagaggttcctgcctaacccagctggggtg cagctggaggatcctgagttccaggccagcaatattatgcatagcattaatggctatgtgtt tgatagcctgcagctgtctgtgtgcctgcatgaggtggcctactggtacatcctgagcattg gggcccagactgactttctgtctgtgttcttctctggctacaccttcaagcataagatggtg tatgaggacaccctgactctgttcccttttctggggagactgtgtttatgagcatggagaa tcctggcctgtggatcctgggctgccataattctgacttcaggaacaggggcatgactgccc tgctgaaagtgagcagctgtgacaagaatactggggactactatgaagacagctatgaggac atctctgcctacctgctgagcaagaacaatgccattgagcccaggagcttcagccagaaccc cccagtgctgaagaggcaccagagagagatcaccaggactaccctgcagtctgaccaggagg agattgactatgatgacaccatttctgtggagatgaagaaggaggactttgacatttatgat gaggatgagaatcagagccccaggagcttccagaagaagactaggcactattttattgctgc tgtggagaggctgtgggactatggcatgagcagctctccccatgtgctgaggaatagggccc agtctggctctgtgcctcagttcaagaaggtggtgttccaggagttcactgatggcagcttt acccagcccctgtataggggggagctgaatgagcacctgggcctgctgggcccctatatcag ggctgaggtggaggacaatattatggtgacctttaggaaccaggccagcaggccctactctt tctatagcagcctgatcagctatgaggaggaccagaggcaggggctgagcccaggaagaat tttgtgaagcctaatgagaccaagacctacttctggaaggtgcagcatcacatggcccccac caaggatgagtttgactgcaaggcttgggcctatttctctgatgtggacctggagaaggatg tgcactctggcctgattggcccctgctggtgtgccacactaacactctgaatcctgcccat ggcaggcaggtgactgtgcaggagtttgccctgttcttcaccatctttgatgagaccaagag ctggtacttcactgagaacatggagaggaactgcagggcccccctgcaacatccagatggagg atcccaccttcaaggagaactacaggtttcatgccatcaatggctacatcatggacactctg cctggcctggtgatggcccaggatcagaggatcaggtggtacctgctgagcatgggctctaa tgagaatatccatagcatccacttctctggccatgtgttcactgtcaggaagaaggaggagt acaagatggctctgtataatctgtaccctggggtgtttgagactgtggagatgctgcccagc aaggctggcatctggagggtggagtgcctgattggggagcacctgcatgctgggatgagcac cctgtttctggtgtactctaacaagtgccagacccccctgggcatggcctctgggcacatca gggatttccagatcactgcttctggccagtatggccagtgggcccccaagctggccaggctg cactactctggcagcatcaatgcctggtctaccaaggagcccttttcttggattaaggtgga cctgctggcccccatgatcatccatggcatcaagacccaggggggccaggcagaagttcagca gcctgtacatcagccagttcatcatcatgtacagcctggatggcaaaaagtggcagacctac aggggcaatagcactgggactctgatggtgttctttggcaatgtggacagctctgggatcaa gcacaatatcttcaaccctcccatcattgctaggtacatcaggctgcaccccacccactata gcatcaggtctaccctgaggatggagctgatgggctgtgacctgaactcttgcagcatgccc ctgggcatggagtccaaagctatctctgatgcccagattactgccagcagctacttcaccaa catgtttgccacctggtctccctctaaggccaggctgcacctgcagggcaggagcaatgcct ggaggccccaggtgaacaatcccaaggagtggctgcaggtggatttccagaaaactatgaag gtgactggggtgaccacccaggggggtgaagtctctgctgaccagcatgtatgtgaaggagtt -continued cctgatctcttctagccaggatggccaccagtggactctgttcttccagaatggcaaggtga aggtgttccagggcaaccaggacagcttcacccctgtggtgaactctctggatccccccctg ctgaccaggtacctgaggattcatccccagagctgggtgcaccagattgctctgagaatgga ggtgctggggtgtgaggctcaggacctgtattga FVIII-BDD encoding CpG reduced nucleic acid variant (SEQ ID NO:82)

atgcagattgagctgtctacttgtttttttctgtgcctgctgaggttctgcttctctgccac caggaggtattacctgggggctgtggagctgagctgggattacatgcagtctgatctggggg agctgcctgtggatgccaggttcccccccagggtgcccaagagcttccccttcaacacctct gtggtgtataagaagaccctgtttgtggagttcactgatcatctgtttaacattgccaagcc caggccccccctggatgggcctgctgggcccaactatccaggctgaggtgtatgacactgtgg tcatcaccctgaagaatatggccagccatcctgtgagcctgcatgctgtgggggtgagctac tggaaggcctctgagggggctgagtatgatgaccagaccagccagagggagaaggaggatga caaggtgttccctgggggcagccacacctatgtgtggcaggtgctgaaggagaatggcccca tggcctctgacccccctgtgcctgacttatagctacctgtctcatgtggacctggtgaaggac ctgaactctggcctgattggggccctgctggtctgtagggaaggcagcctggccaaggagaa gacccagaccctgcacaagtttattctgctgtttgctgtgtttgatgaaggcaagagctggc actctgagaccaagaattctctgatgcaggatagggatgctgcctctgccagggcctggccc aagatgcatactgtgaatggctatgtgaacagaagcctgcctggcctgattggctgccatag gaagtctgtgtattggcatgtgattgggatgggcactacccctgaagtgcacagcattttcc tggagggccacactttcctggtgaggaaccacaggcaggcctctctggagatcagccccatt actttcctgactgcccagaccctgctgatggatctgggccagttcctgctgttctgccacat ctctagccaccagcatgatggcatggaggcctatgtgaaggtggacagctgccctgaggagc cccagctgaggatgaagaataatgaggaggctgaggattatgatgatgacctgactgactct gagatggatgtggtgaggtttgatgatgataatagccccagcttcatccagatcaggtctgt ggccaagaagcatcccaagacctgggtgcactatattgctgctgaagaggaggactgggact atgcccctctggtgctggctcctgatgacaggagctataagagccagtatctgaacaatggg ccccagaggattgggaggaagtacaagaaggtgaggttcatggcctacactgatgagacctt taagaccagggaggccatccagcatgagtctggcattctggggcccctgctgtatggggagg tgggggacactctgctgatcattttcaagaaccaggccagcaggccctacaatatttacccc catggcatcactgatgtgaggcccctgtacagcaggaggctgcccaaggggggtgaagcacct gaaggacttccccatcctgcctggggagatcttcaagtacaagtggactgtgactgtggagg atggccctaccaagtctgaccctaggtgtctgactaggtactacagcagctttgtgaacatg gagagagacctggcttctggcctgattggcccccctgctgatctgctacaaggagtctgtgga tcagaggggcaaccagattatgtctgataagaggaatgtcatcctgttctctgtgtttgatg agaacaggagctggtatctgactgagaacattcagaggttcctgcccaaccctgctggggtg cagctggaggaccctgagttccaggccagcaacatcatgcattctattaatggctatgtgtt tgacagcctgcagctgtctgtgtgcctgcatgaggtggcctactggtacatcctgagcattg ggcccagactgactttctgtctgtgtttttctctgggtacaccttcaagcacaagatggtc tatgaggacaccctgaccctgttcccctttttctggggaaactgtgtttatgagcatggagaa -continued

```
ccctgggctgtggatcctgggctgccacaactctgactttaggaataggggcatgactgccc
tgctgaaggtgagcagctgtgacaagaatactggggattactatgaggacagctatgaggat
atctctgcctacctgctgagcaagaacaatgccattgagcctaggagcttcagccagaaccc
ccctgtgctgaagaggcaccagagggagatcaccaggaccaccctgcagtctgatcaggagg
agattgactatgatgacaccatctctgtggagatgaagaaggaggactttgatatttatgat
gaggatgagaaccagagccccaggagcttccagaagaagaccaggcactatttcattgctgc
tgtggagaggctgtgggactatggcatgagctctagcccccatgtgctgaggaacagggccc
agtctggctctgtgccccagttcaagaaggtggtgttccaggaatttactgatggcagcttt
acccagcccctgtacagaggggagctgaatgagcacctgggcctgctgggcccctacatcag
ggctgaggtggaggataatatcatggtgacctttaggaaccaggcctctaggccctattctt
tttacagcagcctgatcagctatgaggaggaccagaggcaggggctgagcctaggaagaac
tttgtgaagcccaatgagaccaagacctacttttggaaagtgcagcaccacatggcccccac
taaggatgagtttgattgcaaggcctgggcctatttctctgatgtggacctggagaaggatg
tgcactctggcctgattggcccctgctggtgtgccacaccaacactctgaaccctgcccat
ggcaggcaggtgactgtgcaggagtttgccctgttctttaccatctttgatgagactaagag
ctggtatttcactgagaacatggagaggaactgcagagccccttgcaacatccagatggagg
accctaccttcaaggagaactataggttccatgccatcaatgggtacatcatggataccctg
cctggcctggtgatggctcaggaccagaggatcaggtggtacctgctgagcatggggagcaa
tgagaacattcatagcatccacttctctgggcatgtgttcactgtgaggaagaaggaggagt
ataagatggccctgtacaacctgtaccctggggtgtttgagactgtggagatgctgcccagc
aaggctggcatctggagggtggagtgcctgattggggagcacctgcatgctggcatgagcac
tctgttcctggtgtacagcaacaagtgccagacccccctgggcatggcctctggccacatca
gggacttccagattactgcctctgggcagtatgggcagtgggcccccaagctggccaggctg
cactactctgggtctatcaatgcttggagcaccaaggagcctttcagctggatcaaggtgga
tctgctggcccccatgatcattcatgggatcaagacccaggggggccaggcagaagttcagca
gcctgtatatttctcagttcatcatcatgtattctctggatggcaaaaagtggcagacctat
agagggaacagcactgggaccctgatggtgtttttggcaatgtggatagctctggcatcaa
gcacaatatcttcaacccccccattattgccaggtacatcaggctgcaccccacccactact
ctatcaggagcaccctgaggatggagctgatgggctgtgatctgaacagctgctctatgcct
ctggggatggaaagcaaggccatctctgatgcccagatcactgccagcagctatttcaccaa
tatgtttgccacttggagccctagcaaggctaggctgcatctgcagggcaggtctaatgcct
ggaggccccaggtgaacaaccccaaggagtggctgcaggtggacttccagaagactatgaaa
gtgactggggtgaccacccaggggggtgaaaagcctgctgaccagcatgtatgtgaaggagtt
cctgattagcagcagccaggatggccaccagtggaccctgttcttccagaatgggaaggtga
aggtgtttcagggcaatcaggatagcttcaccccagtggtgaacagcctggaccccccctg
ctgaccaggtacctgaggatccacccccagagctgggtgcaccagattgccctgaggatgga
ggtgctgggctgtgaggcccaggatctgtactga
```

FVIII-BDD Encoding CpG Reduced Nucleic Acid Variant
(SEQ ID NO:83)

atgcagattgagctgagcacctgctttttcctgtgcctgctgaggttctgcttctctgctac
caggaggtactacctggggctgtggagctgtcttgggattacatgcagtctgacctggggg
agctgcctgtggatgccaggtttccccccagggtgcccaagtctttcccctttaacacctct
gtggtgtataagaagactctgtttgtggagttcactgatcacctgttcaatattgccaagcc
caggccccccttggatgggcctgctgggccccactatccaggctgaggtgtatgacactgtgg
tcatcaccctgaagaacatggccagccaccctgtgagcctgcatgctgtgggggtgagctac
tggaaggcctctgagggggctgagtatgatgaccagaccagccagagggagaaggaggatga
caaggtgttcccagggggggtctcacacttatgtgtggcaggtgctgaaggagaatgggccca
tggcctctgaccctctgtgcctgacttatagctacctgtctcatgtggatctggtgaaggac
ctgaactctggcctgattggggccctgctggtgtgcagggaggggagcctggccaaggagaa
gacccagaccctgcacaagttcatcctgctgtttgctgtgtttgatgaggggaagagctggc
actctgagaccaagaatagcctgatgcaggacagggatgctgcttctgctagggcctggcct
aagatgcacactgtgaatggctatgtgaacaggagcctgcctggcctgattgggtgtcacag
gaagtctgtgtactggcatgtgattggcatggggactactccagaagtgcacagcatcttcc
tggaggggcacaccttcctggtgaggaatcacaggcaggccagcctggagatttctcccatc
actttcctgactgcccagaccctgctgatggatctggggcagttcctgctgttctgccacat
cagcagccatcagcatgatgggatggaggcctatgtgaaggtggacagctgccctgaggagc
ctcagctgaggatgaagaacaatgaggaggctgaggactatgatgatgatctgactgactct
gagatggatgtggtgaggtttgatgatgacaactctcccagcttcatccagatcaggtctgt
ggccaagaagcaccccaagacctgggtgcactacattgctgctgaggaggaggattgggatt
atgctcccctggtgctggctcctgatgataggagctacaagagccagtatctgaataatggg
ccccagaggattggcaggaagtataagaaggtgaggttcatggcctacactgatgagacctt
taagaccagggaggctattcagcatgagtctggcatcctgggcccccctgctgtatggggagg
tgggggacaccctgctgatcattttcaagaaccaggccagcaggccctataacatctatccc
catgggatcactgatgtgaggcccctgtactctaggaggctgcccaagggggtcaagcacct
gaaggacttccccatcctgcctggggagatcttcaagtacaagtggactgtgactgtggagg
atggccccactaagtctgaccccaggtgcctgactaggtactacagcagctttgtgaacatg
gagagagatctggcctctggcctgattggcccccctgctgatctgctacaaagagtctgtgga
tcagaggggcaaccagatcatgtctgacaagaggaatgtgatcctgttctctgtgtttgatg
agaacagaagctggtacctgactgagaacattcagaggtttctgcccaaccctgctggggtc
cagctggaggaccctgagtttcaggccagcaacatcatgcacagcatcaatgggtatgtgtt
tgacagcctgcagctgtctgtgtgcctgcatgaggtggcctactggtatatcctgagcattg
ggcccagactgatttcctgtctgtgttcttctctggctacactttcaagcacaagatggtg
tatgaggataccctgaccctgttccctttctctggggaaactgtgttcatgagcatggagaa
ccctgggctgtggatcctggggtgccacaattctgatttcaggaacagaggcatgactgctc
tgctgaaggtgtctagctgtgacaagaacactggggactactatgaggacagctatgaggac
atctctgcctacctgctgagcaagaacaatgctattgaacccaggtctttcagccagaaccc
ccctgtgctgaagaggcaccagagggagatcactaggaccaccctgcagtctgatcaggagg
agattgactatgatgacaccatctctgtggagatgaagaaggaggactttgacatctatgat -continued gaggatgagaatcagtctcccaggagcttccagaagaagactaggcattacttcattgctgc tgtggagaggctgtgggactatggcatgagctctagccctcatgtgctgaggaacagggccc agtctggctctgtgccccagttcaagaaggtggtgtttcaggagttcactgatggcagcttc acccagcccctgtacagggggggagctgaatgagcatctgggcctgctgggcccctacatcag ggctgaggtggaggacaacatcatggtgaccttcagaaatcaggctagcaggccctacagct tctacagcagcctgatctcttatgaggaggaccagaggcaggggctgagcccaggaagaac tttgtgaagcccaatgagaccaagacctatttctggaaggtgcagcaccacatggcccccac caaggatgagtttgattgcaaggcctgggcctacttctctgatgtggacctggagaaggatg tgcattctgggctgattggccctctgctggtgtgccacaccaacaccctgaatcctgcccat ggcaggcaggtgactgtgcaggagtttgccctgttctttactatctttgatgagaccaagtc ttggtattttactgagaacatggagaggaactgcagggccccctgcaacatccagatggagg accccaccttcaaggagaactacagattccatgccatcaatggctacattatggacactctg cctggcctggtgatggcccaggaccagaggatcaggtggtacctgctgtctatgggcagcaa tgagaacattcactctatccacttctctgggcatgtgttcactgtgaggaagaaggaggagt acaagatggccctgtacaacctgtaccctggggtgtttgagactgtggagatgctgcctagc aaggctgggatctggagggtggagtgcctgattggggagcacctgcatgctggcatgtctac cctgttcctggtgtacagcaacaagtgccagacccccctgggcatggcctctggccacatca gagattttcagatcactgcctctggccagtatggccagtgggctcctaagctggccaggctg cactactctggcagcatcaatgcctggagcaccaaggagccctttagctggatcaaggtgga cctgctggcccccatgatcatccatggcatcaagactcaggggccaggcagaagttctcta gcctgtacattagccagttcatcatcatgtatagcctggatggcaagaagtggcagacctac aggggcaacagcactgggaccctgatggtgttctttgggaatgtggacagctctgggatcaa gcacaatatcttcaacccccccattattgccaggtatattaggctgcaccccactcactaca gcattaggagcaccctgaggatggagctgatgggctgtgatctgaacagctgcagcatgccc ctgggcatggagtctaaggccatctctgatgcccagatcactgccagctcttacttcaccaa catgtttgccacttggagccccagcaaggccaggctgcacctgcagggcaggagcaatgcct ggaggccccaggtgaacaaccccaaggagtggctgcaggtggatttccagaagactatgaag gtgactggggtgaccactcaggggggtgaagagcctgctgactagcatgtatgtgaaggagtt cctgatcagctctagccaggatggccaccagtggaccctgttctttcagaatggcaaggtga aggtgttccagggcaaccaggactctttcacccctgtggtgaattctctggaccctcccctg ctgactaggtatctgaggattcatccccagagctgggtgcatcagattgccctgaggatgga ggtgctgggctgtgaggcccaggacctgtattga FVIII-BDD encoding CpG reduced nucleic acid variant (SEQ ID NO:84)

atgcagattgagctgagcacctgcttcttcctgtgcctgctgaggttttgcttttctgccac taggaggtactacctgggggctgtggagctgtcttgggattacatgcagtctgacctgggggg agctgccagtggatgccaggttcccccccaagggtgcccaagtcttttcccttcaatacctct gtggtgtacaagaagaccctgtttgtggagtttactgatcatctgtttaacattgccaagcc caggccccccctggatggggctgctgggccccaccatccaggctgaggtgtatgatactgtgg tgattaccctgaagaatatggccagccatcctgtgtctctgcatgctgtgggggtgtcttat -continued tggaaggcctctgagggggctgagtatgatgatcagaccagccagagggagaaggaggatga taaggtgttccctgggggctctcacacctatgtgtggcaggtgctgaaggagaatgggccta tggcctctgacccactgtgcctgacttacagctatctgagccatgtggacctggtgaaggac ctgaactctgggctgattggggccctgctggtgtgcagggagggcagcctggccaaggagaa gactcagaccctgcacaagttcatcctgctgtttgctgtgtttgatgagggcaagtcttggc actctgagaccaagaacagcctgatgcaggatagggatgctgcctctgccagggcctggccc aagatgcacactgtgaatggctatgtgaacaggtctctgcctggcctgattggctgccacag gaagtctgtgtactggcatgtgattggcatgggcaccacccctgaggtgcatagcattttcc tggagggccacaccttcctggtgaggaaccacaggcaggctagcctggagatcagccccatc actttcctgactgcccagaccctgctgatggacctgggccagttcctgctgttctgccacat ctctagccaccagcatgatggcatggaggcctatgtgaaggtggactcttgtcctgaggagc cccagctgaggatgaagaacaatgaggaggctgaggattatgatgatgatctgactgattct gagatggatgtggtgaggtttgatgatgacaacagcccctctttcatccagatcaggtctgt ggccaagaagcaccccaagacctgggtgcactacattgctgctgaggaggaggattgggatt atgccccccctggtgctggcccctgatgacaggagctataagtctcagtacctgaacaatggc ccccagagaattggcaggaagtacaagaaggtgaggttcatggcctatactgatgagacctt caaaaccagggaggccattcagcatgagtctggcatcctggggcccctgctgtatggggagg tgggggacaccctgctgatcatcttcaagaaccaggctagcaggccttacaacatctacccc catgggatcactgatgtgaggcccctgtacagcaggaggctgcctaaggggggtgaagcacct gaaggactttcccattctgcctggggagatcttcaagtataagtggactgtgactgtggagg atgggcccaccaagtctgaccccaggtgcctgactaggtactactctagctttgtgaacatg gagagggacctggcctctgggctgattggcccccctgctgatctgttacaaggagtctgtgga ccagaggggcaaccagatcatgtctgataagaggaatgtgatcctgttctctgtgtttgatg agaacaggagctggtacctgactgagaacatccagagattcctgcccaaccctgctggggtg cagctggaggatcctgagttccaggccagcaacatcatgcattctatcaatgggtatgtgtt tgatagcctgcagctgtctgtgtgtctgcatgaggtggcctactggtacattctgagcattg ggcccagactgacttcctgtctgtgttcttctctggctacactttcaaacacaagatggtg tatgaggacaccctgaccctgttccccttctctggggagactgtgtttatgagcatggagaa ccctgggctgtggattctgggctgccacaactctgacttcagaaacaggggcatgactgccc tgctgaaggtgtcttcttgtgataagaacactggggactattatgaagacagctatgaggac atctctgcctacctgctgagcaagaataatgctattgagcccaggtctttctctcagaaccc ccctgtgctgaagaggcaccagagggagatcaccaggaccaccctgcagtctgatcaggagg agattgactatgatgacactatttctgtggagatgaagaaggaagactttgatatctatgat gaggatgagaaccagagccctaggagcttccagaagaagactaggcattacttcattgctgc tgtggagaggctgtgggactatggcatgagcagcagcccccatgtgctgaggaatagggctc agtctggctctgtgcctcagttcaagaaggtggtgttccaggaattcactgatggcagcttc actcagcccctgtacaggggggagctgaatgagcacctggggctgctgggcccttacatcag ggctgaggtggaggacaatatcatggtgacctttaggaaccaggcctctaggccttacagct tctactctagcctgatctcttatgaagaggaccagaggcaggggggctgagcccaggaagaac tttgtgaagcccaatgagactaagacttacttctggaaggtgcagcaccacatggctcccac -continued caaggatgagtttgactgcaaggcttgggcctacttctctgatgtggacctggagaaggatg tgcactctgggctgattgggcccctgctggtgtgccacactaacactctgaatcctgcccat ggcagacaggtgactgtgcaggagtttgccctgtttttaccatctttgatgagactaagtc ttggtacttcactgagaacatggagaggaactgcagggcccccctgcaacatccagatggagg atcccaccttcaaggagaactacaggtttcatgccatcaatggctacatcatggacaccctg cctggcctggtgatggctcaggaccagaggattaggtggtatctgctgagcatgggcagcaa tgagaatatccactctatccacttctctgggcatgtgttcactgtgaggaagaaggaggagt acaagatggccctgtataacctgtatcctggggtgtttgagactgtggagatgctgcccagc aaggctggcatctggagagtggagtgcctgattggggagcacctgcatgctggcatgagcac tctgtttctggtgtatagcaacaagtgtcagacccctctgggcatggcctctgggcacatta gggactttcagatcactgcttctggccagtatgggcagtgggctcccaagctggccaggctg cactattctggcagcattaatgcctggagcaccaaggagcctttcagctggatcaaggtgga cctgctggcccccatgatcatccatgggatcaagacccaggggctaggcagaagttcagca gcctgtacatcagccagtttatcatcatgtattctctggatggcaagaagtggcagacctac aggggcaattctactggcactctgatggtgttctttgggaatgtggatagctctgggatcaa gcataatatcttcaatcccccattattgctaggtatatcaggctgcaccccacccactata gcatcaggagcaccctgaggatggagctgatggggtgtgacctgaacagctgcagcatgccc ctgggcatggagagcaaggctatttctgatgcccagatcactgccagcagctactttactaa tatgtttgccacctggagccccagcaaggccagactgcacctgcagggcaggtctaatgcct ggaggcctcaggtgaataaccccaaggagtggctgcaggtggacttccagaaaaccatgaag gtgactggggtgactacccaggggtgaagtctctgctgaccagcatgtatgtgaaggagtt cctgatctcttctagccaggatggccaccagtggaccctgttctttcagaatgggaaggtga aggtcttccagggcaaccaggatagcttcacccctgtggtgaatagcctggatcctcctctg ctgaccaggtatctgaggatccacccccagagctgggtgcatcagattgccctgaggatgga ggtgctgggctgtgaggctcaggacctgtactga FVIII-BDD Encoding CpG Reduced Nucleic Acid Variant
(SEQ ID NO:85)

atgcagattgagctgagcacctgtttcttcctgtgcctgctgaggttctgtttctctgccac taggaggtactacctgggggctgtggagctgagctgggactatatgcagtctgacctggggg agctgcctgtggatgccaggttcccccccagggtgcctaagagcttccccttcaatacttct gtggtgtacaagaagactctgtttgtggagtttactgaccacctgttcaacattgctaagcc caggcctccctggatggggctgctgggccccaccatccaggctgaggtgtatgatactgtgg tgattaccctgaagaacatggcctctcatccagtgagcctgcatgctgtgggggtgagctac tggaaggcctctgaaggggctgagtatgatgaccagaccagccagagggagaaggaggatga caaggtgttccctgggggcagccacacctatgtgtggcaggtgctgaaggagaatggcccaa tggcctctgacccccctgtgcctgacttatagctacctgagccatgtggatctggtgaaggac ctgaattctggcctgattggggccctgctggtgtgcagagagggctctctggctaaggagaa gacccagactctgcacaagttcatcctgctgtttgctgtgtttgatgagggcaagagctggc actctgagactaagaatagcctgatgcaggacagggatgctgcttctgccagggcctggccc aagatgcatactgtgaatggctatgtgaacaggagcctgcctggcctgattggctgtcacag -continued gaaatctgtctactggcatgtgattgggatgggcactacccctgaggtgcactctatcttcc
tggagggccataccttcctggtgaggaaccacaggcaggccagcctggagatctctcccatt
accttcctgactgcccagaccctgctgatggatctgggccagttcctgctgttctgccacat
cagcagccaccagcatgatgggatggaggcttatgtgaaggtggatagctgccctgaggagc
cccagctgaggatgaagaacaatgaggaggctgaggactatgatgatgacctgactgactct
gagatggatgtggtgaggtttgatgatgacaactctcccagctttattcagatcaggtctgt
ggctaagaagcaccccaagacttgggtgcactacattgctgctgaggaggaggactgggact
atgcccctctggtgctggctcctgatgacaggtcttacaagtctcagtacctgaataatggc
cctcagaggattggcaggaagtacaagaaggtgaggttcatggcctacactgatgagacctt
caagaccagggaggccatccagcatgagtctggcatcctgggcccccctgctgtatggggagg
tggggggataccctgctgatcatcttcaagaatcaggccagcaggccctacaacatctacccc
catggcatcactgatgtgaggccactgtacagcaggaggctgcccaaggggggtgaagcatct
gaaggacttccccattctgcctggggagatcttcaagtacaaatggactgtgactgtggagg
atggccctaccaagtctgaccccaggtgtctgaccaggtactacagcagctttgtgaatatg
gagagggacctggcctctggcctgattggcccccctgctgatctgctacaaggagtctgtgga
ccagaggggcaatcagatcatgtctgataagaggaatgtgattctgttctctgtgtttgatg
agaacaggagctggtacctgactgagaacatccagaggttcctgcccaatcctgctggggtg
cagctggaggaccctgagttccaggccagcaatatcatgcacagcatcaatggctatgtctt
tgacagcctgcagctgtctgtgtgcctgcatgaggtggcttactggtatattctgagcattg
ggcccagactgatttcctgtctgtgttcttttctggctatacctttaagcacaagatggtg
tatgaggacaccctgaccctgttccccttctctggggagactgtgttcatgtctatggagaa
ccctgggctgtggatcctgggctgccacaactctgacttcaggaacaggggggatgactgccc
tgctgaaggtgtctagctgtgataagaacactggggactattatgaggacagctatgaggac
atctctgcttacctgctgagcaagaacaatgccattgagcccaggtctttcagccagaatcc
ccctgtgctgaagaggcatcagagggagatcaccaggaccaccctgcagtctgatcaggagg
agattgattatgatgacactatctctgtggaaatgaagaaggaggactttgacatctatgat
gaggatgagaaccagagccccaggagcttccagaagaagaccaggcactacttcattgctgc
tgtggagaggctgtgggattatggcatgagcagctctccccatgtgctgaggaacagagccc
agtctggctctgtgcctcagttcaagaaggtggtcttccaggagttcactgatggctctttc
acccagcccctgtacaggggggagctgaatgagcacctgggcctgctggggccctacattag
ggctgaggtggaggataacatcatggtgactttcagaaaccaggccagcaggccttacagct
tttactcttctctgattagctatgaggaggatcagaggcaggggggctgagcctaggaagaac
tttgtgaagcccaatgagaccaagacctatttctggaaggtgcagcaccacatggctcccac
taaggatgagtttgactgcaaggcttgggcctacttctctgatgtggacctggagaaggatg
tgcactctggcctgattgggcccctgctggtgtgccacaccaacaccctgaaccctgcccat
ggcaggcaggtgactgtgcaggagtttgccctgttcttcaccatctttgatgagactaagag
ctggtacttcactgagaacatggagaggaactgcagggccccctgcaacatccagatggagg
accccaccttcaaggagaattacaggttccatgccatcaatggctacattatggacaccctg
cctggcctggtgatggcccaggatcagaggatcaggtggtatctgctgagcatgggctctaa
tgagaacatccacagcatccacttctctggccatgtgtttactgtgaggaagaaggaggaat -continued acaagatggctctgtataacctgtaccctggggtgtttgagactgtggagatgctgcccagc aaggctgggatctggagggtggagtgcctgattggggagcacctgcatgctgggatgagcac cctgttcctggtgtatagcaataagtgccagacccccctgggcatggcttctggccacatca gggatttccagatcactgcttctggccagtatggccagtgggctcccaagctggctaggctg cattactctgggtctatcaatgcctggagcactaaggagcccttcagctggatcaaggtgga cctgctggcccccatgatcattcatggcatcaagacccaggggctaggcagaagttcagca gcctgtacatcagccagttcatcattatgtacagcctggatggcaagaagtggcagacttac aggggcaatagcactgggactctgatggtgttctttggcaatgtggactcttctggcatcaa gcacaacatcttcaaccctcccatcattgccaggtacattaggctgcaccctacccactact ctatcaggagcaccctgaggatggagctgatggggtgtgatctgaactcttgcagcatgcct ctgggcatggaaagcaaagccatctctgatgcccagatcactgcctctagctatttcaccaa tatgtttgccacctggagccctagcaaggccaggctgcacctgcagggcagatctaatgcct ggaggccccaggtgaacaatcccaaggagtggctgcaggtggacttccagaagaccatgaag gtgactggggtgaccactcaggggggtgaagagcctgctgactagcatgtatgtgaaggagtt cctgatctcttctagccaggatggccaccagtggaccctgttcttccagaatggcaaggtga aagtgttccagggcaaccaggatagcttcactcctgtggtgaactctctggaccctcccctg ctgactaggtacctgaggattcatccccagagctgggtgcaccagattgccctgaggatgga ggtgctgggctgtgaggcccaggatctgtactga FVIII-BDD Encoding CpG Reduced Nucleic Acid Variant
(SEQ ID NO:86)

atgcagattgagctgagcacctgcttcttcctgtgcctgctgaggttctgcttctctgccac caggaggtactacctgggggctgtggagctgtcttgggactatatgcagtctgacctggggg agctgccagtggatgccaggttcccccccagggtgcccaagagctttcctttcaacacttct gtggtgtacaagaagaccctgtttgtggagttcactgaccacctgttcaatattgctaagcc caggccaccctggatgggcctgctgggccctaccattcaggctgaggtgtatgacactgtgg tgattactctgaagaatatggccagccaccctgtgagcctgcatgctgtgggggtgtcttac tggaaggcctctgagggggctgagtatgatgatcagacttctcagagggagaaggaggatga taaggtgttccctgggggctctcacacttatgtgtggcaggtgctgaaggagaatggcccca tggcttctgatccactgtgcctgacctactcttacctgagccatgtggacctggtgaaggac ctgaactctggcctgattggggccctgctggtgtgcagggagggcagcctggccaaggagaa gacccagaccctgcataagttcatcctgctgtttgctgtgtttgatgaggggaagagctggc actctgagaccaagaattctctgatgcaggacagggatgctgcctctgccagggcctggcct aagatgcacactgtgaatggctatgtgaacaggtctctgcctggcctgattggctgccacag gaagtctgtgtactggcatgtgattggcatgggcactacccctgaggtgcacagcattttcc tggagggccacaccttcctggtcaggaaccataggcaggcctctctggagatcagccccatc actttcctgactgcccagaccctgctgatggacctgggccagttcctgctgttctgccacat tagcagccaccagcatgatggcatggaggcctatgtgaaggtggactcttgccctgaggagc cccagctgaggatgaagaacaatgaggaagctgaggattatgatgatgacctgactgactct gagatggatgtggtgaggtttgatgatgacaacagccccagcttcatccagatcaggtctgt ggccaagaagcaccccaagacctgggtgcactacattgctgctgaggaggaggattgggact -continued atgctcccctggtgctggctcctgatgataggagctacaagtctcagtacctgaataatggc
ccccagaggattggcaggaagtacaagaaggtgaggttcatggcctacactgatgagacctt
caagaccagagaggctatccagcatgagtctgggatcctggggcccctgctgtatggggagg
tggggacaccctgctgatcatcttcaagaaccaggccagcagaccctacaacatctacccc
catgggatcactgatgtgaggcccctgtacagcaggaggctgcctaaggggtgaagcacct
gaaggacttccccatcctgcctggggagatcttcaagtataagtggactgtgactgtggagg
atgggcccaccaagtctgaccctaggtgcctgactaggtactactctagctttgtgaacatg
gagagggacctggcctctggcctgattggcccctgctgatttgctacaaggagtctgtgga
tcagaggggcaatcagatcatgtctgacaagaggaatgtgatcctgttctctgtgtttgatg
agaataggtcttggtacctgactgagaacatccagaggttcctgcctaatcctgctggggtg
cagctggaggaccctgagtttcaggccagcaacatcatgcacagcatcaatggctatgtgtt
tgactctctgcagctgtctgtgtgcctgcatgaggtggcttactggtatatcctgagcattg
gggctcagactgacttcctgtctgtgttcttttctggctacacttttaagcacaagatggtg
tatgaggacaccctgaccctgttcccctttctggggagactgtgttcatgtctatggagaa
ccctgggctgtggattctgggctgtcacaactctgacttcagaaacaggggcatgactgccc
tgctgaaggtgtctagctgtgacaagaatactggggactactatgaggacagctatgaggac
atttctgcctatctgctgagcaagaacaatgccattgagcccaggagcttttctcagaatcc
ccctgtgctgaagaggcaccagagagagatcaccaggaccactctgcagtctgatcaggagg
agattgattatgatgacactatctctgtggagatgaagaaagaggactttgatatctatgat
gaggatgagaatcagtctcccaggagcttccagaagaagactagacactacttcattgctgc
tgtggagaggctgtgggactatggcatgagctctagccctcatgtgctgaggaacagggccc
agtctgggtctgtgccccagttcaagaaggtggtgttccaggagttcactgatggcagcttt
acccagcccctgtataggggggagctgaatgagcatctgggcctgctgggcccctatattag
ggctgaagtggaggacaacatcatggtgacctttaggaaccaggccagcaggccctacagct
tttacagcagcctgattagctatgaggaggatcagagacaggggctgagcccaggaagaac
tttgtgaagcccaatgagaccaagacctacttctggaaggtgcagcaccacatggcccctac
caaggatgagtttgactgcaaggcctgggcttacttctctgatgtggacctggagaaagatg
tgcactctggcctgattgggcccctgctggtgtgccacaccaacaccctgaaccctgcccat
gggaggcaggtgactgtgcaggagtttgccctgtttttcaccatctttgatgagaccaagag
ctggtacttcactgagaacatggagaggaactgcagggcccccctgtaacatccagatggagg
atcctactttcaaggagaactacaggttccatgccattaatgggtacatcatggacaccctg
cctgggctggtgatggcccaggatcagaggattaggtggtatctgctgtctatgggctctaa
tgagaacatccactctatccacttctctggccatgtgttcactgtgaggaagaaggaggagt
acaagatggccctgtacaacctgtaccctggggtgtttgaaactgtggagatgctgccctct
aaagctgggatctggagggtggagtgcctgattggggagcacctgcatgctggcatgagcac
cctgttcctggtgtacagcaataagtgccagactcccctgggcatggcttctgggcacatca
gggatttccagatcactgcctctggccagtatggccagtgggcccccaagctggctaggctg
cactactctggcagcatcaatgcctggagcaccaaggagcccttctcttggattaaggtgga
cctgctggctcccatgatcattcatggcatcaagacccaggggccaggcagaagttttcta
gcctgtatattagccagttcatcatcatgtatagcctggatgggaagaagtggcagacctac -continued agggggaatagcactggcaccctgatggtgtttttggcaatgtggattcttctggcatcaa gcataacatcttcaatcccccctatcattgccaggtacattaggctgcatcccacccattact ctatcaggagcaccctgaggatggagctgatggggtgtgatctgaacagctgtagcatgccc ctgggcatggagtccaaggctatctctgatgcccagatcactgccagcagctacttcaccaa catgtttgccacctggagccccagcaaggccaggctgcacctgcagggcaggtctaatgcct ggaggccccaggtgaacaatcccaaggagtggctgcaggtggacttccagaagactatgaag gtgactggggtgaccactcagggggtgaagagcctgctgaccagcatgtatgtgaaggagtt cctgatctcttctagccaggatgggcatcagtggaccctgtttttcagaatggcaaagtga aggtgtttcaggggaatcaggacagctttacccctgtggtgaacagcctggatcctcctctg ctgactagatacctgaggatccacccccagagctgggtccaccagattgctctgaggatgga ggtgctggggtgtgaggctcaggacctgtactga FVIII-BDD encoding CpG reduced nucleic acid variant (SEQ ID NO:87)

atgcagattgagctgagcacctgcttctttctgtgcctgctgaggttctgcttctctgccac caggaggtactacctgggggctgtggaactgagctgggactatatgcagtctgacctgggg agctgcctgtggatgccaggttcccccccagggtgcccaagtctttcccctttaacacttct gtggtgtacaagaagaccctgtttgtggagtttactgaccacctgttcaatattgccaagcc caggccccccctggatgggcctgctgggcccaaccatccaggctgaggtgtatgatactgtgg tgatcaccctgaagaacatggccagccaccctgtgagcctgcatgctgtgggggtgagctat tggaaggcttctgagggggctgagtatgatgaccagactagccagagggagaaggaggatga caaggtgttccctgggggtctcatacctatgtgtggcaggtgctgaaggagaatggcccca tggcctctgacccccctgtgcctgacctattcttacctgagccatgtggacctggtcaaggac ctgaactctggcctgattggggctctgctggtgtgcagggagggcagcctggccaaggagaa gactcagactctgcataagttcatcctgctgtttgctgtgtttgatgagggcaagagctggc actctgagaccaagaactctctgatgcaggatagggatgctgcctctgccagggcctggccc aagatgcacactgtgaatggctatgtgaataggtctctgcctggcctgattggctgccatag gaagtctgtgtactggcatgtgattggcatgggcactacccctgaggtgcactctatcttcc tggaggggcacaccttcctggtgaggaaccacaggcaggccagcctggagatctctcccatc accttcctgactgcccagactctgctgatggacctgggccagttcctgctgttctgccatat cagcagccaccagcatgatggcatggaggcctatgtgaaggtggacagctgcccagaggaac cccagctgaggatgaagaacaatgaggaggctgaggactatgatgatgacctgactgactct gagatggatgtggtgaggtttgatgatgacaacagccccagctttattcagatcaggtctgt ggccaagaagcaccccaagacctgggtgcactacattgctgctgaggaggaggactgggatt atgccccccctggtgctggcccctgatgacaggtcttacaagtctcagtacctgaacaatggc cccagaggattgggaggaagtacaagaaggtgaggttcatggcctacactgatgagacctt caagaccagggaggccatccagcatgagtctggcatcctggggcccctgctgtatggggagg tgggggataccctgctgattatcttcaagaaccaggctagcaggccctataacatctacccc catggcattactgatgtgaggcccctgtactctaggagactgcccaagggggtgaagcacct gaaagacttccccatcctgcctggggagatcttcaagtataagtggactgtgactgtggagg atggccccactaagtctgaccccaggtgcctgaccaggtattacagcagctttgtgaatatg -continued gagagggatctggcttctggcctgattgggcctctgctgatttgctacaaggagtctgtgga
tcagagggggaaccagattatgtctgacaagaggaatgtgattctgttctctgtgtttgatg
agaacaggagctggtacctgactgagaatatccagaggttcctgcctaatcctgctggggtg
cagctggaggaccctgagttccaggctagcaacattatgcacagcatcaatggctatgtgtt
tgacagcctgcagctgtctgtgtgcctgcatgaggtggcttactggtacattctgtctattg
ggcccagactgacttcctgtctgtgttcttctctggctacaccttcaagcacaagatggtg
tatgaggacactctgaccctgttccccttctctggggagactgtgttcatgagcatggagaa
tcctgggctgtggattctggggtgccacaactctgatttcaggaacaggggcatgactgccc
tgctgaaggtgagcagctgtgacaagaacactggggattattatgaggacagctatgaggac
atttctgcctacctgctgagcaagaacaatgccattgagcctaggagcttcagccagaatcc
ccctgtgctgaagagacaccagagggagatcactaggaccactctgcagtctgatcaggagg
agattgactatgatgacaccatttctgtggagatgaagaaggaggactttgatatttatgat
gaggatgagaaccagagccccagaagcttccagaagaagaccaggcactacttcattgctgc
tgtggagaggctgtgggattatggcatgtcttctagccccatgtgctgaggaacagggctc
agtctggctctgtgcctcagttcaagaaggtggtgttccaggagttcactgatgggagcttc
acccagcctctgtacagggggggagctgaatgaacatctgggcctgctggggccctacatcag
ggctgaggtggaggataatatcatggtgactttcaggaatcaggcctctaggccctacagct
tctactctagcctgatcagctatgaggaggaccagaggcaggggggctgagcctaggaagaat
tttgtgaaacccaatgagaccaagacctacttttggaaggtgcagcaccacatggcccctac
caaggatgagtttgactgtaaggcctgggcctacttctctgatgtggacctggagaaggatg
tgcattctgggctgattggcccccctgctggtgtgccacaccaacaccctgaaccctgcccat
ggcaggcaggtgactgtgcaggagtttgccctgttcttcaccatctttgatgagactaagag
ctggtatttcactgagaacatggagaggaactgtagggctccctgcaacatccagatggagg
atccaactttcaaggagaactacaggttccatgccatcaatggctacatcatggacaccctg
cctggcctggtgatggcccaggaccagaggattaggtggtacctgctgagcatgggctctaa
tgagaacatccactctatccacttctctggccatgtgtttactgtgaggaagaaggaggagt
acaagatggctctgtacaacctgtaccctggggtgtttgagactgtggagatgctgcctagc
aaggctggcatttggagagtggagtgtctgattggggagcacctgcatgctgggatgtctac
cctgttcctggtgtactctaacaagtgccagaccccccctggggatggcttctgggcacatca
gagattttcagattactgcttctgggcagtatggccagtgggctcccaagctggccagactg
cattactctggctctattaatgcttggagcaccaaggagcctttcagctggatcaaggtgga
cctgctggctcccatgatcatccatggcattaagactcaggggggctaggcagaagttcagca
gcctgtatatttctcagtttattatcatgtattctctggatggcaagaagtggcagacttac
aggggcaacagcactggcaccctgatggtgttctttggcaatgtggacagctctgggatcaa
gcataacatcttcaacccccccattattgccaggtacatcaggctgcaccccacccactatt
ctatcaggagcactctgaggatggagctgatggggtgtgacctgaacagctgctctatgccc
ctgggcatggagagcaaggccatctctgatgcccagatcactgccagctcttatttcaccaa
catgtttgccacctggagccccagcaaggccaggctgcacctgcagggcagaagcaatgcct
ggaggccccaggtgaacaatcctaaggagtggctgcaggtggacttccagaagactatgaag
gtgactggggtgactacccagggggtgaagagcctgctgaccagcatgtatgtgaaggagtt -continued cctgattagcagcagccaggatgggcatcagtggaccctgttcttccagaatgggaaggtga aggtgttccagggcaatcaggacagcttcacccctgtggtgaacagcctggacccccccctg ctgaccaggtacctgaggatccatccccagagctgggtgcaccagattgctctgagaatgga ggtgctgggctgtgaggcccaggacctgtattga FVIII-BDD Encoding CpG Reduced Nucleic Acid Variant
(SEQ ID NO:88)

atgcagattgagctgtctacctgtttttttctgtgcctgctgaggttctgcttctctgctac caggaggtattatctgggggctgtggagctgagctgggactacatgcagtctgacctggggg agctgcctgtggatgccaggtttcctcccagggtgcctaagagcttccccttcaacacctct gtggtgtacaagaagactctgtttgtggagttcactgaccacctgttcaacattgccaagcc caggccccccctggatggggctgctgggccccactatccaggctgaggtgtatgatactgtgg tgattaccctgaagaacatggcctctcaccctgtgtctctgcatgctgtgggggtgagctac tggaaggcttctgagggggctgaatatgatgatcagacctctcagagggagaaggaggatga caaggtgtttcctgggggcagccacacctatgtgtggcaggtgctgaaggagaatgggccca tggcctctgatcccctgtgcctgacctacagctacctgagccatgtggacctggtgaaggac ctgaactctggcctgattggggccctgctggtgtgcagggagggcagcctggccaaggaaaa gacccagaccctgcataagttcatcctgctgtttgctgtgtttgatgagggcaagtcttggc actctgagaccaagaacagcctgatgcaggacagggatgctgcctctgctagggcctggccc aagatgcacactgtgaatgggtatgtgaacagatctctgcctggcctgattggctgccacag gaagtctgtgtactggcatgtgattggcatggggaccacccctgaggtgcatagcatcttcc tggagggggcacaccttcctggtgagaaatcataggcaggccagcctggagattagccccatc accttcctgactgcccagaccctgctgatggacctgggccagttcctgctgttctgccacat ttctagccaccagcatgatggcatggaggcctatgtgaaggtggatagctgccctgaagagc cccagctgaggatgaagaacaatgaggaggctgaggattatgatgatgatctgactgactct gagatggatgtggtgaggtttgatgatgacaacagccccagcttcatccagatcaggtctgt ggccaagaagcaccctaagacctgggtgcactacattgctgctgaagaggaggactgggact atgccccccctggtgctggccccagatgacaggtcttacaagagccagtacctgaataatggc cccagaggattgggaggaagtataagaaagtgaggttcatggcttacactgatgagacctt taagactagggaggccattcagcatgagtctgggattctgggccctctgctgtatggggagg tgggggacaccctgctgatcattttcaagaaccaggccagcaggccctataatatttatccc catgggattactgatgtcaggcccctgtacagcaggaggctgcctaaggggggtgaagcacct gaaggacttccccattctgcctggggagatcttcaagtataagtggactgtgactgtggagg atggccccaccaagtctgatcctaggtgcctgaccaggtactatagcagctttgtgaacatg gagagggacctggcttctggcctgattggcccccctgctgatctgctacaaggaatctgtgga ccagaggggcaaccagattatgtctgacaagaggaatgtgatcctgttttctgtgtttgatg agaataggagctggtatctgactgagaacatccagaggttcctgcccaatcctgctggggtg cagctggaggaccctgagttccaggcttctaacatcatgcatagcatcaatgggtatgtgtt tgactctctgcagctgtctgtgtgcctgcatgaggtggcctattggtacatcctgagcattg ggcccagactgacttcctgtctgtgttcttctctggctacaccttcaagcacaagatggtg tatgaggacaccctgaccctgttccctttctctggggagactgtgttcatgagcatggagaa -continued ccctggcctgtggattctgggctgccataattctgacttcagaaacaggggcatgactgctc tgctgaaggtgagcagctgtgacaagaatactggggactactatgaggactcttatgaggat atttctgcctacctgctgagcaagaacaatgctattgagcccaggagcttcagccagaaccc ccctgtcctgaagaggcatcagagggagatcactaggaccaccctgcagtctgatcaggagg agattgactatgatgacactatctctgtggaaatgaagaaggaggactttgatatctatgat gaggatgagaaccagagccccaggtctttccagaagaagaccaggcactacttcattgctgc tgtggagaggctgtgggactatggcatgtctagcagcccccatgtgctgaggaacagagccc agtctggctctgtgccccagttcaagaaggtggtgtttcaggagttcactgatgggagcttc actcagcccctgtataggggggagctgaatgagcatctgggcctgctggggccctacatcag ggctgaggtggaggataacatcatggtgaccttcaggaaccaggccagcaggccctactctt tctactcttctctgatcagctatgaggaggatcagaggcaggggggctgagcctaggaagaac tttgtcaagcctaatgagactaagacctacttttggaaggtgcagcaccacatggctcccac taaggatgagtttgattgcaaggcctgggcctacttctctgatgtggacctggagaaggatg tgcactctggcctgattggcccccctgctggtgtgtcacaccaataccctgaaccctgcccat ggcaggcaggtcactgtgcaggagtttgccctgtttttcactatctttgatgagactaagtc ttggtacttcactgagaacatggaaaggaattgcagggctccctgcaacatccagatggagg accccaccttcaaggagaactacaggtttcatgccatcaatggctacatcatggacaccctg cctggcctggtgatggctcaggatcagaggattaggtggtatctgctgagcatgggcagcaa tgagaacatccacagcatccacttttctggccatgtgttcactgtgaggaagaaggaggagt acaagatggctctgtacaatctgtaccctggggtgtttgagactgtggagatgctgcccagc aaggctgggatctggagggtggagtgcctgattggggaacacctgcatgctggcatgtctac cctgttcctggtgtactctaacaagtgccagactcccctgggcatggcctctgggcacatca gggacttccagatcactgcctctgggcagtatggccagtgggcccctaagctggctaggctg cattactctggcagcatcaatgcctggagcaccaaggagcccttcagctggatcaaggtgga cctgctggcccctatgatcatccatggcatcaagacccaggggggccagacagaagttctctt ctctgtacatctctcagttcatcatcatgtactctctggatggcaagaagtggcagacctac agggggaattctactggcactctgatggtgttctttgggaatgtggatagctctgggatcaa gcataatattttcaacccccccattattgctaggtacatcaggctgcacccaacccactact ctattaggtctaccctgaggatggagctgatgggctgtgacctgaactcttgtagcatgccc ctgggcatggagagcaaggctatctctgatgcccagatcactgccagcagctactttaccaa catgtttgctacttggagccccagcaaggccaggctgcacctgcagggcaggagcaatgcct ggaggccccaggtgaacaaccccaaggagtggctgcaggtggattttcagaagaccatgaag gtgactggggtgaccactcaggggggtgaaaagcctgctgactagcatgtatgtgaaggagtt tctgatcagcagctctcaggatggccatcagtggaccctgttcttccagaatggcaaggtga aggtgttccagggcaaccaggatagcttcacccctgtggtgaatagcctggaccccccctg ctgaccaggtacctgaggatccatccccagagctgggtgcaccagattgccctgaggatgga ggtgctgggctgtgaagcccaggacctgtactga FVIII V3 cDNA (SEQ ID NO:89)

atgcagattgagctgagcacctgcttcttcctgtgcctgctgaggttctgcttctctgccac caggagatactacctgggggctgtggagctgagctgggactacatgcagtctgacctggggg agctgcctgtggatgccaggttcccccccagagtgcccaagagcttccccttcaacacctct gtggtgtacaagaagaccctgtttgtggagttcactgaccacctgttcaacattgccaagcc caggccccccctggatgggcctgctgggccccaccatccaggctgaggtgtatgacactgtgg tgatcaccctgaagaacatggccagccaccctgtgagcctgcatgctgtgggggtgagctac tggaaggcctctgagggggctgagtatgatgaccagaccagccagagggagaaggaggatga caaggtgttccctgggggcagccacacctatgtgtggcaggtgctgaaggagaatggcccca tggcctctgacccccctgtgcctgacctacagctacctgagccatgtggacctggtgaaggac ctgaactctggcctgattggggccctgctggtgtgcagggagggcagcctggccaaggagaa gacccagaccctgcacaagttcatcctgctgtttgctgtgtttgatgagggcaagagctggc actctgaaaccaagaacagcctgatgcaggacagggatgctgcctctgccagggcctggccc aagatgcacactgtgaatggctatgtgaacaggagcctgcctggcctgattggctgccacag gaagtctgtgtactggcatgtgattggcatgggcaccacccctgaggtgcacagcatcttcc tggagggccacaccttcctggtcaggaaccacaggcaggccagcctggagatcagccccatc accttcctgactgcccagaccctgctgatggacctgggccagttcctgctgttctgccacat cagcagccaccagcatgatggcatggaggcctatgtgaaggtggacagctgccctgaggagc cccagctgaggatgaagaacaatgaggaggctgaggactatgatgatgacctgactgactct gagatggatgtggtgaggtttgatgatgacaacagccccagcttcatccagatcaggtctgt ggccaagaagcaccccaagacctgggtgcactacattgctgctgaggaggaggactgggact atgccccccctggtgctggcccctgatgacaggagctacaagagccagtacctgaacaatggc cccccagaggattggcaggaagtacaagaaggtcaggttcatggcctacactgatgaaacctt caagaccagggaggccatccagcatgagtctggcatcctgggccccctgctgtatggggagg tgggggacaccctgctgatcatcttcaagaaccaggccagcaggccctacaacatctacccc catggcatcactgatgtgaggcccctgtacagcaggaggctgcccaagggggtgaagcacct gaaggacttccccatcctgcctggggagatcttcaagtacaagtggactgtgactgtggagg atggccccaccaagtctgaccccaggtgcctgaccagatactacagcagctttgtgaacatg gagagggacctggcctctggcctgattggccccctgctgatctgctacaaggagtctgtgga ccagaggggcaaccagatcatgtctgacaagaggaatgtgatcctgttctctgtgtttgatg agaacaggagctggtacctgactgagaacatccagaggttcctgcccaaccctgctggggtg cagctggaggaccctgagttccaggccagcaacatcatgcacagcatcaatggctatgtgtt tgacagcctgcagctgtctgtgtgcctgcatgaggtggcctactggtacatcctgagcattg ggcccagactgacttcctgtctgtgttcttctctggctacaccttcaagcacaagatggtg tatgaggacaccctgaccctgttccccttctctggggagactgtgttcatgagcatggagaa ccctggcctgtggattctgggctgccacaactctgacttcaggaacaggggcatgactgccc tgctgaaagtctccagctgtgacaagaacactggggactactatgaggacagctatgaggac atctctgcctacctgctgagcaagaacaatgccattgagcccaggagcttcagccagaacag caggcaccccagcaccaggcagaagcagttcaatgccaccaccatccctgagaatgacatag agaagacagacccatggtttgcccaccggacccccatgcccaagatccagaatgtgagcagc tctgacctgctgatgctgctgaggcagagccccacccccatggcctgagcctgtctgacct -continued gcaggaggccaagtatgaaaccttctctgatgaccccagccctggggccattgacagcaaca acagcctgtctgagatgacccacttcaggccccagctgcaccactctggggacatggtgttc acccctgagtctggcctgcagctgaggctgaatgagaagctgggcaccactgctgccactga gctgaagaagctggacttcaaagtctccagcaccagcaacaacctgatcagcaccatcccct ctgacaacctggctgctggcactgacaacaccagcagcctgggcccccccagcatgcctgtg cactatgacagccagctggacaccaccctgtttggcaagaagagcagcccccctgactgagtc tgggggcccccctgagcctgtctgaggagaacaatgacagcaagctgctggagtctggcctga tgaacagccaggagagcagctggggcaagaatgtgagcaccaggagcttccagaagaagacc aggcactacttcattgctgctgtggagaggctgtgggactatggcatgagcagcagcccccca tgtgctgaggaacagggcccagtctggctctgtgccccagttcaagaaggtggtgttccagg agttcactgatggcagcttcacccagcccctgtacagaggggagctgaatgagcacctgggc ctgctgggcccctacatcagggctgaggtggaggacaacatcatggtgaccttcaggaacca ggccagcaggccctacagcttctacagcagcctgatcagctatgaggaggaccagaggcagg gggctgagcccaggaagaactttgtgaagcccaatgaaaccaagacctacttctggaaggtg cagcaccacatggcccccaccaaggatgagtttgactgcaaggcctgggcctacttctctga tgtggacctggagaaggatgtgcactctggcctgattggcccccctgctggtgtgccacacca acaccctgaaccctgcccatggcaggcaggtgactgtgcaggagtttgccctgttcttcacc atctttgatgaaaccaagagctggtacttcactgagaacatggagaggaactgcagggcccc ctgcaacatccagatggaggaccccaccttcaaggagaactacaggttccatgccatcaatg gctacatcatggacaccctgcctggcctggtgatggcccaggaccagaggatcaggtggtac ctgctgagcatgggcagcaatgagaacatccacagcatccacttctctggccatgtgttcac tgtgaggaagaaggaggagtacaagatggccctgtacaacctgtaccctggggtgtttgaga ctgtggagatgctgcccagcaaggctggcatctggagggtggagtgcctgattggggagcac ctgcatgctggcatgagcaccctgttcctggtgtacagcaacaagtgccagacccccctggg catggcctctggccacatcagggacttccagatcactgcctctggccagtatggccagtggg cccccaagctggccaggctgcactactctggcagcatcaatgcctggagcaccaaggagccc ttcagctggatcaaggtggacctgctggccccccatgatcatccatggcatcaagacccaggg ggccaggcagaagttcagcagcctgtacatcagccagttcatcatcatgtacagcctggatg gcaagaagtggcagacctacaggggcaacagcactggcaccctgatggtgttctttggcaat gtggacagctctggcatcaagcacaacatcttcaacccccccatcattgccagatacatcag gctgcaccccacccactacagcatcaggagcaccctgaggatggagctgatgggctgtgacc tgaacagctgcagcatgcccctgggcatggagagcaaggccatctctgatgcccagatcact gccagcagctacttcaccaacatgtttgccacctggagccccagcaaggccaggctgcacct gcagggcaggagcaatgcctggaggccccaggtcaacaaccccaaggagtggctgcaggtgg acttccagaagaccatgaaggtgactggggtgaccacccaggggggtgaagagcctgctgacc agcatgtatgtgaaggagttcctgatcagcagcagccaggatggccaccagtggaccctgtt cttccagaatggcaaggtgaaggtgttccagggcaaccaggacagcttcacccctgtggtga acagcctggacccccccctgctgaccagatacctgaggattcacccccagagctgggtgcac cagattgccctgaggatggaggtgctgggctgtgaggcccaggacctgtactga FVIII CO3 cDNA (SEQ ID NO:90)

atgcagattgagctgtcaacttgctttttcctgtgcctgctgagattttgtttttccgctac
tagaagatactacctgggggctgtggaactgtcttgggattacatgcagagtgacctgggag
agctgccagtggacgcacgatttccacctagagtccctaaatcattccccttcaacaccagc
gtggtctataagaaaacactgttcgtggagtttactgatcacctgttcaacatcgctaagcc
tcggccaccctggatgggactgctgggaccaacaatccaggcagaggtgtacgacaccgtgg
tcattacactgaaaaacatggcctcacaccccgtgagcctgcatgctgtgggcgtcagctac
tggaaggcttccgaaggggcagagtatgacgatcagacttcccagagagaaaaagaggacga
taaggtgtttcctggcgggtctcatacctatgtgtggcaggtcctgaaagagaatggcccca
tggcttccgaccctctgtgcctgacctactcttatctgagtcacgtggacctggtcaaggat
ctgaacagcggactgatcggagcactgctggtgtgtagggaagggagcctggctaaggagaa
aacccagacactgcataagttcattctgctgttcgccgtgtttgacgaaggaaaatcatggc
acagcgagacaaagaatagtctgatgcaggaccgggatgccgcttcagccagagcttggccc
aaaatgcacactgtgaacggctacgtcaatcgctcactgcctggactgatcggctgccaccg
aaagagcgtgtattggcatgtcatcggaatgggcaccacacctgaagtgcactccattttcc
tggaggggcatacctttctggtccgcaaccaccgacaggcctccctggagatctctccaatt
accttcctgacagctcagactctgctgatggatctgggacagttcctgctgttttgccacat
cagctcccaccagcatgatggcatggaggcctacgtgaaagtggacagctgtcccgaggaac
ctcagctgaggatgaagaacaatgaggaagctgaagactatgacgatgacctgaccgactcc
gagatggatgtggtccgattcgatgacgataacagcccctcctttatccagattagatctgt
ggccaagaaacaccctaagacatgggtccattacatcgcagccgaggaagaggactgggatt
atgcaccactggtgctggcaccagacgatcgatcctacaaatctcagtatctgaacaatgga
ccacagcggattggcagaaagtacaagaaagtgaggttcatggcttataccgatgaaacctt
caagactcgcgaagcaatccagcacgagagcgggattctgggaccactgctgtacggagaag
tgggggacaccctgctgatcatttttaagaaccaggccagcaggccttacaatatctatcca
catggaattacagatgtgcgccctctgtacagccggagactgccaaagggcgtcaaacacct
gaaggacttcccaatcctgcccggggaaatttttaagtataaatggactgtcaccgtcgagg
atggccccactaagagcgaccctaggtgcctgacccgctactattctagtttcgtgaatatg
gaaagggatctggccagcggactgatcggcccactgctgatttgttacaaagagagcgtgga
tcagagaggcaaccagatcatgtccgacaagaggaatgtgattctgttcagtgtctttgacg
aaaaccggtcatggtatctgaccgagaacatccagagattcctgcctaatccagccggagtg
cagctggaagatcctgagtttcaggcttctaacatcatgcatagtattaatggctacgtgtt
cgacagtctgcagctgtcagtgtgtctgcacgaggtcgcttactggtatatcctgagcattg
gagcacagacagatttcctgagcgtgttcttttccggctacacttttaagcataaaatggtg
tatgaggacacactgactctgttccccttcagcggcgaaaccgtgtttatgtccatggagaa
tcccgggctgtggatcctgggatgccacaacagcgatttcaggaatcgcgggatgactgccc
tgctgaaagtgtcaagctgtgacaagaacaccggagactactatgaagattcatacgaggac
atcagcgcatatctgctgtccaaaaacaatgccattgaacccaggtcttttagtcagaatcc
tccagtgctgaagaggcaccagcgcgagatcacccgcactaccctgcagagtgatcaggaag
agatcgactacgacgatacaatttctgtggaaatgaagaaagaggacttcgatatctatgac
gaagatgagaaccagagtcctcgatcattccagaagaaaacccggcattactttattgctgc -continued agtggagcgcctgtgggattatggcatgtcctctagtcctcacgtgctgcgaaatcgggccc agtcagggagcgtcccacagttcaagaaagtggtcttccaggagtttacagacggatccttt actcagccactgtaccggggcgaactgaacgagcacctggggctgctgggaccctatatcag agctgaagtggaggataacattatggtcaccttcagaaatcaggcatctaggccttacagtt tttattcaagcctgatctcttacgaagaggaccagaggcagggagcagaaccacgaaaaaac ttcgtgaagcctaatgagaccaaaacatacttttggaaggtgcagcaccatatggccccaac aaaagacgaattcgattgcaaggcatgggcctatttttctgacgtggatctggagaaggacg tccacagtggcctgatcgggccactgctggtgtgtcatactaacaccctgaatcccgcacac ggcaggcaggtcactgtccaggaattcgccctgttctttaccatctttgatgagacaaaaag ctggtacttcaccgaaaacatggagcgaaattgccgggctccatgtaatattcagatggaag accccacattcaaggagaactaccgctttcatgccatcaatgggtatattatggatactctg cccggactggtcatggctcaggaccagagaatcaggtggtacctgctgagcatggggtccaa cgagaatatccactcaattcatttcagcggacacgtgtttactgtccggaagaaagaagagt ataaaatggccctgtacaacctgtatcccggcgtgttcgaaaccgtcgagatgctgcctagc aaggcagggatctggagagtggaatgcctgattggggagcacctgcatgccggaatgtctac cctgtttctggtgtacagtaataagtgtcagacacccctggggatggcttccggacatatcc gggatttccagattaccgcatctggacagtacggccagtgggcccctaagctggctagactg cactattccgggtctatcaacgcttggtccacaaaagagcctttctcttggattaaggtgga cctgctggcaccaatgatcattcatggcatcaaaactcagggggccaggcagaagttctcct ctctgtacatctcacagtttatcatcatgtacagcctggatggcaagaaatggcagacatac cgcggcaatagcacagggactctgatggtgttctttggcaacgtggacagttcagggatcaa gcacaacattttcaatcccccctatcattgctagatacatcaggctgcacccaacccattatt ctattcgaagtacactgcggatggaactgatggggtgcgatctgaacagttgttcaatgccc ctgggaatggagtccaaggcaatctctgacgcccagattaccgctagctcctacttcactaa tatgtttgctacctggagcccctccaaagcacgactgcatctgcagggacgaagcaacgcat ggcgaccacaggtgaacaatcccaaggagtggctgcaggtcgattttcagaaaactatgaag gtgaccggagtcacaactcagggcgtgaaaagtctgctgacctcaatgtacgtcaaggagtt cctgatctctagttcacaggacggccaccagtggacactgttctttcagaacggaaaggtga aagtcttccagggcaatcaggattcctttacacctgtggtcaactctctggacccacccctg ctgactcgctacctgcgaatccacccacagtcctgggtgcatcagattgcactgagaatgga agtcctgggctgcgaggcccaggacctgtattga AAV-LK03 VP1 Capsid (SEQ ID NO:91)

MAADGYLPDWLEDNISEGIREWWALQPGAPKPKANQQHQDNARGLVLPGY

KYLGPGNGLDKGEPVNAADAAALEHDKAYDQQLKAGDNPYLKYNHADAEF

QERLKEDTSFGGNLGRAVFQAKKRLLEPLGLVEEAAKTAPGKKRPVDQSP

QEPDSSSGVGKSGKQPARKRLNFGQTGDSESVPDPQPLGEPPAAPTSLGS

NTMASGGGAPMADNNEGADGVGNSSGNWHCDSQWLGDRVITTSTRTWALP

TYNNHLYKQISSQSGASNDNHYFGYSTPWGYFDFNRFHCHFSPRDWQRLI

NNNWGFRPKKLSFKLFNIQVKEVTQNDGTTTIANNLTSTVQVFTDSEYQL

-continued

PYVLGSAHQGCLPPFPADVFMVPQYGYLTLNNGSQAVGRSSFYCLEYFPS

QMLRTGNNFQFSYTFEDVPFHSSYAHSQSLDRLMNPLIDQYLYYLNRTQG

TTSGTTNQSRLLFSQAGPQSMSLQARNWLPGPCYRQQRLSKTANDNNNSN

FPWTAASKYHLNGRDSLVNPGPAMASHKDDEEKFFPMHGNLIFGKEGTTA

SNAELDNVMITDEEEIRTTNPVATEQYGTVANNLQSSNTAPTTRTVNDQG

ALPGMVWQDRDVYLQGPIWAKIPHTDGHFHPSPLMGGFGLKHPPPQIMIK

-continued

NTPVPANPPTTFSPAKFASFITQYSTGQVSVEIEWELQKENSKRWNPEIQ

YTSNYNKSVNVDFTVDTNGVYSEPRPIGTRYLTRPL

AAV-SPK VP1 Capsid (SEQ ID NO:92)

MAADGYLPDWLEDNLSEGIREWWDLKPGAPKPKANQQKQDNGRGLVLPGY

KYLGPFNGLDKGEPVNAADAAALEHDKAYDQQLQAGDNPYLRYNHADAEF

QERLQEDTSFGGNLGRAVFQAKKRVLEPLGLVESPVKTAPGKKRPVEPSP

QRSPDSSTGIGKKGQQPAKKRLNFGQTGDSESVPDPQPIGEPPAAPSGVG

PNTMAAGGGAPMADNNEGADGVGSSSGNWHCDSTWLGDRVITTSTRTWAL

PTYNNHLYKQISNGTSGGSTNDNTYFGYSTPWGYFDFNRFHCHFSPRDWQ

RLINNNWGFRPKRLNFKLFNIQVKEVTQNEGTKTIANNLTSTIQVFTDSE

YQLPYVLGSAHQGCLPPFPADVFMIPQYGYLTLNNGSQAVGRSSFYCLEY

FPSQMLRTGNNFEFSYNFEDVPFHSSYAHSQSLDRLMNPLIDQYLYYLSR

TQSTGGTAGTQQLLFSQAGPNNMSAQAKNWLPGPCYRQQRVSTTLSQNNN

SNFAWTGATKYHLNGRDSLVNPGVAMATHKDDEERFFPSSGVLMFGKQGA

GKDNVDYSSVMLTSEEEIKTTNPVATEQYGVVADNLQQQNAAPIVGAVNS

QGALPGMVWQNRDVYLQGPIWAKIPHTDGNFHPSPLMGGFGLKHPPPQIL

IKNTPVPADPPTTFNQAKLASFITQYSTGQVSVEIEWELQKENSKRWNPE

IQYTSNYYKSTNVDFAVNTEGTYSEPRPIGTRYLTRNL

Nucleic Acid Sequence of Intron in AAV-WINT (SEQ ID NO:93)

AGGTAAGTGCCGTGTGTGGTTCCCGCGGGCCTGGCCTCTTTACGGGTTAT

GGCCCTTGCGTGCCTTGAATTACTGACACTGACATCCACTTTTTCTTTTT

CTCCACAG

FIX (SEQ ID NO:94)

ATGCAGAGGGTGAACATGATCATGGCTGAGAGCCCTGGCCTGATCACCAT

CTGCCTGCTGGGCTACCTGCTGTCTGCTGAATGTACAGGTTTGTTTCCTT

TTTTATAATACATTGAGTATGCTTGCCTTTTAGATATAGAAATATCTGAT

TCTGTCTTCTTCACTAAATTTTGATTACATGATTTGACAGCAATATTGAA

GAGTCTAACAGCCAGCACCCAGGTTGGTAAGTACTGGTTCTTTGTTAGCT

AGGTTTTCTTCTTCTTCACTTTTAAAACTAAATAGATGGACAATGCTTAT

GATGCAATAAGGTTTAATAAACACTGTTCAGTTCAGTATTTGGTCATGTA

ATTCCTGTTAAAAAACAGTCATCTCCTTGGTTTAAAAAAATTAAAAGTGG

GAAAACAAAGAAATAGCAGAATATAGTGAAAAAAAATAACCACAGTATTT

TTGTTTGGACTTACCACTTTGAAATCAAATTGGGAAACAAAAGCACAAAC

AGTGGCCTTATTTACACAAAAAGTCTGATTTTAAGATATGTGACAATTCA

AGGTTTCAGAAGTATGTAAGGAGGTGTGTCTCTAATTTTTTAAATTATAT

ATCTTCAATTTAAAGTTTTAGTTAAAACATAAAGATTAACCTTTCATTAG

CAAGCTGTTAGTTATCACCAAAGCTTTTCATGGATTAGGAAAAAATCATT

-continued

TTGTCTCTATCTCAAACATCTTGGAGTTGATATTTGGGGAAACACAATAC

TCAGTTGAGTTCCCTAGGGGAGAAAAGCAAGCTTAAGAATTGACACAAAG

AGTAGGAAGTTAGCTATTGCAACATATATCACTTTGTTTTTTCACAACTA

CAGTGACTTTATTTATTTCCCAGAGGAAGGCATACAGGGAAGAAATTATC

CCATTTGGACAAACAGCATGTTCTCACAGTAAGCACTTATCACACTTACT

TGTCAACTTTCTAGAATCAAATCTAGTAGCTGACAGTACCAGGATCAGGG

GTGCCAACCCTAAGCACCCCCAGAAAGCTGACTGGCCCTGTGGTTCCCAC

TCCAGACATGATGTCAGCTGTGAAATCCACCTCCCTGGACCATAATTAGG

CTTCTGTTCTTCAGGAGACATTTGTTCAAAGTCATTTGGGCAACCATATT

CTGAAAACAGCCCAGCCAGGGTGATGGATCACTTTGCAAAGATCCTCAAT

GAGCTATTTTCAAGTGATGACAAAGTGTGAAGTTAAGGGCTCATTTGAGA

ACTTTCTTTTTCATCCAAAGTAAATTCAAATATGATTAGAAATCTGACCT

TTTATTACTGGAATTCTCTTGACTAAAAGTAAAATTGAATTTTAATTCCT

AAATCTCCATGTGTATACAGTACTGTGGGAACATCACAGATTTTGGCTCC

ATGCCCTAAAGAGAAATTGGCTTTCAGATTATTTGGATTAAAAACAAAGA

CTTTCTTAAGAGATGTAAAATTTTCATGATGTTTTCTTTTTTGCTAAAAC

TAAAGAATTATTCTTTTACATTTCAGTTTTTCTTGATCATGAAAATGCCA

ACAAAATTCTGAATAGACCAAAGAGGTATAACTCTGGCAAGCTTGAAGAG

TTTGTACAGGGGAATCTGGAGAGAGAGTGTATGGAAGAGAAGTGCAGCTT

TGAGGAAGCCAGAGAAGTGTTTGAAAATACAGAGAGAACAACTGAATTTT

GGAAGCAGTATGTGGATGGTGATCAATGTGAGAGCAATCCCTGCTTGAAT

GGGGGGAGCTGTAAAGATGATATCAACAGCTATGAATGTTGGTGTCCCTT

TGGATTTGAGGGGAAAAACTGTGAGCTTGATGTGACCTGTAATATCAAGA

ATGGCAGGTGTGAGCAATTTTGCAAGAATTCTGCTGATAACAAAGTGGTC

TGTAGCTGCACTGAGGGATATAGGCTGGCTGAAAACCAGAAGAGCTGTGA

ACCTGCAGTGCCTTTTCCCTGTGGGAGAGTGTCTGTGAGCCAAACCAGCA

AGCTGACTAGGGCTGAAGCAGTCTTTCCTGATGTAGATTATGTGAATAGC

ACTGAGGCTGAGACAATCCTTGACAATATCACTCAGAGCACACAGAGCTT

CAATGACTTCACCAGGGTGGTAGGAGGGGAGGATGCCAAGCCTGGGCAGT

TCCCCTGGCAGGTAGTGCTCAATGGAAAAGTGGATGCCTTTTGTGGAGGT

TCAATTGTAAATGAGAAGTGGATTGTGACTGCAGCCCACTGTGTGGAAAC

TGGAGTCAAGATTACTGTGGTGGCTGGAGAGCACAATATTGAGGAAACTG

AGCACACTGAGCAGAAGAGGAATGTGATCAGGATTATCCCCCACCACAAC

TACAATGCTGCTATCAACAAGTACAACCATGACATTGCCCTCCTGGAACT

GGATGAACCCCTGGTCTTGAACAGCTATGTGACACCCATCTGTATTGCTG

ATAAAGAGTACACCAACATCTTCTTGAAATTTGGGTCTGGATATGTGTCT

GGCTGGGGCAGGGTGTTCCATAAAGGCAGGTCTGCCCTGGTATTGCAGTA

TTTGAGGGTGCCTCTGGTGGATAGAGCAACCTGCTTGCTGAGCACCAAGT

TTACAATCTACAACAATATGTTCTGTGCAGGGTTCCATGAAGGTGGTAGA

-continued

GACAGCTGCCAGGGAGATTCTGGGGGTCCCCATGTGACTGAGGTGGAGGG

AACCAGCTTCCTGACTGGGATTATCAGCTGGGGTGAGGAGTGTGCTATGA

-continued

AGGGAAAGTATGGGATCTACACAAAAGTATCCAGATATGTGAACTGGATT

AAGGAGAAAACCAAGCTGACTTGA

What is claimed is:

1. A polynucleotide comprising a regulatory element nucleic acid sequence at least 98% identical to the sequence of SEQ ID NO: 58 with or without 5' and/or 3' flanking 5-7 nucleotides or comprising the sequence of SEQ ID NO: 24.

2. A polynucleotide comprising a regulatory element nucleic acid sequence at least 98% identical to the sequence of SEQ ID NO: 58 or comprising the sequence of SEQ ID NO: 24.

3. A polynucleotide comprising a regulatory element nucleic acid sequence at least 98% identical to the sequence of SEQ ID NO: 58 and having reduced CpG(s) at the same positions as set forth in SEQ ID NO: 58; or comprising the sequence of SEQ ID NO: 24.

4. An expression cassette comprising the polynucleotide of claim 3, and a transgene, wherein said regulatory element nucleic acid sequence is operably linked to said transgene.

5. The expression cassette of claim 4, wherein said regulatory element nucleic acid sequence is positioned 5' of said transgene.

6. The expression cassette of claim 5, wherein said transgene encodes a therapeutic protein that is expressed in liver cells and secreted into the systemic circulation.

7. The expression cassette of claim 6, wherein said therapeutic protein is a blood coagulation or clotting factor protein.

8. The expression cassette of claim 7, wherein said blood coagulation or clotting factor protein is Factor IX (FIX), Factor VIII (FVIII), Factor VII (FVII) or Protein C.

9. The expression cassette of claim 6, wherein said therapeutic protein is a lysosomal storage enzyme.

10. The expression cassette of claim 9, wherein said lysosomal storage enzyme is acid alpha-glucosidase (GAA) or alpha-galactosidase (GLA).

11. An adeno-associated virus (AAV) vector comprising the expression cassette of claim 4.

12. The AAV vector of claim 11, wherein said AAV vector comprises:

a) an AAV capsid; and b) AAV inverted terminal repeats (ITRs), wherein said AAV ITR(s) flank the 5' or 3' terminus of said expression cassette.

13. The AAV vector of claim 12, wherein said AAV capsid comprises an amino acid comprising the sequence of SEQ ID NO:91 or SEQ ID NO:92.

14. The AAV vector of claim 11, wherein said ITRs comprise one or more ITRs of any of: AAV1, AAV2, AAV3, AAV3B, AAV4, AAV5, AAV6, AAV7, AAV8, AAV9, AAV10, AAV11, Rh10, or Rh74 AAV serotypes, or a combination thereof.

15. A pharmaceutical composition comprising a plurality of AAV vectors of claim 11 in a biologically compatible carrier or excipient.

16. The pharmaceutical composition of claim 15, further comprising empty AAV capsids.

17. The AAV vector of claim 12, wherein there is no more than 107 nucleotides of untranslated nucleic acid sequence between said regulatory element nucleic acid sequence and the 5' end of said transgene.

18. A polynucleotide comprising a regulatory element nucleic acid sequence comprising the sequence of SEQ ID NO: 58.

19. An expression cassette comprising the polynucleotide of claim 18 and a transgene, wherein said regulatory element nucleic acid sequence is operably linked to said transgene and is positioned 5' of said transgene.

20. The expression cassette of claim 19, wherein said transgene encodes a therapeutic protein.

21. The expression cassette of claim 20, wherein a non-coding nucleic acid is positioned between said regulatory element nucleic acid sequence and said transgene, and said non-coding nucleic acid sequence is not an intron.

22. The expression cassette of claim 20, wherein said therapeutic protein is either Factor IX (FIX), Factor VIII (FVIII), Factor VII (FVII) or Protein C.

23. An adeno-associated virus (AAV) vector comprising the expression cassette of claim 19.

24. The AAV vector of claim 23, wherein said AAV vector comprises:

a) an AAV capsid; and b) a 5' AAV inverted terminal repeats (ITR) flanking the 5' terminus of the expression cassette and a 3' ITR flanking the 3' terminus of the expression cassette.

25. The AAV vector of claim 24, wherein said capsid comprises the amino acid sequence of SEQ ID NOs: 91 or 92.

26. The AAV vector of claim 24, wherein there is no more than 107 nucleotides of untranslated nucleic acid sequence between said regulatory element nucleic acid sequence and the 5' end of said transgene.

27. A polynucleotide comprising a regulatory element nucleic acid sequence comprising the sequence of SEQ ID NO: 24.

28. An expression cassette comprising the polynucleotide of claim 27 and a transgene, wherein said regulatory element nucleic acid sequence is operably linked to said transgene and is positioned 5' of said transgene.

29. The expression cassette of claim 28, wherein said transgene encodes a therapeutic protein.

30. The expression cassette of claim 29, wherein a non-coding nucleic acid is positioned between said regulatory element nucleic acid sequence and said transgene, and said non-coding nucleic acid sequence is not an intron.

31. The expression cassette of claim 29, wherein said therapeutic protein is either Factor IX (FIX), Factor VIII (FVIII), Factor VII (FVII) or Protein C.

32. An adeno-associated virus (AAV) vector comprising the expression cassette of claim 28.

33. The AAV vector of claim 32, wherein said AAV vector comprises:

a) an AAV capsid; and b) a 5' AAV inverted terminal repeats (ITR) flanking the 5' terminus of the expression cassette and a 3' ITR flanking the 3' terminus of the expression cassette.

34. The AAV vector of claim 33, wherein said capsid comprises the amino acid sequence of SEQ ID NOs: 91 or 92.

35. The AAV vector of claim 33, wherein there is no more than 107 nucleotides of untranslated nucleic acid sequence between said regulatory element nucleic acid sequence and the 5' end of said transgene.

* * * * *

SEQUENCE LISTING

<160> NUMBER OF SEQ ID NOS: 98

<210> SEQ ID NO 1
<211> LENGTH: 4960
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 1
cctgcaggca gctgcgcgct cgctcgctca ctgaggccgc ccgggcaaag cccgggcgtc 60
gggcgacctt tggtcgcccg gcctcagtga gcgagcgagc gcgcagagag ggagtggcca 120
actccatcac taggggttcc tgtcgacgtg tctgtctgca catttcgtag agcgagtgtt 180
ccgatactct aatctcccta ggcaaggttc atattgactt aggttactta ttctcctttt 240
gttgactaag tcaataatca gaatcagcag gtttggagtc agcttggcag ggatcagcag 300
cctgggttgg aaggaggggg tataaaagcc ccttcaccag gagaagccgt cacacagatc 360
cacaagctcc tgctagcgtt taaacgccac catgcagatt gagctgagca cctgcttctt 420
cctgtgtctg ctgaggttct gcttctctgc caccaggagg tattacctgg gggctgtgga 480
gctgagctgg gactatatgc agtctgacct gggggagctg cctgtggatg ctaggttccc 540
ccccagggtg cccaagagct tcccctttaa cacttctgtg gtgtacaaga agaccctgtt 600
tgtggagttc actgaccacc tgttcaacat tgccaagccc aggccccct ggatggggct 660 gctggggccc accatccagg ctgaggtgta tgacactgtg gtgatcaccc tgaagaacat 720
ggccagccac cctgtgagcc tgcatgctgt gggggtgagc tactggaagg cttctgaggg 780
ggctgagtat gatgaccaga ctagccagag ggagaaggag gatgacaagg tgtttcctgg 840
gggcagccat acctatgtgt ggcaggtgct gaaggagaat ggccccatgg cctctgaccc 900
cctgtgcctg acctacagct acctgtctca tgtggacctg gtgaaggacc tgaactctgg 960
cctgattggg gctctgctgg tgtgtaggga gggcagcctg gctaaggaaa agacccagac 1020
cctgcataag tttatcctgc tgtttgctgt gtttgatgag ggcaagagct ggcactctga 1080
gaccaagaac agcctgatgc aggataggga tgctgcctct gccagggctt ggcctaagat 1140
gcacactgtg aatgggtatg tgaataggag cctgcctggc ctgattggct gccacaggaa 1200
gtctgtgtac tggcatgtga ttgggatggg caccacccct gaggtccata gcatcttcct 1260
ggagggccac actttcctgg tgaggaacca cagacaggcc tctctggaga tctctcccat 1320
caccttcctg actgctcaga ctctgctgat ggacctgggc cagttcctgc tgttttgcca 1380
tattagcagc caccagcatg atgggatgga ggcctatgtg aaggtggata gctgccctga 1440
ggagcctcag ctgaggatga agaacaatga ggaggctgaa gactatgatg atgacctgac 1500
tgattctgag atggatgtgg tgaggtttga tgatgacaat agccccagct tcattcagat 1560
caggtctgtg gccaagaaac accccaagac ctgggtgcac tacattgctg ctgaggaaga 1620
ggactgggac tatgctcccc tggtgctggc ccctgatgat aggtcttata agagccagta 1680
cctgaacaat gggccccaga ggattggcag gaagtacaag aaggtgaggt tcatggccta 1740

-continued

```
cactgatgaa accttcaaaa ccagggaggc cattcagcat gagtctggca tcctgggccc   1800
tctgctgtat ggggaggtgg gggacaccct gctgatcatc ttcaagaacc aggccagcag   1860
gccctacaac atctatcctc atggcatcac tgatgtgagg cccctgtaca gcaggaggct   1920
gcccaagggg gtgaagcacc tgaaagactt ccccatcctg cctggggaga tctttaagta   1980
taagtggact gtgactgtgg aggatggccc taccaagtct gaccccaggt gtctgaccag   2040
gtactattct agctttgtga acatggagag ggacctggcc tctggcctga ttgggcccct   2100
gctgatctgc tacaaggagt ctgtggacca gaggggcaac cagatcatgt ctgacaagag   2160
gaatgtgatc ctgttttctg tgtttgatga gaataggagc tggtacctga ctgagaacat   2220
ccagaggttt ctgcccaatc ctgctggggt gcagctggag gatcctgagt tccaggccag   2280
caatatcatg catagcatca atggctatgt gtttgacagc ctgcagctgt ctgtgtgcct   2340
gcatgaggtg gcctactggt acatcctgag cattggggcc cagactgact ttctgtctgt   2400
gttcttttct ggctatacct tcaagcacaa gatggtgtat gaggataccc tgaccctgtt   2460
ccccttctct ggggagactg tgttcatgag catggagaat cctgggctgt ggatcctggg   2520
gtgccacaac tctgatttta ggaacagggg gatgactgcc ctgctgaagg tgtctagctg   2580
tgataagaac actggggact actatgagga cagctatgag gacatttctg cttatctgct   2640
gtctaagaat aatgccattg agcccagaag cttcagccag aatccccctg tgctgaagag   2700
acatcagagg gagatcacca gaactaccct gcagtctgat caggaggaga ttgactatga   2760
tgacactatc tctgtggaga tgaagaagga ggactttgac atctatgatg aggatgagaa   2820
tcagtctccc aggagctttc agaagaagac cagacattac ttcattgctg ctgtggagag   2880
gctgtgggac tatggcatga gctctagccc tcatgtgctg aggaacaggg cccagtctgg   2940
ctctgtgccc cagttcaaga aggtggtgtt ccaggaattc actgatggca gcttcaccca   3000
gcccctgtac aggggggagc tgaatgagca cctgggcctg ctggggcctt atatcagggc   3060
tgaggtggag gataatatta tggtgacttt caggaaccag gccagcaggc cctactcttt   3120
ctatagcagc ctgatctctt atgaggagga tcagaggcag gggggctgagc ctaggaagaa   3180
ctttgtgaag cccaatgaga ctaagaccta cttctggaag gtccagcacc acatggcccc   3240
taccaaggat gagtttgact gcaaggcctg ggcctatttc tctgatgtgg atctggagaa   3300
ggatgtccat tctgggctga ttggcccccct gctggtgtgc cacactaaca ctctgaatcc   3360
tgcccatggc aggcaggtga ctgtccagga gtttgccctg ttcttcacta tctttgatga   3420
gaccaagagc tggtacttta ctgagaacat ggagaggaac tgcagagctc cttgcaatat   3480
tcagatggag gaccccacct tcaaggagaa ttacaggttc catgccatta atgggtacat   3540
catggacacc ctgcctggcc tggtgatggc tcaggaccag aggatcaggt ggtacctgct   3600
gagcatgggc tctaatgaga atatccacag catccacttc tctgggcatg tgttcactgt   3660
gaggaagaag gaggagtaca agatggctct gtataatctg taccctgggg tgtttgaaac   3720
tgtggagatg ctgccctcta aggctggcat ctggagggtg gagtgcctga ttggggagca   3780
cctgcatgct ggcatgagca ccctgttcct ggtgtacagc aacaagtgcc agaccccccct   3840
gggcatggcc tctggccaca tcagggactt ccagatcact gcctctggcc agtatggcca   3900
gtgggccccc aagctggcca ggctgcacta ttctggcagc atcaatgcct ggagcaccaa   3960
ggagcccttc agctggatca aggtggacct gctggccccc atgatcattc atggcatcaa   4020
gacccagggg gccaggcaga agttcagctc tctgtacatc tctcagttca tcatcatgta   4080
ctctctggat gggaagaagt ggcagaccta caggggcaac agcactggca ccctgatggt   4140
```

gttctttggg aatgtggact cttctggcat caagcacaac atcttcaatc cccccatcat 4200
tgctaggtat attaggctgc atcccaccca ctacagcatc aggtctaccc tgaggatgga 4260
gctgatgggc tgtgacctga actcttgcag catgcccctg ggcatggagt ctaaggccat 4320
ctctgatgcc cagattactg ccagcagcta cttcaccaac atgtttgcca cctggagccc 4380
ctctaaggcc aggctgcatc tgcaggggag gagcaatgcc tggaggcctc aggtgaacaa 4440
ccccaaggag tggctgcagg tggatttcca gaagaccatg aaggtgactg gggtgaccac 4500
ccagggggtc aagagcctgc tgaccagcat gtatgtgaag gagttcctga tcagcagcag 4560
ccaggatggc caccagtgga ctctgttctt tcagaatggg aaggtgaagg tgtttcaggg 4620
caatcaggac tctttcaccc ctgtggtgaa cagcctggac ccccccctgc tgaccagata 4680
cctgaggatc cacccccagt cttgggtgca tcagattgcc ctgaggatgg aggtgctggg 4740
ctgtgaggct caggatctgt actgagcggc cgcaataaaa gatcagagct ctagagatct 4800
gtgtgttggt tttttgtgta ggaaccccta gtgatggagt tggccactcc ctctctgcgc 4860
gctcgctcgc tcactgaggc cgggcgacca aaggtcgccc gacgcccggg ctttgcccgg 4920
gcggcctcag tgagcgagcg agcgcgcagc tgcctgcagg 4960

<210> SEQ ID NO 2
<211> LENGTH: 225
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 2
gtgtctgtct gcacatttcg tagagcgagt gttccgatac tctaatctcc ctaggcaagg 60
ttcatatttg tgtaggttac ttattctcct tttgttgact aagtcaataa tcagaatcag 120
caggtttgga gtcagcttgg cagggatcag cagcctgggt tggaaggagg gggtataaaa 180
gccccttcac caggagaagc cgtcacacag atccacaagc tcctg 225

<210> SEQ ID NO 3
<211> LENGTH: 225
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3
gtgtctgtct gcacatttcg tagagcgagt gttccgatac tctaatctcc ctaggcaagg 60
ttcatattga cttaggttac ttattctcct tttgttgact aagtcaataa tcagaatcag 120
caggtttgga gtcagcttgg cagggatcag cagcctgggt tggaaggagg gggtataaaa 180
gccccttcac caggagaagc cgtcacacag atccacaagc tcctg 225

<210> SEQ ID NO 4
<211> LENGTH: 225
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 4
gtgtctgtct gcacattttg tagagtgagt gttctgatac tctaatctcc ctaggcaagg 60
ttcatattga cttaggttac ttattctcct tttgttgact aagtcaataa tcagaatcag 120
caggtttgga gtcagcttgg cagggatcag cagcctgggt tggaaggagg gggtataaaa 180
gccccttcac caggagaagc tgtcacacag atccacaagc tcctg 225

<210> SEQ ID NO 5
<211> LENGTH: 236
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 5
acgcgtgtct gtctgcacat tttgtagagt gagtgttctg atactctaat ctccctaggc 60
aaggttcata ttgacttagg ttacttattc tccttttgtt gactaagtca ataatcagaa 120
tcagcaggtt tggagtcagc ttggcaggga tcagcagcct gggttggaag gagggggtat 180
aaaagcccct tcaccaggag aagctgtcac acagatccac aagctcctgt ttaaac 236

<210> SEQ ID NO 6
<211> LENGTH: 225
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 6
gtgtctgtct gcacatttcg tagagtgagt gttctgatac tctaatctcc ctaggcaagg 60
ttcatattga cttaggttac ttattctcct tttgttgact aagtcaataa tcagaatcag 120
caggtttgga gtcagcttgg cagggatcag cagcctgggt tggaaggagg gggtataaaa 180
gccccttcac caggagaagc tgtcacacag atccacaagc tcctg 225

<210> SEQ ID NO 7
<211> LENGTH: 236
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 7
acgcgtgtct gtctgcacat ttcgtagagt gagtgttctg atactctaat ctccctaggc 60
aaggttcata ttgacttagg ttacttattc tccttttgtt gactaagtca ataatcagaa 120
tcagcaggtt tggagtcagc ttggcaggga tcagcagcct gggttggaag gagggggtat 180
aaaagcccct tcaccaggag aagctgtcac acagatccac aagctcctgt ttaaac 236

<210> SEQ ID NO 8
<211> LENGTH: 225
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 8
gtgtctgtct gcacattttg tagagcgagt gttctgatac tctaatctcc ctaggcaagg 60
ttcatattga cttaggttac ttattctcct tttgttgact aagtcaataa tcagaatcag 120

-continued caggtttgga gtcagcttgg cagggatcag cagcctgggt tggaaggagg gggtataaaa 180
gccccttcac caggagaagc tgtcacacag atccacaagc tcctg 225

<210> SEQ ID NO 9
<211> LENGTH: 236
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 9
acgcgtgtct gtctgcacat tttgtagagc gagtgttctg atactctaat ctccctaggc 60
aaggttcata ttgacttagg ttacttattc tccttttgtt gactaagtca ataatcagaa 120
tcagcaggtt tggagtcagc ttggcaggga tcagcagcct gggttggaag gagggggtat 180
aaaagcccct tcaccaggag aagctgtcac acagatccac aagctcctgt ttaaac 236

<210> SEQ ID NO 10
<211> LENGTH: 225
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 10
gtgtctgtct gcacattttg tagagtgagt gttccgatac tctaatctcc ctaggcaagg 60
ttcatattga cttaggttac ttattctcct tttgttgact aagtcaataa tcagaatcag 120
caggtttgga gtcagcttgg cagggatcag cagcctgggt tggaaggagg gggtataaaa 180
gccccttcac caggagaagc tgtcacacag atccacaagc tcctg 225

<210> SEQ ID NO 11
<211> LENGTH: 236
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 11
acgcgtgtct gtctgcacat tttgtagagt gagtgttccg atactctaat ctccctaggc 60
aaggttcata ttgacttagg ttacttattc tccttttgtt gactaagtca ataatcagaa 120
tcagcaggtt tggagtcagc ttggcaggga tcagcagcct gggttggaag gagggggtat 180
aaaagcccct tcaccaggag aagctgtcac acagatccac aagctcctgt ttaaac 236

<210> SEQ ID NO 12
<211> LENGTH: 225
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 12
gtgtctgtct gcacattttg tagagtgagt gttctgatac tctaatctcc ctaggcaagg 60
ttcatattga cttaggttac ttattctcct tttgttgact aagtcaataa tcagaatcag 120
caggtttgga gtcagcttgg cagggatcag cagcctgggt tggaaggagg gggtataaaa 180
gccccttcac caggagaagc cgtcacacag atccacaagc tcctg 225

<210> SEQ ID NO 13
<211> LENGTH: 236
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 13
acgcgtgtct gtctgcacat tttgtagagt gagtgttctg atactctaat ctccctaggc 60
aaggttcata ttgacttagg ttacttattc tccttttgtt gactaagtca ataatcagaa 120
tcagcaggtt tggagtcagc ttggcaggga tcagcagcct gggttggaag gagggggtat 180
aaaagcccct tcaccaggag aagccgtcac acagatccac aagctcctgt ttaaac 236

<210> SEQ ID NO 14
<211> LENGTH: 177
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 14
taggcaaggt tcatattgac ttaggttact tattctcctt ttgcctgctg accttggagc 60
tggggcagag gtcagaggag tcagcttggc agggatcagc agatgaattt tgtaatcagt 120
tcccttgagt cattaaaaaa tataaaacaa agatgagtct agttaataat ctacaat 177

<210> SEQ ID NO 15
<211> LENGTH: 190
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 15
acgcgtaggc aaggttcata ttgacttagg ttacttattc tccttttgcc tgctgacctt 60
ggagctgggg cagaggtcag aggagtcagc ttggcaggga tcagcagatg aattttgtaa 120
tcagttccct tgagtcatta aaaaatataa aacaaagatg agtctagtta ataatctaca 180
atgtttaaac 190

<210> SEQ ID NO 16
<211> LENGTH: 167
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 16
taggcaaggt tcatattgac ttaggttact tattctcctt ttgataactg gggtgacctt 60
ggttaatatt caccagcaga gtcagcttgg cagggatcag cagcctgggt tggaaggagg 120
gggtataaaa tgataactgg ggtgaccttg gttaatattc accagca 167

<210> SEQ ID NO 17
<211> LENGTH: 180
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 17
acgcgtaggc aaggttcata ttgacttagg ttacttattc tccttttgat aactggggtg     60
accttggtta atattcacca gcagagtcag cttggcaggg atcagcagcc tgggttggaa    120
ggagggggta taaaatgata actggggtga ccttggttaa tattcaccag cagtttaaac    180

<210> SEQ ID NO 18
<211> LENGTH: 211
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
actcccttga gtcattaaaa aaatatattt ggtaattcat aaaccttaca aacatttact     60
taacacttac catgaattgg gtaatgtgct caattgactt aggttactta ttctcctttt    120 gaatttttg gcaagaatat tatgaatttt gtaatcagtt ataaaggcag ccaatgaaat    180
acaaagatga gtctagttaa taatctacaa t                                   211

<210> SEQ ID NO 19
<211> LENGTH: 225
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
acgcgtactc ccttgagtca ttaaaaaaat atatttggta attcataaac cttacaaaca     60
tttacttaac acttaccatg aattgggtaa tgtgctcaat tgacttaggt tacttattct    120
ccttttgaat tttttggcaa gaatattatg aattttgtaa tcagttataa aggcagccaa    180
tgaaatacaa agatgagtct agttaataat ctacaatgtt taaac                    225

<210> SEQ ID NO 20
<211> LENGTH: 210
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
taggcaaggt tcatattgac ttaggttact tattctcctt tgggtgactc agatcccagc     60
cagtggactt agcccctgtt tgctcctctg ataactgggg tgaccttggt taatattcac    120
cagcattttt gagtcaataa taatgttaac tgatccctag gctataaaat aatagtgtta    180
actgatccct gtgcagtggt gtgattatag                                     210

<210> SEQ ID NO 21
<211> LENGTH: 223
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
acgcgttagg caaggttcat attgacttag gttacttatt ctcctttggg tgactcagat 60
cccagccagt ggacttagcc cctgtttgct cctctgataa ctggggtgac cttggttaat 120
attcaccagc atttttgagt caataataat gttaactgat ccctaggcta taaaataata 180
gtgttaactg atccctgtgc agtggtgtga ttatagttta aac 223

<210> SEQ ID NO 22
<211> LENGTH: 444
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 22
atgccacctc caacatccac tcgacccctt ggaatttcgg tggagaggag cagaggttgt 60
cctggcgtgg tttaggtagt gtgagagggg tacccgggga tcttgctacc agtggaacag 120
ccactaagga ttctgcagtg agagcagagg gccagctaag tggtactctc ccagagactg 180
tctgactcac gccacccccct ccaccttgga cacaggacgc tgtggtttct gagccaggta 240
caatgactcc tttcggtaag tgcagtggaa gctgtacact gcccaggcaa agcgtccggg 300
cagcgtaggc gggcgactca gatcccagcc agtggactta gcccctgttt gctcctccga 360
taactggggt gaccttggtt aatattcacc agcagcctcc cccgttgccc ctctggatcc 420
actgcttaaa tacggacgag gaca 444

<210> SEQ ID NO 23
<211> LENGTH: 456
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 23
gggcccatgc cacctccaac atccactcga ccccttggaa tttcggtgga gaggagcaga 60
ggttgtcctg gcgtggttta ggtagtgtga gaggggtacc cggggatctt gctaccagtg 120
gaacagccac taaggattct gcagtgagag cagagggcca gctaagtggt actctcccag 180
agactgtctg actcacgcca ccccctccac cttggacaca ggacgctgtg gtttctgagc 240
caggtacaat gactcctttc ggtaagtgca gtggaagctg tacactgccc aggcaaagcg 300
tccgggcagc gtaggcgggc gactcagatc ccagccagtg gacttagccc ctgtttgctc 360
ctccgataac tggggtgacc ttggttaata ttcaccagca gcctcccccg ttgcccctct 420
ggatccactg cttaaatacg gacgaggaca gggccc 456

<210> SEQ ID NO 24
<211> LENGTH: 444
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 24
atgccacctc caacatccac ttgacccctt ggaattttgg tggagaggag cagaggttgt 60
cctggtgtgg tttaggtagt gtgagagggg tacctgggga tcttgctacc agtggaacag 120
ccactaagga ttctgcagtg agagcagagg gccagctaag tggtactctc ccagagactg 180

-continued

```
tctgactcat gccacccccct ccaccttgga cacaggatgc tgtggtttct gagccaggta    240

caatgactcc tttcagtaag tgcagtggaa gctgtacact gcccaggcaa agtgtctggg    300

cagtgtaggt gggtgactca gatcccagcc agtggactta gcccctgttt gctcctctga    360

taactggggt gaccttggtt aatattcacc agcagcctcc cctgttgccc ctctggatcc    420

actgcttaaa tatggatgag gaca                                           444
```

<210> SEQ ID NO 25
<211> LENGTH: 456
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 25

```
gggcccatgc cacctccaac atccacttga ccccttggaa ttttggtgga gaggagcaga     60

ggttgtcctg gtgtggttta ggtagtgtga gaggggtacc tggggatctt gctaccagtg    120

gaacagccac taaggattct gcagtgagag cagagggcca gctaagtggt actctcccag    180

agactgtctg actcatgcca ccccctccac cttggacaca ggatgctgtg gtttctgagc    240

caggtacaat gactcctttc agtaagtgca gtggaagctg tacactgccc aggcaaagtg    300

tctgggcagt gtaggtgggt gactcagatc ccagccagtg gacttagccc ctgtttgctc    360

ctctgataac tggggtgacc ttggttaata ttcaccagca gcctcccctg ttgcccctct    420

ggatccactg cttaaatatg gatgaggaca gggccc                              456
```

<210> SEQ ID NO 26
<211> LENGTH: 444
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 26

```
atgccacctc caacatccac tcgacccctt ggaattttgg tggagaggag cagaggttgt     60

cctggtgtgg tttaggtagt gtgagagggg tacctgggga tcttgctacc agtggaacag    120

ccactaagga ttctgcagtg agagcagagg gccagctaag tggtactctc ccagagactg    180

tctgactcat gccacccccct ccaccttgga cacaggatgc tgtggtttct gagccaggta    240

caatgactcc tttcagtaag tgcagtggaa gctgtacact gcccaggcaa agtgtctggg    300

cagtgtaggt gggtgactca gatcccagcc agtggactta gcccctgttt gctcctctga    360

taactggggt gaccttggtt aatattcacc agcagcctcc cctgttgccc ctctggatcc    420

actgcttaaa tatggatgag gaca                                           444
```

<210> SEQ ID NO 27
<211> LENGTH: 456
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 27

```
gggcccatgc cacctccaac atccactcga ccccttggaa ttttggtgga gaggagcaga     60

ggttgtcctg gtgtggttta ggtagtgtga gaggggtacc tggggatctt gctaccagtg    120
```

gaacagccac taaggattct gcagtgagag cagagggcca gctaagtggt actctcccag 180
agactgtctg actcatgcca ccccctccac cttggacaca ggatgctgtg gtttctgagc 240
caggtacaat gactcctttc agtaagtgca gtggaagctg tacactgccc aggcaaagtg 300
tctgggcagt gtaggtgggt gactcagatc ccagccagtg gacttagccc ctgtttgctc 360
ctctgataac tggggtgacc ttggttaata ttcaccagca gcctcccctg ttgcccctct 420
ggatccactg cttaaatatg gatgaggaca gggccc 456

<210> SEQ ID NO 28
<211> LENGTH: 444
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 28
atgccacctc caacatccac ttgacccctt ggaatttcgg tggagaggag cagaggttgt 60
cctggtgtgg tttaggtagt gtgagagggg tacctgggga tcttgctacc agtggaacag 120
ccactaagga ttctgcagtg agagcagagg gccagctaag tggtactctc ccagagactg 180
tctgactcat gccacccccct ccaccttgga cacaggatgc tgtggtttct gagccaggta 240
caatgactcc tttcagtaag tgcagtggaa gctgtacact gcccaggcaa agtgtctggg 300
cagtgtaggt gggtgactca gatcccagcc agtggactta gcccctgttt gctcctctga 360
taactggggt gaccttggtt aatattcacc agcagcctcc cctgttgccc ctctggatcc 420
actgcttaaa tatggatgag gaca 444

<210> SEQ ID NO 29
<211> LENGTH: 456
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 29
gggcccatgc cacctccaac atccacttga ccccttggaa tttcggtgga gaggagcaga 60
ggttgtcctg gtgtggttta ggtagtgtga gaggggtacc tggggatctt gctaccagtg 120
gaacagccac taaggattct gcagtgagag cagagggcca gctaagtggt actctcccag 180
agactgtctg actcatgcca ccccctccac cttggacaca ggatgctgtg gtttctgagc 240
caggtacaat gactcctttc agtaagtgca gtggaagctg tacactgccc aggcaaagtg 300
tctgggcagt gtaggtgggt gactcagatc ccagccagtg gacttagccc ctgtttgctc 360
ctctgataac tggggtgacc ttggttaata ttcaccagca gcctcccctg ttgcccctct 420
ggatccactg cttaaatatg gatgaggaca gggccc 456

<210> SEQ ID NO 30
<211> LENGTH: 444
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 30
atgccacctc caacatccac ttgacccctt ggaattttgg tggagaggag cagaggttgt 60

```
cctggcgtgg tttaggtagt gtgagagggg tacctgggga tcttgctacc agtggaacag    120

ccactaagga ttctgcagtg agagcagagg gccagctaag tggtactctc ccagagactg    180

tctgactcat gccacccccct ccaccttgga cacaggatgc tgtggtttct gagccaggta    240

caatgactcc tttcagtaag tgcagtggaa gctgtacact gcccaggcaa agtgtctggg    300

cagtgtaggt gggtgactca gatcccagcc agtggactta gcccctgttt gctcctctga    360

taactggggt gaccttggtt aatattcacc agcagcctcc cctgttgccc ctctggatcc    420

actgcttaaa tatggatgag gaca                                           444
```

<210> SEQ ID NO 31
<211> LENGTH: 456
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 31

```
gggcccatgc cacctccaac atccacttga ccccttggaa ttttggtgga gaggagcaga     60

ggttgtcctg gcgtggttta ggtagtgtga gaggggtacc tggggatctt gctaccagtg    120

gaacagccac taaggattct gcagtgagag cagagggcca gctaagtggt actctcccag    180

agactgtctg actcatgcca ccccctccac cttggacaca ggatgctgtg gtttctgagc    240

caggtacaat gactcctttc agtaagtgca gtggaagctg tacactgccc aggcaaagtg    300

tctgggcagt gtaggtgggt gactcagatc ccagccagtg gacttagccc ctgtttgctc    360

ctctgataac tggggtgacc ttggttaata ttcaccagca gcctcccctg ttgcccctct    420

ggatccactg cttaaatatg gatgaggaca gggccc                               456
```

<210> SEQ ID NO 32
<211> LENGTH: 444
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 32

```
atgccacctc caacatccac ttgacccctt ggaattttgg tggagaggag cagaggttgt     60

cctggtgtgg tttaggtagt gtgagagggg tacccgggga tcttgctacc agtggaacag    120

ccactaagga ttctgcagtg agagcagagg gccagctaag tggtactctc ccagagactg    180

tctgactcat gccacccccct ccaccttgga cacaggatgc tgtggtttct gagccaggta    240

caatgactcc tttcagtaag tgcagtggaa gctgtacact gcccaggcaa agtgtctggg    300

cagtgtaggt gggtgactca gatcccagcc agtggactta gcccctgttt gctcctctga    360

taactggggt gaccttggtt aatattcacc agcagcctcc cctgttgccc ctctggatcc    420

actgcttaaa tatggatgag gaca                                           444
```

<210> SEQ ID NO 33
<211> LENGTH: 456
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 33

-continued

```
gggcccatgc cacctccaac atccacttga ccccttggaa ttttggtgga gaggagcaga     60

ggttgtcctg gtgtggttta ggtagtgtga gaggggtacc cggggatctt gctaccagtg    120

gaacagccac taaggattct gcagtgagag cagagggcca gctaagtggt actctcccag    180

agactgtctg actcatgcca ccccctccac cttggacaca ggatgctgtg gtttctgagc    240

caggtacaat gactcctttc agtaagtgca gtggaagctg tacactgccc aggcaaagtg    300

tctgggcagt gtaggtgggt gactcagatc ccagccagtg gacttagccc ctgtttgctc    360

ctctgataac tggggtgacc ttggttaata ttcaccagca gcctcccctg ttgcccctct    420

ggatccactg cttaaatatg gatgaggaca gggccc                              456
```

<210> SEQ ID NO 34
<211> LENGTH: 444
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34

```
atgccacctc caacatccac ttgacccctt ggaattttgg tggagaggag cagaggttgt     60

cctggtgtgg tttaggtagt gtgagagggg tacctgggga tcttgctacc agtggaacag    120

ccactaagga ttctgcagtg agagcagagg gccagctaag tggtactctc ccagagactg    180

tctgactcac gccacccccct ccaccttgga cacaggatgc tgtggtttct gagccaggta    240

caatgactcc tttcagtaag tgcagtggaa gctgtacact gcccaggcaa agtgtctggg    300

cagtgtaggt gggtgactca gatcccagcc agtggactta gcccctgttt gctcctctga    360

taactggggt gaccttggtt aatattcacc agcagcctcc cctgttgccc ctctggatcc    420

actgcttaaa tatggatgag gaca                                           444
```

<210> SEQ ID NO 35
<211> LENGTH: 456
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35

```
gggcccatgc cacctccaac atccacttga ccccttggaa ttttggtgga gaggagcaga     60

ggttgtcctg gtgtggttta ggtagtgtga gaggggtacc tggggatctt gctaccagtg    120

gaacagccac taaggattct gcagtgagag cagagggcca gctaagtggt actctcccag    180

agactgtctg actcacgcca ccccctccac cttggacaca ggatgctgtg gtttctgagc    240

caggtacaat gactcctttc agtaagtgca gtggaagctg tacactgccc aggcaaagtg    300

tctgggcagt gtaggtgggt gactcagatc ccagccagtg gacttagccc ctgtttgctc    360

ctctgataac tggggtgacc ttggttaata ttcaccagca gcctcccctg ttgcccctct    420

ggatccactg cttaaatatg gatgaggaca gggccc                              456
```

<210> SEQ ID NO 36
<211> LENGTH: 444
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36
atgccacctc caacatccac ttgacccctt ggaattttgg tggagaggag cagaggttgt 60
cctggtgtgg tttaggtagt gtgagagggg tacctgggga tcttgctacc agtggaacag 120
ccactaagga ttctgcagtg agagcagagg gccagctaag tggtactctc ccagagactg 180
tctgactcat gccacccccct ccaccttgga cacaggacgc tgtggtttct gagccaggta 240
caatgactcc tttcagtaag tgcagtggaa gctgtacact gcccaggcaa agtgtctggg 300
cagtgtaggt gggtgactca gatcccagcc agtggactta gcccctgttt gctcctctga 360
taactggggt gaccttggtt aatattcacc agcagcctcc cctgttgccc ctctggatcc 420
actgcttaaa tatggatgag gaca 444

<210> SEQ ID NO 37
<211> LENGTH: 456
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 37
gggcccatgc cacctccaac atccacttga ccccttggaa ttttggtgga gaggagcaga 60
ggttgtcctg gtgtggttta ggtagtgtga gaggggtacc tggggatctt gctaccagtg 120
gaacagccac taaggattct gcagtgagag cagagggcca gctaagtggt actctcccag 180
agactgtctg actcatgcca ccccctccac cttggacaca ggacgctgtg gtttctgagc 240
caggtacaat gactcctttc agtaagtgca gtggaagctg tacactgccc aggcaaagtg 300
tctgggcagt gtaggtgggt gactcagatc ccagccagtg gacttagccc ctgtttgctc 360
ctctgataac tggggtgacc ttggttaata ttcaccagca gcctcccctg ttgcccctct 420
ggatccactg cttaaatatg gatgaggaca gggccc 456

<210> SEQ ID NO 38
<211> LENGTH: 444
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 38
atgccacctc caacatccac ttgacccctt ggaattttgg tggagaggag cagaggttgt 60
cctggtgtgg tttaggtagt gtgagagggg tacctgggga tcttgctacc agtggaacag 120
ccactaagga ttctgcagtg agagcagagg gccagctaag tggtactctc ccagagactg 180
tctgactcat gccacccccct ccaccttgga cacaggatgc tgtggtttct gagccaggta 240
caatgactcc tttcggtaag tgcagtggaa gctgtacact gcccaggcaa agtgtctggg 300
cagtgtaggt gggtgactca gatcccagcc agtggactta gcccctgttt gctcctctga 360
taactggggt gaccttggtt aatattcacc agcagcctcc cctgttgccc ctctggatcc 420
actgcttaaa tatggatgag gaca 444

<210> SEQ ID NO 39
<211> LENGTH: 456
<212> TYPE: DNA
<213> ORGANISM: Artificial Sequence
<220> FEATURE:
<223> OTHER INFORMATION: Description of Artificial Sequence: Synthetic -continued polynucleotide

<400> SEQUENCE: 39
gggcccatgc cacctccaac atccacttga ccccttggaa ttttggtgga gaggagcaga 60
ggttgtcctg gtgtggttta ggtagtgtga gaggggtacc tggggatctt gctaccagtg 120
gaacagccac taaggattct gcagtgagag cagagggcca gctaagtggt actctcccag 180
agactgtctg actcatgcca ccccctccac cttggacaca ggatgctgtg gtttctgagc 240
caggtacaat gactcctttc ggtaagtgca gtggaagctg tacactgccc aggcaaagtg 300
tctgggcagt gtaggtgggt gactcagatc ccagccagtg gacttagccc ctgtttgctc 360
ctctgataac tggggtgacc ttggttaata ttcaccagca gcctcccctg ttgcccctct 420
ggatccactg cttaaatatg gatgaggaca gggccc 456

<210> SEQ ID NO 40
<211> LENGTH: 444
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 40
atgccacctc caacatccac ttgacccctt ggaattttgg tggagaggag cagaggttgt 60
cctggtgtgg tttaggtagt gtgagagggg tacctgggga tcttgctacc agtggaacag 120
ccactaagga ttctgcagtg agagcagagg gccagctaag tggtactctc ccagagactg 180
tctgactcat gccacccccc ccaccttgga cacaggatgc tgtggtttct gagccaggta 240
caatgactcc tttcagtaag tgcagtggaa gctgtacact gcccaggcaa agcgtctggg 300
cagtgtaggt gggtgactca gatcccagcc agtggactta gcccctgttt gctcctctga 360
taactggggt gaccttggtt aatattcacc agcagcctcc cctgttgccc ctctggatcc 420
actgcttaaa tatggatgag gaca 444

<210> SEQ ID NO 41
<211> LENGTH: 456
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 41
gggcccatgc cacctccaac atccacttga ccccttggaa ttttggtgga gaggagcaga 60
ggttgtcctg gtgtggttta ggtagtgtga gaggggtacc tggggatctt gctaccagtg 120
gaacagccac taaggattct gcagtgagag cagagggcca gctaagtggt actctcccag 180
agactgtctg actcatgcca ccccctccac cttggacaca ggatgctgtg gtttctgagc 240
caggtacaat gactcctttc agtaagtgca gtggaagctg tacactgccc aggcaaagcg 300
tctgggcagt gtaggtgggt gactcagatc ccagccagtg gacttagccc ctgtttgctc 360
ctctgataac tggggtgacc ttggttaata ttcaccagca gcctcccctg ttgcccctct 420
ggatccactg cttaaatatg gatgaggaca gggccc 456

<210> SEQ ID NO 42
<211> LENGTH: 444
<212> TYPE: DNA
<213> ORGANISM: Artificial Sequence -continued

```
<220> FEATURE:
<223> OTHER INFORMATION: Description of Artificial Sequence: Synthetic
      polynucleotide

<400> SEQUENCE: 42

atgccacctc caacatccac ttgacccctt ggaattttgg tggagaggag cagaggttgt     60

cctggtgtgg tttaggtagt gtgagagggg tacctgggga tcttgctacc agtggaacag    120

ccactaagga ttctgcagtg agagcagagg gccagctaag tggtactctc ccagagactg    180

tctgactcat gccacccccct ccaccttgga cacaggatgc tgtggtttct gagccaggta    240

caatgactcc tttcagtaag tgcagtggaa gctgtacact gcccaggcaa agtgtccggg    300

cagtgtaggt gggtgactca gatcccagcc agtggactta gcccctgttt gctcctctga    360

taactggggt gaccttggtt aatattcacc agcagcctcc cctgttgccc ctctggatcc    420

actgcttaaa tatggatgag gaca                                            444


<210> SEQ ID NO 43
<211> LENGTH: 456
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43

gggcccatgc cacctccaac atccacttga ccccttggaa ttttggtgga gaggagcaga     60

ggttgtcctg gtgtggttta ggtagtgtga gaggggtacc tggggatctt gctaccagtg    120

gaacagccac taaggattct gcagtgagag cagagggcca gctaagtggt actctcccag    180

agactgtctg actcatgcca ccccctccac cttggacaca ggatgctgtg gtttctgagc    240

caggtacaat gactcctttc agtaagtgca gtggaagctg tacactgccc aggcaaagtg    300

tccgggcagt gtaggtgggt gactcagatc ccagccagtg gacttagccc ctgtttgctc    360

ctctgataac tggggtgacc ttggttaata ttcaccagca gcctcccctg ttgcccctct    420

ggatccactg cttaaatatg gatgaggaca gggccc                               456


<210> SEQ ID NO 44
<211> LENGTH: 444
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44

atgccacctc caacatccac ttgacccctt ggaattttgg tggagaggag cagaggttgt     60

cctggtgtgg tttaggtagt gtgagagggg tacctgggga tcttgctacc agtggaacag    120

ccactaagga ttctgcagtg agagcagagg gccagctaag tggtactctc ccagagactg    180

tctgactcat gccacccccct ccaccttgga cacaggatgc tgtggtttct gagccaggta    240

caatgactcc tttcagtaag tgcagtggaa gctgtacact gcccaggcaa agtgtctggg    300

cagcgtaggt gggtgactca gatcccagcc agtggactta gcccctgttt gctcctctga    360

taactggggt gaccttggtt aatattcacc agcagcctcc cctgttgccc ctctggatcc    420

actgcttaaa tatggatgag gaca                                            444


<210> SEQ ID NO 45
<211> LENGTH: 456
```

<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 45
gggcccatgc cacctccaac atccacttga ccccttggaa ttttggtgga gaggagcaga 60
ggttgtcctg gtgtggttta ggtagtgtga gaggggtacc tggggatctt gctaccagtg 120
gaacagccac taaggattct gcagtgagag cagagggcca gctaagtggt actctcccag 180
agactgtctg actcatgcca ccccctccac cttggacaca ggatgctgtg gtttctgagc 240
caggtacaat gactcctttc agtaagtgca gtggaagctg tacactgccc aggcaaagtg 300
tctgggcagc gtaggtgggt gactcagatc ccagccagtg gacttagccc ctgtttgctc 360
ctctgataac tggggtgacc ttggttaata ttcaccagca gcctcccctg ttgcccctct 420
ggatccactg cttaaatatg gatgaggaca gggccc 456

<210> SEQ ID NO 46
<211> LENGTH: 444
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 46
atgccacctc caacatccac ttgacccctt ggaattttgg tggagaggag cagaggttgt 60
cctggtgtgg tttaggtagt gtgagagggg tacctgggga tcttgctacc agtggaacag 120
ccactaagga ttctgcagtg agagcagagg gccagctaag tggtactctc ccagagactg 180
tctgactcat gccacccccct ccaccttgga cacaggatgc tgtggtttct gagccaggta 240
caatgactcc tttcagtaag tgcagtggaa gctgtacact gcccaggcaa agtgtctggg 300
cagtgtaggc gggtgactca gatcccagcc agtggactta gcccctgttt gctcctctga 360
taactggggt gaccttggtt aatattcacc agcagcctcc cctgttgccc ctctggatcc 420
actgcttaaa tatggatgag gaca 444

<210> SEQ ID NO 47
<211> LENGTH: 456
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 47
gggcccatgc cacctccaac atccacttga ccccttggaa ttttggtgga gaggagcaga 60
ggttgtcctg gtgtggttta ggtagtgtga gaggggtacc tggggatctt gctaccagtg 120
gaacagccac taaggattct gcagtgagag cagagggcca gctaagtggt actctcccag 180
agactgtctg actcatgcca ccccctccac cttggacaca ggatgctgtg gtttctgagc 240
caggtacaat gactcctttc agtaagtgca gtggaagctg tacactgccc aggcaaagtg 300
tctgggcagt gtaggcgggt gactcagatc ccagccagtg gacttagccc ctgtttgctc 360
ctctgataac tggggtgacc ttggttaata ttcaccagca gcctcccctg ttgcccctct 420
ggatccactg cttaaatatg gatgaggaca gggccc 456

<210> SEQ ID NO 48
<211> LENGTH: 444
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 48
atgccacctc caacatccac ttgacccctt ggaattttgg tggagaggag cagaggttgt 60
cctggtgtgg tttaggtagt gtgagagggg tacctgggga tcttgctacc agtggaacag 120
ccactaagga ttctgcagtg agagcagagg gccagctaag tggtactctc ccagagactg 180
tctgactcat gccacccct ccaccttgga cacaggatgc tgtggtttct gagccaggta 240
caatgactcc tttcagtaag tgcagtggaa gctgtacact gcccaggcaa agtgtctggg 300
cagtgtaggt gggcgactca gatcccagcc agtggactta gcccctgttt gctcctctga 360
taactggggt gaccttggtt aatattcacc agcagcctcc cctgttgccc ctctggatcc 420
actgcttaaa tatggatgag gaca 444

<210> SEQ ID NO 49
<211> LENGTH: 456
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 49
gggcccatgc cacctccaac atccacttga ccccttggaa ttttggtgga gaggagcaga 60
ggttgtcctg gtgtggttta ggtagtgtga gaggggtacc tggggatctt gctaccagtg 120
gaacagccac taaggattct gcagtgagag cagagggcca gctaagtggt actctcccag 180
agactgtctg actcatgcca ccccctccac cttggacaca ggatgctgtg gtttctgagc 240
caggtacaat gactcctttc agtaagtgca gtggaagctg tacactgccc aggcaaagtg 300
tctgggcagt gtaggtgggc gactcagatc ccagccagtg gacttagccc ctgtttgctc 360
ctctgataac tggggtgacc ttggttaata ttcaccagca gcctcccctg ttgcccctct 420
ggatccactg cttaaatatg gatgaggaca gggccc 456

<210> SEQ ID NO 50
<211> LENGTH: 444
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 50
atgccacctc caacatccac ttgacccctt ggaattttgg tggagaggag cagaggttgt 60
cctggtgtgg tttaggtagt gtgagagggg tacctgggga tcttgctacc agtggaacag 120
ccactaagga ttctgcagtg agagcagagg gccagctaag tggtactctc ccagagactg 180
tctgactcat gccacccct ccaccttgga cacaggatgc tgtggtttct gagccaggta 240
caatgactcc tttcagtaag tgcagtggaa gctgtacact gcccaggcaa agtgtctggg 300
cagtgtaggt gggtgactca gatcccagcc agtggactta gcccctgttt gctcctccga 360
taactggggt gaccttggtt aatattcacc agcagcctcc cctgttgccc ctctggatcc 420
actgcttaaa tatggatgag gaca 444

<210> SEQ ID NO 51
<211> LENGTH: 456
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51
gggcccatgc cacctccaac atccacttga ccccttggaa ttttggtgga gaggagcaga 60
ggttgtcctg gtgtggttta ggtagtgtga gaggggtacc tggggatctt gctaccagtg 120
gaacagccac taaggattct gcagtgagag cagagggcca gctaagtggt actctcccag 180
agactgtctg actcatgcca ccccctccac cttggacaca ggatgctgtg gtttctgagc 240
caggtacaat gactcctttc agtaagtgca gtggaagctg tacactgccc aggcaaagtg 300
tctgggcagt gtaggtgggt gactcagatc ccagccagtg gacttagccc ctgtttgctc 360
ctccgataac tggggtgacc ttggttaata ttcaccagca gcctcccctg ttgcccctct 420
ggatccactg cttaaatatg gatgaggaca gggccc 456

<210> SEQ ID NO 52
<211> LENGTH: 444
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52
atgccacctc caacatccac ttgacccctt ggaattttgg tggagaggag cagaggttgt 60
cctggtgtgg tttaggtagt gtgagagggg tacctgggga tcttgctacc agtggaacag 120
ccactaagga ttctgcagtg agagcagagg gccagctaag tggtactctc ccagagactg 180
tctgactcat gccacccccct ccaccttgga cacaggatgc tgtggtttct gagccaggta 240
caatgactcc tttcagtaag tgcagtggaa gctgtacact gcccaggcaa agtgtctggg 300
cagtgtaggt gggtgactca gatcccagcc agtggactta gcccctgttt gctcctctga 360
taactggggt gaccttggtt aatattcacc agcagcctcc cccgttgccc ctctggatcc 420
actgcttaaa tatggatgag gaca 444

<210> SEQ ID NO 53
<211> LENGTH: 456
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53
gggcccatgc cacctccaac atccacttga ccccttggaa ttttggtgga gaggagcaga 60
ggttgtcctg gtgtggttta ggtagtgtga gaggggtacc tggggatctt gctaccagtg 120
gaacagccac taaggattct gcagtgagag cagagggcca gctaagtggt actctcccag 180
agactgtctg actcatgcca ccccctccac cttggacaca ggatgctgtg gtttctgagc 240
caggtacaat gactcctttc agtaagtgca gtggaagctg tacactgccc aggcaaagtg 300
tctgggcagt gtaggtgggt gactcagatc ccagccagtg gacttagccc ctgtttgctc 360
ctctgataac tggggtgacc ttggttaata ttcaccagca gcctcccccg ttgcccctct 420
ggatccactg cttaaatatg gatgaggaca gggccc 456

<210> SEQ ID NO 54
<211> LENGTH: 444
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 54
atgccacctc caacatccac ttgacccctt ggaattttgg tggagaggag cagaggttgt 60
cctggtgtgg tttaggtagt gtgagagggg tacctgggga tcttgctacc agtggaacag 120
ccactaagga ttctgcagtg agagcagagg gccagctaag tggtactctc ccagagactg 180
tctgactcat gccacccccct ccaccttgga cacaggatgc tgtggtttct gagccaggta 240
caatgactcc tttcagtaag tgcagtggaa gctgtacact gcccaggcaa agtgtctggg 300
cagtgtaggt gggtgactca gatcccagcc agtggactta gcccctgttt gctcctctga 360
taactggggt gaccttggtt aatattcacc agcagcctcc cctgttgccc ctctggatcc 420
actgcttaaa tacggatgag gaca 444

<210> SEQ ID NO 55
<211> LENGTH: 456
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 55
gggcccatgc cacctccaac atccacttga ccccttggaa ttttggtgga gaggagcaga 60
ggttgtcctg gtgtggttta ggtagtgtga gaggggtacc tggggatctt gctaccagtg 120
gaacagccac taaggattct gcagtgagag cagagggcca gctaagtggt actctcccag 180
agactgtctg actcatgcca ccccctccac cttggacaca ggatgctgtg gtttctgagc 240
caggtacaat gactcctttc agtaagtgca gtggaagctg tacactgccc aggcaaagtg 300
tctgggcagt gtaggtgggt gactcagatc ccagccagtg gacttagccc ctgtttgctc 360
ctctgataac tggggtgacc ttggttaata ttcaccagca gcctcccctg ttgcccctct 420
ggatccactg cttaaatacg gatgaggaca gggccc 456

<210> SEQ ID NO 56
<211> LENGTH: 444
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 56
atgccacctc caacatccac ttgacccctt ggaattttgg tggagaggag cagaggttgt 60
cctggtgtgg tttaggtagt gtgagagggg tacctgggga tcttgctacc agtggaacag 120
ccactaagga ttctgcagtg agagcagagg gccagctaag tggtactctc ccagagactg 180
tctgactcat gccacccccct ccaccttgga cacaggatgc tgtggtttct gagccaggta 240
caatgactcc tttcagtaag tgcagtggaa gctgtacact gcccaggcaa agtgtctggg 300
cagtgtaggt gggtgactca gatcccagcc agtggactta gcccctgttt gctcctctga 360

```
taactggggt gaccttggtt aatattcacc agcagcctcc cctgttgccc ctctggatcc    420

actgcttaaa tatggacgag gaca                                           444


<210> SEQ ID NO 57
<211> LENGTH: 456
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57

gggcccatgc cacctccaac atccacttga ccccttggaa ttttggtgga gaggagcaga     60

ggttgtcctg gtgtggttta ggtagtgtga gaggggtacc tggggatctt gctaccagtg    120

gaacagccac taaggattct gcagtgagag cagagggcca gctaagtggt actctcccag    180

agactgtctg actcatgcca ccccctccac cttggacaca ggatgctgtg gtttctgagc    240

caggtacaat gactcctttc agtaagtgca gtggaagctg tacactgccc aggcaaagtg    300

tctgggcagt gtaggtgggt gactcagatc ccagccagtg gacttagccc ctgtttgctc    360

ctctgataac tggggtgacc ttggttaata ttcaccagca gcctcccctg ttgcccctct    420

ggatccactg cttaaatatg gacgaggaca gggccc                              456


<210> SEQ ID NO 58
<211> LENGTH: 439
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58

atgccacctc caacatccac ttgacccctt ggaattttgg tggagaggag cagaggttgt     60

cctggtgtgg tttaggtagt gtgagagggg tacctgggga tcttgctacc agtggaacag    120

ccactaagga ttctgcagtg agagcagagg gccagctaag tggtactctc ccagagactg    180

tctgactcag ccaccccctc caccttggac acaggatgct gtggtttctg agccaggtac    240

aatgactcct ttggtaagtg cagtggaagc tgtacactgc ccaggcaaag gtctgggcag    300

gtagggggtg actcagatcc cagccagtgg acttagcccc tgtttgctcc tctgataact    360

ggggtgacct tggttaatat tcaccagcag cctcccctgt tgcccctctg gatccactgc    420

ttaaatatgg atgaggaca                                                 439


<210> SEQ ID NO 59
<211> LENGTH: 451
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59

gggcccatgc cacctccaac atccacttga ccccttggaa ttttggtgga gaggagcaga     60

ggttgtcctg gtgtggttta ggtagtgtga gaggggtacc tggggatctt gctaccagtg    120

gaacagccac taaggattct gcagtgagag cagagggcca gctaagtggt actctcccag    180

agactgtctg actcagccac cccctccacc ttggacacag gatgctgtgg tttctgagcc    240

aggtacaatg actcctttgg taagtgcagt ggaagctgta cactgcccag gcaaaggtct    300
```

gggcaggtag ggggtgactc agatcccagc cagtggactt agcccctgtt tgctcctctg 360
ataactgggg tgaccttggt taatattcac cagcagcctc ccctgttgcc cctctggatc 420
cactgcttaa atatggatga ggacagggcc c 451

<210> SEQ ID NO 60
<211> LENGTH: 443
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 60
atgccacctc caacatccac ttgacccctt ggaattttgg tggagaggag cagaggttgt 60
cctggtgtgg tttaggtagt gtgagagggg tacctgggga tcttgctacc agtggaacag 120
ccactaagga ttctgcagtg agagcagagg gccagctaag tggtactctc ccagagactg 180
tctgactcat gccacccct ccaccttgga cacaggacgc tgtggtttct gagccaggta 240
caatgactcc tttggtaagt gcagtggaag ctgtacactg cccaggcaaa gtgtctgggc 300
agtgtaggtg ggcgactcag atcccagcca gtggacttag cccctgtttg ctcctccgat 360
aactggggtg accttggtta atattcacca gcagcctccc ccgttgcccc tctggatcca 420
ctgcttaaat acggacgagg aca 443

<210> SEQ ID NO 61
<211> LENGTH: 455
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 61
gggcccatgc cacctccaac atccacttga ccccttggaa ttttggtgga gaggagcaga 60
ggttgtcctg gtgtggttta ggtagtgtga gaggggtacc tggggatctt gctaccagtg 120
gaacagccac taaggattct gcagtgagag cagagggcca gctaagtggt actctcccag 180
agactgtctg actcatgcca ccccctccac cttggacaca ggacgctgtg gtttctgagc 240
caggtacaat gactcctttg gtaagtgcag tggaagctgt acactgccca ggcaaagtgt 300
ctgggcagtg taggtgggcg actcagatcc cagccagtgg acttagcccc tgtttgctcc 360
tccgataact ggggtgacct tggttaatat tcaccagcag cctcccccgt tgcccctctg 420
gatccactgc ttaaatacgg acgaggacag ggccc 455

<210> SEQ ID NO 62
<211> LENGTH: 268
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 62
atgccacctc caaggagcag aggtgatctt gctaccagtg gagagcagag ggccagctct 60
cccagagact gtctgactca gccacccct ccaccttgga cacaggaggt ttctgagcca 120
tcctttcagt aagtgcatgt acactgccca gctgggcagc tcagatccca gccagtggac 180
ttagcccctg tttgctcctc tgataactgg ggtgaccttg gttaatattc accagcagcc 240
tgttgcccct ctggatccac tgcttaaa 268

<210> SEQ ID NO 63
<211> LENGTH: 280
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 63
gggcccatgc cacctccaag gagcagaggt gatcttgcta ccagtggaga gcagagggcc 60
agctctccca gagactgtct gactcagcca ccccctccac cttggacaca ggaggtttct 120
gagccatcct ttcagtaagt gcatgtacac tgcccagctg ggcagctcag atcccagcca 180
gtggacttag cccctgtttg ctcctctgat aactggggtg accttggtta atattcacca 240
gcagcctgtt gcccctctgg atccactgct taaagggccc 280

<210> SEQ ID NO 64
<211> LENGTH: 444
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 64
atgccacctc caacatccac ttgacccctt ggaattttgg tggagaggag cagaggttgt 60
cctggtgtgg tttaggtagt gtgagagggg tacctgggga tcttgctacc agtggaacag 120
ccactaagga ttctgcagtg agagcagagg gccagctaag tggtactctc ccagagactg 180
tctgactcac cccacccccct ccaccttgga cacaggacac tgtggtttct gagccaggta 240
caatgactcc ttttggtaag tgcagtggaa gctgtacact gcccaggcaa agtgtctggg 300
cagtgtaggt gggtgactca gatcccagcc agtggactta gcccctgttt gctcctctga 360
taactggggt gaccttggtt aatattcacc agcagcctcc cctgttgccc ctctggatcc 420
actgcttaaa tatggatgag gaca 444

<210> SEQ ID NO 65
<211> LENGTH: 456
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 65
gggcccatgc cacctccaac atccacttga ccccttggaa ttttggtgga gaggagcaga 60
ggttgtcctg gtgtggttta ggtagtgtga gaggggtacc tggggatctt gctaccagtg 120
gaacagccac taaggattct gcagtgagag cagagggcca gctaagtggt actctcccag 180
agactgtctg actcacccca ccccctccac cttggacaca ggacactgtg gtttctgagc 240
caggtacaat gactcctttt ggtaagtgca gtggaagctg tacactgccc aggcaaagtg 300
tctgggcagt gtaggtgggt gactcagatc ccagccagtg gacttagccc ctgtttgctc 360
ctctgataac tggggtgacc ttggttaata ttcaccagca gcctcccctg ttgcccctct 420
ggatccactg cttaaatatg gatgaggaca gggccc 456

<210> SEQ ID NO 66
<211> LENGTH: 444
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 66
atgccacctc caacatccac ttgacccctt ggaattttgg tggagaggag cagaggttgt 60
cctggtgtgg tttaggtagt gtgagagggg tacctgggga tcttgctacc agtggaacag 120
ccactaagga ttctgcagtg agagcagagg gccagctaag tggtactctc ccagagactg 180
tctgactcac gccacccct ccaccttgga cacaggacac tgtggtttct gagccaggta 240
caatgactcc ttttggtaag tgcagtggaa gctgtacact gcccaggcaa agtgtctggg 300
cagtgtaggt gggtgactca gatcccagcc agtggactta gcccctgttt gctcctctga 360
taactggggt gaccttggtt aatattcacc agcagcctcc cctgttgccc ctctggatcc 420
actgcttaaa tatggatgag gaca 444

<210> SEQ ID NO 67
<211> LENGTH: 456
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 67
gggcccatgc cacctccaac atccacttga ccccttggaa ttttggtgga gaggagcaga 60
ggttgtcctg gtgtggttta ggtagtgtga gaggggtacc tggggatctt gctaccagtg 120
gaacagccac taaggattct gcagtgagag cagagggcca gctaagtggt actctcccag 180
agactgtctg actcacgcca ccccctccac cttggacaca ggacactgtg gtttctgagc 240
caggtacaat gactcctttt ggtaagtgca gtggaagctg tacactgccc aggcaaagtg 300
tctgggcagt gtaggtgggt gactcagatc ccagccagtg gacttagccc ctgtttgctc 360
ctctgataac tggggtgacc ttggttaata ttcaccagca gcctcccctg ttgcccctct 420
ggatccactg cttaaatatg gatgaggaca gggccc 456

<210> SEQ ID NO 68
<211> LENGTH: 1457
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 68

Met Gln Ile Glu Leu Ser Thr Cys Phe Phe Leu Cys Leu Leu Arg Phe
1 5 10 15

Cys Phe Ser Ala Thr Arg Arg Tyr Tyr Leu Gly Ala Val Glu Leu Ser
20 25 30

Trp Asp Tyr Met Gln Ser Asp Leu Gly Glu Leu Pro Val Asp Ala Arg
35 40 45

Phe Pro Pro Arg Val Pro Lys Ser Phe Pro Phe Asn Thr Ser Val Val
50 55 60

Tyr Lys Lys Thr Leu Phe Val Glu Phe Thr Asp His Leu Phe Asn Ile
65 70 75 80

-continued

```
Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
```

-continued

```
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Pro Pro Val Leu
        755                 760                 765

Lys Arg His Gln Arg Glu Ile Thr Arg Thr Thr Leu Gln Ser Asp Gln
    770                 775                 780

Glu Glu Ile Asp Tyr Asp Asp Thr Ile Ser Val Glu Met Lys Lys Glu
785                 790                 795                 800

Asp Phe Asp Ile Tyr Asp Glu Asp Glu Asn Gln Ser Pro Arg Ser Phe
                805                 810                 815

Gln Lys Lys Thr Arg His Tyr Phe Ile Ala Ala Val Glu Arg Leu Trp
            820                 825                 830

Asp Tyr Gly Met Ser Ser Ser Pro His Val Leu Arg Asn Arg Ala Gln
        835                 840                 845

Ser Gly Ser Val Pro Gln Phe Lys Lys Val Val Phe Gln Glu Phe Thr
    850                 855                 860

Asp Gly Ser Phe Thr Gln Pro Leu Tyr Arg Gly Glu Leu Asn Glu His
865                 870                 875                 880

Leu Gly Leu Leu Gly Pro Tyr Ile Arg Ala Glu Val Glu Asp Asn Ile
                885                 890                 895

Met Val Thr Phe Arg Asn Gln Ala Ser Arg Pro Tyr Ser Phe Tyr Ser
            900                 905                 910

Ser Leu Ile Ser Tyr Glu Glu Asp Gln Arg Gln Gly Ala Glu Pro Arg
        915                 920                 925
```

```
Lys Asn Phe Val Lys Pro Asn Glu Thr Lys Thr Tyr Phe Trp Lys Val
    930                 935                 940

Gln His His Met Ala Pro Thr Lys Asp Glu Phe Asp Cys Lys Ala Trp
945                 950                 955                 960

Ala Tyr Phe Ser Asp Val Asp Leu Glu Lys Asp Val His Ser Gly Leu
                965                 970                 975

Ile Gly Pro Leu Leu Val Cys His Thr Asn Thr Leu Asn Pro Ala His
            980                 985                 990

Gly Arg Gln Val Thr Val Gln Glu  Phe Ala Leu Phe Phe  Thr Ile Phe
        995                 1000                1005

Asp Glu  Thr Lys Ser Trp Tyr  Phe Thr Glu Asn Met  Glu Arg Asn
    1010                1015                1020

Cys Arg  Ala Pro Cys Asn Ile  Gln Met Glu Asp Pro  Thr Phe Lys
    1025                1030                1035

Glu Asn  Tyr Arg Phe His Ala  Ile Asn Gly Tyr Ile  Met Asp Thr
    1040                1045                1050

Leu Pro  Gly Leu Val Met Ala  Gln Asp Gln Arg Ile  Arg Trp Tyr
    1055                1060                1065

Leu Leu  Ser Met Gly Ser Asn  Glu Asn Ile His Ser  Ile His Phe
    1070                1075                1080

Ser Gly  His Val Phe Thr Val  Arg Lys Lys Glu Glu  Tyr Lys Met
    1085                1090                1095

Ala Leu  Tyr Asn Leu Tyr Pro  Gly Val Phe Glu Thr  Val Glu Met
    1100                1105                1110

Leu Pro  Ser Lys Ala Gly Ile  Trp Arg Val Glu Cys  Leu Ile Gly
    1115                1120                1125

Glu His  Leu His Ala Gly Met  Ser Thr Leu Phe Leu  Val Tyr Ser
    1130                1135                1140

Asn Lys  Cys Gln Thr Pro Leu  Gly Met Ala Ser Gly  His Ile Arg
    1145                1150                1155

Asp Phe  Gln Ile Thr Ala Ser  Gly Gln Tyr Gly Gln  Trp Ala Pro
    1160                1165                1170

Lys Leu  Ala Arg Leu His Tyr  Ser Gly Ser Ile Asn  Ala Trp Ser
    1175                1180                1185

Thr Lys  Glu Pro Phe Ser Trp  Ile Lys Val Asp Leu  Leu Ala Pro
    1190                1195                1200

Met Ile  Ile His Gly Ile Lys  Thr Gln Gly Ala Arg  Gln Lys Phe
    1205                1210                1215

Ser Ser  Leu Tyr Ile Ser Gln  Phe Ile Ile Met Tyr  Ser Leu Asp
    1220                1225                1230

Gly Lys  Lys Trp Gln Thr Tyr  Arg Gly Asn Ser Thr  Gly Thr Leu
    1235                1240                1245

Met Val  Phe Phe Gly Asn Val  Asp Ser Ser Gly Ile  Lys His Asn
    1250                1255                1260

Ile Phe  Asn Pro Pro Ile Ile  Ala Arg Tyr Ile Arg  Leu His Pro
    1265                1270                1275

Thr His  Tyr Ser Ile Arg Ser  Thr Leu Arg Met Glu  Leu Met Gly
    1280                1285                1290

Cys Asp  Leu Asn Ser Cys Ser  Met Pro Leu Gly Met  Glu Ser Lys
    1295                1300                1305

Ala Ile  Ser Asp Ala Gln Ile  Thr Ala Ser Ser Tyr  Phe Thr Asn
    1310                1315                1320
```

-continued

Met Phe Ala Thr Trp Ser Pro Ser Lys Ala Arg Leu His Leu Gln
1325 1330 1335

Gly Arg Ser Asn Ala Trp Arg Pro Gln Val Asn Asn Pro Lys Glu
1340 1345 1350

Trp Leu Gln Val Asp Phe Gln Lys Thr Met Lys Val Thr Gly Val
1355 1360 1365

Thr Thr Gln Gly Val Lys Ser Leu Leu Thr Ser Met Tyr Val Lys
1370 1375 1380

Glu Phe Leu Ile Ser Ser Ser Gln Asp Gly His Gln Trp Thr Leu
1385 1390 1395

Phe Phe Gln Asn Gly Lys Val Lys Val Phe Gln Gly Asn Gln Asp
1400 1405 1410

Ser Phe Thr Pro Val Val Asn Ser Leu Asp Pro Pro Leu Leu Thr
1415 1420 1425

Arg Tyr Leu Arg Ile His Pro Gln Ser Trp Val His Gln Ile Ala
1430 1435 1440

Leu Arg Met Glu Val Leu Gly Cys Glu Ala Gln Asp Leu Tyr
1445 1450 1455

<210> SEQ ID NO 69
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 69

Ser Phe Ser Gln Asn Pro Pro Val Leu Lys Arg His Gln Arg
1 5 10

<210> SEQ ID NO 70
<211> LENGTH: 4374
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 70
atgcaaatag agctctccac ctgcttcttt ctgtgccttt tgcgattctg ctttagtgcc 60
accagaagat actacctggg tgcagtggaa ctgtcatggg actatatgca aagtgatctc 120
ggtgagctgc ctgtggacgc aagatttcct cctagagtgc caaaatcttt tccattcaac 180
acctcagtcg tgtacaaaaa gactctgttt gtagaattca cggatcacct tttcaacatc 240
gctaagccaa ggccaccctg gatgggtctg ctaggtccta ccatccaggc tgaggtttat 300
gatacagtgg tcattacact taagaacatg gcttcccatc ctgtcagtct tcatgctgtt 360
ggtgtatcct actggaaagc ttctgaggga gctgaatatg atgatcagac cagtcaaagg 420
gagaaagaag atgataaagt cttccctggt ggaagccata catatgtctg gcaggtcctg 480
aaagagaatg gtccaatggc ctctgaccca ctgtgcctta cctactcata tctttctcat 540
gtggacctgg taaaagactt gaattcaggc ctcattggag ccctactagt atgtagagaa 600
gggagtctgg ccaaggaaaa gacacagacc ttgcacaaat ttatactact ttttgctgta 660
tttgatgaag ggaaaagttg gcactcagaa acaaagaact ccttgatgca ggatagggat 720
gctgcatctg ctcgggcctg gcctaaaatg cacacagtca atggttatgt aaacaggtct 780
ctgccaggtc tgattggatg ccacaggaaa tcagtctatt ggcatgtgat tggaatgggc 840

-continued

```
accactcctg aagtgcactc aatattcctc gaaggtcaca catttcttgt gaggaaccat    900
cgccaggcgt ccttggaaat ctcgccaata actttcctta ctgctcaaac actcttgatg    960
gaccttggac agtttctact gttttgtcat atctcttccc accaacatga tggcatggaa   1020
gcttatgtca aagtagacag ctgtccagag gaacccaac tacgaatgaa aaataatgaa    1080
gaagcggaag actatgatga tgatcttact gattctgaaa tggatgtggt caggtttgat   1140
gatgacaact ctccttcctt tatccaaatt cgctcagttg ccaagaagca tcctaaaact   1200
tgggtacatt acattgctgc tgaagaggag gactgggact atgctccctt agtcctcgcc   1260
cccgatgaca gaagttataa aagtcaatat ttgaacaatg gccctcagcg gattggtagg   1320
aagtacaaaa aagtccgatt tatggcatac acagatgaaa cctttaagac tcgtgaagct   1380
attcagcatg aatcaggaat cttgggacct ttactttatg gggaagttgg agacacactg   1440
ttgattatat ttaagaatca agcaagcaga ccatataaca tctaccctca cggaatcact   1500
gatgtccgtc ctttgtattc aaggagatta ccaaaaggtg taaaacattt gaaggatttt   1560
ccaattctgc caggagaaat attcaaatat aaatggacag tgactgtaga agatgggcca   1620
actaaatcag atcctcggtg cctgacccgc tattactcta gtttcgttaa tatggagaga   1680
gatctagctt caggactcat tggccctctc ctcatctgct acaaagaatc tgtagatcaa   1740
agaggaaacc agataatgtc agacaagagg aatgtcatcc tgttttctgt atttgatgag   1800
aaccgaagct ggtacctcac agagaatata caacgctttc tccccaatcc agctggagtg   1860
cagcttgagg atccagagtt ccaagcctcc aacatcatgc acagcatcaa tggctatgtt   1920
tttgatagtt tgcagttgtc agtttgtttg catgaggtgg catactggta cattctaagc   1980
attggagcac agactgactt cctttctgtc ttcttctctg gatatacctt caaacacaaa   2040
atggtctatg aagacacact caccctattc ccattctcag gagaaactgt cttcatgtcg   2100
atggaaaacc caggtctatg gattctgggg tgccacaact cagactttcg gaacagaggc   2160
atgaccgcct tactgaaggt ttctagttgt gacaagaaca ctggtgatta ttacgaggac   2220
agttatgaag atatttcagc atacttgctg agtaaaaaca atgccattga accaagaagc   2280
ttctcccaaa acccaccagt cttgaaacgc catcaacggg aaataactcg tactactctt   2340
cagtcagatc aagaggaaat tgactatgat gataccatat cagttgaaat gaagaaggaa   2400
gattttgaca tttatgatga ggatgaaaat cagagccccc gcagctttca aaagaaaaca   2460
cgacactatt ttattgctgc agtggagagg ctctgggatt atgggatgag tagctcccca   2520
catgttctaa gaaacagggc tcagagtggc agtgtccctc agttcaagaa agttgttttc   2580
caggaattta ctgatggctc ctttactcag cccttatacc gtggagaact aaatgaacat   2640
ttgggactcc tggggccata tataagagca gaagttgaag ataatatcat ggtaactttc   2700
agaaatcagg cctctcgtcc ctattccttc tattctagcc ttatttctta tgaggaagat   2760
cagaggcaag gagcagaacc tagaaaaaac tttgtcaagc ctaatgaaac caaaacttac   2820
ttttggaaag tgcaacatca tatggcaccc actaaagatg agtttgactg caaagcctgg   2880
gcttatttct ctgatgttga cctggaaaaa gatgtgcact caggcctgat tggacccctt   2940
ctggtctgcc acactaacac actgaaccct gctcatggga gacaagtgac agtacaggaa   3000
tttgctctgt tttcaccat ctttgatgag accaaaagct ggtacttcac tgaaaatatg    3060
gaaagaaact gcagggctcc ctgcaatatc cagatggaag atcccacttt taaagagaat   3120
tatcgcttcc atgcaatcaa tggctacata atggatacac tacctggctt agtaatggct   3180
```

caggatcaaa ggattcgatg gtatctgctc agcatgggca gcaatgaaaa catccattct 3240
attcatttca gtggacatgt gttcaccgta cgaaaaaaag aggagtataa aatggcactg 3300
tacaatctct atccaggtgt ttttgagaca gtggaaatgt taccatccaa agctggaatt 3360
tggcgggtgg aatgccttat tggcgagcat ctacatgctg ggatgagcac actttttctg 3420
gtgtacagca ataagtgtca gactcccctg ggaatggctt ctggacacat tagagatttt 3480
cagattacag cttcaggaca atatggacag tgggccccaa agctggccag acttcattat 3540
tccggatcaa tcaatgcctg gagcaccaag gagccctttt cttggatcaa ggtggatctg 3600
ttggcaccaa tgattattca cggcatcaag acccagggtg cccgtcagaa gttctccagc 3660
ctctacatct ctcagtttat catcatgtat agtcttgatg ggaagaagtg gcagacttat 3720
cgaggaaatt ccactggaac cttaatggtc ttctttggca atgtggattc atctgggata 3780
aaacacaata tttttaaccc tccaattatt gctcgataca tccgtttgca cccaactcat 3840
tatagcattc gcagcactct tcgcatggag ttgatgggct gtgatttaaa tagttgcagc 3900
atgccattgg gaatggagag taaagcaata tcagatgcac agattactgc ttcatcctac 3960
tttaccaata tgtttgccac ctggtctcct tcaaaagctc gacttcacct ccaagggagg 4020
agtaatgcct ggagacctca ggtgaataat ccaaaagagt ggctgcaagt ggacttccag 4080
aagacaatga aagtcacagg agtaactact cagggagtaa aatctctgct taccagcatg 4140
tatgtgaagg agttcctcat ctccagcagt caagatggcc atcagtggac tctctttttt 4200
cagaatggca aagtaaaggt ttttcaggga aatcaagact ccttcacacc tgtggtgaac 4260
tctctagacc caccgttact gactcgctac cttcgaattc acccccagag ttgggtgcac 4320
cagattgccc tgaggatgga ggttctgggc tgcgaggcac aggacctcta ctga 4374

<210> SEQ ID NO 71
<211> LENGTH: 4374
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 71
atgcagattg agctgtctac ctgcttcttc ctgtgcctgc tgaggttctg cttctctgct 60
accaggaggt actacctggg ggctgtggag ctgagctggg attacatgca gtctgacctg 120
ggggagctgc ctgtggatgc caggtttccc cccagggtgc ccaagagctt ccccttcaat 180
acctctgtgg tgtataagaa gaccctgttt gtggagttca ctgatcatct gttcaacatt 240
gctaaaccca ggccccccctg gatggggctg ctgggcccta ccatccaggc tgaggtgtat 300
gacactgtgg tgatcactct gaagaacatg gctagccatc ctgtgtctct gcatgctgtg 360
ggggtgagct actggaaggc ttctgagggg gctgagtatg atgatcagac tagccagagg 420
gagaaggagg atgacaaggt gttccctggg ggctctcaca cctatgtctg gcaggtgctg 480
aaggagaatg gccccatggc ctctgatcct ctgtgtctga cctatagcta cctgagccat 540
gtggacctgg tgaaggacct gaactctggc ctgattgggg ccctgctggt gtgtagggag 600
gggagcctgg ccaaggagaa gacccagacc ctgcacaagt tcattctgct gtttgctgtg 660
tttgatgagg gcaagagctg gcattctgaa accaagaaca gcctgatgca ggacagggat 720
gctgcctctg ctagggcctg gcccaagatg cacactgtga atgggtatgt caataggtct 780
ctgcctggcc tgattggctg ccacaggaag tctgtgtact ggcatgtgat tgggatgggc 840

-continued

```
accaccccctg aggtgcacag catctttctg gagggccaca ccttcctggt gaggaatcac    900
agacaggcca gcctggagat cagccccatc accttcctga ctgcccagac cctgctgatg    960
gacctgggcc agtttctgct gttctgccac atctctagcc accagcatga tggcatggag   1020
gcctatgtga aggtggactc ctgccctgag gagccccagc tgaggatgaa gaataatgag   1080
gaggctgagg actatgatga tgacctgact gactctgaga tggatgtggt gagatttgat   1140
gatgacaatt ctcccagctt cattcagatc aggtctgtgg ccaagaagca tcccaagacc   1200
tgggtgcact acattgctgc tgaggaggag gactgggact atgcccccct ggtgctggcc   1260
cctgatgaca ggagctataa gagccagtac ctgaataatg gcccccagag gattgggagg   1320
aagtataaga aggtgaggtt catggcctat actgatgaaa ccttcaagac cagagaggcc   1380
atccagcatg agtctgggat cctggggccc ctgctgtatg gggaggtggg ggacaccctg   1440
ctgatcatct tcaagaacca ggccagcagg ccctacaaca tctaccctca tggcatcact   1500
gatgtgaggc ctctgtacag cagaaggctg cccaaggggg tgaagcatct gaaggacttc   1560
cccattctgc ctggggagat tttcaagtac aagtggactg tgactgtgga ggatggccca   1620
accaagtctg accctaggtg cctgactagg tactacagca gctttgtgaa tatggagagg   1680
gacctggcct ctggcctgat tggcccccctg ctgatctgct acaaggagtc tgtggatcag   1740
aggggcaacc agatcatgtc tgacaagagg aatgtgatcc tgttctctgt gtttgatgag   1800
aacaggagct ggtacctgac tgagaacatt cagaggtttc tgcccaaccc tgctggggtg   1860
cagctggagg accctgaatt ccaggcctct aacatcatgc acagcattaa tggctatgtg   1920
tttgacagcc tgcagctgtc tgtgtgcctg catgaggtgg cctactggta cattctgagc   1980
attggggccc agactgactt cctgtctgtg ttcttctctg gctacacctt taagcacaag   2040
atggtgtatg aggataccct gaccctgttt cctttctctg ggagactgt gttcatgagc    2100
atggagaacc ctggcctgtg gatcctgggc tgccacaact ctgacttcag gaacaggggg   2160
atgactgctc tgctgaaggt gagcagctgt gataagaaca ctggggacta ctatgaggac   2220
agctatgagg acatctctgc ctatctgctg agcaagaata atgctattga gcccaggagc   2280
ttctctcaga accccccctgt gctgaagagg caccagaggg agatcaccag aactactctg   2340
cagtctgacc aggaggagat tgactatgat gacaccatct ctgtggagat gaagaaggag   2400
gattttgata tttatgatga ggatgaaaac cagagcccca ggagctttca gaagaagact   2460
aggcactatt tcattgctgc tgtggagagg ctgtgggact atggcatgtc ttctagcccc   2520
catgtgctga ggaacagggc ccagtctggc tctgtgcccc agttcaagaa ggtggtgttc   2580
caggagttca ctgatggcag cttcactcag cccctgtaca ggggggagct gaatgagcac   2640
ctggggctgc tgggccctta tatcagggct gaggtggagg ataacatcat ggtgaccttc   2700
aggaaccagg ccagcaggcc ctacagcttc tactctagcc tgatcagcta tgaggaggac   2760
cagaggcagg gggctgagcc caggaagaac tttgtgaagc ccaatgagac caagacttat   2820
ttctggaagg tgcagcacca tatggccccc accaaggatg agtttgattg caaagcctgg   2880
gcctacttct ctgatgtgga cctggagaag gatgtgcact ctgggctgat tggcccccctg   2940
ctggtgtgcc acaccaacac tctgaaccct gcccatggca ggcaggtgac tgtgcaggag   3000
tttgccctgt tcttcaccat ctttgatgag actaagagct ggtacttcac tgagaacatg   3060
gagaggaact gcagggcccc ctgcaatatc cagatggagg accccacctt taaggaaaat   3120
tataggtttc atgccattaa tggctacatc atggacaccc tgcctggcct ggtgatggcc   3180
caggaccaga ggatcaggtg gtacctgctg agcatgggca gcaatgagaa cattcacagc   3240
```

atccacttct ctggccatgt gttcactgtg aggaagaagg aggagtacaa gatggccctg 3300
tataatctgt accctggggt gtttgagact gtggagatgc tgcccagcaa ggctggcatc 3360
tggagggtgg agtgcctgat tggggagcac ctgcatgctg gcatgagcac cctgttcctg 3420
gtgtattcta acaagtgtca gacccccctg ggcatggcct ctggccatat cagggacttc 3480
cagatcactg cctctggcca gtatgggcag tgggccccca agctggccag gctgcattac 3540
tctggcagca tcaatgcctg gagcaccaag gagccattca gctggattaa ggtggacctg 3600
ctggctccaa tgattatcca tggcatcaag acccaggggg ccaggcagaa gtttagcagc 3660
ctgtacatct ctcagtttat catcatgtac tctctggatg gcaaaaagtg gcagacctac 3720
aggggcaatt ctactggcac tctgatggtg ttctttggca atgtggacag ctctgggatc 3780
aagcacaaca tctttaaccc ccctatcatt gccaggtaca ttaggctgca ccccacccat 3840
tacagcatca ggagcaccct gaggatggag ctgatgggct gtgatctgaa cagctgcagc 3900
atgcccctgg gcatggagag caaggctatc tctgatgccc agattactgc cagcagctac 3960
ttcaccaata tgtttgccac ctggagcccc agcaaggcca ggctgcacct gcagggcagg 4020
tctaatgcct ggaggcccca ggtgaacaac cccaaggagt ggctgcaggt ggacttccag 4080
aagaccatga aggtgactgg ggtgaccacc cagggggtga agagcctgct gactagcatg 4140
tatgtgaagg agttcctgat cagcagcagc caggatggcc atcagtggac cctgttcttc 4200
cagaatggca aggtgaaggt gttccagggc aatcaggaca gcttcacccc tgtggtgaac 4260
agcctggacc ccccctgct gaccagatac ctgaggatcc acccccagag ctgggtgcat 4320
cagattgccc tgaggatgga ggtgctgggg tgtgaggccc aggacctgta ctga 4374

<210> SEQ ID NO 72
<211> LENGTH: 4374
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 72
atgcagattg agctgtctac ctgctttttc ctgtgtctgc tgaggttctg cttctctgcc 60
actaggaggt actacctggg ggctgtggag ctgtcttggg attacatgca gtctgatctg 120
ggggagctgc ctgtggatgc caggtttcct cccagggtgc ccaagtcttt ccccttcaat 180
acctctgtgg tgtataagaa gaccctgttt gtggagttta ctgatcacct gttcaacatt 240
gccaagccca ggccccttg gatgggcctg ctggggccca ccatccaggc tgaggtgtat 300
gacactgtgg tgatcaccct gaagaacatg gcctctcacc ctgtgagcct gcatgctgtg 360
ggggtgagct actggaaggc ctctgagggg gctgagtatg atgaccagac cagccagagg 420
gagaaggagg atgataaggt gttccctggg gggagccaca cttatgtgtg gcaggtgctg 480
aaggagaatg gcccaatggc ctctgatccc ctgtgcctga cctattctta cctgagccat 540
gtggacctgg tgaaggacct gaactctggc ctgattgggg ccctgctggt gtgcagggag 600
ggctctctgg ctaaggagaa gacccagacc ctgcacaagt tcatcctgct gtttgctgtg 660
tttgatgagg ggaagagctg gcactctgag accaagaaca gcctgatgca ggacagggat 720
gctgcctctg ccagggcctg gcccaaaatg cacactgtga atggctatgt gaataggagc 780
ctgcctggcc tgattggctg ccacaggaag tctgtgtatt ggcatgtgat tggcatgggc 840
accacccctg aggtgcactc tatcttcctg gagggccata ctttcctggt gaggaatcat 900

-continued

```
aggcaggcca gcctggagat tagccccatt acctttctga ctgcccagac cctgctgatg    960
gacctgggcc agttcctgct gttttgccac atcagctctc accagcatga tggcatggag   1020
gcctatgtga aggtggatag ctgccctgag gagccccagc tgaggatgaa gaacaatgag   1080
gaggctgagg attatgatga tgatctgact gattctgaaa tggatgtggt gaggtttgat   1140
gatgacaata gcccctcttt catccagatc aggtctgtgg ccaagaagca tcctaagacc   1200
tgggtgcact acattgctgc tgaggaggag gactgggact atgctcccct ggtgctggcc   1260
cctgatgaca ggtcttacaa gagccagtac ctgaacaatg gcccccagag aattgggagg   1320
aagtataaga aggtgagatt catggcttac actgatgaga ccttcaagac tagggaggcc   1380
atccagcatg agtctggcat tctgggcccc ctgctgtatg ggggaggtggg ggacaccctg   1440
ctgatcatct tcaagaacca ggcctctagg ccctacaata tttaccccca tgggatcact   1500
gatgtgaggc ccctgtacag caggaggctg cctaaggggg tgaagcatct gaaggacttc   1560
cccatcctgc ctggggagat cttcaagtat aagtggactg tgactgtgga agatggcccc   1620
accaagtctg accctaggtg cctgaccagg tactactctt cttttgtgaa catggagagg   1680
gacctggcct ctggcctgat tggcccccctg ctgatctgct acaaggagtc tgtggaccag   1740
agggggaacc agattatgtc tgacaagagg aatgtgattc tgttctctgt gtttgatgag   1800
aacaggagct ggtatctgac tgagaacatc cagaggttcc tgcccaatcc tgctggggtg   1860
cagctggagg accctgagtt ccaggccagc aacatcatgc acagcatcaa tgggtatgtg   1920
tttgattctc tgcagctgtc tgtgtgcctg catgaggtgg cctactggta catcctgagc   1980
attggggctc agactgattt cctgtctgtg ttcttttctg gctacacctt taagcataag   2040
atggtgtatg aggacactct gaccctgttt cccttctctg gggagactgt gtttatgagc   2100
atggagaacc ctggcctgtg gatcctgggc tgccacaact ctgatttcag gaacaggggc   2160
atgactgctc tgctgaaggt gtcttcttgt gacaagaaca ctggggacta ttatgaggac   2220
agctatgagg acatctctgc ctacctgctg agcaagaaca atgctattga gcccagatct   2280
ttcagccaga accccccctgt gctgaagagg caccagaggg agatcactag gaccaccctg   2340
cagtctgacc aggaggagat tgactatgat gacactatct ctgtggagat gaagaaggag   2400
gactttgata tctatgatga ggatgagaac cagtctccca ggagcttcca gaaaaagacc   2460
aggcactact tcattgctgc tgtggagagg ctgtgggact atggcatgtc ttctagcccc   2520
catgtgctga ggaacagggc ccagtctggg tctgtgcccc agttcaagaa ggtggtgttc   2580
caggagttca ctgatgggag cttcacccag cctctgtaca ggggggagct gaatgagcac   2640
ctggggctgc tgggccctta tattagggct gaggtggagg acaacatcat ggtgactttc   2700
aggaatcagg cctctaggcc ctatagcttc tacagctctc tgatcagcta tgaggaggat   2760
cagaggcagg gggctgagcc caggaagaac tttgtgaagc ccaatgagac caagacctac   2820
ttctggaagg tgcagcacca catggctcct accaaggatg agtttgactg caaggcctgg   2880
gcctactttt ctgatgtgga cctggagaag gatgtgcact ctggcctgat tggcccccctg   2940
ctggtgtgtc ataccaacac cctgaaccct gcccatggca ggcaggtgac tgtgcaggag   3000
tttgccctgt tcttcaccat ctttgatgag accaagagct ggtactttac tgagaacatg   3060
gagaggaatt gcagagcccc ttgcaacatc cagatggagg acccaacctt caaagagaac   3120
tacaggttcc atgccatcaa tgggtacatc atggacaccc tgcctggcct ggtgatggct   3180
caggaccaga ggatcaggtg gtatctgctg agcatgggca gcaatgagaa tatccatagc   3240
```

-continued attcacttct ctggccatgt gttcactgtg aggaagaagg aggagtacaa gatggccctg 3300
tataacctgt accctggggt gtttgagact gtggagatgc tgccaagcaa ggctgggatt 3360
tggagggtgg agtgcctgat tggggagcac ctgcatgctg gcatgtctac cctgttcctg 3420
gtgtactcca ataagtgcca gacccccctg ggcatggcct ctggccacat cagggacttc 3480
cagatcactg cctctggcca gtatgggcag tgggccccaa agctggccag gctgcactat 3540
tctgggagca tcaatgcttg gagcaccaag gagccttca gctggattaa ggtggatctg 3600
ctggccccca tgatcattca tggcatcaaa acccaggggg ctagacagaa gttttctagc 3660
ctgtacatca gccagttcat catcatgtac agcctggatg gcaagaagtg gcagacttac 3720
aggggcaata gcactggcac cctgatggtg ttttttggca atgtggacag ctctggcatc 3780
aagcacaaca tctttaaccc ccccattatt gccaggtata tcaggctgca tcccacccac 3840
tattctatta ggtctactct gagaatggag ctgatgggct gtgacctgaa cagctgtagc 3900
atgcccctgg ggatggagag caaggctatc tctgatgccc agatcactgc cagctcttat 3960
ttcaccaata tgtttgccac ctggtctccc tctaaggcca ggctgcacct gcagggcagg 4020
agcaatgctt ggaggcccca ggtgaataac cccaaggagt ggctgcaggt ggacttccag 4080
aagaccatga aggtgactgg ggtgactacc caggggggtga agtctctgct gactagcatg 4140
tatgtgaagg agttcctgat cagcagcagc caggatgggc atcagtggac tctgttcttc 4200
cagaatggca aggtgaaggt cttccagggg aaccaggata gcttcactcc tgtggtgaac 4260
tctctggacc ccccctgct gactaggtat ctgaggatcc acccccagag ctgggtgcac 4320
cagattgccc tgaggatgga ggtgctgggc tgtgaggccc aggacctgta ttga 4374

<210> SEQ ID NO 73
<211> LENGTH: 4374
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 73
atgcagattg aactgtctac ttgtttcttc ctgtgcctgc tgaggttttg cttctctgct 60
actaggaggt actatctggg ggctgtggag ctgtcttggg actatatgca gtctgacctg 120
ggggagctgc ctgtggatgc taggtttccc cccagggtgc ccaagagctt cccctttaac 180
acctctgtgg tgtataagaa gactctgttt gtggagttca ctgaccatct gttcaacatt 240
gccaagccaa ggccccctg gatgggcctg ctgggcccca ccatccaggc tgaggtgtat 300
gacactgtgg tgattactct gaagaacatg gccagccatc ctgtgagcct gcatgctgtg 360
ggggtgtctt actggaaggc ctctgagggg gctgagtatg atgaccagac ctctcagagg 420
gagaaggagg atgacaaggt gttccctggg ggctctcata cctatgtgtg gcaggtcctg 480
aaggagaatg ggcccatggc ctctgacccc ctgtgcctga cctactctta tctgtctcat 540
gtggacctgg tgaaggacct gaactctggc ctgattgggg ccctgctggt gtgcagggag 600
ggcagcctgg ctaaggagaa gacccagact ctgcacaagt tcatcctgct gtttgctgtg 660
tttgatgagg gcaagagctg gcactctgag accaagaaca gcctgatgca ggacagggat 720
gctgcctctg ctagggcctg gcccaagatg cacactgtga atgggtatgt gaacaggagc 780
ctgccaggcc tgattggctg ccataggaag tctgtgtatt ggcatgtgat tgggatgggg 840
actacccctg aggtccacag cattttcctg gaggggcata cctttctggt gaggaaccac 900

-continued

```
aggcaggcct ctctggagat ctctcccatt actttcctga ctgcccagac cctgctgatg    960
gacctgggcc agttcctgct gttctgccac atcagcagcc accagcatga tggcatggag   1020
gcctatgtga aggtggatag ctgccctgag gagccccagc tgaggatgaa aaacaatgag   1080
gaggctgagg attatgatga tgacctgact gattctgaga tggatgtggt gaggtttgat   1140
gatgataaca gccccagctt catccagatt aggtctgtgg ccaagaagca tcccaagacc   1200
tgggtgcact acattgctgc tgaggaggag gattgggact atgctcctct ggtgctggcc   1260
cctgatgaca ggagctacaa gagccagtac ctgaataatg gcccccagag gattggcagg   1320
aagtataaga aggtgaggtt catggcctac actgatgaga cctttaagac cagggaggcc   1380
atccagcatg aatctgggat cctgggcccc ctgctgtatg gggaggtggg ggacaccctg   1440
ctgattatct ttaagaacca ggctagcagg ccctacaaca tttacccccca tggcattact  1500
gatgtgaggc ccctgtacag caggaggctg cccaaggggg tgaagcacct gaaggatttc   1560
cccattctgc ctggggagat ctttaagtac aaatggactg tgactgtgga ggatggccct   1620
actaagtctg atcccaggtg tctgaccaga tactacagca gctttgtgaa tatggagagg   1680
gacctggctt ctggcctgat tggcccccctg ctgatctgct acaaggagtc tgtggaccag  1740
aggggcaatc agattatgtc tgacaagagg aatgtgatcc tgttctctgt gtttgatgag   1800
aacagaagct ggtacctgac tgagaacatc cagaggttcc tgcccaaccc tgctggggtg   1860
cagctggagg accctgagtt ccaggctagc aatatcatgc acagcattaa tggctatgtg   1920
tttgacagcc tgcagctgtc tgtgtgcctg catgaggtgg cctattggta cattctgagc   1980
attggggccc agactgattt cctgtctgtg ttcttttctg gctacacctt caagcacaag   2040
atggtgtatg aggatactct gaccctgttt cccttctctg ggagactgt gttcatgagc    2100
atggagaacc ctggcctgtg gatcctgggc tgtcacaact ctgacttcag gaacaggggc   2160
atgactgccc tgctgaaggt gagctcttgt gataagaaca ctggggacta ctatgaggac   2220
tcttatgagg acatctctgc ctacctgctg agcaagaaca atgctattga gcccaggagc   2280
ttctctcaga atccccctgt gctgaagagg catcagaggg agatcactag gactaccctg   2340
cagtctgacc aggaagagat tgactatgat gacaccatct ctgtggaaat gaagaaggag   2400
gactttgata tctatgatga ggatgaaaac cagagcccca ggagcttcca gaagaagacc   2460
aggcattact tcattgctgc tgtggagagg ctgtgggact atgggatgag ctcttctccc   2520
catgtgctga ggaatagggc tcagtctggc tctgtcccac agttcaagaa ggtggtgttt   2580
caggagttca ctgatggcag cttcactcag cccctgtaca ggggggagct gaatgagcat   2640
ctgggcctgc tggggcccta catcagggct gaggtggagg ataacattat ggtgactttc   2700
aggaaccagg cctctaggcc ctacagcttc tacagcagcc tgatcagcta tgaggaggac   2760
cagaggcagg gggctgagcc caggaagaac tttgtgaagc ccaatgagac taagacctat   2820
ttctggaagg tgcagcatca catggctccc actaaagatg agtttgactg caaggcctgg   2880
gcctacttct ctgatgtgga tctggagaag gatgtgcatt ctgggctgat tggccctctg   2940
ctggtctgcc atactaacac cctgaatcct gcccatggca ggcaggtgac tgtgcaggag   3000
tttgccctgt tctttaccat ctttgatgag accaagtctt ggtacttcac tgagaacatg   3060
gagaggaact gcagggcccc ctgtaacatc cagatggagg accccacctt taaggagaac   3120
tacaggttcc atgccatcaa tggctacatc atggacactc tgcctggcct ggtgatggcc   3180
caggaccaga ggatcaggtg gtacctgctg tctatgggct ctaatgagaa cattcattct   3240
atccacttct ctggccatgt gtttactgtg aggaagaagg aggagtacaa gatggccctg   3300
```

```
tacaatctgt accctggggt gtttgaaact gtggagatgc tgccctctaa ggctggcatc   3360

tggagggtgg agtgcctgat tggggaacac ctgcatgctg gcatgagcac cctgttcctg   3420

gtctatagca ataagtgcca gacccccctg ggatggcct ctgggcatat cagagacttc    3480

cagatcactg cctctggcca gtatggccag tgggccccca agctggccag gctgcactac   3540

tctggcagca ttaatgcctg gagcaccaag gagcccttct cttggatcaa ggtggacctg   3600

ctggctccca tgatcatcca tgggatcaag acccaggggg ccaggcagaa gttcagcagc   3660

ctgtacatct ctcagttcat catcatgtac tctctggatg gcaagaagtg gcagacctac   3720

aggggcaata gcactgggac cctgatggtg ttctttggga atgtggacag ctctggcatc   3780

aagcacaata tcttcaaccc ccccatcatt gccaggtaca tcagactgca ccccactcat   3840

tacagcatca ggagcactct gaggatggag ctgatgggct gtgacctgaa tagctgctct   3900

atgcccctgg gcatggagag caaggccatt tctgatgccc agattactgc ctcttcttac   3960

ttcactaata tgtttgccac ctggagcccc agcaaggcca ggctgcatct gcaggggagg   4020

agcaatgcct ggaggcccca ggtgaacaac cccaaggagt ggctgcaggt ggacttccag   4080

aagactatga aggtgactgg ggtgaccact caggggggtga agagcctgct gaccagcatg  4140

tatgtgaagg agttcctgat ctcttctagc caggatgggc accagtggac cctgtttttc   4200

cagaatggga aggtgaaggt gtttcagggc aatcaggaca gctttactcc tgtggtgaac   4260

agcctggacc ccccccctgct gactaggtac ctgaggattc acccccagag ctgggtgcac  4320

cagattgccc tgaggatgga ggtgctgggc tgtgaggccc aggatctgta ctga         4374
```

<210> SEQ ID NO 74
<211> LENGTH: 4374
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 74

```
atgcagattg agctgtctac ctgcttcttt ctgtgcctgc tgaggttctg tttctctgcc     60

actaggaggt attatctggg ggctgtggag ctgtcctggg actacatgca gtctgatctg    120

ggggagctgc ctgtggatgc caggttccct cccagggtgc ccaagtcttt ccctttcaat    180

acctctgtgg tgtacaagaa gactctgttt gtggagttta ctgatcacct gtttaacatt    240

gccaagccca ggccccccctg gatggggctg ctgggcccca ccatccaggc tgaggtgtat   300

gacactgtgg tgattactct gaagaatatg gcttctcacc ctgtgagcct gcatgctgtg    360

ggggtgagct actggaaggc ctctgagggg gctgagtatg atgaccagac cagccagagg    420

gagaaggagg atgacaaggt gttccctggg ggcagccaca cttatgtgtg gcaggtgctg    480

aaggagaatg gcccaatggc ctctgacccc ctgtgcctga cctacagcta tctgagccat    540

gtggatctgg tgaaggatct gaactctggc ctgattgggg ccctgctggt gtgcagggag    600

ggctctctgg ccaaggagaa gactcagact ctgcacaagt tcatcctgct gtttgctgtg    660

tttgatgagg gcaagagctg gcactctgag accaagaact ctctgatgca ggatagggat    720

gctgcttctg ccagggcctg gcccaagatg cacactgtga atgggtatgt gaataggagc    780

ctgcctgggc tgattgggtg tcacaggaag tctgtgtact ggcatgtgat tggcatgggc    840

accactcctg aggtgcacag catctttctg gagggccaca cttttctggt gaggaatcac    900

aggcaggcca gcctggagat cagccccatc accttcctga ctgcccagac cctgctgatg    960
```

-continued

```
gatctgggcc agttcctgct gttttgccat atcagcagcc atcagcatga tgggatggag   1020
gcttatgtga aggtggactc ttgccctgag gagcctcagc tgaggatgaa gaataatgaa   1080
gaggctgagg actatgatga tgatctgact gactctgaga tggatgtggt gaggtttgat   1140
gatgacaaca gccccagctt tatccagatt aggtctgtgg ccaagaagca ccccaagacc   1200
tgggtgcatt acattgctgc tgaggaagag gattgggact atgcccccct ggtgctggcc   1260
cctgatgaca ggagctacaa gtctcagtac ctgaacaatg gccctcagag gattggcagg   1320
aagtacaaga aggtgaggtt catggcttac actgatgaga ccttcaagac cagggaggcc   1380
attcagcatg aatctgggat cctgggcccc ctgctgtatg gggaggtggg ggacaccctg   1440
ctgattattt tcaagaacca ggccagcagg ccctacaaca tttatcctca tggcattact   1500
gatgtgagac ccctgtacag caggaggctg cctaaggggg tgaagcacct gaaggacttc   1560
cccatcctgc ctggggagat cttcaagtac aagtggactg tgactgtgga ggatggcccc   1620
actaagtctg accccaggtg cctgactagg tactactcca gctttgtgaa catggagagg   1680
gacctggcct ctggcctgat tggcccccctg ctgatctgct acaaggagtc tgtggatcag   1740
aggggcaacc agatcatgtc tgacaagaga aatgtgatcc tgttctctgt gtttgatgag   1800
aataggtctt ggtacctgac tgagaacatc cagaggtttc tgcctaatcc tgctggggtg   1860
cagctggagg atcctgagtt ccaggcctct aacattatgc acagcatcaa tgggtatgtg   1920
tttgacagcc tgcagctgtc tgtgtgcctg catgaggtgg cctactggta catcctgagc   1980
attggggccc agactgactt tctgtctgtg ttcttctctg gctacacctt taagcataag   2040
atggtgtatg aggacaccct gactctgttc cccttctctg ggagactgt gttcatgagc   2100
atggagaacc caggcctgtg gatcctgggc tgccacaact ctgatttcag gaataggggc   2160
atgactgccc tgctgaaggt gagcagctgt gataagaaca ctggggacta ttatgaggat   2220
agctatgagg acatctctgc ctacctgctg agcaagaaca atgccattga gcccaggagc   2280
ttcagccaga atcctcctgt gctgaagagg caccagaggg agatcaccag gaccaccctg   2340
cagtctgatc aggaggagat tgactatgat gacactatct ctgtggagat gaagaaggag   2400
gactttgaca tctatgatga ggatgagaat cagagcccca ggagcttcca gaagaagact   2460
agacactact ttattgctgc tgtggagagg ctgtgggact atggcatgag ctcttctccc   2520
catgtgctga gaaacagggc ccagtctggc tctgtgcccc agttcaagaa ggtggtcttc   2580
caggagttca ctgatggctc tttcacccag cctctgtata gaggggagct gaatgagcac   2640
ctgggcctgc tgggccctta catcagggct gaggtggagg acaatatcat ggtgaccttc   2700
aggaaccagg ctagcaggcc ctactctttc tacagcagcc tgatcagcta tgaggaggac   2760
cagaggcagg gggctgagcc taggaagaat tttgtgaagc ccaatgagac caagacctac   2820
ttctggaagg tgcagcacca catggctccc actaaggatg agtttgactg caaggcctgg   2880
gcctactttt ctgatgtgga cctggagaag gatgtgcatt ctggcctgat tggcccccctg   2940
ctggtctgcc acaccaatac tctgaaccct gctcatggga gacaggtgac tgtgcaggag   3000
tttgccctgt tcttcaccat ctttgatgag accaagtcct ggtactttac tgagaacatg   3060
gagaggaatt gcagggcccc ttgcaacatc cagatggagg accccacctt caaggaaaat   3120
tataggttcc atgccatcaa tggctacatc atggacaccc tgcctggcct ggtgatggcc   3180
caggaccaga ggatcaggtg gtatctgctg tctatgggct ctaatgagaa catccacagc   3240
atccatttct ctggccatgt gttcactgtg aggaagaagg aggagtataa gatggctctg   3300
```

-continued

```
tacaacctgt accctggggt ctttgagact gtggagatgc tgcccagcaa ggctggcatt   3360

tggagggtgg agtgcctgat tggggaacac ctgcatgctg ggatgagcac cctgttcctg   3420

gtgtactcta acaagtgcca gaccccactg ggcatggctt ctggccacat cagggatttc   3480

cagattactg cctctggcca gtatggccag tgggctccca agctggctag gctgcactac   3540

tctgggagca tcaatgcctg gtctactaag gagccttttct cttggatcaa agtggacctg   3600

ctggccccta tgatcatcca tgggatcaag actcaggggg ccaggcagaa gttcagcagc   3660

ctgtacatct ctcagttcat cattatgtac agcctggatg gcaagaagtg gcagacctac   3720

aggggcaaca gcactggcac cctgatggtg ttctttggga atgtggacag ctctgggatt   3780

aagcacaaca tctttaaccc ccccatcatt gccaggtata tcaggctgca ccctacccac   3840

tacagcatta ggagcaccct gaggatggag ctgatgggct gtgacctgaa cagctgcagc   3900

atgcccctgg ggatggagag caaggccatt tctgatgctc agatcactgc ttctagctac   3960

ttcactaaca tgtttgccac ctggtctccc agcaaggcta gactgcacct gcaggggagg   4020

agcaatgcct ggaggcccca ggtgaataat cccaaggagt ggctgcaggt ggatttccag   4080

aaaaccatga aggtgactgg ggtgactacc caggggggtga agtctctgct gaccagcatg   4140

tatgtgaagg agttcctgat cagcagcagc caggatgggc atcagtggac cctgttcttt   4200

cagaatggga aggtgaaggt gtttcagggc aatcaggaca gcttcacccc tgtggtgaac   4260

agcctggacc cccccctgct gaccaggtac ctgaggatcc acccccagag ctgggtgcat   4320

cagattgccc tgaggatgga ggtgctgggc tgtgaggccc aggacctgta ctga         4374
```

<210> SEQ ID NO 75
<211> LENGTH: 4374
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 75

```
atgcagattg agctgtctac ttgcttcttc ctgtgcctgc tgaggttctg cttctctgcc     60

actaggaggt attacctggg ggctgtggag ctgagctggg actatatgca gtctgacctg    120

ggggagctgc ctgtggatgc caggtttcct cccagggtgc ctaagagctt ccccttcaac    180

acctctgtgg tgtacaagaa gactctgttt gtggagttta ctgatcatct gttcaacatt    240

gccaagccca ggcctccttg gatggggctg ctgggcccca ccatccaggc tgaggtgtat    300

gacactgtgg tgattaccct gaagaatatg gccagccatc ctgtgagcct gcatgctgtg    360

ggggtgagct attggaaggc ctctgagggg gctgagtatg atgatcagac tagccagagg    420

gagaaggagg atgacaaggt gttccctggg gggagccata cctatgtgtg gcaggtgctg    480

aaggagaatg gccccatggc ctctgaccct ctgtgcctga cttatagcta cctgagccat    540

gtggatctgg tgaaggacct gaactctggc ctgattgggg ccctgctggt gtgcagggag    600

ggcagcctgg ccaaggagaa gactcagacc ctgcacaagt tcatcctgct gtttgctgtg    660

tttgatgagg ggaagtcctg gcactctgag actaagaaca gcctgatgca ggatagggat    720

gctgcttctg ccagggcctg gcctaagatg cacactgtga atggctatgt gaataggagc    780

ctgcctggcc tgattggctg ccataggaag tctgtgtact ggcatgtgat tgggatgggc    840

accaccccctg aggtgcactc tattttcctg gagggccata ctttcctggt gaggaaccat    900

aggcaggcca gcctggagat cagccccatc actttcctga ctgcccagac tctgctgatg    960
```

-continued gacctgggcc agttcctgct gttctgccac atcagcagcc atcagcatga tggcatggag 1020
gcttatgtga aggtggacag ctgccctgag gagcctcagc tgaggatgaa gaataatgag 1080
gaggctgagg actatgatga tgacctgact gactctgaga tggatgtggt gaggtttgat 1140
gatgacaact ctccctcttt catccagatc aggtctgtgg ccaagaagca ccctaagacc 1200
tgggtgcact acattgctgc tgaggaggag gattgggact atgcccccct ggtgctggcc 1260
ccagatgaca ggagctacaa gtcccagtac ctgaacaatg gcccccagag gattggcagg 1320
aagtacaaga aggtgaggtt catggcttat actgatgaga ctttcaagac cagggaggcc 1380
atccagcatg agtctggcat cctgggccct ctgctgtatg gggaggtggg ggacaccctg 1440
ctgattatct tcaagaacca ggcttctagg ccctacaata tctaccctca tggcatcact 1500
gatgtgaggc ccctgtacag caggaggctg cccaaggggg tgaagcatct gaaggatttc 1560
cccatcctgc ctggggagat ctttaagtat aagtggactg tgactgtgga ggatggcccc 1620
actaagtctg accccaggtg cctgaccagg tattacagca gctttgtgaa catggagagg 1680
gatctggctt ctgggctgat tggcccccctg ctgatctgct acaaggagtc tgtggaccag 1740
aggggcaacc agatcatgtc tgacaagagg aatgtgatcc tgttctctgt gtttgatgag 1800
aataggagct ggtacctgac tgagaacatc cagaggtttc tgcccaatcc tgctggggtg 1860
cagctggagg atcctgagtt tcaggcctct aatatcatgc acagcatcaa tggctatgtg 1920
tttgactctc tgcagctgtc tgtgtgcctg catgaggtgg cctattggta catcctgagc 1980
attggggccc agactgactt tctgtctgtg ttttttctg gctacacctt caagcacaag 2040
atggtgtatg aggatactct gactctgttc ccttttttctg ggagactgt gttcatgtct 2100
atggagaacc ctgggctgtg gattctgggc tgccacaatt ctgacttcag gaacagaggc 2160
atgactgctc tgctgaaggt gagcagctgt gacaagaaca ctggggacta ctatgaggac 2220
tcttatgagg acatttctgc ctacctgctg agcaagaaca atgccattga gcccagaagc 2280
ttttctcaga acccccctgt gctgaagagg caccagaggg agatcaccag gaccaccctg 2340
cagtctgacc aggaggagat tgactatgat gatactattt ctgtggagat gaagaaggag 2400
gactttgaca tctatgatga ggatgagaac cagagcccca ggtctttcca gaagaagact 2460
aggcactact ttattgctgc tgtggagagg ctgtgggact atgggatgtc tagctctcct 2520
catgtgctga ggaacagggc ccagtctggc tctgtgcccc agtttaaaaa ggtggtgttc 2580
caggaattca ctgatggcag ctttacccag cctctgtaca gggggggagct gaatgagcac 2640
ctggggctgc tggggcctta cattagggct gaggtggagg acaacatcat ggtgaccttc 2700
aggaatcagg ccagcaggcc ctactctttc tacagcagcc tgatctctta tgaggaggac 2760
cagaggcagg gggctgaacc caggaagaac tttgtgaagc ccaatgagac caagacctac 2820
ttctggaagg tgcagcacca catggctccc accaaggatg agtttgattg caaggcctgg 2880
gcttacttct ctgatgtgga tctggagaag gatgtgcact ctgggctgat tggcccccctg 2940
ctggtgtgcc acaccaacac tctgaaccct gcccatggca gacaggtgac tgtgcaggag 3000
tttgccctgt tcttcactat ctttgatgag actaagagct ggtacttcac tgagaacatg 3060
gagaggaatt gcagggcccc ttgcaacatc cagatggagg accccacctt taaggagaac 3120
tacaggtttc atgccattaa tggctacatc atggacaccc tgcctggcct ggtgatggcc 3180
caggaccaga ggatcaggtg gtacctgctg tctatgggga gcaatgagaa catccacagc 3240
attcacttct ctggccatgt gttcactgtg aggaagaagg aggagtacaa gatggccctg 3300
tacaacctgt accctggggt gtttgagact gtggagatgc tgcccagcaa ggctgggatc 3360

-continued tggagggtgg agtgcctgat tggggagcac ctgcatgctg ggatgagcac cctgttcctg 3420
gtgtatagca acaagtgcca gaccccccctg ggcatggcct ctggccacat cagagacttt 3480
cagattactg cctctggcca gtatgggcag tgggcccccca agctggccag gctgcactat 3540
tctggctcta ttaatgcctg gagcactaag gagcccttca gctggattaa ggtggacctg 3600
ctggctccca tgatcatcca tggcatcaag actcaggggg ccaggcagaa gttctcttct 3660
ctgtacatca gccagttcat tatcatgtac tccctggatg gcaagaagtg gcagacctat 3720
aggggcaaca gcactggcac cctgatggtg ttctttggga atgtggacag ctctggcatc 3780
aagcataata tcttcaatcc ccccatcatt gctaggtaca tcaggctgca ccccacccac 3840
tactctatta ggtctaccct gaggatggag ctgatgggct gtgacctgaa cagctgcagc 3900
atgcctctgg gcatggagag caaagccatc tctgatgccc agatcactgc cagcagctac 3960
tttaccaaca tgtttgctac ttggagcccc agcaaggcca ggctgcacct gcaggggagg 4020
tctaatgcct ggaggcccca ggtgaacaac cccaaggagt ggctgcaggt ggacttccag 4080
aagactatga aggtgactgg ggtgaccacc caggggggtga agagcctgct gacctctatg 4140
tatgtgaagg agttcctgat tagcagcagc caggatggcc accagtggac cctgtttttc 4200
cagaatggga aggtgaaggt gtttcagggg aaccaggaca gcttcactcc tgtggtgaac 4260
tctctggacc ccccccctgct gaccaggtat ctgaggatcc accctcagag ctgggtgcac 4320
cagattgccc tgaggatgga ggtgctgggc tgtgaggccc aggacctgta ctga 4374

<210> SEQ ID NO 76
<211> LENGTH: 4374
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 76
atgcagattg agctgagcac ctgcttcttc ctgtgcctgc tgaggttttg cttctctgcc 60
accaggaggt actacctggg ggctgtggag ctgagctggg attacatgca gtctgacctg 120
ggggagctgc ctgtggatgc caggttccct cccagggtgc ccaagtcttt ccccttcaac 180
acttctgtgg tgtacaagaa gaccctgttt gtggagttta ctgaccacct gttcaacatt 240
gccaagccca ggcctccctg gatgggcctg ctgggcccca ccattcaggc tgaggtgtat 300
gacactgtgg tcatcaccct gaaaaatatg gctagccacc ctgtgtctct gcatgctgtg 360
ggggtgagct actggaaggc ctctgagggg gctgagtatg atgaccagac tagccagagg 420
gagaaggagg atgacaaggt gttccctggg ggcagccaca cttatgtgtg gcaggtgctg 480
aaagagaatg gccccatggc ttctgatccc ctgtgtctga cctatagcta cctgagccat 540
gtggatctgg tgaaggacct gaactctggc ctgattgggg ccctgctggt gtgcagggag 600
ggcagcctgg ctaaggagaa gacccagacc ctgcataagt tcatcctgct gtttgctgtg 660
tttgatgagg gcaagagctg gcactctgag actaagaaca gcctgatgca ggatagggat 720
gctgcttctg ccagggcctg gcccaagatg cacactgtga atgggtatgt gaacaggagc 780
ctgcctggcc tgattggctg ccataggaag tctgtctatt ggcatgtgat tggcatgggc 840
actactcctg aggtgcacag catctttctg gagggccaca ccttcctggt gaggaaccac 900
aggcaggcca gcctggagat ctctcccatc actttcctga ctgctcagac cctgctgatg 960
gacctgggcc agttcctgct gttctgtcac atctctagcc accagcatga tggcatggag 1020

-continued

```
gcctatgtga aggtggatag ctgccctgag gaaccccagc tgaggatgaa gaacaatgag   1080
gaggctgagg attatgatga tgatctgact gattctgaga tggatgtggt gaggtttgat   1140
gatgacaatt ctcctagctt cattcagatc agatctgtgg ccaaaaagca tcctaagact   1200
tgggtgcatt atattgctgc tgaggaggag gattgggatt atgccccccct ggtgctggct   1260
cctgatgata ggagctacaa gtctcagtac ctgaataatg ggccccagag gattggcagg   1320
aagtacaaga aggtgaggtt catggcctac actgatgaga ccttcaagac cagggaggcc   1380
attcagcatg agtctgggat tctggggccc ctgctgtatg ggaggtggg ggataccctg   1440
ctgatcattt tcaagaacca ggccagcagg ccctacaaca tctaccccca tgggattact   1500
gatgtgaggc ccctgtactc taggaggctg cctaaggggg tgaagcacct gaaggatttt   1560
cctatcctgc ctggggaaat cttcaagtac aagtggactg tgactgtgga ggatggcccc   1620
actaagtctg atcccaggtg tctgaccagg tattatagct cttttgtgaa catggagagg   1680
gatctggcct ctgggctgat tggccctctg ctgatctgct acaaggagtc tgtggaccag   1740
aggggcaacc agatcatgtc tgacaagagg aatgtgatcc tgttctctgt gtttgatgag   1800
aacaggagct ggtatctgac tgagaacatc cagaggtttc tgcccaatcc tgctggggtg   1860
cagctggagg atcctgagtt ccaggctagc aacatcatgc acagcatcaa tgggtatgtg   1920
tttgacagcc tgcagctgtc tgtgtgtctg catgaggtgg cctactggta tatcctgtct   1980
attggggccc agactgactt cctgtctgtg ttttttctg ggtatacttt taagcacaag   2040
atggtgtatg aggacaccct gactctgttc cccttctctg ggagactgt gtttatgagc   2100
atggagaacc ctggcctgtg gatcctgggc tgccacaatt ctgacttcag gaataggggg   2160
atgactgccc tgctgaaggt gagcagctgt gataagaata ctggggacta ctatgaggac   2220
tcttatgagg acatttctgc ctatctgctg tctaagaaca atgccattga acccaggagc   2280
ttctctcaga acccccctgt gctgaagagg caccagaggg aaatcaccag aactactctg   2340
cagtctgatc aggaggaaat tgactatgat gacactattt ctgtggagat gaagaaggag   2400
gactttgaca tctatgatga ggatgagaac cagagcccaa ggagcttcca gaagaagact   2460
aggcactact tcattgctgc tgtggagagg ctgtgggact atggcatgag cagcagcccc   2520
catgtgctga gaaacagggc ccagtctggg tctgtgcccc agttcaagaa ggtggtgttc   2580
caggagttca ctgatgggag cttcacccag cccctgtata ggggggagct gaatgagcac   2640
ctgggcctgc tgggccccta tattagggct gaggtggagg acaacatcat ggtgaccttc   2700
aggaatcagg cctctaggcc ctacagcttc tacagcagcc tgattagcta tgaggaggat   2760
cagaggcagg gggctgaacc caggaagaac tttgtgaagc ccaatgagac caagacctat   2820
ttctggaagg tgcagcatca catggccccc accaaggatg agtttgactg caaggcctgg   2880
gcctacttct ctgatgtgga tctggagaag gatgtgcact ctggcctgat tggcccccctg   2940
ctggtgtgcc acaccaacac cctgaaccct gctcatggca ggcaggtgac tgtgcaggag   3000
tttgccctgt tcttcaccat ctttgatgag actaagtctt ggtacttcac tgagaatatg   3060
gagaggaatt gcagggcccc ctgcaatatt cagatggaag accccacctt caaggagaat   3120
tacaggttcc atgccattaa tggctacatc atggataccc tgcctggcct ggtgatggcc   3180
caggatcaga ggatcaggtg gtacctgctg agcatgggca gcaatgagaa catccactct   3240
atccacttct ctggccatgt gtttactgtg aggaagaagg aggagtataa gatggccctg   3300
tacaacctgt accctggggt ctttgagact gtggagatgc tgccttctaa ggctggcatt   3360
```

-continued

```
tggagggtgg agtgcctgat tggggaacac ctgcatgctg gcatgtctac cctgttcctg   3420

gtgtacagca ataagtgcca gacccccctg ggcatggcct ctgggcatat cagggatttc   3480

cagatcactg cctctggcca gtatggccag tgggccccaa agctggctag gctgcactac   3540

tctgggagca tcaatgcctg gagcactaag gagcccttca gctggatcaa ggtggacctg   3600

ctggccccca tgattatcca tgggattaag actcaggggg ccaggcagaa gttcagcagc   3660

ctgtacatca gccagttcat tatcatgtac agcctggatg gcaagaagtg gcagacctat   3720

aggggcaact ctactgggac cctgatggtg ttctttggga atgtggatag ctctgggatc   3780

aagcacaata tcttcaaccc ccccatcatt gccaggtata tcaggctgca ccccacccac   3840

tacagcatta ggtctaccct gaggatggag ctgatgggct gtgatctgaa cagctgtagc   3900

atgcctctgg gcatggagtc taaggccatt tctgatgccc agattactgc tagcagctac   3960

ttcaccaaca tgtttgccac ctggtctccc agcaaggcca ggctgcatct gcagggcagg   4020

tctaatgctt ggaggcccca ggtgaacaac ccaaaggagt ggctgcaggt ggatttccag   4080

aagactatga aggtgactgg ggtgaccact caggggggtga agtctctgct gacctctatg   4140

tatgtgaagg agttcctgat ctctagcagc caggatggcc atcagtggac cctgttcttc   4200

cagaatggca aggtgaaagt gttccagggc aatcaggata gcttcactcc agtggtgaac   4260

agcctggatc cccctctgct gactaggtac ctgaggatcc acccccagag ctgggtgcac   4320

cagattgccc tgaggatgga ggtgctgggc tgtgaggccc aggacctgta ctga         4374
```

<210> SEQ ID NO 77
<211> LENGTH: 4374
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77

```
atgcagattg agctgagcac ctgcttcttc ctgtgtctgc tgaggttctg cttctctgcc     60

accaggaggt attacctggg ggctgtggag ctgagctggg actatatgca gtctgacctg    120

ggggagctgc ctgtggatgc taggttcccc cccagggtgc ccaagagctt cccctttaac    180

acttctgtgg tgtacaagaa gaccctgttt gtggagttca ctgaccacct gttcaacatt    240

gccaagccca ggccccctg gatggggctg ctggggccca ccatccaggc tgaggtgtat    300

gacactgtgg tgatcaccct gaagaacatg gccagccacc ctgtgagcct gcatgctgtg    360

ggggtgagct actggaaggc ttctgagggg gctgagtatg atgaccagac tagccagagg    420

gagaaggagg atgacaaggt gtttcctggg ggcagccata cctatgtgtg gcaggtgctg    480

aaggagaatg gccccatggc ctctgacccc ctgtgcctga cctacagcta cctgtctcat    540

gtggacctgg tgaaggacct gaactctggc ctgattgggg ctctgctggt gtgtagggag    600

ggcagcctgg ctaaggaaaa gacccagacc ctgcataagt ttatcctgct gtttgctgtg    660

tttgatgagg gcaagagctg gcactctgag accaagaaca gcctgatgca ggatagggat    720

gctgcctctg ccagggcttg gcctaagatg cacactgtga atgggtatgt gaataggagc    780

ctgcctggcc tgattggctg ccacaggaag tctgtgtact ggcatgtgat tgggatgggc    840

accaccccctg aggtccatag catcttcctg gagggccaca ctttcctggt gaggaaccac    900

agacaggcct ctctggagat ctctcccatc accttcctga ctgctcagac tctgctgatg    960

gacctgggcc agttcctgct gttttgccat attagcagcc accagcatga tgggatggag   1020
```

-continued

```
gcctatgtga aggtggatag ctgccctgag gagcctcagc tgaggatgaa gaacaatgag   1080
gaggctgaag actatgatga tgacctgact gattctgaga tggatgtggt gaggtttgat   1140
gatgacaata gccccagctt cattcagatc aggtctgtgg ccaagaaaca ccccaagacc   1200
tgggtgcact acattgctgc tgaggaagag gactgggact atgctcccct ggtgctggcc   1260
cctgatgata ggtcttataa gagccagtac ctgaacaatg ggccccagag gattggcagg   1320
aagtacaaga aggtgaggtt catggcctac actgatgaaa ccttcaaaac cagggaggcc   1380
attcagcatg agtctggcat cctgggccct ctgctgtatg ggaggtggg ggacaccctg    1440
ctgatcatct tcaagaacca ggccagcagg ccctacaaca tctatcctca tggcatcact   1500
gatgtgaggc ccctgtacag caggaggctg cccaaggggg tgaagcacct gaaagacttc   1560
cccatcctgc ctggggagat ctttaagtat aagtggactg tgactgtgga ggatggccct   1620
accaagtctg accccaggtg tctgaccagg tactattcta gctttgtgaa catggagagg   1680
gacctggcct ctggcctgat tggcccctg ctgatctgct acaaggagtc tgtggaccag    1740
aggggcaacc agatcatgtc tgacaagagg aatgtgatcc tgttttctgt gtttgatgag   1800
aataggagct ggtacctgac tgagaacatc cagaggtttc tgcccaatcc tgctggggtg   1860
cagctggagg atcctgagtt ccaggccagc aatatcatgc atagcatcaa tggctatgtg   1920
tttgacagcc tgcagctgtc tgtgtgcctg catgaggtgg cctactggta catcctgagc   1980
attggggccc agactgactt tctgtctgtg ttcttttctg gctatacctt caagcacaag   2040
atggtgtatg aggataccct gaccctgttc cccttctctg ggagactgt gttcatgagc    2100
atggagaatc ctgggctgtg gatcctgggg tgccacaact ctgattttag gaacaggggg   2160
atgactgccc tgctgaaggt gtctagctgt gataagaaca ctggggacta ctatgaggac   2220
agctatgagg acatttctgc ttatctgctg tctaagaata atgccattga gcccagaagc   2280
ttcagccaga atccccctgt gctgaagaga catcagaggg agatcaccag aactaccctg   2340
cagtctgatc aggaggagat tgactatgat gacactatct ctgtggagat gaagaaggag   2400
gactttgaca tctatgatga ggatgagaat cagtctccca ggagctttca gaagaagacc   2460
agacattact tcattgctgc tgtggagagg ctgtgggact atggcatgag ctctagccct   2520
catgtgctga ggaacagggc ccagtctggc tctgtgcccc agttcaagaa ggtggtgttc   2580
caggaattca ctgatggcag cttcacccag cccctgtaca gggggagct gaatgagcac    2640
ctgggcctgc tggggcctta tatcagggct gaggtggagg ataatattat ggtgactttc   2700
aggaaccagg ccagcaggcc ctactctttc tatagcagcc tgatctctta tgaggaggat   2760
cagaggcagg ggctgagcc taggaagaac tttgtgaagc ccaatgagac taagacctac    2820
ttctggaagg tccagcacca catggcccct accaaggatg agtttgactg caaggcctgg   2880
gcctatttct ctgatgtgga tctggagaag gatgtccatt ctgggctgat tggcccccctg  2940
ctggtgtgcc acactaacac tctgaatcct gcccatggca ggcaggtgac tgtccaggag   3000
tttgccctgt tcttcactat ctttgatgag accaagagct ggtactttac tgagaacatg   3060
gagaggaact gcagagctcc ttgcaatatt cagatggagg accccacctt caaggagaat   3120
tacaggttcc atgccattaa tgggtacatc atggacaccc tgcctggcct ggtgatggct   3180
caggaccaga ggatcaggtg gtacctgctg agcatgggct ctaatgagaa tatccacagc   3240
atccacttct ctgggcatgt gttcactgtg aggaagaagg aggagtacaa gatggctctg   3300
tataatctgt accctggggt gtttgaaact gtggagatgc tgccctctaa ggctggcatc   3360
tggagggtgg agtgcctgat tggggagcac ctgcatgctg gcatgagcac cctgttcctg   3420
```

gtgtacagca acaagtgcca gaccccccctg ggcatggcct ctggccacat cagggacttc 3480
cagatcactg cctctggcca gtatggccag tgggccccca agctggccag gctgcactat 3540
tctggcagca tcaatgcctg gagcaccaag gagcccttca gctggatcaa ggtggacctg 3600
ctggccccca tgatcattca tggcatcaag acccaggggg ccaggcagaa gttcagctct 3660
ctgtacatct ctcagttcat catcatgtac tctctggatg ggaagaagtg gcagacctac 3720
aggggcaaca gcactggcac cctgatggtg ttctttggga atgtggactc ttctggcatc 3780
aagcacaaca tcttcaatcc ccccatcatt gctaggtata ttaggctgca tcccacccac 3840
tacagcatca ggtctaccct gaggatggag ctgatgggct gtgacctgaa ctcttgcagc 3900
atgcccctgg gcatggagtc taaggccatc tctgatgccc agattactgc cagcagctac 3960
ttcaccaaca tgtttgccac ctggagcccc tctaaggcca ggctgcatct gcaggggagg 4020
agcaatgcct ggaggcctca ggtgaacaac cccaaggagt ggctgcaggt ggatttccag 4080
aagaccatga aggtgactgg ggtgaccacc caggggggtca agagcctgct gaccagcatg 4140
tatgtgaagg agttcctgat cagcagcagc caggatggcc accagtggac tctgttcttt 4200
cagaatggga aggtgaaggt gtttcagggc aatcaggact ctttcacccc tgtggtgaac 4260
agcctggacc cccccctgct gaccagatac ctgaggatcc acccccagtc ttgggtgcat 4320
cagattgccc tgaggatgga ggtgctgggc tgtgaggctc aggatctgta ctga 4374

<210> SEQ ID NO 78
<211> LENGTH: 4374
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 78
atgcagattg agctgagcac ttgctttttt ctgtgcctgc tgaggttttg tttttctgcc 60
accaggaggt actacctggg ggctgtggag ctgagctggg actatatgca gtctgatctg 120
ggggagctgc ctgtggatgc caggttcccc cccagggtgc ccaagtcttt tcccttcaac 180
acctctgtgg tgtataagaa gaccctgttt gtggagttca ctgaccacct gttcaacatt 240
gctaagccta ggccccccctg gatgggcctg ctgggcccta ccattcaggc tgaggtgtat 300
gacactgtgg tgatcaccct gaagaacatg gccagccatc ctgtgagcct gcatgctgtg 360
ggggtctctt actggaaggc ctctgagggg gctgagtatg atgaccagac cagccagaga 420
gagaaggagg atgacaaggt cttccctggg ggctctcaca cctatgtgtg gcaggtgctg 480
aaggaaaatg gccccatggc ctctgacccc ctgtgcctga cctacagcta tctgagccat 540
gtggatctgg tgaaggacct gaattctggc ctgattgggg ccctgctggt gtgcagggag 600
ggcagcctgg ccaaggagaa gacccagacc ctgcacaagt ttatcctgct gtttgctgtg 660
tttgatgagg gcaagtcttg gcactctgag actaagaaca gcctgatgca ggacagggat 720
gctgcctctg ccagggcctg gcccaagatg cacactgtga atggctatgt gaacaggagc 780
ctgcctgggc tgattggctg ccacaggaag tctgtgtact ggcatgtgat tggcatgggc 840
accacccctg aggtgcacag catcttcctg gaaggccaca ctttcctggt gaggaaccat 900
aggcaggcca gcctggagat cagccctatc accttcctga ctgcccagac cctgctgatg 960
gatctggggc agttcctgct gttctgccac atctctagcc accagcatga tgggatggag 1020
gcctatgtga aggtggacag ctgcccagag gagcctcagc tgaggatgaa aaacaatgaa 1080

-continued

```
gaggctgagg attatgatga tgatctgact gactctgaga tggatgtggt gagatttgat   1140
gatgacaata gccctagctt tattcagatc aggtctgtgg ctaagaagca ccccaagacc   1200
tgggtgcatt acattgctgc tgaggaggag gactgggatt atgctcctct ggtgctggcc   1260
cctgatgata ggagctacaa gagccagtac ctgaataatg gccctcagag gattggcagg   1320
aagtacaaga aggtgaggtt catggcttac actgatgaga ccttcaagac tagggaggcc   1380
atccagcatg agtctgggat cctggggccc ctgctgtatg gggaggtggg ggacaccctg   1440
ctgatcatct tcaagaacca ggctagcagg ccttacaaca tctatcccca tgggatcact   1500
gatgtgagac ctctgtacag caggaggctg cccaaggggg tcaagcatct gaaagacttc   1560
cccatcctgc ctggggagat ctttaagtat aagtggactg tgactgtgga ggatgggccc   1620
accaagtctg accccaggtg cctgaccagg tattacagca gctttgtgaa catggagagg   1680
gatctggcct ctgggctgat tggcccccctg ctgatctgtt acaaggaatc tgtggatcag   1740
aggggcaatc agatcatgtc tgacaagagg aatgtgatcc tgttctctgt gtttgatgag   1800
aataggtctt ggtacctgac tgaaaacatc cagaggttcc tgcccaaccc tgctggggtc   1860
cagctggagg atcctgagtt ccaggctagc aacatcatgc acagcatcaa tgggtatgtg   1920
tttgatagcc tgcagctgtc tgtgtgcctg catgaggtgg cctactggta catcctgtct   1980
attggggccc agactgactt cctgtctgtg ttcttttctg gctacacctt caagcacaag   2040
atggtgtatg aggacaccct gaccctgttc cccttctctg ggagactgt ctttatgagc   2100
atggagaacc ctgggctgtg gatcctgggc tgccacaact ctgatttcag gaataggggc   2160
atgactgctc tgctgaaggt gagctcttgt gacaagaaca ctggggatta ctatgaggac   2220
agctatgagg acatttctgc ctacctgctg agcaagaaca atgccattga gcctaggagc   2280
tttagccaga atcctcctgt cctgaagagg caccagaggg agatcaccag gaccaccctg   2340
cagtctgacc aggaggagat tgactatgat gataccatct ctgtggagat gaagaaggag   2400
gactttgaca tctatgatga ggatgagaat cagtctccca ggagcttcca gaagaagacc   2460
aggcactatt tcattgctgc tgtggagagg ctgtgggact atggcatgag cagctctcct   2520
catgtgctga ggaatagggc tcagtctggc tctgtgcccc agttcaagaa agtggtgttt   2580
caggagttca ctgatggctc tttcacccag cctctgtata ggggggagct gaatgagcac   2640
ctggggctgc tgggccccta tatcagggct gaggtggagg ataacatcat ggtgaccttc   2700
aggaaccagg cctctaggcc ctacagcttc tatagcagcc tgatcagcta tgaggaggac   2760
cagaggcagg gggctgagcc caggaagaac tttgtgaagc ccaatgagac caagacttac   2820
ttctggaagg tgcagcatca catggccccc accaaggatg agtttgactg taaggcctgg   2880
gcctacttct ctgatgtgga tctggagaag gatgtgcact ctggcctgat tggcccccctg   2940
ctggtgtgcc ataccaatac tctgaaccct gctcatggca ggcaggtgac tgtgcaggag   3000
tttgctctgt tcttcactat ctttgatgag accaagtctt ggtatttcac tgagaatatg   3060
gagaggaact gcagggcccc ctgcaacatc cagatggagg accccacctt taaggagaac   3120
tataggtttc atgccatcaa tggctacatc atggacaccc tgcctggcct ggtgatggcc   3180
caggatcaga ggatcaggtg gtacctgctg agcatggggt ctaatgagaa catccacagc   3240
atccacttct ctggccatgt gtttactgtg agaaagaagg aggagtacaa gatggctctg   3300
tacaatctgt accctggggt ctttgagact gtggagatgc tgcctagcaa ggctgggatc   3360
tggagggtgg agtgcctgat tggggaacat ctgcatgctg ggatgtctac tctgttcctg   3420
```

gtgtacagca acaagtgcca gaccccccctg ggcatggctt ctggccatat cagggacttt 3480
cagattactg cctctgggca gtatggccag tgggccccca agctggctag gctgcattat 3540
tctggcagca tcaatgcctg gtctactaag gagcccttca gctggatcaa ggtggatctg 3600 ctggcccccca tgatcatcca tggcatcaag acccaggggg ccaggcagaa gtttagctct 3660
ctgtacatta gccagttcat catcatgtac agcctggatg ggaagaagtg gcagacctac 3720
aggggcaatt ctactggcac cctgatggtg ttctttggca atgtggacag ctctggcatc 3780
aagcacaaca tctttaaccc ccctatcatt gctaggtaca tcaggctgca tcccacccat 3840
tacagcatca ggagcaccct gaggatggag ctgatgggct gtgacctgaa ctcttgcagc 3900
atgcccctgg gcatggagag caaggccatt tctgatgccc agattactgc cagcagctac 3960
ttcactaaca tgtttgccac ctggtctccc agcaaggcca ggctgcacct gcagggcagg 4020
agcaatgcct ggaggcccca ggtgaacaac cccaaggagt ggctgcaggt ggatttccag 4080
aagaccatga aggtgactgg ggtgaccacc cagggggtga agagcctgct gactagcatg 4140
tatgtgaagg agttcctgat cagctctagc caggatggcc accagtggac tctgtttttc 4200
cagaatggca aggtgaaggt gttccagggc aaccaggact ctttcactcc tgtggtgaac 4260
agcctggacc cccccctgct gaccaggtat ctgaggattc acccccagtc ttgggtgcat 4320
cagattgccc tgaggatgga ggtgctgggc tgtgaggccc aggatctgta ctga 4374

<210> SEQ ID NO 79
<211> LENGTH: 4374
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 79
atgcagattg agctgagcac ctgcttcttc ctgtgtctgc tgagattttg cttttctgcc 60
actaggaggt attacctggg ggctgtggag ctgtcttggg actacatgca gtctgatctg 120
ggggagctgc ctgtggatgc caggttccca cctagggtgc ctaagagctt tcccttcaat 180
acctctgtgg tgtacaagaa gaccctgttt gtggagttca ctgaccacct gttcaacatt 240
gccaagccta ggccccccctg gatgggcctg ctgggcccta ccatccaggc tgaagtgtat 300
gacactgtgg tgatcaccct gaagaacatg gccagccacc ctgtgagcct gcatgctgtg 360
ggggtgtctt actggaaggc ctctgagggg gctgagtatg atgatcagac cagccagagg 420
gagaaggaag atgacaaggt gttccctggg ggcagccaca cctatgtctg gcaggtgctg 480
aaggagaatg gccccatggc ctctgatccc ctgtgcctga cctactctta cctgagccat 540
gtggacctgg tgaaggatct gaattctggc ctgattgggg ccctgctggt gtgcagggag 600
ggcagcctgg ccaaggagaa gacccagacc ctgcataagt tcatcctgct gtttgctgtg 660
tttgatgaag ggaagagctg gcactctgag actaagaaca gcctgatgca ggacagggat 720
gctgcttctg ccagggcctg gcccaagatg cacactgtga atggctatgt gaatagaagc 780
ctgcctggcc tgattgggtg ccacaggaag tctgtgtact ggcatgtgat tgggatgggc 840 actaccccctg aggtgcatag catcttcctg gaaggccata ccttcctggt gaggaatcat 900
aggcaggctt ctctggaaat ttctcccatc actttcctga ctgctcagac cctgctgatg 960
gacctgggcc agttcctgct gttctgccac atcagctctc accagcatga tgggatggag 1020
gcctatgtga aggtggacag ctgtcctgag gagccccagc tgaggatgaa gaacaatgag 1080

-continued gaggctgagg actatgatga tgacctgact gactctgaga tggatgtggt caggtttgat 1140
gatgacaata gcccctcttt catccagatc aggtctgtgg ccaagaagca ccccaagact 1200
tgggtgcact acattgctgc tgaggaggag gattgggatt atgcccctct ggtgctggcc 1260
cctgatgaca ggagctataa gtctcagtac ctgaataatg gcccccagag gattgggagg 1320
aagtataaga aggtgaggtt tatggcctac actgatgaga ccttcaagac cagggaggcc 1380
atccagcatg agtctggcat cctgggcccc ctgctgtatg gggaggtggg ggataccctg 1440
ctgatcatct tcaagaacca ggcctctagg ccctacaata tctaccctca tggcatcact 1500
gatgtgagac ccctgtatag caggaggctg cctaaggggg tgaagcacct gaaggacttc 1560
cccatcctgc ctggggagat cttcaagtat aagtggactg tgactgtgga ggatggcccc 1620
accaagtctg accccaggtg cctgaccagg tattacagct cttttgtgaa catggagagg 1680
gatctggcct ctgggctgat tggcccactg ctgatctgct acaaggagtc tgtggatcag 1740
aggggcaatc agatcatgtc tgacaagagg aatgtgatcc tgttttctgt gtttgatgaa 1800
aataggtctt ggtatctgac tgagaacatc cagaggtttc tgcccaatcc tgctggggtg 1860
cagctggagg atcctgagtt tcaggcctct aatatcatgc attctatcaa tggctatgtg 1920
tttgacagcc tgcagctgtc tgtgtgcctg catgaggtgg cctactggta catcctgagc 1980
attggggctc agactgactt cctgtctgtg ttcttttctg gctatacttt caagcacaag 2040
atggtgtatg aggacactct gaccctgttc cccttctctg ggagactgt gttcatgtct 2100 atggaaaatc ctgggctgtg gattctgggc tgccacaatt ctgacttcag gaatagggg 2160 atgactgccc tgctgaaggt gtctagctgt gataagaaca ctggggatta ctatgaggac 2220
tcttatgaag atatctctgc ctatctgctg agcaagaaca atgccattga gcccaggagc 2280
ttcagccaga acccccctgt gctgaagagg caccagaggg agatcaccag gaccactctg 2340
cagtctgatc aggaggagat tgactatgat gacactatct ctgtggagat gaagaaggag 2400
gattttgaca tttatgatga ggatgagaac cagtctccca ggagcttcca gaagaagacc 2460
aggcattact ttattgctgc tgtggagagg ctgtgggact atgggatgag cagctctcct 2520
catgtgctga ggaacagggc ccagtctggg tctgtgcccc agttcaagaa ggtggtgttc 2580
caggagttca ctgatgggag cttcacccag cccctgtata ggggggagct gaatgagcac 2640
ctgggcctgc tgggccccta catcagggct gaggtggagg ataatatcat ggtgaccttc 2700
aggaaccagg ctagcaggcc ttacagcttt tacagcagcc tgatctctta tgaagaagac 2760
cagaggcagg gggctgagcc caggaagaat tttgtgaagc ctaatgagac caagacttat 2820
ttttggaagg tgcagcatca catggctcct accaaggatg agtttgactg caaggcctgg 2880
gcctactttt ctgatgtgga tctggagaag gatgtgcact ctggcctgat tggccctctg 2940
ctggtgtgcc atactaacac tctgaaccct gcccatggga ggcaggtgac tgtgcaggag 3000
tttgccctgt tcttcactat ttttgatgag accaagtctt ggtatttcac tgagaacatg 3060
gagaggaact gcagggctcc ctgcaacatc cagatggaag accccacctt caaggagaac 3120
tataggttcc atgccatcaa tgggtacatc atggataccc tgcctggcct ggtgatggcc 3180
caggatcaga ggattaggtg gtatctgctg agcatgggct ctaatgagaa catccacagc 3240
atccatttct ctggccatgt gttcactgtg aggaagaagg aggagtacaa gatggctctg 3300
tacaacctgt atcctggggt gtttgagact gtggagatgc tgcccagcaa ggctggcatc 3360
tggagggtgg aatgcctgat tggggagcac ctgcatgctg gcatgagcac tctgttcctg 3420
gtgtatagca acaagtgcca gacccccctg ggcatggcct ctggccatat cagggatttc 3480

-continued

```
cagatcactg cttctggcca gtatggccag tgggccccca agctggccag gctgcactat   3540

tctggcagca tcaatgcctg gagcactaag gagccttttt cttggatcaa ggtggacctg   3600

ctggccccta tgattattca tggcatcaag acccaggggg ccaggcagaa gttctctagc   3660

ctgtacatct ctcagttcat cattatgtat agcctggatg gcaagaagtg gcagacctac   3720

aggggcaata gcactggcac cctgatggtg ttttttggga atgtggactc ttctgggatc   3780

aagcacaaca tctttaaccc ccccatcatt gccaggtata ttaggctgca ccccacccac   3840

tacagcatca ggagcaccct gaggatggag ctgatgggct gtgatctgaa ttcttgctct   3900

atgcccctgg gcatggagag caaggccatc tctgatgccc agatcactgc cagctcttac   3960

ttcaccaaca tgtttgccac ctggtctcct agcaaggcca ggctgcatct gcagggcagg   4020

agcaatgcct ggaggcccca ggtgaacaac cccaaggagt ggctgcaggt ggacttccag   4080

aagaccatga aggtgactgg ggtgaccact caggggggtga agagcctgct gacctctatg   4140

tatgtgaagg agttcctgat cagcagcagc caggatggcc accagtggac tctgttcttc   4200

cagaatggga aggtgaaggt gttccagggc aaccaggata gctttacccc tgtggtgaac   4260

agcctggacc ctcctctgct gaccagatac ctgaggatcc atcctcagag ctgggtgcac   4320

cagattgccc tgaggatgga ggtgctgggc tgtgaggccc aggatctgta ctga         4374
```

<210> SEQ ID NO 80
<211> LENGTH: 4374
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 80

```
atgcagattg agctgagcac ttgcttcttc ctgtgcctgc tgaggttctg cttttctgct     60

actaggaggt actacctggg ggctgtggag ctgagctggg attacatgca gtctgacctg    120

ggggagctgc cagtggatgc caggttcccc cccagggtgc ccaagtcttt tcctttcaac    180

acctctgtgg tgtacaagaa gaccctgttt gtggagttca ctgaccacct gttcaacatt    240

gccaagccca ggccccctg gatggggctg ctggggccca ccatccaggc tgaggtgtat    300

gacactgtgg tgattaccct gaagaacatg gctagccacc ctgtgagcct gcatgctgtg    360

ggggtgagct attggaaggc ctctgagggg gctgagtatg atgatcagac cagccagagg    420

gaaaaggagg atgacaaggt gttccctggg ggcagccata cttatgtgtg gcaggtgctg    480

aaggagaatg ggcccatggc ctctgacccc ctgtgcctga cttacagcta tctgagccat    540

gtggacctgg tgaaggatct gaactctggc ctgattgggg ctctgctggt gtgcagggag    600

ggcagcctgg ctaaggagaa gactcagact ctgcataagt tcatcctgct gtttgctgtg    660

tttgatgaag gcaagagctg gcactctgag accaagaact ctctgatgca ggatagggat    720

gctgcctctg ccagggcttg gcccaagatg cacactgtga atggctatgt gaacaggagc    780

ctgcctggcc tgattgggtg ccacaggaag tctgtgtact ggcatgtgat tggcatgggc    840

accacccctg aggtgcacag cattttcctg gagggccaca ccttcctggt gaggaatcac    900

aggcaggcca gcctggagat cagccccatc accttcctga ctgcccagac cctgctgatg    960

gacctggggc agtttctgct gttctgccac atcagcagcc atcagcatga tggcatggag   1020

gcctatgtga aggtggactc ttgccctgag gagccccagc tgaggatgaa gaacaatgag   1080

gaggctgagg attatgatga tgacctgact gactctgaga tggatgtggt gaggtttgat   1140
```

-continued gatgacaata gccccagctt catccagatt aggtctgtgg ccaagaagca ccctaagacc 1200
tgggtgcact acattgctgc tgaggaggag gattgggatt atgccccccct ggtgctggct 1260
cctgatgaca ggtcttataa gagccagtac ctgaacaatg ggccccagag gattggcagg 1320
aagtacaaga aggtgaggtt catggcttac actgatgaga ccttcaagac tagggaggcc 1380
atccagcatg agtctggcat cctgggcccc ctgctgtatg gggaggtggg ggataccctg 1440
ctgatcatct tcaagaacca ggccagcagg ccctacaaca tttaccctca tggcatcact 1500
gatgtgaggc ccctgtacag caggagactg cccaaggggg tgaagcacct gaaggatttt 1560
cccattctgc ctggggagat cttcaagtac aagtggactg tgactgtgga ggatggcccc 1620
accaagtctg atcccaggtg cctgactagg tactactctt cttttgtgaa tatggagagg 1680
gatctggcct ctggcctgat tggcccccctg ctgatctgct acaaggagtc tgtggaccag 1740
aggggcaacc agatcatgtc tgacaagagg aatgtgatcc tgttctctgt gtttgatgag 1800
aataggagct ggtacctgac tgagaatatc cagaggttcc tgcctaatcc tgctggggtc 1860
cagctggagg atcctgagtt ccaggctagc aacattatgc acagcatcaa tggctatgtg 1920
tttgattctc tgcagctgtc tgtgtgcctg catgaggtgg cttactggta catcctgtct 1980
attggggccc agactgattt cctgtctgtg ttcttctctg gctacacttt caagcataag 2040
atggtgtatg aggataccct gaccctgttc cccttctctg ggagactgt gttcatgtct 2100
atggagaacc ctggcctgtg gatcctgggc tgtcataact ctgacttcag aaacaggggc 2160
atgactgccc tgctgaaggt gagcagctgt gacaagaaca ctggggacta ctatgaggac 2220
agctatgagg atatctctgc ttatctgctg agcaagaata atgccattga gcccaggagc 2280
ttcagccaga accccccctgt gctgaagagg caccagaggg agatcactag gactaccctg 2340
cagtctgatc aggaggagat tgactatgat gacaccatct ctgtggagat gaagaaggag 2400
gactttgaca tctatgatga ggatgagaac cagtccccca ggtctttcca gaagaagacc 2460
aggcactact tcattgctgc tgtggagagg ctgtgggact atggcatgag ctctagcccc 2520
catgtgctga ggaacagggc tcagtctggc tctgtgcccc agttcaagaa ggtggtcttc 2580
caggagttca ctgatggctc ttttacccag cctctgtaca gaggggagct gaatgagcac 2640
ctgggcctgc tgggccccta catcagggct gaggtggagg ataatatcat ggtgaccttc 2700
agaaaccagg cctctaggcc ctacagcttc tacagcagcc tgatctctta tgaggaggat 2760
cagaggcagg gggctgagcc caggaagaac tttgtgaagc ccaatgagac caagacctac 2820
ttctggaagg tgcagcacca tatggcccct actaaggatg agtttgactg caaggcctgg 2880
gcttattttt ctgatgtgga cctggagaag gatgtgcact ctgggctgat tggcccccctg 2940
ctggtgtgcc acaccaacac cctgaaccct gcccatggca ggcaggtgac tgtgcaggag 3000
tttgccctgt tcttcactat ctttgatgag accaagagct ggtacttcac tgagaacatg 3060
gagagaaatt gtagggctcc ctgcaatatc cagatggagg accccacctt caaagaaaat 3120
tacagattcc atgccatcaa tgggtacatc atggataccc tgcctgggct ggtgatggct 3180
caggaccaga ggatcaggtg gtacctgctg agcatggggt ctaatgagaa catccactct 3240
atccatttct ctggccatgt gttcactgtg agaaagaagg aggagtataa gatggctctg 3300
tacaacctgt acccaggggt gtttgagact gtggaaatgc tgcccagcaa agctgggatc 3360
tggagggtgg agtgcctgat tggggagcac ctgcatgctg gcatgtctac cctgttcctg 3420
gtgtacagca acaagtgcca gactcccctg ggcatggcct ctgggcacat cagggatttt 3480

```
cagatcactg cctctggcca gtatggccag tgggcccccca agctggccag gctgcactac   3540

tctggcagca ttaatgcttg gagcactaag gagcccttca gctggatcaa ggtggatctg   3600

ctggccccca tgatcatcca tggcatcaag acccaggggg ccaggcagaa gttctctagc   3660

ctgtacattt ctcagttcat catcatgtac agcctggatg ggaagaagtg gcagacctac   3720

agggggaaca gcactgggac cctgatggtg ttctttggca atgtggatag ctctggcatc   3780

aagcacaata tcttcaatcc ccccattatt gccaggtaca ttaggctgca tcctactcac   3840

tactctatta ggagcaccct gaggatggag ctgatggggt gtgacctgaa cagctgttct   3900

atgcccctgg gcatggagtc taaggctatc tctgatgccc agatcactgc cagcagctac   3960

ttcactaata tgtttgccac ctggagccct agcaaggcca gactgcacct gcagggcagg   4020

agcaatgcct ggaggcccca ggtgaacaac cccaaggagt ggctgcaggt ggacttccag   4080

aagaccatga aggtgactgg ggtgaccact caggggggtga agagcctgct gaccagcatg   4140

tatgtgaagg agttcctgat cagcagcagc caggatggcc accagtggac cctgttcttc   4200

cagaatggga aggtgaaggt gttccagggc aaccaggact ctttcacccc tgtggtgaac   4260

agcctggatc ctcccctgct gaccaggtac ctgaggatcc acccccagag ctgggtgcac   4320

cagattgctc tgaggatgga agtgctgggc tgtgaggccc aggatctgta ctga         4374
```

<210> SEQ ID NO 81
<211> LENGTH: 4374
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 81

```
atgcagattg agctgagcac ctgcttcttc ctgtgcctgc tgaggttttg cttctctgct     60

accaggaggt actacctggg ggctgtggag ctgagctggg actatatgca gtctgacctg    120

ggggagctgc ctgtggatgc taggttccct cccagggtgc ccaagagctt cccctttaat    180

acctctgtgg tgtacaagaa aaccctgttt gtggagttca ctgaccatct gttcaacatt    240

gccaagccca ggccccccttg gatgggcctg ctgggcccca ccattcaggc tgaggtgtat    300

gacactgtgg tcattaccct gaagaacatg gcttctcacc ctgtgagcct gcatgctgtg    360

ggggtgagct actggaaggc ctctgagggg gctgagtatg atgaccagac cagccagagg    420

gagaaggagg atgataaggt gttccctggg ggcagccaca cctatgtgtg gcaggtgctg    480

aaggagaatg gccccatggc ctctgatccc ctgtgcctga cctactctta tctgtctcat    540

gtggacctgg tgaaggacct gaactctggc ctgattgggg ctctgctggt gtgcagggag    600

ggctctctgg ccaaggagaa gacccagacc ctgcacaagt ttattctgct gtttgctgtc    660

tttgatgagg gcaagagctg gcattctgag accaagaaca gcctgatgca ggacagggat    720

gctgcctctg ccagggcctg gcccaaaatg cacactgtga atggctatgt gaacaggagc    780

ctgcctggcc tgattggctg ccacaggaag tctgtgtact ggcatgtgat tggcatgggc    840

accaccccctg aggtgcacag catcttcctg gagggccaca cctttctggt gaggaatcac    900

aggcaggcca gcctggagat tagccccatc accttcctga ctgcccagac cctgctgatg    960

gacctgggcc agttcctgct gttctgccac atcagcagcc accagcatga tggcatggag   1020

gcctatgtga aggtggatag ctgccctgag gagccccagc tgaggatgaa aaacaatgag   1080

gaggctgagg attatgatga tgacctgact gactctgaga tggatgtggt gaggtttgat   1140
```

-continued gatgacaata gccccagctt tattcagatt aggtctgtgg ctaagaagca ccccaagact 1200
tgggtgcact acattgctgc tgaggaggag gattgggact atgcccctct ggtcctggcc 1260
cctgatgata ggtcttacaa gagccagtat ctgaacaatg gcccccagag gattggcagg 1320
aagtacaaga aggtgaggtt catggcctac actgatgaga cctttaagac cagggaggcc 1380
attcagcatg agtctgggat cctgggcccc ctgctgtatg gggaggtggg ggacactctg 1440
ctgatcatct tcaagaacca ggccagcagg ccttataaca tctaccctca tgggatcact 1500
gatgtgaggc ccctgtactc tagaaggctg cccaaggggg tcaagcacct gaaggatttt 1560
cccatcctgc ctggggagat tttcaagtac aagtggactg tgactgtgga ggatggcccc 1620
accaagtctg accctaggtg cctgaccagg tactacagct cttttgtgaa catggagagg 1680
gacctggcct ctggcctgat tggccctctg ctgatttgct acaaggagtc tgtggaccag 1740
aggggcaacc agatcatgtc tgacaagagg aatgtgatcc tgttttctgt gtttgatgag 1800
aacaggtctt ggtacctgac tgagaacatc cagaggttcc tgcctaaccc agctggggtg 1860
cagctggagg atcctgagtt ccaggccagc aatattatgc atagcattaa tggctatgtg 1920
tttgatagcc tgcagctgtc tgtgtgcctg catgaggtgg cctactggta catcctgagc 1980
attggggccc agactgactt tctgtctgtg ttcttctctg gctacacctt caagcataag 2040
atggtgtatg aggacaccct gactctgttc cctttttctg ggagactgt gtttatgagc 2100 atggagaatc ctggcctgtg gatcctgggc tgccataatt ctgacttcag gaacaggggc 2160
atgactgccc tgctgaaagt gagcagctgt gacaagaata ctggggacta ctatgaagac 2220
agctatgagg acatctctgc ctacctgctg agcaagaaca atgccattga gcccaggagc 2280
ttcagccaga accccccagt gctgaagagg caccagagag agatcaccag gactaccctg 2340
cagtctgacc aggaggagat tgactatgat gacaccattt ctgtggagat gaagaaggag 2400
gactttgaca tttatgatga ggatgagaat cagagcccca ggagcttcca gaagaagact 2460
aggcactatt ttattgctgc tgtggagagg ctgtgggact atggcatgag cagctctccc 2520
catgtgctga ggaatagggc ccagtctggc tctgtgcctc agttcaagaa ggtggtgttc 2580
caggagttca ctgatggcag ctttacccag cccctgtata ggggggagct gaatgagcac 2640
ctgggcctgc tgggccccta tatcagggct gaggtggagg acaatattat ggtgaccttt 2700
aggaaccagg ccagcaggcc ctactctttc tatagcagcc tgatcagcta tgaggaggac 2760
cagaggcagg gggctgagcc caggaagaat tttgtgaagc ctaatgagac caagacctac 2820
ttctggaagg tgcagcatca catggccccc accaaggatg agtttgactg caaggcttgg 2880
gcctatttct ctgatgtgga cctggagaag gatgtgcact ctggcctgat tggccccctg 2940
ctggtgtgcc acactaacac tctgaatcct gcccatggca ggcaggtgac tgtgcaggag 3000
tttgccctgt tcttcaccat ctttgatgag accaagagct ggtacttcac tgagaacatg 3060
gagaggaact gcagggcccc ctgcaacatc cagatggagg atcccacctt caaggagaac 3120
tacaggtttc atgccatcaa tggctacatc atggacactc tgcctggcct ggtgatggcc 3180
caggatcaga ggatcaggtg gtacctgctg agcatgggct ctaatgagaa tatccatagc 3240
atccacttct ctggccatgt gttcactgtc aggaagaagg aggagtacaa gatggctctg 3300
tataatctgt accctggggt gtttgagact gtggagatgc tgcccagcaa ggctggcatc 3360
tggagggtgg agtgcctgat tggggagcac ctgcatgctg ggatgagcac cctgtttctg 3420
gtgtactcta acaagtgcca gacccccctg ggcatggcct ctgggcacat cagggatttc 3480
cagatcactg cttctggcca gtatggccag tgggccccca agctggccag gctgcactac 3540

```
tctggcagca tcaatgcctg gtctaccaag gagccctttt cttggattaa ggtggacctg   3600

ctggccccca tgatcatcca tggcatcaag acccaggggg ccaggcagaa gttcagcagc   3660

ctgtacatca gccagttcat catcatgtac agcctggatg gcaaaaagtg gcagacctac   3720

aggggcaata gcactgggac tctgatggtg ttctttggca atgtggacag ctctgggatc   3780

aagcacaata tcttcaaccc tcccatcatt gctaggtaca tcaggctgca ccccacccac   3840

tatagcatca ggtctaccct gaggatggag ctgatgggct gtgacctgaa ctcttgcagc   3900

atgcccctgg gcatggagtc caaagctatc tctgatgccc agattactgc cagcagctac   3960

ttcaccaaca tgtttgccac ctggtctccc tctaaggcca ggctgcacct gcagggcagg   4020

agcaatgcct ggaggcccca ggtgaacaat cccaaggagt ggctgcaggt ggatttccag   4080

aaaactatga aggtgactgg ggtgaccacc caggggggtga agtctctgct gaccagcatg   4140

tatgtgaagg agttcctgat ctcttctagc caggatggcc accagtggac tctgttcttc   4200

cagaatggca aggtgaaggt gttccagggc aaccaggaca gcttcacccc tgtggtgaac   4260

tctctggatc ccccccctgct gaccaggtac ctgaggattc atccccagag ctgggtgcac   4320

cagattgctc tgagaatgga ggtgctgggg tgtgaggctc aggacctgta ttga         4374
```

<210> SEQ ID NO 82
<211> LENGTH: 4374
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 82

```
atgcagattg agctgtctac ttgttttttt ctgtgcctgc tgaggttctg cttctctgcc     60

accaggaggt attacctggg ggctgtggag ctgagctggg attacatgca gtctgatctg    120

ggggagctgc ctgtggatgc caggttcccc cccagggtgc ccaagagctt ccccttcaac    180

acctctgtgg tgtataagaa gaccctgttt gtggagttca ctgatcatct gtttaacatt    240

gccaagccca ggcccccctg gatgggcctg ctgggcccaa ctatccaggc tgaggtgtat    300

gacactgtgg tcatcaccct gaagaatatg gccagccatc ctgtgagcct gcatgctgtg    360

ggggtgagct actggaaggc ctctgagggg gctgagtatg atgaccagac cagccagagg    420

gagaaggagg atgacaaggt gttccctggg ggcagccaca cctatgtgtg gcaggtgctg    480

aaggagaatg gccccatggc ctctgacccc ctgtgcctga cttatagcta cctgtctcat    540

gtggacctgg tgaaggacct gaactctggc ctgattgggg ccctgctggt ctgtagggaa    600

ggcagcctgg ccaaggagaa gacccagacc ctgcacaagt ttattctgct gtttgctgtg    660

tttgatgaag gcaagagctg gcactctgag accaagaatt ctctgatgca ggatagggat    720

gctgcctctg ccagggcctg gcccaagatg catactgtga atggctatgt gaacagaagc    780

ctgcctggcc tgattggctg ccataggaag tctgtgtatt ggcatgtgat tgggatgggc    840

actacccctg aagtgcacag cattttcctg gagggccaca ctttcctggt gaggaaccac    900

aggcaggcct ctctggagat cagccccatt actttcctga ctgcccagac cctgctgatg    960

gatctgggcc agttcctgct gttctgccac atctctagcc accagcatga tggcatggag   1020

gcctatgtga aggtggacag ctgccctgag gagccccagc tgaggatgaa gaataatgag   1080

gaggctgagg attatgatga tgacctgact gactctgaga tggatgtggt gaggtttgat   1140

gatgataata gccccagctt catccagatc aggtctgtgg ccaagaagca tcccaagacc   1200
```

-continued tgggtgcact atattgctgc tgaagaggag gactgggact atgcccctct ggtgctggct 1260
cctgatgaca ggagctataa gagccagtat ctgaacaatg ggccccagag gattgggagg 1320
aagtacaaga aggtgaggtt catggcctac actgatgaga cctttaagac cagggaggcc 1380
atccagcatg agtctggcat tctggggccc ctgctgtatg gggaggtggg ggacactctg 1440
ctgatcattt tcaagaacca ggccagcagg ccctacaata tttacccccca tggcatcact 1500 gatgtgaggc ccctgtacag caggaggctg cccaaggggg tgaagcacct gaaggacttc 1560
cccatcctgc ctggggagat cttcaagtac aagtggactg tgactgtgga ggatggccct 1620
accaagtctg accctaggtg tctgactagg tactacagca gctttgtgaa catggagaga 1680
gacctggctt ctggcctgat tggcccccctg ctgatctgct acaaggagtc tgtggatcag 1740
aggggcaacc agattatgtc tgataagagg aatgtcatcc tgttctctgt gtttgatgag 1800
aacaggagct ggtatctgac tgagaacatt cagaggttcc tgcccaaccc tgctggggtg 1860
cagctggagg accctgagtt ccaggccagc aacatcatgc attctattaa tggctatgtg 1920
tttgacagcc tgcagctgtc tgtgtgcctg catgaggtgg cctactggta catcctgagc 1980
attggggccc agactgactt tctgtctgtg tttttctctg ggtacacctt caagcacaag 2040
atggtctatg aggacaccct gaccctgttc cccttttctg ggaaaactgt gtttatgagc 2100
atggagaacc ctgggctgtg gatcctgggc tgccacaact ctgactttag gaataggggc 2160
atgactgccc tgctgaaggt gagcagctgt gacaagaata ctggggatta ctatgaggac 2220
agctatgagg atatctctgc ctacctgctg agcaagaaca atgccattga gcctaggagc 2280
ttcagccaga acccccctgt gctgaagagg caccagaggg agatcaccag gaccaccctg 2340
cagtctgatc aggaggagat tgactatgat gacaccatct ctgtggagat gaagaaggag 2400
gactttgata tttatgatga ggatgagaac cagagcccca ggagcttcca gaagaagacc 2460
aggcactatt tcattgctgc tgtggagagg ctgtgggact atggcatgag ctctagcccc 2520
catgtgctga ggaacagggc ccagtctggc tctgtgcccc agttcaagaa ggtggtgttc 2580
caggaattta ctgatggcag ctttacccag cccctgtaca gaggggagct gaatgagcac 2640
ctgggcctgc tgggccccta catcagggct gaggtggagg ataatatcat ggtgaccttt 2700
aggaaccagg cctctaggcc ctattctttt tacagcagcc tgatcagcta tgaggaggac 2760
cagaggcagg gggctgagcc taggaagaac tttgtgaagc ccaatgagac caagacctac 2820
ttttggaaag tgcagcacca catggccccc actaaggatg agtttgattg caaggcctgg 2880
gcctatttct ctgatgtgga cctggagaag gatgtgcact ctggcctgat tggcccccctg 2940 ctggtgtgcc acaccaacac tctgaaccct gcccatggca ggcaggtgac tgtgcaggag 3000
tttgccctgt tctttaccat ctttgatgag actaagagct ggtatttcac tgagaacatg 3060
gagaggaact gcagagcccc ttgcaacatc cagatggagg accctacctt caaggagaac 3120
tataggttcc atgccatcaa tggctacatc atggataccc tgcctggcct ggtgatggct 3180
caggaccaga ggatcaggtg gtacctgctg agcatgggga gcaatgagaa cattcatagc 3240
atccacttct ctgggcatgt gttcactgtg aggaagaagg aggagtataa gatggccctg 3300
tacaacctgt accctggggt gtttgagact gtggagatgc tgcccagcaa ggctggcatc 3360
tggagggtgg agtgcctgat tggggagcac ctgcatgctg gcatgagcac tctgttcctg 3420
gtgtacagca acaagtgcca gacccccctg ggcatggcct ctggccacat cagggacttc 3480
cagattactg cctctgggca gtatgggcag tgggccccca agctggccag gctgcactac 3540

```
tctgggtcta tcaatgcttg gagcaccaag gagcctttca gctggatcaa ggtggatctg   3600

ctggccccca tgatcattca tgggatcaag acccaggggg ccaggcagaa gttcagcagc   3660

ctgtatattt ctcagttcat catcatgtat tctctggatg gcaaaaagtg gcagacctat   3720

agagggaaca gcactgggac cctgatggtg ttttttggca atgtggatag ctctggcatc   3780

aagcacaata tcttcaaccc ccccattatt gccaggtaca tcaggctgca ccccacccac   3840

tactctatca ggagcaccct gaggatggag ctgatgggct gtgatctgaa cagctgctct   3900

atgcctctgg ggatggaaag caaggccatc tctgatgccc agatcactgc cagcagctat   3960

ttcaccaata tgtttgccac ttggagccct agcaaggcta ggctgcatct gcagggcagg   4020

tctaatgcct ggaggcccca ggtgaacaac cccaaggagt ggctgcaggt ggacttccag   4080

aagactatga aagtgactgg ggtgaccacc cagggggtga aaagcctgct gaccagcatg   4140

tatgtgaagg agttcctgat tagcagcagc caggatggcc accagtggac cctgttcttc   4200

cagaatggga aggtgaaggt gtttcagggc aatcaggata gcttcacccc agtggtgaac   4260

agcctggacc ccccctgct gaccaggtac ctgaggatcc acccccagag ctgggtgcac   4320

cagattgccc tgaggatgga ggtgctgggc tgtgaggccc aggatctgta ctga         4374
```

<210> SEQ ID NO 83
<211> LENGTH: 4374
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 83

```
atgcagattg agctgagcac ctgctttttc ctgtgcctgc tgaggttctg cttctctgct     60

accaggaggt actacctggg ggctgtggag ctgtcttggg attacatgca gtctgacctg    120

ggggagctgc ctgtggatgc caggtttccc cccagggtgc ccaagtcttt cccctttaac    180

acctctgtgg tgtataagaa gactctgttt gtggagttca ctgatcacct gttcaatatt    240

gccaagccca ggcccccttg gatgggcctg ctgggcccca ctatccaggc tgaggtgtat    300

gacactgtgg tcatcaccct gaagaacatg gccagccacc ctgtgagcct gcatgctgtg    360

ggggtgagct actggaaggc ctctgagggg gctgagtatg atgaccagac cagccagagg    420

gagaaggagg atgacaaggt gttcccaggg gggtctcaca cttatgtgtg gcaggtgctg    480

aaggagaatg ggcccatggc ctctgaccct ctgtgcctga cttatagcta cctgtctcat    540

gtggatctgg tgaaggacct gaactctggc ctgattgggg ccctgctggt gtgcagggag    600

gggagcctgg ccaaggagaa gacccagacc ctgcacaagt tcatcctgct gtttgctgtg    660

tttgatgagg ggaagagctg gcactctgag accaagaata gcctgatgca ggacagggat    720

gctgcttctg ctagggcctg gcctaagatg cacactgtga atggctatgt gaacaggagc    780

ctgcctggcc tgattgggtg tcacaggaag tctgtgtact ggcatgtgat tggcatgggg    840

actactccag aagtgcacag catcttcctg gaggggcaca ccttcctggt gaggaatcac    900

aggcaggcca gcctggagat ttctcccatc actttcctga ctgcccagac cctgctgatg    960

gatctggggc agttcctgct gttctgccac atcagcagcc atcagcatga tgggatggag   1020

gcctatgtga aggtggacag ctgccctgag gagcctcagc tgaggatgaa gaacaatgag   1080

gaggctgagg actatgatga tgatctgact gactctgaga tggatgtggt gaggtttgat   1140

gatgacaact ctcccagctt catccagatc aggtctgtgg ccaagaagca ccccaagacc   1200
```

-continued tgggtgcact acattgctgc tgaggaggag gattgggatt atgctcccct ggtgctggct 1260
cctgatgata ggagctacaa gagccagtat ctgaataatg ggccccagag gattggcagg 1320
aagtataaga aggtgaggtt catggcctac actgatgaga cctttaagac cagggaggct 1380
attcagcatg agtctggcat cctgggcccc ctgctgtatg gggaggtggg ggacaccctg 1440
ctgatcattt tcaagaacca ggccagcagg ccctataaca tctatcccca tgggatcact 1500
gatgtgaggc ccctgtactc taggaggctg cccaaggggg tcaagcacct gaaggacttc 1560
cccatcctgc ctggggagat cttcaagtac aagtggactg tgactgtgga ggatggcccc 1620
actaagtctg accccaggtg cctgactagg tactacagca gctttgtgaa catggagaga 1680
gatctggcct ctggcctgat tggcccccctg ctgatctgct acaaagagtc tgtggatcag 1740
aggggcaacc agatcatgtc tgacaagagg aatgtgatcc tgttctctgt gtttgatgag 1800
aacagaagct ggtacctgac tgagaacatt cagaggtttc tgcccaaccc tgctggggtc 1860
cagctggagg accctgagtt tcaggccagc aacatcatgc acagcatcaa tgggtatgtg 1920
tttgacagcc tgcagctgtc tgtgtgcctg catgaggtgg cctactggta tatcctgagc 1980
attggggccc agactgattt cctgtctgtg ttcttctctg gctacacttt caagcacaag 2040
atggtgtatg aggataccct gaccctgttc cctttctctg ggaaactgt gttcatgagc 2100
atggagaacc ctgggctgtg gatcctgggg tgccacaatt ctgatttcag gaacagaggc 2160
atgactgctc tgctgaaggt gtctagctgt gacaagaaca ctggggacta ctatgaggac 2220
agctatgagg acatctctgc ctacctgctg agcaagaaca atgctattga acccaggtct 2280
ttcagccaga accccctgt gctgaagagg caccagaggg agatcactag gaccaccctg 2340
cagtctgatc aggaggagat tgactatgat gacaccatct ctgtggagat gaagaaggag 2400
gactttgaca tctatgatga ggatgagaat cagtctccca ggagcttcca gaagaagact 2460
aggcattact tcattgctgc tgtggagagg ctgtgggact atggcatgag ctctagccct 2520
catgtgctga ggaacagggc ccagtctggc tctgtgcccc agttcaagaa ggtggtgttt 2580
caggagttca ctgatggcag cttcacccag cccctgtaca ggggggagct gaatgagcat 2640
ctgggcctgc tgggccccta catcagggct gaggtggagg acaacatcat ggtgaccttc 2700
agaaatcagg ctagcaggcc ctacagcttc tacagcagcc tgatctctta tgaggaggac 2760
cagaggcagg gggctgagcc caggaagaac tttgtgaagc ccaatgagac caagacctat 2820
ttctggaagg tgcagcacca catggccccc accaaggatg agtttgattg caaggcctgg 2880
gcctacttct ctgatgtgga cctggagaag gatgtgcatt ctgggctgat tggccctctg 2940
ctggtgtgcc acaccaacac cctgaatcct gcccatggca ggcaggtgac tgtgcaggag 3000
tttgccctgt tctttactat ctttgatgag accaagtctt ggtattttac tgagaacatg 3060
gagaggaact gcagggcccc ctgcaacatc cagatggagg accccacctt caaggagaac 3120
tacagattcc atgccatcaa tggctacatt atggacactc tgcctggcct ggtgatggcc 3180
caggaccaga ggatcaggtg gtacctgctg tctatgggca gcaatgagaa cattcactct 3240
atccacttct ctgggcatgt gttcactgtg aggaagaagg aggagtacaa gatggccctg 3300
tacaacctgt accctggggt gtttgagact gtggagatgc tgcctagcaa ggctgggatc 3360
tggagggtgg agtgcctgat tggggagcac ctgcatgctg gcatgtctac cctgttcctg 3420
gtgtacagca acaagtgcca gacccccctg ggcatggcct ctggccacat cagagatttt 3480
cagatcactg cctctggcca gtatggccag tgggctccta agctggccag gctgcactac 3540
tctggcagca tcaatgcctg gagcaccaag gagcccttta gctggatcaa ggtggacctg 3600
ctggccccca tgatcatcca tggcatcaag actcaggggg ccaggcagaa gttctctagc 3660
ctgtacatta gccagttcat catcatgtat agcctggatg gcaagaagtg gcagacctac 3720
aggggcaaca gcactgggac cctgatggtg ttctttggga atgtggacag ctctgggatc 3780
aagcacaata tcttcaaccc ccccattatt gccaggtata ttaggctgca ccccactcac 3840
tacagcatta ggagcaccct gaggatggag ctgatgggct gtgatctgaa cagctgcagc 3900
atgcccctgg gcatggagtc taaggccatc tctgatgccc agatcactgc cagctcttac 3960
ttcaccaaca tgtttgccac ttggagcccc agcaaggcca ggctgcacct gcagggcagg 4020
agcaatgcct ggaggcccca ggtgaacaac cccaaggagt ggctgcaggt ggatttccag 4080
aagactatga aggtgactgg ggtgaccact caggggggtga agagcctgct gactagcatg 4140
tatgtgaagg agttcctgat cagctctagc caggatggcc accagtggac cctgttcttt 4200
cagaatggca aggtgaaggt gttccagggc aaccaggact ctttcacccc tgtggtgaat 4260
tctctggacc ctcccctgct gactaggtat ctgaggattc atccccagag ctgggtgcat 4320
cagattgccc tgaggatgga ggtgctgggc tgtgaggccc aggacctgta ttga 4374

<210> SEQ ID NO 84
<211> LENGTH: 4374
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 84
atgcagattg agctgagcac ctgcttcttc ctgtgcctgc tgaggttttg cttttctgcc 60
actaggaggt actacctggg ggctgtggag ctgtcttggg attacatgca gtctgacctg 120
ggggagctgc cagtggatgc caggttcccc ccaagggtgc ccaagtcttt tcccttcaat 180
acctctgtgg tgtacaagaa gaccctgttt gtggagttta ctgatcatct gtttaacatt 240
gccaagccca ggccccccctg gatggggctg ctgggcccca ccatccaggc tgaggtgtat 300
gatactgtgg tgattaccct gaagaatatg gccagccatc ctgtgtctct gcatgctgtg 360
ggggtgtctt attggaaggc ctctgagggg gctgagtatg atgatcagac cagccagagg 420
gagaaggagg atgataaggt gttccctggg ggctctcaca cctatgtgtg gcaggtgctg 480
aaggagaatg ggcctatggc ctctgaccca ctgtgcctga cttacagcta tctgagccat 540
gtggacctgg tgaaggacct gaactctggg ctgattgggg ccctgctggt gtgcagggag 600
ggcagcctgg ccaaggagaa gactcagacc ctgcacaagt tcatcctgct gtttgctgtg 660
tttgatgagg gcaagtcttg gcactctgag accaagaaca gcctgatgca ggatagggat 720
gctgcctctg ccagggcctg gcccaagatg cacactgtga atggctatgt gaacaggtct 780
ctgcctggcc tgattggctg ccacaggaag tctgtgtact ggcatgtgat tggcatgggc 840
accacccctg aggtgcatag cattttcctg gagggccaca ccttcctggt gaggaaccac 900
aggcaggcta gcctggagat cagccccatc actttcctga ctgcccagac cctgctgatg 960
gacctgggcc agttcctgct gttctgccac atctctagcc accagcatga tggcatggag 1020
gcctatgtga aggtggactc ttgtcctgag gagccccagc tgaggatgaa gaacaatgag 1080
gaggctgagg attatgatga tgatctgact gattctgaga tggatgtggt gaggtttgat 1140
gatgacaaca gcccctcttt catccagatc aggtctgtgg ccaagaagca ccccaagacc 1200
tgggtgcact acattgctgc tgaggaggag gattgggatt atgccccccct ggtgctggcc 1260

-continued

```
cctgatgaca ggagctataa gtctcagtac ctgaacaatg gcccccagag aattggcagg   1320
aagtacaaga aggtgaggtt catggcctat actgatgaga ccttcaaaac cagggaggcc   1380
attcagcatg agtctggcat cctggggccc ctgctgtatg gggaggtggg ggacaccctg   1440
ctgatcatct tcaagaacca ggctagcagg ccttacaaca tctacccccca tgggatcact   1500
gatgtgaggc ccctgtacag caggaggctg cctaaggggg tgaagcacct gaaggacttt   1560
cccattctgc ctggggagat cttcaagtat aagtggactg tgactgtgga ggatgggccc   1620
accaagtctg accccaggtg cctgactagg tactactcta gctttgtgaa catggagagg   1680
gacctggcct ctgggctgat tggcccccctg ctgatctgtt acaaggagtc tgtggaccag   1740
aggggcaacc agatcatgtc tgataagagg aatgtgatcc tgttctctgt gtttgatgag   1800
aacaggagct ggtacctgac tgagaacatc cagagattcc tgcccaaccc tgctggggtg   1860
cagctggagg atcctgagtt ccaggccagc aacatcatgc attctatcaa tgggtatgtg   1920
tttgatagcc tgcagctgtc tgtgtgtctg catgaggtgg cctactggta cattctgagc   1980
attggggccc agactgactt cctgtctgtg ttcttctctg gctacacttt caaacacaag   2040
atggtgtatg aggacaccct gaccctgttc cccttctctg ggagactgt gtttatgagc   2100
atggagaacc ctgggctgtg gattctgggc tgccacaact ctgacttcag aaacaggggc   2160
atgactgccc tgctgaaggt gtcttcttgt gataagaaca ctggggacta ttatgaagac   2220
agctatgagg acatctctgc ctacctgctg agcaagaata atgctattga gcccaggtct   2280
ttctctcaga acccccctgt gctgaagagg caccagaggg agatcaccag gaccaccctg   2340
cagtctgatc aggaggagat tgactatgat gacactattt ctgtggagat gaagaaggaa   2400
gactttgata tctatgatga ggatgagaac cagagcccta ggagcttcca gaagaagact   2460
aggcattact tcattgctgc tgtggagagg ctgtgggact atggcatgag cagcagcccc   2520
catgtgctga ggaatagggc tcagtctggc tctgtgcctc agttcaagaa ggtggtgttc   2580
caggaattca ctgatggcag cttcactcag cccctgtaca ggggggagct gaatgagcac   2640
ctggggctgc tgggccctta catcagggct gaggtggagg acaatatcat ggtgaccttt   2700
aggaaccagg cctctaggcc ttacagcttc tactctagcc tgatctctta tgaagaggac   2760
cagaggcagg gggctgagcc caggaagaac tttgtgaagc ccaatgagac taagacttac   2820
ttctggaagg tgcagcacca catggctccc accaaggatg agtttgactg caaggcttgg   2880
gcctacttct ctgatgtgga cctggagaag gatgtgcact ctgggctgat tgggcccctg   2940
ctggtgtgcc acactaacac tctgaatcct gcccatggca gacaggtgac tgtgcaggag   3000
tttgccctgt tttttaccat ctttgatgag actaagtctt ggtacttcac tgagaacatg   3060
gagaggaact gcagggcccc ctgcaacatc cagatggagg atcccacctt caaggagaac   3120
tacaggtttc atgccatcaa tggctacatc atggacaccc tgcctggcct ggtgatggct   3180
caggaccaga ggattaggtg gtatctgctg agcatgggca gcaatgagaa tatccactct   3240
atccacttct ctgggcatgt gttcactgtg aggaagaagg aggagtacaa gatggccctg   3300
tataacctgt atcctggggt gtttgagact gtggagatgc tgcccagcaa ggctggcatc   3360
tggagagtgg agtgcctgat tggggagcac ctgcatgctg gcatgagcac tctgtttctg   3420
gtgtatagca acaagtgtca gacccctctg ggcatggcct ctgggcacat tagggacttt   3480
cagatcactg cttctggcca gtatgggcag tgggctccca agctggccag gctgcactat   3540
tctggcagca ttaatgcctg gagcaccaag gagcctttca gctggatcaa ggtggacctg   3600
```

```
ctggccccca tgatcatcca tgggatcaag acccaggggg ctaggcagaa gttcagcagc   3660

ctgtacatca gccagtttat catcatgtat tctctggatg gcaagaagtg gcagacctac   3720

aggggcaatt ctactggcac tctgatggtg ttctttggga atgtggatag ctctgggatc   3780

aagcataata tcttcaatcc ccccattatt gctaggtata tcaggctgca ccccacccac   3840

tatagcatca ggagcaccct gaggatggag ctgatggggt gtgacctgaa cagctgcagc   3900

atgcccctgg gcatggagag caaggctatt tctgatgccc agatcactgc cagcagctac   3960

tttactaata tgtttgccac ctggagcccc agcaaggcca gactgcacct gcagggcagg   4020

tctaatgcct ggaggcctca ggtgaataac cccaaggagt ggctgcaggt ggacttccag   4080

aaaaccatga aggtgactgg ggtgactacc caggggtga agtctctgct gaccagcatg   4140

tatgtgaagg agttcctgat ctcttctagc caggatggcc accagtggac cctgttcttt   4200

cagaatggga aggtgaaggt cttccagggc aaccaggata gcttcacccc tgtggtgaat   4260

agcctggatc ctcctctgct gaccaggtat ctgaggatcc acccccagag ctgggtgcat   4320

cagattgccc tgaggatgga ggtgctgggc tgtgaggctc aggacctgta ctga         4374
```

<210> SEQ ID NO 85
<211> LENGTH: 4374
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 85

```
atgcagattg agctgagcac ctgtttcttc ctgtgcctgc tgaggttctg tttctctgcc     60

actaggaggt actacctggg ggctgtggag ctgagctggg actatatgca gtctgacctg    120

ggggagctgc ctgtggatgc caggttcccc cccagggtgc ctaagagctt ccccttcaat    180

acttctgtgg tgtacaagaa gactctgttt gtggagttta ctgaccacct gttcaacatt    240

gctaagccca ggcctccctg gatggggctg ctgggcccca ccatccaggc tgaggtgtat    300

gatactgtgg tgattaccct gaagaacatg gcctctcatc cagtgagcct gcatgctgtg    360

ggggtgagct actggaaggc ctctgaaggg gctgagtatg atgaccagac cagccagagg    420

gagaaggagg atgacaaggt gttccctggg ggcagccaca cctatgtgtg gcaggtgctg    480

aaggagaatg gcccaatggc ctctgacccc ctgtgcctga cttatagcta cctgagccat    540

gtggatctgg tgaaggacct gaattctggc ctgattgggg ccctgctggt gtgcagagag    600

ggctctctgg ctaaggagaa gacccagact ctgcacaagt tcatcctgct gtttgctgtg    660

tttgatgagg gcaagagctg gcactctgag actaagaata gcctgatgca ggacagggat    720

gctgcttctg ccagggcctg gcccaagatg catactgtga atggctatgt gaacaggagc    780

ctgcctggcc tgattggctg tcacaggaaa tctgtctact ggcatgtgat tgggatgggc    840

actacccctg aggtgcactc tatcttcctg gagggccata ccttcctggt gaggaaccac    900

aggcaggcca gcctggagat ctctcccatt accttcctga ctgcccagac cctgctgatg    960

gatctgggcc agttcctgct gttctgccac atcagcagcc accagcatga tgggatggag   1020

gcttatgtga aggtggatag ctgccctgag gagccccagc tgaggatgaa gaacaatgag   1080

gaggctgagg actatgatga tgacctgact gactctgaga tggatgtggt gaggtttgat   1140

gatgacaact ctcccagctt tattcagatc aggtctgtgg ctaagaagca ccccaagact   1200

tgggtgcact acattgctgc tgaggaggag gactgggact atgcccctct ggtgctggct   1260
```

-continued

```
cctgatgaca ggtcttacaa gtctcagtac ctgaataatg gccctcagag gattggcagg   1320
aagtacaaga aggtgaggtt catggcctac actgatgaga ccttcaagac cagggaggcc   1380
atccagcatg agtctggcat cctgggcccc ctgctgtatg gggaggtggg ggataccctg   1440
ctgatcatct tcaagaatca ggccagcagg ccctacaaca tctacccccca tggcatcact   1500
gatgtgaggc cactgtacag caggaggctg cccaaggggg tgaagcatct gaaggacttc   1560
cccattctgc ctggggagat cttcaagtac aaatggactg tgactgtgga ggatggccct   1620
accaagtctg accccaggtg tctgaccagg tactacagca gctttgtgaa tatggagagg   1680
gacctggcct ctggcctgat tggcccccctg ctgatctgct acaaggagtc tgtggaccag   1740
aggggcaatc agatcatgtc tgataagagg aatgtgattc tgttctctgt gtttgatgag   1800
aacaggagct ggtacctgac tgagaacatc cagaggttcc tgcccaatcc tgctggggtg   1860
cagctggagg accctgagtt ccaggccagc aatatcatgc acagcatcaa tggctatgtc   1920
tttgacagcc tgcagctgtc tgtgtgcctg catgaggtgg cttactggta tattctgagc   1980
attggggccc agactgattt cctgtctgtg ttcttttctg gctatacctt taagcacaag   2040
atggtgtatg aggacaccct gaccctgttc cccttctctg ggagactgt gttcatgtct   2100
atggagaacc ctgggctgtg gatcctgggc tgccacaact ctgacttcag gaacaggggg   2160
atgactgccc tgctgaaggt gtctagctgt gataagaaca ctggggacta ttatgaggac   2220
agctatgagg acatctctgc ttacctgctg agcaagaaca atgccattga gcccaggtct   2280
ttcagccaga atccccctgt gctgaagagg catcagaggg agatcaccag gaccaccctg   2340
cagtctgatc aggaggagat tgattatgat gacactatct ctgtggaaat gaagaaggag   2400
gactttgaca tctatgatga ggatgagaac cagagcccca ggagcttcca gaagaagacc   2460
aggcactact tcattgctgc tgtggagagg ctgtgggatt atggcatgag cagctctccc   2520
catgtgctga ggaacagagc ccagtctggc tctgtgcctc agttcaagaa ggtggtcttc   2580
caggagttca ctgatggctc tttcacccag cccctgtaca gggggggagct gaatgagcac   2640
ctgggcctgc tggggcccta cattagggct gaggtggagg ataacatcat ggtgactttc   2700
agaaaccagg ccagcaggcc ttacagcttt tactcttctc tgattagcta tgaggaggat   2760
cagaggcagg gggctgagcc taggaagaac tttgtgaagc ccaatgagac caagacctat   2820
ttctggaagg tgcagcacca catggctccc actaaggatg agtttgactg caaggcttgg   2880
gcctacttct ctgatgtgga cctggagaag gatgtgcact ctggcctgat tgggcccctg   2940
ctggtgtgcc acaccaacac cctgaaccct gcccatggca ggcaggtgac tgtgcaggag   3000
tttgccctgt tcttcaccat ctttgatgag actaagagct ggtacttcac tgagaacatg   3060
gagaggaact gcagggcccc ctgcaacatc cagatggagg accccacctt caaggagaat   3120
tacaggttcc atgccatcaa tggctacatt atggacaccc tgcctggcct ggtgatggcc   3180
caggatcaga ggatcaggtg gtatctgctg agcatgggct ctaatgagaa catccacagc   3240
atccacttct ctggccatgt gtttactgtg aggaagaagg aggaatacaa gatggctctg   3300
tataacctgt accctggggt gtttgagact gtggagatgc tgcccagcaa ggctgggatc   3360
tggagggtgg agtgcctgat tggggagcac ctgcatgctg ggatgagcac cctgttcctg   3420
gtgtatagca ataagtgcca gacccccctg ggcatggctt ctggccacat cagggatttc   3480
cagatcactg cttctggcca gtatggccag tgggctccca agctggctag gctgcattac   3540
tctgggtcta tcaatgcctg gagcactaag gagcccttca gctggatcaa ggtggacctg   3600
ctggccccca tgatcattca tggcatcaag acccaggggg ctaggcagaa gttcagcagc   3660
```

ctgtacatca gccagttcat cattatgtac agcctggatg gcaagaagtg gcagacttac 3720
aggggcaata gcactgggac tctgatggtg ttctttggca atgtggactc ttctggcatc 3780
aagcacaaca tcttcaaccc tcccatcatt gccaggtaca ttaggctgca ccctacccac 3840
tactctatca ggagcaccct gaggatggag ctgatggggt gtgatctgaa ctcttgcagc 3900
atgcctctgg gcatggaaag caaagccatc tctgatgccc agatcactgc ctctagctat 3960
ttcaccaata tgtttgccac ctggagccct agcaaggcca ggctgcacct gcagggcaga 4020
tctaatgcct ggaggcccca ggtgaacaat cccaaggagt ggctgcaggt ggacttccag 4080
aagaccatga aggtgactgg ggtgaccact caggggggtga agagcctgct gactagcatg 4140
tatgtgaagg agttcctgat ctcttctagc caggatggcc accagtggac cctgttcttc 4200
cagaatggca aggtgaaagt gttccagggc aaccaggata gcttcactcc tgtggtgaac 4260
tctctggacc ctcccctgct gactaggtac ctgaggattc atccccagag ctgggtgcac 4320
cagattgccc tgaggatgga ggtgctgggc tgtgaggccc aggatctgta ctga 4374

<210> SEQ ID NO 86
<211> LENGTH: 4374
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 86
atgcagattg agctgagcac ctgcttcttc ctgtgcctgc tgaggttctg cttctctgcc 60
accaggaggt actacctggg ggctgtggag ctgtcttggg actatatgca gtctgacctg 120
ggggagctgc cagtggatgc caggttcccc cccagggtgc ccaagagctt tcctttcaac 180
acttctgtgg tgtacaagaa gaccctgttt gtggagttca ctgaccacct gttcaatatt 240
gctaagccca ggccaccctg gatgggcctg ctgggcccta ccattcaggc tgaggtgtat 300
gacactgtgg tgattactct gaagaatatg gccagccacc ctgtgagcct gcatgctgtg 360
ggggtgtctt actggaaggc ctctgagggg gctgagtatg atgatcagac ttctcagagg 420
gagaaggagg atgataaggt gttccctggg ggctctcaca cttatgtgtg gcaggtgctg 480
aaggagaatg gccccatggc ttctgatcca ctgtgcctga cctactctta cctgagccat 540
gtggacctgg tgaaggacct gaactctggc ctgattgggg ccctgctggt gtgcagggag 600
ggcagcctgg ccaaggagaa gacccagacc ctgcataagt tcatcctgct gtttgctgtg 660
tttgatgagg ggaagagctg gcactctgag accaagaatt ctctgatgca ggacagggat 720
gctgcctctg ccagggcctg gcctaagatg cacactgtga atggctatgt gaacaggtct 780
ctgcctggcc tgattggctg ccacaggaag tctgtgtact ggcatgtgat tggcatgggc 840
actacccctg aggtgcacag cattttcctg gagggccaca ccttcctggt caggaaccat 900
aggcaggcct ctctggagat cagccccatc actttcctga ctgcccagac cctgctgatg 960
gacctgggcc agttcctgct gttctgccac attagcagcc accagcatga tggcatggag 1020
gcctatgtga aggtggactc ttgccctgag gagccccagc tgaggatgaa gaacaatgag 1080
gaagctgagg attatgatga tgacctgact gactctgaga tggatgtggt gaggtttgat 1140
gatgacaaca gccccagctt catccagatc aggtctgtgg ccaagaagca ccccaagacc 1200
tgggtgcact acattgctgc tgaggaggag gattgggact atgctcccct ggtgctggct 1260
cctgatgata ggagctacaa gtctcagtac ctgaataatg gcccccagag gattggcagg 1320

-continued

```
aagtacaaga aggtgaggtt catggcctac actgatgaga ccttcaagac cagagaggct   1380
atccagcatg agtctgggat cctggggccc ctgctgtatg ggaggtgggg ggacaccctg   1440
ctgatcatct tcaagaacca ggccagcaga ccctacaaca tctacccccca tgggatcact   1500
gatgtgaggc ccctgtacag caggaggctg cctaaggggg tgaagcacct gaaggacttc   1560
cccatcctgc ctggggagat cttcaagtat aagtggactg tgactgtgga ggatgggccc   1620
accaagtctg accctaggtg cctgactagg tactactcta gctttgtgaa catggagagg   1680
gacctggcct ctggcctgat tggcccccctg ctgatttgct acaaggagtc tgtggatcag   1740
aggggcaatc agatcatgtc tgacaagagg aatgtgatcc tgttctctgt gtttgatgag   1800
aataggtctt ggtacctgac tgagaacatc cagaggttcc tgcctaatcc tgctggggtg   1860
cagctggagg accctgagtt tcaggccagc aacatcatgc acagcatcaa tggctatgtg   1920
tttgactctc tgcagctgtc tgtgtgcctg catgaggtgg cttactggta tatcctgagc   1980
attggggctc agactgactt cctgtctgtg ttcttttctg gctacacttt taagcacaag   2040
atggtgtatg aggacaccct gaccctgttc cccttttctg gggagactgt gttcatgtct   2100
atggagaacc ctgggctgtg gattctgggc tgtcacaact ctgacttcag aaacaggggc   2160
atgactgccc tgctgaaggt gtctagctgt gacaagaata ctggggacta ctatgaggac   2220
agctatgagg acatttctgc ctatctgctg agcaagaaca atgccattga gcccaggagc   2280
ttttctcaga atccccctgt gctgaagagg caccagagag agatcaccag gaccactctg   2340
cagtctgatc aggaggagat tgattatgat gacactatct ctgtggagat gaagaaagag   2400
gactttgata tctatgatga ggatgagaat cagtctccca ggagcttcca gaagaagact   2460
agacactact tcattgctgc tgtggagagg ctgtgggact atggcatgag ctctagccct   2520
catgtgctga ggaacagggc ccagtctggg tctgtgcccc agttcaagaa ggtggtgttc   2580
caggagttca ctgatggcag ctttacccag cccctgtata ggggggagct gaatgagcat   2640
ctgggcctgc tgggccccta tattagggct gaagtggagg acaacatcat ggtgaccttt   2700
aggaaccagg ccagcaggcc ctacagcttt tacagcagcc tgattagcta tgaggaggat   2760
cagagacagg ggctgagccc caggaagaac tttgtgaagc ccaatgagac caagacctac   2820
ttctggaagg tgcagcacca catggcccct accaaggatg agtttgactg caaggcctgg   2880
gcttacttct ctgatgtgga cctggagaaa gatgtgcact ctggcctgat tgggcccctg   2940
ctggtgtgcc acaccaacac cctgaaccct gcccatggga ggcaggtgac tgtgcaggag   3000
tttgccctgt tttcaccat ctttgatgag accaagagct ggtacttcac tgagaacatg   3060
gagaggaact gcagggcccc ctgtaacatc cagatggagg atcctacttt caaggagaac   3120
tacaggttcc atgccattaa tgggtacatc atggacaccc tgcctgggct ggtgatggcc   3180
caggatcaga ggattaggtg gtatctgctg tctatgggct ctaatgagaa catccactct   3240
atccacttct ctggccatgt gttcactgtg aggaagaagg aggagtacaa gatggccctg   3300
tacaacctgt accctggggt gtttgaaact gtggagatgc tgccctctaa agctgggatc   3360
tggagggtgg agtgcctgat tggggagcac ctgcatgctg gcatgagcac cctgttcctg   3420
gtgtacagca ataagtgcca gactcccctg ggcatggctt ctgggcacat cagggatttc   3480
cagatcactg cctctggcca gtatggccag tgggccccca agctggctag gctgcactac   3540
tctggcagca tcaatgcctg gagcaccaag gagcccttct cttggattaa ggtggacctg   3600
ctggctccca tgatcattca tggcatcaag acccaggggg ccaggcagaa gttttctagc   3660
```

ctgtatatta gccagttcat catcatgtat agcctggatg ggaagaagtg gcagacctac 3720 aggggggaata gcactggcac cctgatggtg ttttttggca atgtggattc ttctggcatc 3780
aagcataaca tcttcaatcc ccctatcatt gccaggtaca ttaggctgca tcccacccat 3840
tactctatca ggagcaccct gaggatggag ctgatggggt gtgatctgaa cagctgtagc 3900
atgcccctgg gcatggagtc caaggctatc tctgatgccc agatcactgc cagcagctac 3960
ttcaccaaca tgtttgccac ctggagcccc agcaaggcca ggctgcacct gcagggcagg 4020
tctaatgcct ggaggcccca ggtgaacaat cccaaggagt ggctgcaggt ggacttccag 4080
aagactatga aggtgactgg ggtgaccact cagggggtga agagcctgct gaccagcatg 4140
tatgtgaagg agttcctgat ctcttctagc caggatgggc atcagtggac cctgtttttt 4200
cagaatggca aagtgaaggt gtttcagggg aatcaggaca gctttacccc tgtggtgaac 4260
agcctggatc ctcctctgct gactagatac ctgaggatcc acccccagag ctgggtccac 4320
cagattgctc tgaggatgga ggtgctgggg tgtgaggctc aggacctgta ctga 4374

<210> SEQ ID NO 87
<211> LENGTH: 4374
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 87
atgcagattg agctgagcac ctgcttcttt ctgtgcctgc tgaggttctg cttctctgcc 60
accaggaggt actacctggg ggctgtggaa ctgagctggg actatatgca gtctgacctg 120
ggggagctgc ctgtggatgc caggttcccc cccagggtgc ccaagtcttt cccctttaac 180
acttctgtgg tgtacaagaa gaccctgttt gtggagttta ctgaccacct gttcaatatt 240
gccaagccca ggcccccctg gatgggcctg ctgggcccaa ccatccaggc tgaggtgtat 300
gatactgtgg tgatcaccct gaagaacatg gccagccacc ctgtgagcct gcatgctgtg 360
ggggtgagct attggaaggc ttctgagggg gctgagtatg atgaccagac tagccagagg 420
gagaaggagg atgacaaggt gttccctggg ggtctcata cctatgtgtg gcaggtgctg 480
aaggagaatg gccccatggc ctctgacccc ctgtgcctga cctattctta cctgagccat 540
gtggacctgg tcaaggacct gaactctggc ctgattgggg ctctgctggt gtgcagggag 600
ggcagcctgg ccaaggagaa gactcagact ctgcataagt tcatcctgct gtttgctgtg 660
tttgatgagg gcaagagctg gcactctgag accaagaact ctctgatgca ggatagggat 720
gctgcctctg ccagggcctg gcccaagatg cacactgtga atggctatgt gaataggtct 780
ctgcctggcc tgattggctg ccataggaag tctgtgtact ggcatgtgat tggcatgggc 840
actacccctg aggtgcactc tatcttcctg gaggggcaca ccttcctggt gaggaaccac 900
aggcaggcca gcctggagat ctctcccatc accttcctga ctgcccagac tctgctgatg 960
gacctgggcc agttcctgct gttctgccat atcagcagcc accagcatga tggcatggag 1020
gcctatgtga aggtggacag ctgcccagag gaaccccagc tgaggatgaa gaacaatgag 1080
gaggctgagg actatgatga tgacctgact gactctgaga tggatgtggt gaggtttgat 1140
gatgacaaca gccccagctt tattcagatc aggtctgtgg ccaagaagca ccccaagacc 1200
tgggtgcact acattgctgc tgaggaggag gactgggatt atgcccccct ggtgctggcc 1260
cctgatgaca ggtcttacaa gtctcagtac ctgaacaatg gcccccagag gattgggagg 1320

-continued aagtacaaga aggtgaggtt catggcctac actgatgaga ccttcaagac cagggaggcc 1380
atccagcatg agtctggcat cctggggccc ctgctgtatg gggaggtggg ggataccctg 1440
ctgattatct tcaagaacca ggctagcagg ccctataaca tctaccccca tggcattact 1500
gatgtgaggc ccctgtactc taggagactg cccaaggggg tgaagcacct gaaagacttc 1560
cccatcctgc ctggggagat cttcaagtat aagtggactg tgactgtgga ggatggcccc 1620
actaagtctg accccaggtg cctgaccagg tattacagca gctttgtgaa tatggagagg 1680
gatctggctt ctggcctgat tgggcctctg ctgatttgct acaaggagtc tgtggatcag 1740
agggggaacc agattatgtc tgacaagagg aatgtgattc tgttctctgt gtttgatgag 1800
aacaggagct ggtacctgac tgagaatatc cagaggttcc tgcctaatcc tgctggggtg 1860
cagctggagg accctgagtt ccaggctagc aacattatgc acagcatcaa tggctatgtg 1920
tttgacagcc tgcagctgtc tgtgtgcctg catgaggtgg cttactggta cattctgtct 1980
attggggccc agactgactt cctgtctgtg ttcttctctg gctacacctt caagcacaag 2040
atggtgtatg aggacactct gaccctgttc cccttctctg gggagactgt gttcatgagc 2100
atggagaatc ctgggctgtg gattctgggg tgccacaact ctgatttcag gaacaggggc 2160
atgactgccc tgctgaaggt gagcagctgt gacaagaaca ctggggatta ttatgaggac 2220
agctatgagg acatttctgc ctacctgctg agcaagaaca atgccattga gcctaggagc 2280
ttcagccaga atcccccctgt gctgaagaga caccagaggg agatcactag gaccactctg 2340
cagtctgatc aggaggagat tgactatgat gacaccattt ctgtggagat gaagaaggag 2400
gactttgata tttatgatga ggatgagaac cagagcccca gaagcttcca gaagaagacc 2460
aggcactact tcattgctgc tgtggagagg ctgtgggatt atggcatgtc ttctagcccc 2520
catgtgctga ggaacagggc tcagtctggc tctgtgcctc agttcaagaa ggtggtgttc 2580
caggagttca ctgatgggag cttcacccag cctctgtaca ggggggagct gaatgaacat 2640
ctgggcctgc tggggcccta catcagggct gaggtggagg ataatatcat ggtgactttc 2700
aggaatcagg cctctaggcc ctacagcttc tactctagcc tgatcagcta tgaggaggac 2760
cagaggcagg gggctgagcc taggaagaat tttgtgaaac ccaatgagac caagacctac 2820
ttttggaagg tgcagcacca catggcccct accaaggatg agtttgactg taaggcctgg 2880
gcctacttct ctgatgtgga cctggagaag gatgtgcatt ctgggctgat tggcccccctg 2940
ctggtgtgcc acaccaacac cctgaaccct gcccatggca ggcaggtgac tgtgcaggag 3000
tttgccctgt tcttcaccat ctttgatgag actaagagct ggtatttcac tgagaacatg 3060
gagaggaact gtagggctcc ctgcaacatc cagatggagg atccaacttt caaggagaac 3120
tacaggttcc atgccatcaa tggctacatc atggacaccc tgcctggcct ggtgatggcc 3180
caggaccaga ggattaggtg gtacctgctg agcatgggct ctaatgagaa catccactct 3240
atccacttct ctggccatgt gtttactgtg aggaagaagg aggagtacaa gatggctctg 3300
tacaacctgt accctggggt gtttgagact gtggagatgc tgcctagcaa ggctggcatt 3360
tggagagtgg agtgtctgat tggggagcac ctgcatgctg ggatgtctac cctgttcctg 3420
gtgtactcta acaagtgcca gacccccctg gggatggctt ctgggcacat cagagatttt 3480
cagattactg cttctgggca gtatggccag tgggctccca agctggccag actgcattac 3540
tctggctcta ttaatgcttg gagcaccaag gagcctttca gctggatcaa ggtggacctg 3600
ctggctccca tgatcatcca tggcattaag actcaggggg ctaggcagaa gttcagcagc 3660
ctgtatattt ctcagtttat tatcatgtat tctctggatg gcaagaagtg gcagacttac 3720
aggggcaaca gcactggcac cctgatggtg ttctttggca atgtggacag ctctgggatc 3780
aagcataaca tcttcaaccc ccccattatt gccaggtaca tcaggctgca ccccacccac 3840
tattctatca ggagcactct gaggatggag ctgatggggt gtgacctgaa cagctgctct 3900
atgcccctgg gcatggagag caaggccatc tctgatgccc agatcactgc cagctcttat 3960
ttcaccaaca tgtttgccac ctggagcccc agcaaggcca ggctgcacct gcagggcaga 4020
agcaatgcct ggaggcccca ggtgaacaat cctaaggagt ggctgcaggt ggacttccag 4080
aagactatga aggtgactgg ggtgactacc cagggggtga agagcctgct gaccagcatg 4140
tatgtgaagg agttcctgat tagcagcagc caggatgggc atcagtggac cctgttcttc 4200
cagaatggga aggtgaaggt gttccagggc aatcaggaca gcttcacccc tgtggtgaac 4260
agcctggacc ccccccctgct gaccaggtac ctgaggatcc atccccagag ctgggtgcac 4320
cagattgctc tgagaatgga ggtgctgggc tgtgaggccc aggacctgta ttga 4374

<210> SEQ ID NO 88
<211> LENGTH: 4374
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 88
atgcagattg agctgtctac ctgttttttt ctgtgcctgc tgaggttctg cttctctgct 60
accaggaggt attatctggg ggctgtggag ctgagctggg actacatgca gtctgacctg 120
ggggagctgc ctgtggatgc caggtttcct cccagggtgc ctaagagctt ccccttcaac 180
acctctgtgg tgtacaagaa gactctgttt gtggagttca ctgaccacct gttcaacatt 240
gccaagccca ggccccccctg gatggggctg ctgggcccca ctatccaggc tgaggtgtat 300
gatactgtgg tgattaccct gaagaacatg gcctctcacc ctgtgtctct gcatgctgtg 360
ggggtgagct actggaaggc ttctgagggg gctgaatatg atgatcagac ctctcagagg 420
gagaaggagg atgacaaggt gtttcctggg ggcagccaca cctatgtgtg gcaggtgctg 480
aaggagaatg ggcccatggc ctctgatccc ctgtgcctga cctacagcta cctgagccat 540
gtggacctgg tgaaggacct gaactctggc ctgattgggg ccctgctggt gtgcagggag 600
ggcagcctgg ccaaggaaaa gacccagacc ctgcataagt tcatcctgct gtttgctgtg 660
tttgatgagg gcaagtcttg gcactctgag accaagaaca gcctgatgca ggacagggat 720
gctgcctctg ctagggcctg gcccaagatg cacactgtga atgggtatgt gaacagatct 780
ctgcctggcc tgattggctg ccacaggaag tctgtgtact ggcatgtgat tggcatgggg 840
accacccctg aggtgcatag catcttcctg gaggggcaca ccttcctggt gagaaatcat 900
aggcaggcca gcctggagat tagccccatc accttcctga ctgcccagac cctgctgatg 960
gacctgggcc agttcctgct gttctgccac atttctagcc accagcatga tggcatggag 1020
gcctatgtga aggtggatag ctgccctgaa gagccccagc tgaggatgaa gaacaatgag 1080
gaggctgagg attatgatga tgatctgact gactctgaga tggatgtggt gaggtttgat 1140
gatgacaaca gccccagctt catccagatc aggtctgtgg ccaagaagca ccctaagacc 1200
tgggtgcact acattgctgc tgaagaggag gactgggact atgccccccct ggtgctggcc 1260 ccagatgaca ggtcttacaa gagccagtac ctgaataatg gcccccagag gattgggagg 1320
aagtataaga aagtgaggtt catggcttac actgatgaga cctttaagac tagggaggcc 1380
attcagcatg agtctgggat tctgggccct ctgctgtatg gggaggtggg ggacaccctg 1440
ctgatcattt tcaagaacca ggccagcagg ccctataata tttatcccca tgggattact 1500
gatgtcaggc ccctgtacag caggaggctg cctaaggggg tgaagcacct gaaggacttc 1560
cccattctgc ctggggagat cttcaagtat aagtggactg tgactgtgga ggatggcccc 1620
accaagtctg atcctaggtg cctgaccagg tactatagca gctttgtgaa catggagagg 1680
gacctggctt ctggcctgat tggccccctg ctgatctgct acaaggaatc tgtggaccag 1740
aggggcaacc agattatgtc tgacaagagg aatgtgatcc tgttttctgt gtttgatgag 1800
aataggagct ggtatctgac tgagaacatc cagaggttcc tgcccaatcc tgctggggtg 1860
cagctggagg accctgagtt ccaggcttct aacatcatgc atagcatcaa tgggtatgtg 1920
tttgactctc tgcagctgtc tgtgtgcctg catgaggtgg cctattggta catcctgagc 1980
attggggccc agactgactt cctgtctgtg ttcttctctg gctacacctt caagcacaag 2040
atggtgtatg aggacaccct gaccctgttc cctttctctg ggagactgt gttcatgagc 2100 atggagaacc ctggcctgtg gattctgggc tgccataatt ctgacttcag aaacaggggc 2160
atgactgctc tgctgaaggt gagcagctgt gacaagaata ctggggacta ctatgaggac 2220
tcttatgagg atatttctgc ctacctgctg agcaagaaca atgctattga gcccaggagc 2280
ttcagccaga accccctgt cctgaagagg catcagaggg agatcactag gaccaccctg 2340
cagtctgatc aggaggagat tgactatgat gacactatct ctgtggaaat gaagaaggag 2400
gactttgata tctatgatga ggatgagaac cagagcccca ggtctttcca gaagaagacc 2460
aggcactact tcattgctgc tgtggagagg ctgtgggact atggcatgtc tagcagcccc 2520
catgtgctga ggaacagagc ccagtctggc tctgtgcccc agttcaagaa ggtggtgttt 2580
caggagttca ctgatgggag cttcactcag cccctgtata ggggggagct gaatgagcat 2640
ctgggcctgc tggggcccta catcagggct gaggtggagg ataacatcat ggtgaccttc 2700
aggaaccagg ccagcaggcc ctactctttc tactcttctc tgatcagcta tgaggaggat 2760
cagaggcagg gggctgagcc taggaagaac tttgtcaagc ctaatgagac taagacctac 2820
ttttggaagg tgcagcacca catggctccc actaaggatg agtttgattg caaggcctgg 2880
gcctacttct ctgatgtgga cctggagaag gatgtgcact ctggcctgat tggccccctg 2940
ctggtgtgtc acaccaatac cctgaaccct gcccatggca ggcaggtcac tgtgcaggag 3000
tttgccctgt tttcactat ctttgatgag actaagtctt ggtacttcac tgagaacatg 3060
gaaaggaatt gcagggctcc ctgcaacatc cagatggagg accccacctt caaggagaac 3120
tacaggtttc atgccatcaa tggctacatc atggacaccc tgcctggcct ggtgatggct 3180
caggatcaga ggattaggtg gtatctgctg agcatgggca gcaatgagaa catccacagc 3240
atccactttt ctggccatgt gttcactgtg aggaagaagg aggagtacaa gatggctctg 3300
tacaatctgt accctggggt gtttgagact gtggagatgc tgcccagcaa ggctgggatc 3360
tggagggtgg agtgcctgat tggggaacac ctgcatgctg gcatgtctac cctgttcctg 3420
gtgtactcta acaagtgcca gactcccctg ggcatggcct ctgggcacat cagggacttc 3480
cagatcactg cctctgggca gtatggccag tgggccccta agctggctag gctgcattac 3540
tctggcagca tcaatgcctg gagcaccaag gagcccttca gctggatcaa ggtggacctg 3600
ctggccccta tgatcatcca tggcatcaag acccaggggg ccagacagaa gttctcttct 3660
ctgtacatct ctcagttcat catcatgtac tctctggatg gcaagaagtg gcagacctac 3720
agggggaatt ctactggcac tctgatggtg ttctttggga atgtggatag ctctgggatc 3780
aagcataata ttttcaaccc ccccattatt gctaggtaca tcaggctgca cccaacccac 3840
tactctatta ggtctaccct gaggatggag ctgatgggct gtgacctgaa ctcttgtagc 3900
atgcccctgg gcatggagag caaggctatc tctgatgccc agatcactgc cagcagctac 3960
tttaccaaca tgtttgctac ttggagcccc agcaaggcca ggctgcacct gcagggcagg 4020
agcaatgcct ggaggcccca ggtgaacaac cccaaggagt ggctgcaggt ggattttcag 4080
aagaccatga aggtgactgg ggtgaccact caggggggtga aaagcctgct gactagcatg 4140
tatgtgaagg agtttctgat cagcagctct caggatggcc atcagtggac cctgttcttc 4200
cagaatggca aggtgaaggt gttccagggc aaccaggata gcttcacccc tgtggtgaat 4260
agcctggacc ccccccctgct gaccaggtac ctgaggatcc atccccagag ctgggtgcac 4320
cagattgccc tgaggatgga ggtgctgggc tgtgaagccc aggacctgta ctga 4374

<210> SEQ ID NO 89
<211> LENGTH: 4890
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 89
atgcagattg agctgagcac ctgcttcttc ctgtgcctgc tgaggttctg cttctctgcc 60
accaggagat actacctggg ggctgtggag ctgagctggg actacatgca gtctgacctg 120
ggggagctgc ctgtggatgc caggttcccc cccagagtgc ccaagagctt ccccttcaac 180
acctctgtgg tgtacaagaa gaccctgttt gtggagttca ctgaccacct gttcaacatt 240
gccaagccca ggccccccctg gatgggcctg ctgggcccca ccatccaggc tgaggtgtat 300
gacactgtgg tgatcaccct gaagaacatg gccagccacc ctgtgagcct gcatgctgtg 360
ggggtgagct actggaaggc ctctgagggg gctgagtatg atgaccagac cagccagagg 420
gagaaggagg atgacaaggt gttccctggg ggcagccaca cctatgtgtg gcaggtgctg 480
aaggagaatg gccccatggc ctctgacccc ctgtgcctga cctacagcta cctgagccat 540
gtggacctgg tgaaggacct gaactctggc ctgattgggg ccctgctggt gtgcagggag 600
ggcagcctgg ccaaggagaa gacccagacc ctgcacaagt tcatcctgct gtttgctgtg 660
tttgatgagg gcaagagctg gcactctgaa accaagaaca gcctgatgca ggacagggat 720
gctgcctctg ccagggcctg gcccaagatg cacactgtga atggctatgt gaacaggagc 780
ctgcctggcc tgattggctg ccacaggaag tctgtgtact ggcatgtgat tggcatgggc 840 accaccccctg aggtgcacag catcttcctg gagggccaca ccttcctggt caggaaccac 900
aggcaggcca gcctggagat cagccccatc accttcctga ctgcccagac cctgctgatg 960
gacctgggcc agttcctgct gttctgccac atcagcagcc accagcatga tggcatggag 1020
gcctatgtga aggtggacag ctgccctgag gagccccagc tgaggatgaa gaacaatgag 1080
gaggctgagg actatgatga tgacctgact gactctgaga tggatgtggt gaggtttgat 1140
gatgacaaca gccccagctt catccagatc aggtctgtgg ccaagaagca ccccaagacc 1200
tgggtgcact acattgctgc tgaggaggag gactgggact atgccccccct ggtgctggcc 1260 cctgatgaca ggagctacaa gagccagtac ctgaacaatg gcccccagag gattggcagg 1320
aagtacaaga aggtcaggtt catggcctac actgatgaaa ccttcaagac cagggaggcc 1380

-continued

```
atccagcatg agtctggcat cctgggcccc ctgctgtatg gggaggtggg ggacaccctg   1440
ctgatcatct tcaagaacca ggccagcagg ccctacaaca tctacccccca tggcatcact   1500
gatgtgaggc ccctgtacag caggaggctg cccaaggggg tgaagcacct gaaggacttc   1560
cccatcctgc ctggggagat cttcaagtac aagtggactg tgactgtgga ggatggcccc   1620
accaagtctg accccaggtg cctgaccaga tactacagca gctttgtgaa catggagagg   1680
gacctggcct ctggcctgat tggcccccctg ctgatctgct acaaggagtc tgtggaccag   1740
aggggcaacc agatcatgtc tgacaagagg aatgtgatcc tgttctctgt gtttgatgag   1800
aacaggagct ggtacctgac tgagaacatc cagaggttcc tgcccaaccc tgctggggtg   1860
cagctggagg accctgagtt ccaggccagc aacatcatgc acagcatcaa tggctatgtg   1920
tttgacagcc tgcagctgtc tgtgtgcctg catgaggtgg cctactggta catcctgagc   1980
attggggccc agactgactt cctgtctgtg ttcttctctg gctacacctt caagcacaag   2040
atggtgtatg aggacaccct gaccctgttc cccttctctg ggagactgt gttcatgagc   2100
atggagaacc ctggcctgtg gattctgggc tgccacaact ctgacttcag gaacaggggc   2160
atgactgccc tgctgaaagt ctccagctgt gacaagaaca ctggggacta ctatgaggac   2220
agctatgagg acatctctgc ctacctgctg agcaagaaca atgccattga gcccaggagc   2280
ttcagccaga acagcaggca ccccagcacc aggcagaagc agttcaatgc caccaccatc   2340
cctgagaatg acatagagaa gacagaccca tggtttgccc accggacccc catgcccaag   2400
atccagaatg tgagcagctc tgacctgctg atgctgctga ggcagagccc caccccccat   2460
ggcctgagcc tgtctgacct gcaggaggcc aagtatgaaa ccttctctga tgaccccagc   2520
cctggggcca ttgacagcaa caacagcctg tctgagatga cccacttcag gccccagctg   2580
caccactctg gggacatggt gttcacccct gagtctggcc tgcagctgag gctgaatgag   2640
aagctgggca ccactgctgc cactgagctg aagaagctgg acttcaaagt ctccagcacc   2700
agcaacaacc tgatcagcac catcccctct gacaacctgg ctgctggcac tgacaacacc   2760
agcagcctgg gccccccag catgcctgtg cactatgaca gccagctgga caccaccctg   2820
tttggcaaga agagcagccc cctgactgag tctgggggcc ccctgagcct gtctgaggag   2880
aacaatgaca gcaagctgct ggagtctggc ctgatgaaca gccaggagag cagctggggc   2940
aagaatgtga gcaccaggag cttccagaag aagaccaggc actacttcat tgctgctgtg   3000
gagaggctgt gggactatgg catgagcagc agcccccatg tgctgaggaa cagggcccag   3060
tctggctctg tgccccagtt caagaaggtg gtgttccagg agttcactga tggcagcttc   3120
acccagcccc tgtacagagg ggagctgaat gagcacctgg gcctgctggg cccctacatc   3180
agggctgagg tggaggacaa catcatggtg accttcagga accaggccag caggccctac   3240
agcttctaca gcagcctgat cagctatgag gaggaccaga ggcagggggc tgagcccagg   3300
aagaactttg tgaagcccaa tgaaaccaag acctacttct ggaaggtgca gcaccacatg   3360
gcccccacca aggatgagtt tgactgcaag gcctgggcct acttctctga tgtggacctg   3420
gagaaggatg tgcactctgg cctgattggc cccctgctgg tgtgccacac caacaccctg   3480
aaccctgccc atggcaggca ggtgactgtg caggagtttg ccctgttctt caccatcttt   3540
gatgaaacca agagctggta cttcactgag aacatggaga ggaactgcag ggccccctgc   3600
aacatccaga tggaggaccc caccttcaag gagaactaca ggttccatgc catcaatggc   3660
tacatcatgg acaccctgcc tggcctggtg atggcccagg accagaggat caggtggtac   3720
ctgctgagca tgggcagcaa tgagaacatc cacagcatcc acttctctgg ccatgtgttc   3780
```

actgtgagga agaaggagga gtacaagatg gccctgtaca acctgtaccc tggggtgttt 3840
gagactgtgg agatgctgcc cagcaaggct ggcatctgga gggtggagtg cctgattggg 3900
gagcacctgc atgctggcat gagcaccctg ttcctggtgt acagcaacaa gtgccagacc 3960
cccctgggca tggcctctgg ccacatcagg gacttccaga tcactgcctc tggccagtat 4020
ggccagtggg cccccaagct ggccaggctg cactactctg gcagcatcaa tgcctggagc 4080
accaaggagc ccttcagctg gatcaaggtg gacctgctgg cccccatgat catccatggc 4140
atcaagaccc agggggccag gcagaagttc agcagcctgt acatcagcca gttcatcatc 4200
atgtacagcc tggatggcaa gaagtggcag acctacaggg gcaacagcac tggcaccctg 4260
atggtgttct ttggcaatgt ggacagctct ggcatcaagc acaacatctt caaccccccc 4320
atcattgcca gatacatcag gctgcacccc acccactaca gcatcaggag caccctgagg 4380
atggagctga tgggctgtga cctgaacagc tgcagcatgc ccctgggcat ggagagcaag 4440
gccatctctg atgcccagat cactgccagc agctacttca ccaacatgtt tgccacctgg 4500
agccccagca aggccaggct gcacctgcag ggcaggagca atgcctggag gccccaggtc 4560
aacaacccca aggagtggct gcaggtggac ttccagaaga ccatgaaggt gactggggtg 4620
accacccagg gggtgaagag cctgctgacc agcatgtatg tgaaggagtt cctgatcagc 4680
agcagccagg atggccacca gtggaccctg ttcttccaga atggcaaggt gaaggtgttc 4740
cagggcaacc aggacagctt cacccctgtg gtgaacagcc tggacccccc cctgctgacc 4800
agatacctga ggattcaccc ccagagctgg gtgcaccaga ttgccctgag gatggaggtg 4860
ctgggctgtg aggcccagga cctgtactga 4890

<210> SEQ ID NO 90
<211> LENGTH: 4374
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 90
atgcagattg agctgtcaac ttgctttttc ctgtgcctgc tgagattttg tttttccgct 60
actagaagat actacctggg ggctgtggaa ctgtcttggg attacatgca gagtgacctg 120
ggagagctgc cagtggacgc acgatttcca cctagagtcc ctaaatcatt ccccttcaac 180
accagcgtgg tctataagaa aacactgttc gtggagttta ctgatcacct gttcaacatc 240
gctaagcctc ggccaccctg gatgggactg ctgggaccaa caatccaggc agaggtgtac 300
gacaccgtgg tcattacact gaaaaacatg gcctcacacc ccgtgagcct gcatgctgtg 360
ggcgtcagct actggaaggc ttccgaaggg gcagagtatg acgatcagac ttcccagaga 420
gaaaaagagg acgataaggt gtttcctggc gggtctcata cctatgtgtg gcaggtcctg 480
aaagagaatg gccccatggc ttccgaccct ctgtgcctga cctactctta tctgagtcac 540
gtggacctgg tcaaggatct gaacagcgga ctgatcggag cactgctggt gtgtagggaa 600
gggagcctgg ctaaggagaa aacccagaca ctgcataagt tcattctgct gttcgccgtg 660
tttgacgaag gaaaatcatg gcacagcgag acaaagaata gtctgatgca ggaccgggat 720
gccgcttcag ccagagcttg gcccaaaatg cacactgtga acggctacgt caatcgctca 780
ctgcctggac tgatcggctg ccaccgaaag agcgtgtatt ggcatgtcat cggaatgggc 840
accacacctg aagtgcactc cattttcctg gaggggcata cctttctggt ccgcaaccac 900

-continued

```
cgacaggcct ccctggagat ctctccaatt accttcctga cagctcagac tctgctgatg    960
gatctgggac agttcctgct gttttgccac atcagctccc accagcatga tggcatggag   1020
gcctacgtga aagtggacag ctgtcccgag gaacctcagc tgaggatgaa gaacaatgag   1080
gaagctgaag actatgacga tgacctgacc gactccgaga tggatgtggt ccgattcgat   1140
gacgataaca gcccctcctt tatccagatt agatctgtgg ccaagaaaca ccctaagaca   1200
tgggtccatt acatcgcagc cgaggaagag gactgggatt atgcaccact ggtgctggca   1260
ccagacgatc gatcctacaa atctcagtat ctgaacaatg gaccacagcg gattggcaga   1320
aagtacaaga aagtgaggtt catggcttat accgatgaaa ccttcaagac tcgcgaagca   1380
atccagcacg agagcgggat tctgggacca ctgctgtacg gagaagtggg ggacaccctg   1440
ctgatcattt ttaagaacca ggccagcagg ccttacaata tctatccaca tggaattaca   1500
gatgtgcgcc ctctgtacag ccggagactg ccaaagggcg tcaaacacct gaaggacttc   1560
ccaatcctgc ccggggaaat ttttaagtat aaatggactg tcaccgtcga ggatggcccc   1620
actaagagcg accctaggtg cctgacccgc tactattcta gtttcgtgaa tatggaaagg   1680
gatctggcca gcggactgat cggcccactg ctgatttgtt acaaagagag cgtggatcag   1740
agaggcaacc agatcatgtc cgacaagagg aatgtgattc tgttcagtgt ctttgacgaa   1800
aaccggtcat ggtatctgac cgagaacatc cagagattcc tgcctaatcc agccggagtg   1860
cagctggaag atcctgagtt tcaggcttct aacatcatgc atagtattaa tggctacgtg   1920
ttcgacagtc tgcagctgtc agtgtgtctg cacgaggtcg cttactggta tatcctgagc   1980
attggagcac agacagattt cctgagcgtg ttcttttccg gctacacttt taagcataaa   2040
atggtgtatg aggacacact gactctgttc cccttcagcg gcgaaaccgt gtttatgtcc   2100
atggagaatc ccgggctgtg gatcctggga tgccacaaca gcgatttcag gaatcgcggg   2160
atgactgccc tgctgaaagt gtcaagctgt gacaagaaca ccggagacta ctatgaagat   2220
tcatacgagg acatcagcgc atatctgctg tccaaaaaca atgccattga acccaggtct   2280
tttagtcaga atcctccagt gctgaagagg caccagcgcg agatcacccg cactaccctg   2340
cagagtgatc aggaagagat cgactacgac gatacaattt ctgtggaaat gaagaaagag   2400
gacttcgata tctatgacga agatgagaac cagagtcctc gatcattcca gaagaaaacc   2460
cggcattact ttattgctgc agtggagcgc ctgtgggatt atggcatgtc ctctagtcct   2520
cacgtgctgc gaaatcgggc ccagtcaggg agcgtcccac agttcaagaa agtggtcttc   2580
caggagttta cagacggatc ctttactcag ccactgtacc ggggcgaact gaacgagcac   2640
ctggggctgc tgggacccta tatcagagct gaagtggagg ataacattat ggtcaccttc   2700
agaaatcagg catctaggcc ttacagtttt tattcaagcc tgatctctta cgaagaggac   2760
cagaggcagg gagcagaacc acgaaaaaac ttcgtgaagc ctaatgagac caaaacatac   2820
ttttggaagg tgcagcacca tatggcccca acaaaagacg aattcgattg caaggcatgg   2880
gcctattttt ctgacgtgga tctggagaag gacgtccaca gtggcctgat cgggccactg   2940
ctggtgtgtc atactaacac cctgaatccc gcacacggca ggcaggtcac tgtccaggaa   3000
ttcgccctgt tctttaccat ctttgatgag acaaaaagct ggtacttcac cgaaaacatg   3060
gagcgaaatt gccgggctcc atgtaatatt cagatggaag accccacatt caaggagaac   3120
taccgctttc atgccatcaa tgggtatatt atggatactc tgcccggact ggtcatggct   3180
caggaccaga gaatcaggtg gtacctgctg agcatggggt ccaacgagaa tatccactca   3240
```

```
attcatttca gcggacacgt gtttactgtc cggaagaaag aagagtataa aatggccctg   3300

tacaacctgt atcccggcgt gttcgaaacc gtcgagatgc tgcctagcaa ggcagggatc   3360

tggagagtgg aatgcctgat tggggagcac ctgcatgccg gaatgtctac cctgtttctg   3420

gtgtacagta ataagtgtca gacacccctg ggatggcttc ccggacatat ccgggatttc   3480

cagattaccg catctggaca gtacggccag tgggccccta agctggctag actgcactat   3540

tccgggtcta tcaacgcttg gtccacaaaa gagcctttct cttggattaa ggtggacctg   3600

ctggcaccaa tgatcattca tggcatcaaa actcaggggg ccaggcagaa gttctcctct   3660

ctgtacatct cacagtttat catcatgtac agcctggatg gcaagaaatg gcagacatac   3720

cgcggcaata gcacagggac tctgatggtg ttctttggca acgtggacag ttcagggatc   3780

aagcacaaca ttttcaatcc ccctatcatt gctagataca tcaggctgca cccaacccat   3840

tattctattc gaagtacact gcggatggaa ctgatggggt gcgatctgaa cagttgttca   3900

atgcccctgg gaatggagtc caaggcaatc tctgacgccc agattaccgc tagctcctac   3960

ttcactaata tgtttgctac ctggagcccc tccaaagcac gactgcatct gcagggacga   4020

agcaacgcat ggcgaccaca ggtgaacaat cccaaggagt ggctgcaggt cgattttcag   4080

aaaactatga aggtgaccgg agtcacaact cagggcgtga aagtctgct gacctcaatg    4140

tacgtcaagg agttcctgat ctctagttca caggacggcc accagtggac actgttcttt   4200

cagaacggaa aggtgaaagt cttccagggc aatcaggatt cctttacacc tgtggtcaac   4260

tctctggacc cacccctgct gactcgctac ctgcgaatcc acccacagtc ctgggtgcat   4320

cagattgcac tgagaatgga agtcctgggc tgcgaggccc aggacctgta ttga         4374
```

<210> SEQ ID NO 91
<211> LENGTH: 736
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 91

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Gln Pro Gly Ala Pro Lys Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Asp Gln Ser Pro Gln Glu Pro Asp Ser Ser Ser Gly Val Gly
145                 150                 155                 160
```

-continued

```
Lys Ser Gly Lys Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Thr Ser Leu Gly Ser Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Lys Leu Ser Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Gln Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Asn Arg Thr
        435                 440                 445

Gln Gly Thr Thr Ser Gly Thr Thr Asn Gln Ser Arg Leu Leu Phe Ser
    450                 455                 460

Gln Ala Gly Pro Gln Ser Met Ser Leu Gln Ala Arg Asn Trp Leu Pro
465                 470                 475                 480

Gly Pro Cys Tyr Arg Gln Gln Arg Leu Ser Lys Thr Ala Asn Asp Asn
                485                 490                 495

Asn Asn Ser Asn Phe Pro Trp Thr Ala Ala Ser Lys Tyr His Leu Asn
            500                 505                 510

Gly Arg Asp Ser Leu Val Asn Pro Gly Pro Ala Met Ala Ser His Lys
        515                 520                 525

Asp Asp Glu Glu Lys Phe Phe Pro Met His Gly Asn Leu Ile Phe Gly
    530                 535                 540

Lys Glu Gly Thr Thr Ala Ser Asn Ala Glu Leu Asp Asn Val Met Ile
545                 550                 555                 560

Thr Asp Glu Glu Glu Ile Arg Thr Thr Asn Pro Val Ala Thr Glu Gln
                565                 570                 575

Tyr Gly Thr Val Ala Asn Asn Leu Gln Ser Ser Asn Thr Ala Pro Thr
```

580 585 590

Thr Arg Thr Val Asn Asp Gln Gly Ala Leu Pro Gly Met Val Trp Gln
595 600 605

Asp Arg Asp Val Tyr Leu Gln Gly Pro Ile Trp Ala Lys Ile Pro His
610 615 620

Thr Asp Gly His Phe His Pro Ser Pro Leu Met Gly Gly Phe Gly Leu
625 630 635 640

Lys His Pro Pro Pro Gln Ile Met Ile Lys Asn Thr Pro Val Pro Ala
645 650 655

Asn Pro Pro Thr Thr Phe Ser Pro Ala Lys Phe Ala Ser Phe Ile Thr
660 665 670

Gln Tyr Ser Thr Gly Gln Val Ser Val Glu Ile Glu Trp Glu Leu Gln
675 680 685

Lys Glu Asn Ser Lys Arg Trp Asn Pro Glu Ile Gln Tyr Thr Ser Asn
690 695 700

Tyr Asn Lys Ser Val Asn Val Asp Phe Thr Val Asp Thr Asn Gly Val
705 710 715 720

Tyr Ser Glu Pro Arg Pro Ile Gly Thr Arg Tyr Leu Thr Arg Pro Leu
725 730 735

<210> SEQ ID NO 92
<211> LENGTH: 738
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 92

Met Ala Ala Asp Gly Tyr Leu Pro Asp Trp Leu Glu Asp Asn Leu Ser
1 5 10 15

Glu Gly Ile Arg Glu Trp Trp Asp Leu Lys Pro Gly Ala Pro Lys Pro
20 25 30

Lys Ala Asn Gln Gln Lys Gln Asp Asn Gly Arg Gly Leu Val Leu Pro
35 40 45

Gly Tyr Lys Tyr Leu Gly Pro Phe Asn Gly Leu Asp Lys Gly Glu Pro
50 55 60

Val Asn Ala Ala Asp Ala Ala Ala Leu Glu His Asp Lys Ala Tyr Asp
65 70 75 80

Gln Gln Leu Gln Ala Gly Asp Asn Pro Tyr Leu Arg Tyr Asn His Ala
85 90 95

Asp Ala Glu Phe Gln Glu Arg Leu Gln Glu Asp Thr Ser Phe Gly Gly
100 105 110

Asn Leu Gly Arg Ala Val Phe Gln Ala Lys Lys Arg Val Leu Glu Pro
115 120 125

Leu Gly Leu Val Glu Ser Pro Val Lys Thr Ala Pro Gly Lys Lys Arg
130 135 140

Pro Val Glu Pro Ser Pro Gln Arg Ser Pro Asp Ser Ser Thr Gly Ile
145 150 155 160

Gly Lys Lys Gly Gln Gln Pro Ala Lys Lys Arg Leu Asn Phe Gly Gln
165 170 175

Thr Gly Asp Ser Glu Ser Val Pro Asp Pro Gln Pro Ile Gly Glu Pro
180 185 190

Pro Ala Ala Pro Ser Gly Val Gly Pro Asn Thr Met Ala Ala Gly Gly
195 200 205

```
Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Asn Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Ser Thr Gly Gly Thr Ala Gly Thr Gln Gln Leu Leu
    450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
        515                 520                 525

His Lys Asp Asp Glu Glu Arg Phe Phe Pro Ser Ser Gly Val Leu Met
    530                 535                 540

Phe Gly Lys Gln Gly Ala Gly Lys Asp Asn Val Asp Tyr Ser Ser Val
545                 550                 555                 560

Met Leu Thr Ser Glu Glu Glu Ile Lys Thr Thr Asn Pro Val Ala Thr
                565                 570                 575

Glu Gln Tyr Gly Val Val Ala Asp Asn Leu Gln Gln Gln Asn Ala Ala
            580                 585                 590

Pro Ile Val Gly Ala Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
```

```
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ala Lys Leu Ala Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
                725                 730                 735

Asn Leu


<210> SEQ ID NO 93
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 93

aggtaagtgc cgtgtgtggt tcccgcgggc ctggcctctt tacgggttat ggcccttgcg     60

tgccttgaat tactgacact gacatccact ttttcttttt ctccacag                 108


<210> SEQ ID NO 94
<211> LENGTH: 2824
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 94

atgcagaggg tgaacatgat catggctgag agccctggcc tgatcaccat ctgcctgctg     60

ggctacctgc tgtctgctga atgtacaggt ttgtttcctt ttttataata cattgagtat    120

gcttgccttt tagatataga aatatctgat tctgtcttct tcactaaatt ttgattacat    180

gatttgacag caatattgaa gagtctaaca gccagcaccc aggttggtaa gtactggttc    240

tttgttagct aggttttctt cttcttcact tttaaaacta aatagatgga caatgcttat    300

gatgcaataa ggtttaataa acactgttca gttcagtatt tggtcatgta attcctgtta    360

aaaaacagtc atctccttgg tttaaaaaaa ttaaaagtgg gaaaacaaag aaatagcaga    420

atatagtgaa aaaaaataac cacagtattt ttgtttggac ttaccacttt gaaatcaaat    480

tgggaaacaa aagcacaaac agtggcctta tttacacaaa aagtctgatt ttaagatatg    540

tgacaattca aggtttcaga agtatgtaag gaggtgtgtc tctaattttt taaattatat    600

atcttcaatt taaagtttta gttaaaacat aaagattaac ctttcattag caagctgtta    660

gttatcacca aagcttttca tggattagga aaaaatcatt ttgtctctat ctcaaacatc    720

ttggagttga tatttgggga aacacaatac tcagttgagt tccctagggg agaaaagcaa    780

gcttaagaat tgacacaaag agtaggaagt tagctattgc aacatatatc actttgtttt    840

ttcacaacta cagtgacttt atttatttcc cagaggaagg catacaggga agaaattatc    900

ccatttggac aaacagcatg ttctcacagt aagcacttat cacacttact tgtcaacttt    960
```

-continued

```
ctagaatcaa atctagtagc tgacagtacc aggatcaggg gtgccaaccc taagcacccc   1020

cagaaagctg actggccctg tggttcccac tccagacatg atgtcagctg tgaaatccac   1080

ctccctggac cataattagg cttctgttct tcaggagaca tttgttcaaa gtcatttggg   1140

caaccatatt ctgaaaacag cccagccagg gtgatggatc actttgcaaa gatcctcaat   1200

gagctatttt caagtgatga caaagtgtga agttaagggc tcatttgaga actttctttt   1260

tcatccaaag taaattcaaa tatgattaga aatctgacct tttattactg gaattctctt   1320

gactaaaagt aaaattgaat tttaattcct aaatctccat gtgtatacag tactgtggga   1380

acatcacaga ttttggctcc atgccctaaa gagaaattgg ctttcagatt atttggatta   1440

aaaacaaaga ctttcttaag agatgtaaaa ttttcatgat gttttctttt ttgctaaaac   1500

taaagaatta ttcttttaca tttcagtttt tcttgatcat gaaaatgcca acaaaattct   1560

gaatagacca aagaggtata actctggcaa gcttgaagag tttgtacagg ggaatctgga   1620

gagagagtgt atggaagaga agtgcagctt tgaggaagcc agagaagtgt ttgaaaatac   1680

agagagaaca actgaatttt ggaagcagta tgtggatggt gatcaatgtg agagcaatcc   1740

ctgcttgaat ggggggagct gtaaagatga tatcaacagc tatgaatgtt ggtgtccctt   1800

tggatttgag gggaaaaact gtgagcttga tgtgacctgt aatatcaaga atggcaggtg   1860

tgagcaattt tgcaagaatt ctgctgataa caaagtggtc tgtagctgca ctgagggata   1920

taggctggct gaaaaccaga agagctgtga acctgcagtg ccttttccct gtgggagagt   1980

gtctgtgagc caaaccagca agctgactag ggctgaagca gtctttcctg atgtagatta   2040

tgtgaatagc actgaggctg agacaatcct tgacaatatc actcagagca cacagagctt   2100

caatgacttc accagggtgg taggaggggga ggatgccaag cctgggcagt tcccctggca   2160

ggtagtgctc aatggaaaag tggatgcctt ttgtggaggt tcaattgtaa atgagaagtg   2220

gattgtgact gcagcccact gtgtggaaac tggagtcaag attactgtgg tggctggaga   2280

gcacaatatt gaggaaactg agcacactga gcagaagagg aatgtgatca ggattatccc   2340

ccaccacaac tacaatgctg ctatcaacaa gtacaaccat gacattgccc tcctggaact   2400

ggatgaaccc ctggtcttga acagctatgt gacacccatc tgtattgctg ataaagagta   2460

caccaacatc ttcttgaaat ttgggtctgg atatgtgtct ggctggggca gggtgttcca   2520

taaaggcagg tctgccctgg tattgcagta tttgagggtg cctctggtgg atagagcaac   2580

ctgcttgctg agcaccaagt ttacaatcta caacaatatg ttctgtgcag ggttccatga   2640

aggtggtaga gacagctgcc agggagattc tgggggtccc catgtgactg aggtggaggg   2700

aaccagcttc ctgactggga ttatcagctg ggtgaggag tgtgctatga agggaaagta   2760

tgggatctac acaaaagtat ccagatatgt gaactggatt aaggagaaaa ccaagctgac   2820

ttga                                                                2824
```

<210> SEQ ID NO 95
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 95

```
tgaggaggct gaagactatg a                                               21
```

-continued

```
<210> SEQ ID NO 96
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96

ccacagacct gatctgaatg aa                                          22


<210> SEQ ID NO 97
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 97

tgaggtttga tgatgaca                                               18


<210> SEQ ID NO 98
<211> LENGTH: 9
<212> TYPE: PRT
<213> ORGANISM: Unknown
<220> FEATURE:
<223> OTHER INFORMATION: Description of Unknown:
      CD4-plus T cell epitope sequence

<400> SEQUENCE: 98

Gly Arg Val Arg Val Asn Ser Ala Tyr
1               5
```